US008263063B2

(12) United States Patent
Konradi et al.

(10) Patent No.: US 8,263,063 B2
(45) Date of Patent: Sep. 11, 2012

(54) MULTIMERIC VLA-4 ANTAGONISTS COMPRISING POLYMER MOIETIES

(75) Inventors: Andrei W. Konradi, Burlingame, CA (US); Michael A. Pleiss, Sunnyvale, CA (US); Christopher M. Semko, Fremont, CA (US); Theodore Yednock, Forest Knolls, CA (US); Jenifer L. Smith, South San Francisco, CA (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 12/877,496

(22) Filed: Sep. 8, 2010

(65) Prior Publication Data

US 2011/0002876 A1  Jan. 6, 2011

Related U.S. Application Data

(62) Division of application No. 11/177,748, filed on Jul. 8, 2005, now Pat. No. 7,794,700.

(60) Provisional application No. 60/586,975, filed on Jul. 8, 2004.

(51) Int. Cl.
*A61K 31/74* (2006.01)

(52) U.S. Cl. .................................. 424/78.27

(58) Field of Classification Search ........................ None
See application file for complete search history.

(56) References Cited

U.S. PATENT DOCUMENTS

| 6,479,492 | B1 | 11/2002 | Konradi et al. |
| 6,489,300 | B1 | 12/2002 | Thorsett et al. |
| 6,492,372 | B1 | 12/2002 | Konradi et al. |
| 6,525,026 | B2 | 2/2003 | Thorsett et al. |
| 6,900,179 | B2 | 5/2005 | Thorsett et al. |
| 6,903,088 | B2 | 6/2005 | Konradi et al. |
| 6,911,439 | B2 | 6/2005 | Konradi et al. |
| 6,939,855 | B2 | 9/2005 | Yednock et al. |
| 7,005,433 | B2 | 2/2006 | Konradi et al. |
| 7,026,328 | B2 | 4/2006 | Konradi et al. |
| 7,049,306 | B2 | 5/2006 | Konradi et al. |
| 7,135,477 | B2 | 11/2006 | Konradi et al. |
| 7,205,310 | B2 | 4/2007 | Konradi et al. |
| 7,378,529 | B2 | 5/2008 | Konradi et al. |
| 7,427,628 | B2 | 9/2008 | Konradi et al. |
| 2005/0261293 | A1 | 11/2005 | Konradi et al. |
| 2006/0013799 | A1 | 1/2006 | Konradi et al. |
| 2007/0037804 | A1 | 2/2007 | Stappenbeck et al. |
| 2007/0099921 | A1 | 5/2007 | Konradi et al. |

FOREIGN PATENT DOCUMENTS

| EP | 0 503 548 | 9/1992 |
| WO | 99/06390 | 2/1999 |
| WO | 99/06391 | 2/1999 |
| WO | 00/18759 A1 | 4/2000 |
| WO | 00/43369 | 7/2000 |
| WO | 00/43372 | 7/2000 |
| WO | 01/54690 | 8/2001 |
| WO | 02/08202 | 1/2002 |
| WO | 03/084984 | 10/2003 |
| WO | 03/099809 | 12/2003 |
| WO | 2004/066931 | 8/2004 |
| WO | 2004/066932 | 8/2004 |
| WO | 2005/000246 | 1/2005 |
| WO | 2005/000244 | 6/2005 |
| WO | 2005/070921 | 8/2005 |
| WO | 2005/097162 | 10/2005 |
| WO | 2005/111020 | 11/2005 |
| WO | 2006/010054 | 1/2006 |
| WO | 2006/127584 | 11/2006 |
| WO | 2007/008563 | 1/2007 |
| WO | 2009/075806 | 6/2009 |

OTHER PUBLICATIONS

Dorwald F. A. Side Reactions in Organic Synthesis, 2005, Wiley: VCH, Weinheim p. IX of Preface.*
Chen et al., "Evidence that ligand and metal ion binding to integrin $\alpha 4\beta 1$ are regulated through a coupled Equilibrium", (2001) Journ. of Biol. Chem., 276: 36520-36529.
Hagg and Kratz, "Polymer Therapeutics: Concepts and Applications", (2006) Angew. Chem. Int. Ed., 45:1198-1215.
Huryn et al., "Synthesis, Characterization and Evaluation of Prodrugs of VLA-4 Antagonists", (2004) Bioorganic & Medicinal Chemistry Letters, 14:1651-1654.
Jones et al., "Multivalent Poly(ethylene glycol)-Containing Conjugates for in Vivo Antibody Suppression," (2003) Bioconjugate Chem., 14:1067-1076.
Pepinsky et al., "Design, Synthesis, and Analysis of a Polyethelene Glycol-Modified (PEGylated) Small Molecule Inhibitor of Integrin $\alpha 4\beta 1$ with Improved Pharmaceutical Properties", (2005) JPET, vol. 312: No. 2, 742-750.
Dorwald F.A., Side Reactions in Organic Synthesis, (2005), Wiley; VCH, Weinheim p. IX of Preface.

(Continued)

*Primary Examiner* — Jeffrey Murray
(74) *Attorney, Agent, or Firm* — McDonnell Boehnen Hulbert & Berghoff LLP

(57) ABSTRACT

Disclosed are conjugates exhibiting VLA-4 antagonistic properties. Certain of these conjugates also inhibit leukocyte adhesion and, in particular, leukocyte adhesion mediated by VLA-4. The conjugates of this invention are characterized as containing more than one VLA-4 inhibiting compound covalently attached to a bio-compatible polymer, such as polyethylene glycol. Conjugates of the invention are defined by formula I,

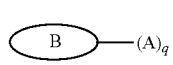

I wherein A, B, and q are described in the specification. Such conjugates are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis, and myocardial ischemia. The conjugates can also be administered for the treatment of inflammatory brain diseases such as multiple sclerosis.

30 Claims, No Drawings

OTHER PUBLICATIONS

Borisy, et al., Proceedings of the National Academy of Sciences of the United States of America, (2003)100(13) 7977-7982.

Pepinsky, et al., (Oct. 14, 2004), JPET online publication DOL:10.1124/jpet.104.075648.

Pepinsky et al., Abstract Mentioning online publication of Oct. 14, 2004 and print publication (JPET 2005).

Huryn, et al., "The Identification and Optimization of Orally Efficacious, Small Molecule VLA-4 Antagonists", (2004) Current Topics in Medicinal Chemistry vol. 4, pp. 1473-1484.

Veronese F M et al, "Biioconjugation in pharmaceutical chemistry" (1999) Farmaco, Societa Chimica Italiana, Pavia, IT, vol. 54, pp. 497-516, XP00828090.

* cited by examiner

MULTIMERIC VLA-4 ANTAGONISTS COMPRISING POLYMER MOIETIES

CROSS REFERENCE TO RELATED APPLICATIONS

This application claims priority from U.S. Provisional Application Ser. No. 60/586,975 filed Jul. 8, 2004, which is incorporated herein by reference in its entirety.

BACKGROUND OF THE INVENTION

1. Field of the Invention

This invention relates to conjugates which inhibit leukocyte adhesion and, in particular, leukocyte adhesion mediated at least in part by VLA-4. The conjugates of this invention are characterized as containing more than one VLA-4 inhibiting compound covalently attached to a bio-compatible polymer, such as polyethylene glycol.

2. State of the Art

The physical interaction of inflammatory leukocytes with each other and other cells of the body plays an important role in regulating immune and inflammatory responses [Springer, T. A. Nature, 346, 425, (1990); Springer, T. A. Cell 76, 301, (1994)]. Many of these interactions are mediated by specific cell surface molecules collectively referred to as cell adhesion molecules. These adhesion molecules have been sub-divided into different groups on the basis of their structure. One family of adhesion molecules which is believed to play a important role in regulating immune and inflammatory responses is the integrin family. This family of cell surface glycoproteins has a typical non-covalently linked heterodimer structure.

The particular integrin subgroup of interest herein involves the alpha 4 ($\alpha 4$) chain, which can pair with two different beta chains beta1 ($\beta 1$) and beta7 ($\beta 7$) [Sonnenberg, A. ibid]. The $\alpha 4\beta 1$ pairing occurs on many circulating leukocytes (for example lymphocytes, monocytes and eosinophils) although it is absent or only present at low levels on circulating neutrophils. VLA-4 (Very Late Antigen-4, also referred to as $\alpha_4\beta_1$ integrin and as CD49d/CD29), first identified by Hemler and Takada[1] is a member of the $\beta 1$ integrin family of cell surface receptors. VLA-4 consists of an $\alpha 4$ chain and a $\beta 1$ chain. There are at least nine $\beta 1$ integrins, all sharing the same $\beta 1$ chain and each having a distinct $\alpha$ chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells.

VLA-4 ($\alpha 4\beta 1$ integrin) binds to an adhesion molecule called Vascular Cell Adhesion Molecule-1 (or VCAM-1) which is frequently up-regulated on endothelial cells at sites of inflammation [Osborne, L. Cell, 62, 3 (1990)]. VCAM-1 is a non-matrix molecule which is an expressed receptor that is believed to be responsible for trafficking leukocytes into the central nervous system (CNS). $\alpha 4\beta 1$ has also been shown to bind to at least three sites in the matrix molecule fibronectin [Humphries, M. J. et al. Ciba Foundation Symposium, 189, 177, (1995)]. Distinct epitopes of VLA-4 are responsible for the fibronectin and VCAM-1 binding activities and each has been demonstrated to be independently inhibited.[2] Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992).

The integrin generated by the pairing of $\alpha 4$ and $\beta 7$ has been termed LPAM-1 [Holzmann, B. and Weissman, I. EMBO J. 8, 1735, (1989)] and like $\alpha 4\beta 1$, can bind to VCAM-1 and fibronectin. In addition, .alpha.4.beta.7 binds to an adhesion molecule believed to be involved in the homing of leukocytes to mucosal tissue termed MAdCAM-1 [Berlin, C. et al. Cell, 74, 185, (1993)]. The interaction between. $\alpha 4137$ and MAdCAM-1 may also be important at sites of inflammation outside of mucosal tissue [Yang, X-D. et al. PNAS, 91, 12604 (1994)].

Intercellular adhesion mediated by VLA-4 and other cell surface receptors is associated with a number of inflammatory responses. At the site of an injury or other inflammatory stimuli, activated vascular endothelial cells express molecules that are adhesive for leukocytes. The mechanics of leukocyte adhesion to endothelial cells involve, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as multiple sclerosis (MS), meningitis, encephalitis, and a disease model called experimental autoimmune encephalomyelitis (EAE), are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive cell damage and death resulting in impaired nerve conduction and paralysis. Similar occurrences in encephalitis and meningitis indicate that these diseases can be treated with suitable cell adhesion inhibitors.

In other organ systems, tissue damage also occurs via an adhesion mechanism resulting in migration or activation of leukocytes. For example, inflammatory bowel disease[15] (including ulcerative colitis and Crohn's disease), are at least partially caused by leukocyte trafficking across the intestinal endothelium via an $\alpha 4\beta 7$ interaction with MadCAM and possibly $\alpha 4\beta 1$ interaction with VCAM-1 expressed in this tissue as well. Asthma[6-8], rheumatoid arthritis[18-21] and tissue transplant rejection[22] are all thought to have components based in interaction of $\alpha 4\beta 1$ with VCAM-1 and/or fibronectin, probably both. it has been shown that the initial insult following myocardial (heart tissue) ischemia can be further complicated by leukocyte entry to the injured tissue causing still further injury (Vedder et al.[5]). Other inflammatory or medical conditions mediated by an adhesion molecule mechanism include, by way of example, Alzheimer's disease, atherosclerosie[9-10], AIDS dementia[11], diabetes[12-14] (including acute juvenile onset diabetes, tumor metastasis[23-28], stroke, and other cerebral traumas, nephritis, retinitis, atopic dermatitis, psoriasis, and acute leukocyte-mediated lung injury such as that which occurs in adult respiratory distress syndrome.

One group of VLA-4 antagonists showing promise as anti-inflammatory agents is the class of sulfonylated-Pro-Phe compounds as set forth in, for example, U.S. Pat. No. 6,489,300.[31] These compounds are very potent antagonists of VLA-4NCAM-1 binding.

Owing to extensive first pass liver metabolism, these compounds are poorly orally available. Because many of the disease conditions treatable by these compounds are chronic conditions, a prolonged serum half-life for the administered compound would increase the usefulness of these kinds of compounds in treating disease in mammals.

The half-life of a drug is a measure of the time that it takes for the amount of drug in the body to decrease by one half, through normal metabolic and elimination pathways. VLA-4 inhibitors, including those disclosed in U.S. Pat. No. 6,489, 300, suffer from short half-lives of around 10 to 20 minutes, even when intravenously administered in a pharmaceutical formulation. In order for the patient to retain an effective amount of the drug in their system for a reasonable period of time, either very large quantities of the drug must be administered and/or the drug must be administered many times in a day.

VLA-4 inhibitors with such short half-lives are not commercially viable therapeutic candidates. Therefore, there is a need for VLA-4 inhibitors with significantly enhanced serum half-lives; preferably in the range of hours to days.

SUMMARY OF THE INVENTION

This invention provides conjugates exhibiting VLA-4 antagonistic properties. The conjugates of this invention are characterized as containing more than one VLA-4 antagonists covalently attached to a polymer. Without being limited to any theory, the improved serum half-life is believed to be associated with covalent conjugation of active compounds to a polymer. In addition, attachment of multiple copies of such compounds to the polymer minimizes degradation of biological efficacy.

In one aspect, the invention provides conjugates of formula I below:

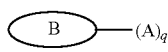

I

B is a bio-compatible polymer moiety optionally covalently attached to a branched-arm hub molecule;
q is from about 2 to about 20;
A at each occurrence is independently a compound of formula II

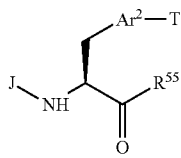

II or a pharmaceutically acceptable salt thereof, wherein
J is selected from:
  a) a group of formula (a):

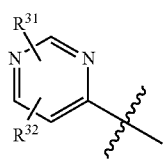

(a)

wherein $R^{31}$ is a covalent bond to the polymer moiety which optionally comprises a linker, or $R^{31}$ is selected from the group consisting of —H, $R^{31'}$, —NH$_2$, —NHR$^{31'}$, -N(R$^{31'}$)$_2$, —NC$_3$-C$_6$cyclic, —OR$^{31'}$, and —SR$^{31'}$, wherein each $R^{31'}$ is independently an optionally substituted straight or branched C$_1$-C$_6$alkyl, optionally substituted C$_3$-C$_6$cycloalkyl, optionally substituted aryl, or optionally substituted heteroaryl, and $R^{32}$ is a covalent bond to the polymer moiety which optionally comprises a linker, or $R^{32}$ is selected from the group consisting of —H, —NO$_2$, haloalkyl, and —N(MR$^{41}$)R$^{42}$ wherein M is a covalent bond, —C(O)— or —SO$_2$—, and $R^{41}$ is $R^{41'}$, N(R$^{41'}$)$_2$) or —OR$^{41'}$, wherein each $R^{41'}$ is independently hydrogen, an optionally substituted straight or branched C$_1$-C$_6$alkyl, optionally substituted cycloalkyl, optionally substituted aryl, optionally substituted heterocyclic or an optionally substituted heteroaryl, wherein optional substitutions are halide, C$_1$-C$_6$alkyl, or —OC$_1$-C$_6$alkyl, and $R^{42}$ is hydrogen, $R^{41'}$, alkynyl, or substituted alkynyl; and
b) a group of formula (b):

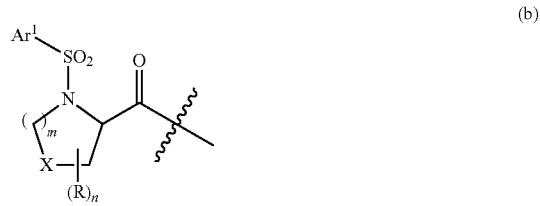

(b)

wherein R is selected from the group consisting of a covalent bond to the polymer moiety, hydrogen, aryl, substituted aryl, heteroaryl, substituted heteroaryl, amino, hydroxyl, substituted amino, alkyl, substituted alkyl, alkyloxy, aryloxy, heteroaryloxy, heterocyclyloxy, thiol, arylthio, heteroarylthio, heterocyclylthio and substituted alkyl wherein each amino, substituted amino, alkyl, substituted alkyl, aryl, substituted aryl, heteroaryl, and substituted heteroaryl is optionally covalently bound to the polymer moiety wherein, in each case, the polymer moiety optionally comprises a linker which covalently links the polymer moiety;

$Ar^1$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to $Ar^1$;

$Ar^2$ is selected from the group consisting of aryl, substituted aryl, heteroaryl, substituted heteroaryl, alkyl, substituted alkyl, alkylamino, and substituted alkylamino, wherein $Ar^2$ is optionally covalently bound to the polymer moiety and wherein the polymer moiety optionally comprises a linker which covalently links the polymer moiety to $Ar^2$;

X is selected from the group consisting of —NR$^1$—, —O—, —S—, —SO—, —SO$_2$ and optionally substituted —CH$_2$— which is optionally covalently bound to the polymer moiety wherein, in each case, the polymer moiety optionally comprises a linker which covalently links the polymer moiety;

where $R^1$ is selected from the group consisting of hydrogen and alkyl;

T is selected from:
a) a group of formula (c)

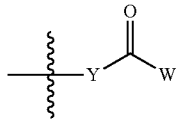

wherein Y is selected from the group consisting of —O— and —NR¹— wherein R¹ is selected from the group consisting of hydrogen and alkyl;
W is selected from the group consisting of a covalent bond to a polymer moiety which optionally comprises a linker and —NR²R³ wherein R² and R³ are independently selected from the group consisting of hydrogen, alkyl, substituted alkyl, and where R² and R³, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;
m is an integer equal to 0, 1 or 2;
n is an integer equal to 0, 1 or 2; and
b) a group of formula (d)

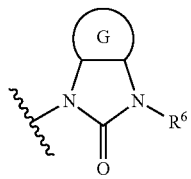

wherein G is an optionally substituted aryl or optionally substituted heteroaryl 5 or 6 membered ring containing 0 to 3 nitrogens, wherein said aryl or heteroary optionally further comprises a covalent bond to a polymer moiety which optionally comprises a linker;
R⁶ is a covalent bond to a polymer moiety which optionally comprises a linker, or R⁶ is —H, alkyl, substituted alkyl, or —CH₂C(O)R¹⁷, wherein R¹⁷ is —OH, —OR¹⁸, or —NHR¹⁸, wherein R¹⁸ is alkyl, substituted alkyl, aryl, substituted aryl, heteroaryl, or substituted heteroaryl;
R⁵⁵ is —OH or a hydrolyzable ester, or R⁵⁵ forms a hydrolyzable polymer ester with the polymer moiety, optionally through a linker;
provided that:
A. at least one of Ar¹, J, Ar², R⁵⁵ and T (more preferably one of J and T) contains a covalent bond to the polymer moiety;
B. when X is —O—, then m is two; and
C. the conjugate of formula I has a molecular weight of no more than about 80,000.

The invention also provides pharmaceutical compositions which compositions comprise, for example, a pharmaceutically acceptable carrier and a therapeutically effective amount of a conjugate of the invention or mixtures thereof.

The invention also provides methods for treating a disease mediated, at least in part, by VLA-4 in a patient, which method comprises administering a pharmaceutical composition comprising a pharmaceutically acceptable carrier and a therapeutically effective amount of a conjugate of the invention or mixtures thereof.

The invention also includes the use of a conjugate of the invention, and pharmaceutically acceptable salts thereof, for the manufacture of a medicament for use in treating a disease mediated, at least in part, by VLA-4 in a patient.

The conjugates and pharmaceutical compositions may be used to treat disease conditions mediated, at least in part, by VLA-4 or leukocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, Sjogren's disease, atopic dermatitis, psoriasis, myocardial ischemia and acute leukocyte-mediated lung injury such as that which occurs in adult respiratory distress syndrome.

Other disease conditions which may be treated using conjugates and compositions of the present invention include, but are not limited to, inflammatory conditions such as erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Preferably, the conjugates and pharmaceutically compositions of this invention are used in methods for treating asthma, rheumatoid arthritis and multiple sclerosis. As to this latter disease, the conjugates of this invention not only provide an anti-inflammatory effect when administered in vivo but further find use in treating conditions and diseases associated with demyelination.

The invention also provides methods of preparing the conjugates of the invention and the intermediates used in those methods.

DETAILED DESCRIPTION OF THE INVENTION

As noted above, this invention relates to conjugates which inhibit leukocyte adhesion and, in particular, leukocyte adhesion mediated, at least in part, by VLA-4.

In one preferred embodiment, only one of Ar¹, J, Ar², and T contains a covalent bond to a polymer moiety.

In another preferred embodiment, the polymer moiety is attached to the —NR²R³ group.

In a further preferred embodiment, when X in the conjugates of the invention is NR¹, then m is two.

In yet another preferred embodiment, q is an integer of from 2 to about 20 and more preferably from 2 to about 8.

Preferred conjugates of formula I include those of formula Ia below:

and pharmaceutically acceptable salts thereof, wherein
B is a a di-valent, tri-valent, tetra-valent or higher valency bio-compatible polymer moiety or optionally more than one biocompatible polymers covalently joined by a functional group linkage or by a branched-arm hub molecule or both to form a di-valent, tri-valent, tetra-valent or higher valency polymer moiety;
q is from 2 to about 20;
A at each occurrence is independently a compound of formula IIa

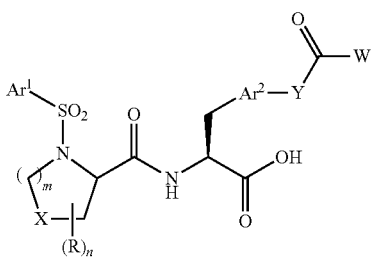

wherein
R is selected from the group consisting of a covalent bond to the polymer moiety, amino, substituted amino, alkyl and substituted alkyl wherein each amino, substituted amino, alkyl and substituted alkyl is optionally covalently bound to the polymer moiety wherein, in each case, the polymer moiety optionally comprises a linker which covalently links the polymer moiety;
$Ar^1$ is selected from the group consisting of aryl, substituted aryl, heteroaryl and substituted heteroaryl;
$Ar^2$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to $Ar^2$;
X is selected from the group consisting of —$NR^1$—, —O—, —S—, —SO—, —$SO_2$— and optionally substituted —$CH_2$— where $R^1$ is selected from the group consisting of hydrogen and alkyl;
Y is selected from the group consisting of —O— and —$NR^1$— wherein $R^1$ is selected from the group consisting of hydrogen and alkyl;
W is selected from the group consisting of a covalent bond to the polymer moiety which optionally comprises a linker and —$NR^2R^3$ wherein $R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to the polymer moiety optionally through a linker;
m is an integer equal to 0, 1 or 2;
n is an integer equal to 0, 1 or 2; and
pharmaceutically acceptable salts thereof;
provided that:
A. at least one of R, $Ar^2$, W and —$NR^2R^3$ contain a covalent bond to the polymer moiety;
B. when R is covalently bound to the polymer moiety, n is one and X is not —O—, —S—, —SO—, or —$SO_2$—;
C. when X is —O— or —$NR^1$—, then m is two; and
D. the conjugate of formula Ia has a molecular weight of no more than 60,000.

Preferred conjugates of formula I include those of formula Ib below:

wherein each A is independently a compound of formula IIb below:

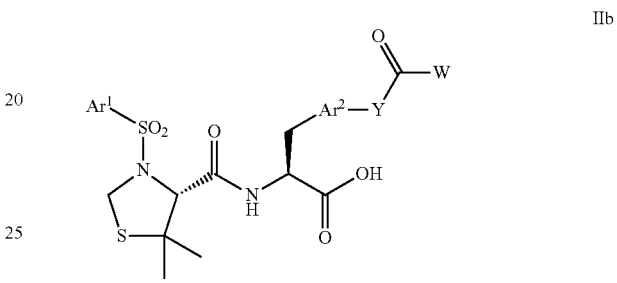

and wherein q is 2 to about 20;
B is as defined above;
$Ar^1$ is selected from the group consisting of aryl, substituted aryl, heteroaryl and substituted heteroaryl;
$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;
Y is selected from the group consisting of —O— and —$NR^1$— wherein $R^1$ is selected from the group consisting of hydrogen and alkyl;
W is selected from the group consisting of a covalent bond to a polymer moiety which optionally comprises a linker and —$NR^2R^3$ wherein $R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to the polymer moiety which further optionally comprises a linker;
provided that at least one of $Ar^2$, W and —$NR^2R^3$ is covalently bound to a polymer moiety which optionally comprises a linker;
and further provided that the conjugate of formula Ib has a molecular weight of no more than 60,000.

Preferred conjugates of formula I include those of formula Ic below:

wherein each A is independently a compound of formula IIc below:

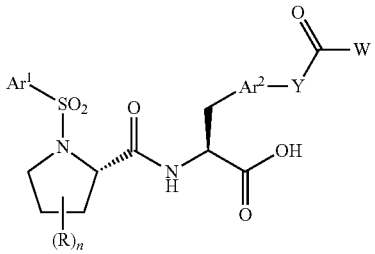

IIc and wherein q is 2 to about 20;

B is as defined above;

R is selected from the group consisting of a covalent bond to a polymer moiety, amino, substituted amino, alkyl and substituted alkyl wherein each amino, substituted amino, alkyl and substituted alkyl is optionally covalently bound to the polymer moiety wherein, in each case, the polymer moiety optionally comprises a linker which covalently links the polymer moiety;

$Ar^1$ is selected from the group consisting of aryl, substituted aryl, heteroaryl and substituted heteroaryl;

$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;

Y is selected from the group consisting of —O— and —$NR^1$— wherein $R^1$ is selected from the group consisting of hydrogen and alkyl;

W is selected from the group consisting of a covalent bond to a polymer moiety which optionally comprises a linker and —$NR^2R^3$ wherein $R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;

n is an integer equal to 0, 1 or 2; and pharmaceutically acceptable salts thereof;

provided that at least one of R, $Ar^2$, W and —$NR^2R^3$ is covalently bound to a polymer moiety which optionally comprises a linker;

and further provided that the conjugate of formula Ic has a molecular weight of no more than 60,000.

Preferred conjugates of formula I include those of formula Id below:

Id wherein each A is independently a compound of formula IId below:

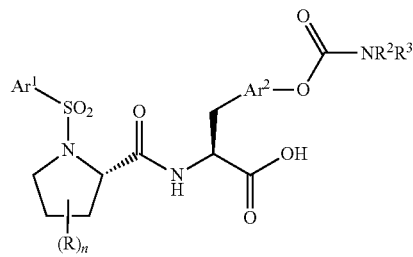

IId and wherein q is 2 to about 20;

B is as defined above;

R is selected from the group consisting of a covalent bond to a polymer moiety, amino, substituted amino, alkyl and substituted alkyl wherein each amino, substituted amino, alkyl and substituted alkyl is optionally covalently bound to a polymer moiety wherein, in each case, the polymer moiety optionally comprises a linker which covalently links the polymer moiety;

$Ar^1$ is selected from the group consisting of aryl, substituted aryl, heteroaryl and substituted heteroaryl;

$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;

$R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;

n is an integer equal to 0, 1 or 2; and pharmaceutically acceptable salts thereof;

provided that at least one of R, $Ar^2$, and —$NR^2R^3$ is covalently bound to a polymer which optionally comprises a linker;

and further provided that the conjugate of formula Id has a molecular weight of no more than about 80,000.

Preferred conjugates of formula I include those of formula Ie below:

Ie wherein each A is independently a compound of formula IIe below:

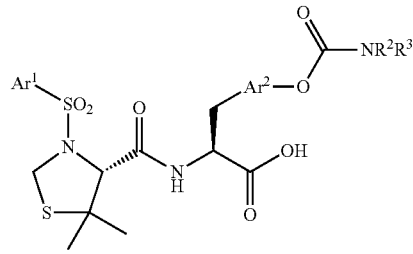

IIe and wherein q is 2 to about 20;

B is as defined above;

Ar¹ is selected from the group consisting of aryl, substituted aryl, heteroaryl and substituted heteroaryl;

Ar² is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to Ar²;

R² and R³ are independently selected from the group consisting of hydrogen, alkyl, substituted alkyl, and where R² and R³, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker; and pharmaceutically acceptable salts thereof;

provided that at least one of Ar² and —NR²R³ is covalently bound to a polymer moiety which optionally comprises a linker;

and further provided that the conjugate of formula Ie has a molecular weight of not more than 60,000.

Preferred conjugates of formula I include those of formula If below:

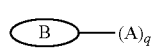

If wherein each A is independently a compound of formula IIf below:

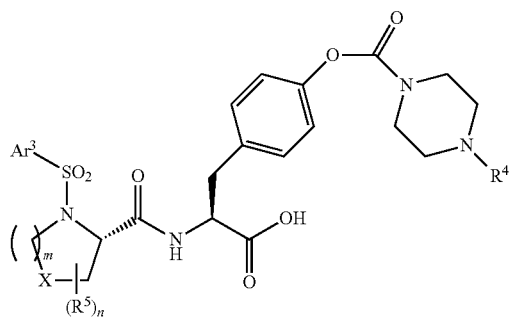

IIf and wherein q is 2 to about 20;

B is as defined above;

R⁴ is covalently bound to a polymer moiety which optionally comprises a linker;

R⁵ is selected from the group consisting of alkyl and substituted alkyl;

Ar³ is selected from the group consisting of aryl, substituted aryl, heteroaryl and substituted heteroaryl;

X is selected from the group consisting of —NR¹—, —O—, —S—, —SO—, —SO₂— and optionally substituted —CH₂— where R¹ is selected from the group consisting of hydrogen and alkyl;

m is an integer equal to 0, 1 or 2;

n is an integer equal to 0, 1 or 2; and pharmaceutically acceptable salts thereof;

provided that:

A. when R is covalently bound to the polymer moiety, n is one and X is not —O—, —S—, —SO—, or —SO₂—;

B. when X is —O— or —NR¹—, then m is two; and

C. the conjugate of formula If has a molecular weight of no more than 60,000.

Preferred conjugates of formula I include those of formula Ig below:

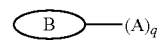

Ig wherein each A is independently a compound of formula IIg below:

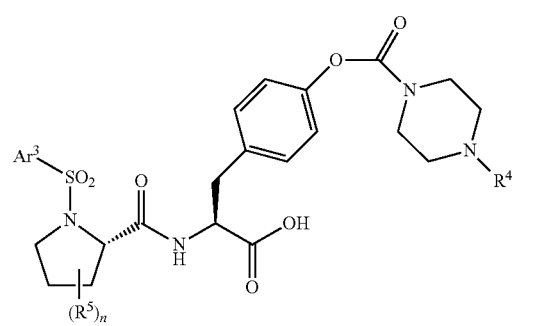

IIg and wherein q is 2 to about 20;

B is as defined above;

R⁴ is covalently bound to a polymer moiety which optionally comprises a linker;

R⁵ is selected from the group consisting of alkyl and substituted alkyl;

Ar³ is selected from the group consisting of aryl, substituted aryl, heteroaryl and substituted heteroaryl;

n is an integer equal to 0, 1 or 2; and pharmaceutically acceptable salts thereof;

provided that the conjugate of formula Ig has a molecular weight of not more than 60,000.

Preferred conjugates of formula I include those of formula Ih below:

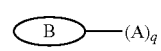

Ih wherein each A is independently a compound of formula IIh below:

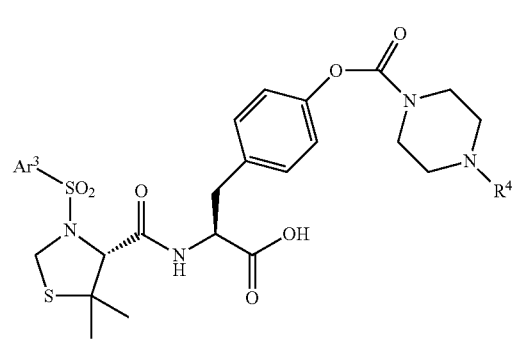

IIh and wherein q is 2 to about 20;

$R^4$ is covalently bound to a polymer moiety which optionally comprises a linker;

$Ar^3$ is selected from the group consisting of aryl, substituted aryl, heteroaryl and substituted heteroaryl;

pharmaceutically acceptable salts thereof;

provided that the conjugate of formula Ih has a molecular weight of not more than 60,000.

Preferred conjugates of formula I include those of formula II below:

Ii wherein each A is independently a compound of formula IIi below:

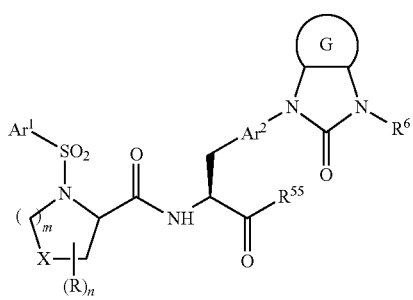

IIi or a pharmaceutically acceptable salt thereof,
and wherein q is 2 to about 20;
and provided that the conjugate of formula II has a molecular weight of no more than 60,000.

Preferred conjugates of formula I include those of formula Ij below:

Ij wherein each A is independently a compound of formula IIj below:

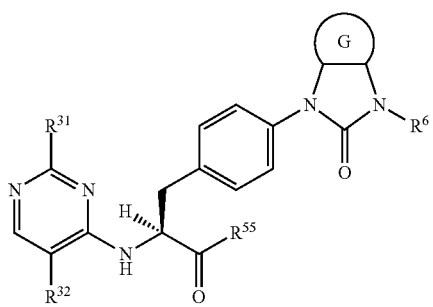

IIj or a pharmaceutically acceptable salt thereof,
and wherein q is about 2 to about 20;
and provided that the conjugate of formula Ij has a molecular weight of no more than about 80,000.

Preferred conjugates of formula I include those of formula Ik below:

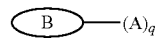

Ik wherein each A is independently a compound of formula IIk below:

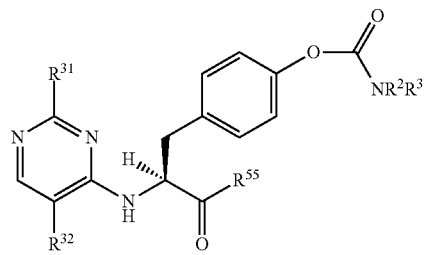

IIk or a pharmaceutically acceptable salt thereof.

Preferred conjugates of formula I include those of formula IL below:

IL wherein each A is independently a compound of formula IIL below:

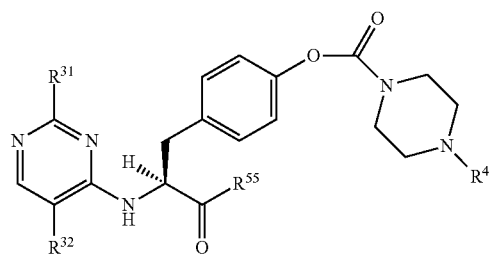

IIL or a pharmaceutically acceptable salt thereof, wherein $R^4$ is covalently bound to the polymer moiety which optionally comprises a linker.

Preferably, $Ar^1$ in formulae IIa-IIe and $Ar^3$ in formulae IIf-IIh are independently selected from the group consisting of:
phenyl,
4-methylphenyl,
4-t-butylphenyl,
2,4,6-trimethylphenyl,
2-fluorophenyl,
3-fluorophenyl,
4-fluorophenyl,
2,4-difluorophenyl,
3,4-difluorophenyl,
3,5-difluorophenyl,
2-chlorophenyl,
3-chlorophenyl,
4-chlorophenyl, 3,4-dichlorophenyl,
3,5-dichlorophenyl,
3-chloro-4-fluorophenyl,
4-bromophenyl,
2-methoxyphenyl,
3-methoxyphenyl,
4-methoxyphenyl,
3,4-dimethoxyphenyl,
4-t-butoxyphenyl,
4-(3'-dimethylamino-n-propoxy)-phenyl,
2-carboxyphenyl,
2-(methoxycarbonyl)phenyl,
4-($H_2NC(O)$-)phenyl,
4-($H_2NC(S)$-)phenyl,
4-cyanophenyl,
4-trifluoromethylphenyl,
4-trifluoromethoxyphenyl,
3,5-di-(trifluoromethyl)phenyl,
4-nitrophenyl,
4-aminophenyl,
4-($CH_3C(O)NH$—)phenyl,
4-(phenylNHC(O)NH—)phenyl,
4-amidinophenyl,
4-methylamidinophenyl,
4-[$CH_3SC(=NH)$-]phenyl,
4-chloro-3-[$H_2NS(O)_2$-]phenyl,
1-naphthyl,
2-naphthyl,
pyridin-2-yl,
pyridin-3-yl,
pyridin-4-yl,
pyrimidin-2-yl,
quinolin-8-yl,
2-(trifluoroacetyl)-1,2,3,4-tetrahydroisoquinolin-7-yl,
2-thienyl,
5-chloro-2-thienyl,
2,5-dichloro-4-thienyl,
1-N-methylimidazol-4-yl,
1-N-methylpyrazol-3-yl,
1-N-methylpyrazol-4-yl,
1-N-butylpyrazol-4-yl,
1-N-methyl-3-methyl-5-chloropyrazol-4-yl,
1-N-methyl-5-methyl-3-chloropyrazol-4-yl,
2-thiazolyl and
5-methyl-1,3,4-thiadiazol-2-yl.

Preferably, when A is of the formulae IIa, IIb, IIc, IId, and IIe, and $Ar^1$ is bound to a polymer moiety, then $Ar^1$ is of the formula:

—$Ar^1$-Z-$(CH_2CHR^7O)_p R^8$ wherein $Ar^1$ is selected from the group consisting of aryl, substituted aryl, heteroaryl, and substituted heteroaryl, Z is selected from the group consisting of a covalent bond, a linking group of from 1 to 40 atoms, —O—, and —$NR^9$—, where $R^9$ is selected from the group consisting of hydrogen and alkyl, $R^7$ is selected from the group consisting of hydrogen and methyl;

$R^8$ is selected from the group consisting of -$(L)_w$-A when p is greater than about 300 and (L)-B-$(A)_{q-1}$, wherein A is represented by any of formulae IIa through IIh above, L is a linking group of from 1 to 40 atoms and w is zero or one: and p is an integer of from about 200 to 1360.

When A is of the Formulae IIa or IIf, and R is not bound to a polymer moiety, the substituent of the following formula:

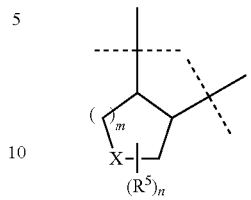

where $R^5$, X, m and n are as defined above, is preferably selected from the group consisting of azetidinyl, thiazolidinyl, piperidinyl, piperazinyl, morpholino, thiomorpholinyl, pyrrolidinyl, 4-hydroxypyrrolidinyl, 4-oxopyrrolidinyl, 4-fluoropyrrolidinyl, 4,4-difluoropyrrolidinyl, 4-(thiomorpholin-4-ylC(O)O-)pyrrolidinyl, 4-[$CH_3S(O)_2O$-]pyrrolidinyl, 3-phenylpyrrolidinyl, 3-thiophenylpyrrolidinyl, 4-amino-pyrrolidinyl, 3-methoxypyrrolidinyl, 4,4-dimethylpyrrolidinyl, 4-N-Cbz-piperazinyl, 4-[$CH_3S(O)_2$-]piperazinyl, 5,5-dimethylthiazolindin-4-yl, 1,1-dioxo-thiazolidinyl, 1,1-dioxo-5,5-dimethylthiazolidin-2-yl and 1,1-dioxothiomorpholinyl.

Preferably, when A is of the formulae IIa and the substituent of the formula:

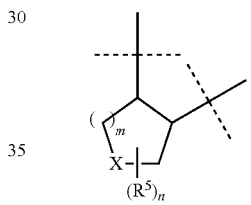

is bound to the polymer moiety, then preferably the substituent is of the formula:

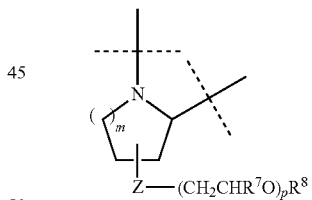

wherein m is an integer equal to zero, one or two;

Z is selected from the group consisting of a covalent bond, a linking group of from 1 to 40 atoms, —O—, —$NR^9$—, where $R^9$ is selected from the group consisting of hydrogen and alkyl, $R^7$ is selected from the group consisting of hydrogen and methyl;

p is an integer of from 0 to about 1360;

$R^8$ is selected from the group consisting of —B-$(A)_{q-1}$, and A when p is greater than about 300, and A is represented by any of formulae IIa through IIh above.

When A is of the formula IIa, IIb, IIc, IId, IIe and when $Ar^2$ is bound to a polymer moiety, then preferably $Ar^2$ is selected from the group consisting of phenyl, substituted phenyl, 2-pyridinyl, 3-pyridinyl, 4-pyridinyl, and 4-pyridin-2-onyl.

When A is of the formula IIa, IIb, IIc, IId, IIe and when $Ar^2$ is bound to a polymer moiety, then $Ar^2$ is preferably represented by the formula:

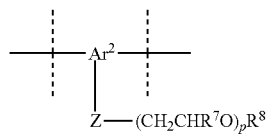

where $Ar^2$ is selected from the group consisting of aryl, substituted aryl, heteroaryl and substituted heteroaryl;

Z is selected from the group consisting of a covalent bond, a linking group of from 1 to 40 atoms, —O—, —NR$^9$—, amide, carbamate and urea, where $R^9$ is selected from the group consisting of hydrogen and alkyl, $R^7$ is selected from the group consisting of hydrogen and methyl;

p is an integer of from 0 to about 1360;

$R^8$ is selected from the group consisting of —B-(A)$_{q-1}$, and A when p is greater than about 300, and A is represented by any of formulae IIa through IIh above.

In one preferred embodiment, —YC(O)W is —OC(O)NR$^2$R$^3$.

When A is of the formulae IIa, IIb, or IIc, —YC(O)W is —OC(O)NR$^2$R$^3$ and neither $R^2$ nor $R^3$ are bound to a polymer moiety, then preferably —OC(O)NR$^2$R$^3$ is selected from the group consisting of:
(CH$_3$)$_2$NC(O)O—,
(piperidin-1-yl)-C(O)O—,
(piperidin-4-yl)-C(O)O—,
(1-methyl piperidin-4-yl)-C(O)O—,
(4-hydroxypiperidin-1-yl)-C(O)O—,
(4-formyloxypiperidin-1-yl)-C(O)O—,
(4-ethoxycarbonylpiperidin-1-yl)-C(O)O—,
(4-carboxylpiperidin-1-yl)-C(O)O—,
(3-hydroxymethylpiperidin-1-yl)-C(O)O—,
(4-hydroxymethylpiperidin-1-yl)-C(O)O—,
(4-phenyl-1-Boc-piperidin-4-yl)-C(O)O—,
(4-piperidon-1-yl ethylene ketal)-C(O)O—,
(piperazin-4-yl)-C(O)O—,
(1-Boc-piperazin-4-yl)-C(O)O—,
(4-methylpiperazin-1-yl)-C(O)O—,
(4-methylhomopiperazin-1-yl)-C(O)O—,
(4-(2-hydroxyethyl)piperazin-1-yl)-C(O)O—,
(4-phenylpiperazin-1-yl)-C(O)O—,
(4-(pyridin-2-yl)piperazin-1]-yl)-C(O)O—,
(4-(4-trifluoromethylpyridin-2-yl)piperazin-1-yl)-C(O)O—,
(4-(pyrimidin-2-yl)piperazin-1-yl)-C(O)O—,
(4-acetylpiperazin-1-yl)-C(O)O—,
(4-(phenyl-C(O)-)piperazin-1-yl)-C(O)O—,
(4-(pyridin-4'-yl-C(O)-)piperazin-1-yl)-C(O)O—,
(4-(phenyl-NHC(O)-)piperazin-1-yl)-C(O)O—,
(4-(phenyl-NHC(S)-)piperazin-1-yl)-C(O)O—,
(4-methanesulfonylpiperazin-1-yl)-C(O)O—,
(4-trifluoromethanesulfonylpiperazin-1-yl)-C(O)O—,
(morpholin-4-yl)-C(O)O—,
(thiomorpholin-4-yl)-C(O)O—,
(thiomorpholin-4'-ylsulfone)-C(O)O—,
(pyrrolidin-1-yl)-C(O)O—,
(2-methylpyrrolidin-1-yl)-C(O)O—,
(2-(methoxycarbonyl)pyrrolidin-1-yl)-C(O)O—,
(2-(hydroxymethyl)pyrrolidin-1-yl)-C(O)O—,
(2-(N,N-dimethylamino)ethyl)(CH$_3$)NC(O)O—,
(2-(N-methyl-N-toluene-4-sulfonylamino)ethyl)(CH$_3$)N—C(O)O—,
(2-(morpholin-4-yl)ethyl)(CH$_3$)NC(O)O—,
(2-(hydroxy)ethyl)(CH$_3$)NC(O)O—,
bis(2-(hydroxy)ethyl)NC(O)O—,
(2-(formyloxy)ethyl)(CH$_3$)NC(O)O—,
(CH$_3$OC(O)CH$_2$)HNC(O)O—, and
2-(phenylNHC(O)O—)ethyl-]HNC(O)O—.

When A is of the formulae IIa, IIb, or IIc, —YC(O)W is —OC(O)NR$^2$R$^3$ and $R^2$ and/or $R^3$ are/is bound to the polymer moiety, the polymer moiety is preferably represented by the formula:

Z is selected from the group consisting of a covalent bond, a linking group of from 1 to 40 atoms, —O—, —NR$^9$—, amide, carbamate and urea, where $R^9$ is selected from the group consisting of hydrogen and alkyl, $R^7$ is selected from the group consisting of hydrogen and methyl;

p is an integer of from 0 to about 1360;

$R^8$ is selected from the group consisting of —B-(A)$_{q-1}$, and A when p is greater than about 300, and A is represented by any of formulae IIa through IIh above.

In the compounds of formula IIi and IIj, it is preferred that that the group of

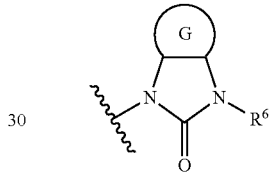

is of the formula:

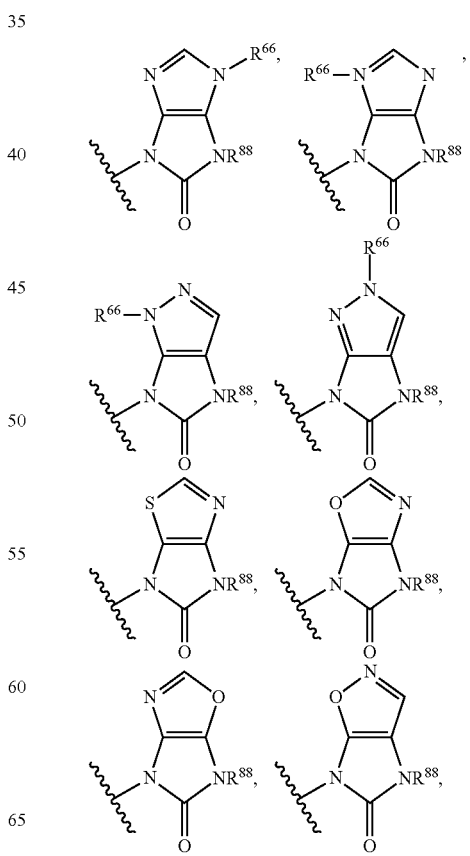

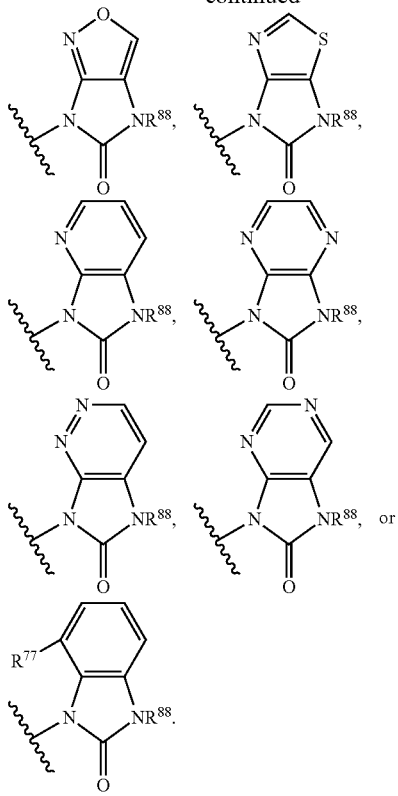

wherein R⁶⁶ is a covalent bond to the polymer moiety which optionally comprises a linker, or R⁶⁶ is hydrogen or straight or branched C₁-C₆alkyl; R⁷⁷ is a covalent bond to a polymer moiety which optionally comprises a linker, or R⁷⁷ is hydrogen, halogen or straight or branched C₁-C₆alkoxy; and R⁸⁸ is a covalent bond to the polymer moiety which optionally comprises a linker, or R⁸⁸ is hydrogen or straight or branched C₁-C₆alkyl Preferably, one of R⁶⁶, R⁷⁷, and R⁸⁸ is a covalent bond to the polymer moiety which optionally comprises a linker.

Preferred compounds of formula IIi are also those of the formula IIi-a:

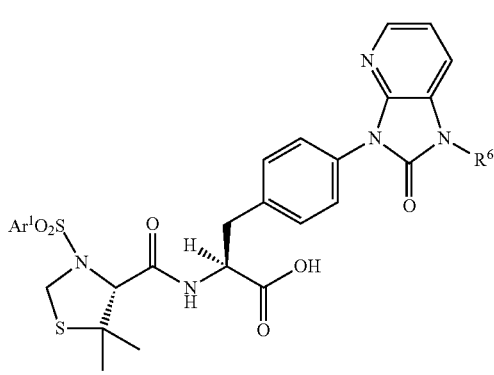

IIi-a and pharmaceutically acceptable salts thereof, wherein
Ar¹ is selected from the group consisting of alkyl, substituted alkyl, aryl, substituted aryl, cycloalkyl, substituted cycloalkyl, heterocyclic, substituted heterocyclic, heteroaryl and substituted heteroaryl; and R⁶ is a covalent bond to a polymer moiety which optionally comprises a linker.

Preferred compounds of Formula IIi-a include those wherein Ar¹ is phenyl or a 5- or 6-membered heteroaryl group having at least one nitrogen atom, each of which is optionally substituted with halogen, hydroxy, C₁-C₆ alkoxy, C₁-C₆ alkyl, nitro, trifluoromethyl, amino, mono- or di(C₁-C₆)alkylamino, amino(C₁-C₆)alkyl, C₂-C₆ acyl, C₂-C₆ acylamino, or amino(C₁-C₆)acyl. Ar¹ is pyridyl optionally substituted with halogen, hydroxy, C₁-C₆ alkyl, C₁-C₆ alkoxy, nitro, trifluoromethyl, amino, mono- or di(C₁-C₆)alkylamino, amino(C₁-C₆)alkyl, C₂-C₆ acyl, C₂-C₆ acylamino, or amino(C₁-C₆)acyl. Particularly preferred compounds of Formula IIi-a include those where Ar¹ is pyridyl optionally substituted with C₁-C₆ alkyl, hydroxy, halogen, C₁-C₆ alkoxy, nitro, trifluoromethyl, amino, or mono- or di(C₁-C₆)alkylamino.

Preferred compounds of formula IIj are also those of the formula IIj-a:

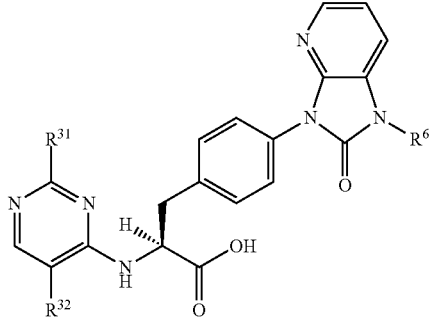

IIj-a and pharmaceutically acceptable salts thereof, wherein
R⁶ is a covalent bond to a polymer moiety which optionally comprises a linker.

Preferred compounds of Formula IIj-a include those where R³¹ is amino or mono- or di(C₁-C₆)alkylamino; and R³² is —H, —NO₂ or haloalkyl, more preferably trifluoromethylmethyl.

Still other preferred compounds of Formula IIj-a are those where
R³¹ is amino or mono- or di(C₁-C₆)alkylamino; and
R³² is —N(MR⁴¹)R⁴²; where M is —SO₂— or —CO—;
R⁴¹ is C₁-C₆ alkyl optionally substituted with halogen, hydroxy, C₁-C₆ alkoxy, amino, or mono- or di(C₁-C₆)alkylamino; or
  phenyl or a 5- or 6-membered heteroaryl containing at least one nitrogen, each of which is optionally substituted with halogen, hydroxy, C₁-C₆ alkyl, C₁-C₆ alkoxy, C₃-C₇ cycloalkyl, amino, nitro, trifluoromethyl, or mono- or di(C₁-C₆)alkylamino; and
R⁴² is hydrogen, C₁-C₆alkyl, or C₃-C₇cycloalkyl.

Further preferred compounds of formula II-j-a include those wherein
R⁴¹ groups within Formula IIj-a are C₁-C₄ alkyl optionally substituted with halogen, hydroxy, C₁-C₆ alkoxy, amino, or mono- or di(C₁-C₆)alkylamino; or
  pyridyl or pyrimidinyl, each of which is optionally substituted with halogen, hydroxy, C₁-C₃ alkyl, C₁-C₃ alkoxy, amino, or mono- or di(C₁-C₄)alkylamino; and
R⁴² is hydrogen, C₁-C₄alkyl, or C₃-C₇cycloalkyl.

In one example, the conjugates of this invention are divalent and are represented by formula III:

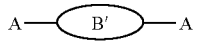

III where each A is independently as defined above and B' is —Z'—(CH$_2$CHR$^7$O)$_p$—Z'— where each Z' is independently a covalent bond or a linking group, R$^7$ is hydrogen or methyl and p is an integer of from about 100 to 1360.

In another example, the conjugates of this invention are trivalent to decavalent and are preferably represented by formula IV:

IV where each A is independently as defined above and t is an integer from 3 to 10.

DEFINITIONS

As used herein, "alkyl" refers to monovalent saturated aliphatic hydrocarbyl groups having from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, spirocycloalkyl, heteroaryl, substituted heteroaryl, heterocyclic, and substituted heterocyclic.

"Optionally substituted alkyl" encompasses "alkyl" and "substituted alkyl" as defined above.

"Optionally substituted —CH$_2$—" refers to a group that is either unsubstituted or is substituted with 1 or 2 substituents selected from the group consisting of alkoxy, substituted alkoxy, thioalkoxy, substituted thioalkoxy, acyl, acylamino, acyloxy, amino, substituted amino, aminoacyl, aryl, substituted aryl, aryloxy, substituted aryloxy, cyano, halogen, hydroxyl, sulfhydryl, nitro, carboxyl, carboxyl esters, cycloalkyl, substituted cycloalkyl, spirocycloalkyl, heteroaryl, substituted heteroaryl, heterocyclic, and substituted heterocyclic. Preferred substituents on "optionally substituted —CH$_2$—" are hydroxy, alkoxy, amino, monoalkyl amino, dialkylamino, sulfhydryl, thioalkoxy, and halogen (preferably F). Preferably, when "optionally substituted —CH$_2$—" is substituted, it is substituted with one group.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R10 is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Cyano" refers to the group —CN.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" is hydrogen.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Cycloalkenyl" refers to cyclic alkenyl groups of from 4 to 10 carbon atoms having single or multiple cyclic rings and further having at least 1 and preferably from 1 to 2 internal sites of ethylenic or vinyl (>C=C<) unsaturation.

"Substituted cycloalkyl" and "substituted cycloalkenyl" refers to an cycloalkyl or cycloalkenyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" or "heterocyclyl" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thioaryl" refers to the group —S-aryl, where aryl is defined above.

"Substituted thioaryl" refers to the group —S-substituted aryl, where substituted aryl is defined above.

"Thioheteroaryl" refers to the group —S-heteroaryl, where heteroaryl is as defined above.

"Substituted thioheteroaryl" refers to the group —S-substituted heteroaryl, where substituted thioheteroaryl is defined above.

"Thioheterocyclic" refers to the group —S-heterocyclic and "substituted thioheterocyclic" refers to the group —S-substituted heterocyclic, where heterocyclic and substituted heterocyclic.

"Heterocyclyloxy" refers to the group heterocyclyl-O— and "substituted heterocyclyl-O— refers to the group substituted heterocyclyl-O— where heterocyclyl and substituted heterocyclyl are as defined above.

"Thiocycloalkyl" refers to the group —S-cycloalkyl and "substituted thiocycloalkyl" refers to the group —S-substituted cycloalkyl, where cycloalkyl and substituted cycloalkyl are as defined above.

"Hydrolyzable ester" refers to a group that is hydrolyzed in vivo to produce the parent acid. Examples of such groups include alkoxy, substituted alkoxy, cycloalkoxy, substituted cycloalkoxy, aryloxy and substituted aryloxy. A preferred hydrolyzable ester is alkoxy.

"Hydrolyzable polymer ester" refers to a biocompatible polymer that is hydrolyzed in vivo to produce the parent acid. A preferred hydrolyzable polymer ester is PEG.

The terms "compound" and "active compound" are used to refer to the VLA-4 antagonist portion of a conjugate of the invention or to a VLA-4 antagonist as it exists prior to conjugation to a polymer.

The terms "Linker", "linking group" or "linker of from 1 to 40 atoms" refer to a group or groups that (1) covalently links the polymer to the active compound and/or (2) covalently link the polymer, oligomer, and/or monomer portions comprising the polymer moiety one to another; non-limiting illustrations of the latter include polymer-linker-polymer, oligomer-linker-oligomer, monomer-linker-monomer, oligomer-linker-oligomer-linker, and the like. Within any particular conjugate, the linker connecting the polymer, oligomer, and/or monomer portions of a polymer moiety together, and the linker bonding a polymer moiety to an active compound may be the same or different (i.e., may have the same or different chemical structures).

The linker that covalently links the polymer, oligomer, and/or monomer portions, such as polyalkylene oxide portions, of a polymer moiety one to another is also referred to as a "branched-arm hub", or "branched-arm hub molecule". Branched-arm hubs are molecules that covalently bond three or more polymer, oligomer, and/or monomer portions to them, providing tri-valent or higher valent polymer moieties for conjugation with the active compound. Non-limiting examples of such hub molecules are glycerol (1,2,3-propanetriol), pentaerythitol, lysine, 1,2,4-benzenetriol, glucose (in its pyranose form), ethylenediamine tetraacetic acid, amino acids, 3- or 4-aminosalicylic acid, 1,3-diamino-2-hydroxypropane, glucosamine, and sialic acid.

Representative functional group linkages, of which a linking group may have one or more, are amides (—C(O)NR$^3$—), ethers (—O—), thioethers (—S—), carbamates (—OC(O)NR$^3$—), thiocarbamates (—OC(S)NR$^3$—), ureas (—NR$^3$C(O)NR$^3$—), thioureas (—NR$^3$C(S)NR$^3$—), amino groups (—NR$^3$—), carbonyl groups (—C(O)—), alkoxy groups (—O-alkylene-), etc. The linker may be homogenous or heterogeneous in its atom content (e.g., linkers containing only carbon atoms or linkers containing carbon atoms as well as one or more heteroatoms present on the linker. Preferably, the linker contains 1 to 25 carbon atoms and 0 to 15 heteroatoms selected from oxygen, NR$^3$, sulfur, —S(O)— and —S(O)$_2$—, where R$^3$ is hydrogen, alkyl or substituted alkyl. The linker may also be chiral or achiral, linear, branched or cyclic.

Intervening between the functional group linkages or bonds within the linker, the linker may further contain spacer groups including, but not limited to, spacers selected from alkyl, substituted alkyl, aryl, substituted aryl, cycloalkyl, substituted cycloalkyl, heteroaryl, substituted heteroaryl, heterocyclic, substituted heterocyclic, and combinations thereof. The spacer may be homogenous or heterogeneous in its atom content (e.g., spacers containing only carbon atoms or spacers containing carbon atoms as well as one or more heteroatoms present on the spacer. Preferably, the spacer contains 1 to 25 carbon atoms and 0 to 15 heteroatoms selected from oxygen, NR$^3$, sulfur, —S(O)— and —S(O)$_2$—, where R$^3$ is as defined above. The spacer may also be chiral or achiral, linear, branched or cyclic.

Non-limiting examples of spacers are straight or branched alkylene chains, phenylene, biphenylene, etc. rings, all of which are capable of carrying one or more than one functional group capable of forming a linkage with the active compound and one or more polyalkylene oxide moieties. One particular example of a polyfunctional linker-spacer group is lysine, which may link any of the active compounds to two polymer moieties via the two amino groups substituted on a C$_4$ alkylene chain. Other non-limiting examples include p-aminobenzoic acid and 3,5-diaminobenzoic acid which have 2 and 3 functional groups respectively available for linkage formation. Other such polyfunctional linkage plus spacer groups can be readily envisaged by one of skill in the art.

The terms "polymer" and "polymer moiety" refers to biocompatible, water-soluble, substantially non-immunogenic, polymers which are capable of being coupled to more than one VLA-4 antagonist of formula II. Preferably the polymer is non-ionic and biocompatible as measured by lack of toxicity at the molecular weights and dosages used. The terms also encompass molecules in which 3 or more polymers are connected to a branched-arm hub molecule, as discussed above. The terms further encompass molecules in which the polymer, oligomer, and/or monomer portions thereof are connected by one or more linkers.

Examples of suitable polymers include, but are not limited to: polyoxyalkylene polymers such as polyethylene glycol (PEG), polyvinylpyrrolidone (PVP), polyacrylamide (PAAm), polydimethylacrylamide (PDAAm), polyvinyl alcohol (PVA), dextran, poly(L-glutamic acid) (PGA), styrene maleic anhydride (SMA), poly-N-(2-hydroxypropyl) methacrylamide (HPMA), polydivinylether maleic anhydride (DIVEMA) (Kameda, Y. et al., Biomaterials 25: 3259-3266, 2004; Thanou, M. et al, Current Opinion in Investigational Drugs 4(6): 701-709, 2003; Veronese, F. M., et al., II Farmaco 54: 497-516, 1999).

Preferred polymers are polyoxyalkylenes. By "polyoxyalkylenes" is meant macromolecules that include at least one polyalkylene oxide portion that is optionally covalently bonded to one or more additional polyakylene oxides, wherein the polyalkylene oxides are the same or different. Non-limiting examples include polyethylene glycol (PEG), polypropylene glycol (PPG), polyisopropylene glycol (PIPG), PEG-PEG, PEG-PPG, PPG-PIPG, and the like. Also included within the definition of polyoxyalkylenes are macromolecules wherein the polyalkylene oxide portions are optionally connected to each other by a linker. Illustrative examples are PEG-linker-PEG, PEG-linker-PIPG, and the like. More specific examples include the commercially available poly[di(ethylene glycol)adipates, poly[di(ethylene glycol)phthalate diols, and the like. Other examples are block copolymers of oxyalkylene, polyethylene glycol, polypropylene glycol, and polyoxyethylenated polyol units.

At least one of its termini, the polymer is covalently attached to non-polymer substituted compound of Formula II optionally through a linker using conventional chemical techniques providing for covalent linkage of the polymer to the non-polymer substituted compound of Formula II.

When a linker is employed, the linker is covalently bonded to at least one of the polymer termini which, in turn, is covalently attached to the otherwise, non-polymer substituted compound of Formula II. Reaction chemistries resulting in such linkages are well known in the art. Such reaction chemistries involve the use of complementary functional groups on the linker, the non-polymer substituted compound of Formula II and the polymer. Preferably, the complementary functional groups on the linker are selected relative to the functional groups available on the polymer for bonding or which can be introduced onto the polymer for bonding. Again, such complementary functional groups are well known in the art. For example, reaction between a carboxylic acid of either the linker or the polymer and a primary or secondary amine of the polymer or the linker in the presence of suitable, well-known activating agents results in formation of an amide bond covalently linking the polymer moiety to the linker; reaction between an amine group of either the linker or the polymer group and a sulfonyl halide of the polymer or the linker results in formation of a sulfonamide bond covalently linking the polymer moiety to the linker; and reaction between an alcohol or phenol group of either the linker or the polymer and an alkyl or aryl halide of the polymer or the linker results in formation of an ether bond covalently linking the polymer group to the linker.

It is understood, of course, that if the appropriate substituents are found on the non-polymer substituted compound of Formula II then the optional linker may not be needed as there can be direct linkage of the polymer to the non-polymer substituted compound of Formula II.

Table I below illustrates numerous complementary reactive groups and the resulting bonds formed by reaction there between. One of ordinary skill in the art can select the appropriate solvents and reaction conditions to effect these linkages.

TABLE I

Representative Complementary Binding Chemistries

| First Reactive Group | Second Reactive Group | Linkage |
|---|---|---|
| Hydroxyl | Isocyanate | Urethane |
| Amine | Epoxide | β-hydroxyamine |
| sulfonyl halide | Amine | Sulfonamide |
| Carboxyl | Amine | Amide |
| Hydroxyl | alkyl/aryl halide | Ether |
| Aldehyde (under reductive amination conditions) | Amine | Amine |

Preferred linkers include, by way of example, the following —O—, —NR³—, —NR³C(O)O—, —OC(O)NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, -alkylene-C(O)NR³—, —NR³C(O)O-alkylene-, —NR³C(O)NR³-alkylene-, —OC(O)NR³-alkylene, —NR³-alkylene-, —O-alkylene-, —NR³C(O)-alkylene-, —C(O)NR³-alkylene-, -alkylene-NR³C(O)O-alkylene-, -alkylene-NR³C(O)NR³-alkylene-, -alkylene-OC(O)NR³-alkylene-, -alkylene-NR³-alkylene-, alkylene-O-alkylene-, -alkylene-NR³C(O)-alkylene-, —C(O)NR³-alkylene-, —NR³C(O)O-alkyleneoxy-, —NR³C(O)NR³-alkyleneoxy-, —OC(O) NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy- where R³ is as defined above and

where

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR³—, —NR³C(O)O—, —OC(O)NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, -alkylene-C(O)NR³—, —NR³C(O)O-alkylene-, —NR³C(O)NR³-alkylene-, —OC(O)NR³-alkylene-, —NR³-alkylene-, —O-alkylene-, —NR³C(O)-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy-, —C(O)NR³-alkylene-, -alkylene-NR³C(O)O-alkylene-, -alkylene-NR³C(O)NR³-alkylene-, -alkylene-OC(O) NR³-alkylene-, -alkylene-NR³-alkylene-, alkylene-O-alkylene-, -alkylene-NR³C(O)— alkylene-, and —C(O)NR³-alkylene-, where R³ is as defined above.

Preferred alkylene groups in the above linkers include $C_1$-$C_{15}$ alkylene groups, more preferably $C_1$-$C_6$ alkylene groups, and most preferably $C_1$-$C_3$ alkylene groups. Preferred heterocyclic groups include piperazinyl, piperidinyl, homopiperazinyl, homopiperidinyl, pyrrolidinyl, and imidazolidinyl. Preferred alkoxy groups are —$(CH_2$—$CH_2O)_{1-15}$.

The term "oxyalkylene" refers to —$OCH_2CHR^d$— where $R^d$ is alkyl. Polymerized oxyalkylenes are referred to as polyoxyalkylenes, polyalkylene oxides or polyalkylene glycols, non-limiting examples of which include PEG, poly propylene glycol, polybutylene glycol, polyisopropylene glycol, and the like.

Such polymers are optionally mono-capped with a substituent preferably selected from alkyl, aryl, substituted alkyl, substituted aryl and a branched-arm hub molecule as described above. Inclusive of such polymers are those diamino capped polyoxyalkylene polymers which are known in the art as Jeffamines®. Generally, Jeffamines® (available from Huntsman Performance Products, The Woodlands, Tex.) contain primary amino groups attached to the terminus of a polyether backbone. They are thus "polyether amines." The polyether backbone is based either on propylene oxide (PO), ethylene oxide (EO), or mixed EO/PO, or other backbone segments. Jeffamines® may be monoamines, diamines, and triamines, and are available in a variety of molecular weights, ranging up to about 5,000.

Still further, polymerized oxyalkylenes can optionally contain one or more non-oxyalkylene units such as the commercially available poly[di(ethylene glycol)adipates, poly[di(ethylene glycol)phthalate diols, and the like. Also included are block copolymers of oxyalkylene, polyethylene glycol, polypropylene glycol, and polyoxyethylenated polyol units.

Polyoxyalkylenes, such as PEG, are usually provided as a water soluble, waxy solid. Generally, as the polymer's molecular weight increases, its viscosity and freezing point also increase. Commercial preparations are usually characterized by the "average molecular weight" of the constituent polymers.

Typically, the average molecular weight of the total amount of polymer arising from single or multiple polymer moieties in the conjugates of the invention is between about 100 to 100,000; preferably from about 20,000 to 60,000; more preferably from about 30,000 to about 50,000. It is apparent to those skilled in the art that polymers of this type will be polydisperse. Polydispersity refers to the fact that polymer molecules, even ones of the same type, come in different sizes (chain lengths, for linear or multi-armed polymers). Therefore average molecular weight will depend on the method of averaging. The polydispersity index, a common measure of the variability of molecular weights is the ratio of the weight average molecular weight to the number average molecular weight. It indicates the distribution of individual molecular weights in a batch of polymers. The number average molecular weight is a way of determining the molecular weight of a polymer. The number average molecular weight is the common average of the molecular weights of the individual polymers. It is determined by measuring the molecular weight of n polymer molecules, summing the weights, and dividing by n. The number average molecular weight of a polymer can be determined by osmometry, end-group titration, and colligative properties.

The weight average molecular weight can be determined by light scattering, small angle neutron scattering (SANS), X-ray scattering, and sedimentation velocity. The ratio of the weight average to the number average is called the polydispersity index. A theoretical sample of polymer having no dispersity would have a polydispersity index of 1. Preferred range of polydispersity index for the present invention is from about 1.10 to about 1.05. More preferred is a range from about 1.05 to the upper limit of commercially feasible synthesis, which to date is about 1.02.

Other suitable polymers such as polyvinylpyrrolidone (PVP), polyacrylamide (PAAm), polydimethylacrylamide (PDAAm), polyvinyl alcohol (PVA), dextran, poly(L-glutamic acid) (PGA), styrene maleic anhydride (SMA), poly-N-(2-hydroxypropyl)methacrylamide (HPMA), polydivinylether maleic anhydride (DIVEMA) are well known in the art and have molecular weights of from about 100 to 100,000; preferably from about 10,000 to 80,000; more preferably from about 20,000 to about 70,000.

Non-limiting examples of PEGs that can be used in the invention include the following:

| | |
|---|---|
| HO(alkylene-O)$_{pp}$R$^{bb}$ | mono-capped mono-hydroxy PEG (mPEG) |
| H$_2$N(alkylene-O)$_{pp}$R$^{bb}$ | mono-capped mono-amino PEG |
| HO(alkylene-O)$_{pp}$R—OH | non-capped di-hydroxy PEG |
| H$_2$N(alkylene-O)$_{pp}$R—OH | non-capped mono-amino PEG |
| HO(alkylene-O)$_{pp}$R$^{bb}$ | branched mono-hydroxy PEG |
| HO(alkylene-O)$_{pp}$R$^{bb}$ | dendrimeric mono-hydroxy PEG | where pp and alkylene are as defined herein and R$^{bb}$ is preferably selected from the group consisting of alkyl, substituted alkyl, aryl and substituted aryl.

Various PEG examples are shown below:

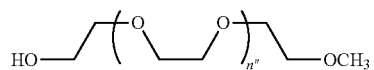

mono-capped mono-hydroxy PEG (mPEG)

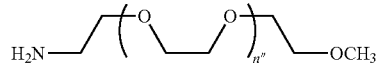

mono-capped mono-amine PEG

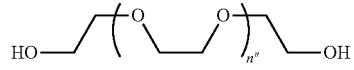

non-capped di-hydroxy PEG

Branched PEGs:
PEG Reagents available from NOF (20 kDa 4-arm)

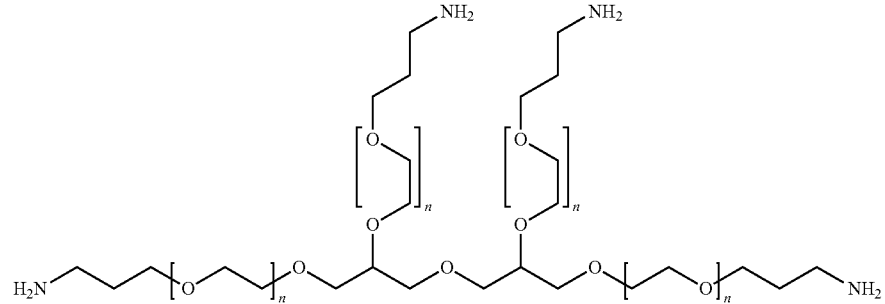

20 kDa 4-arm PEG tetra-amine
Diglycerine core
Cat # Sunbright DG-200PA

PEG Reagents available from Nektar (40 kDa 8-arm)

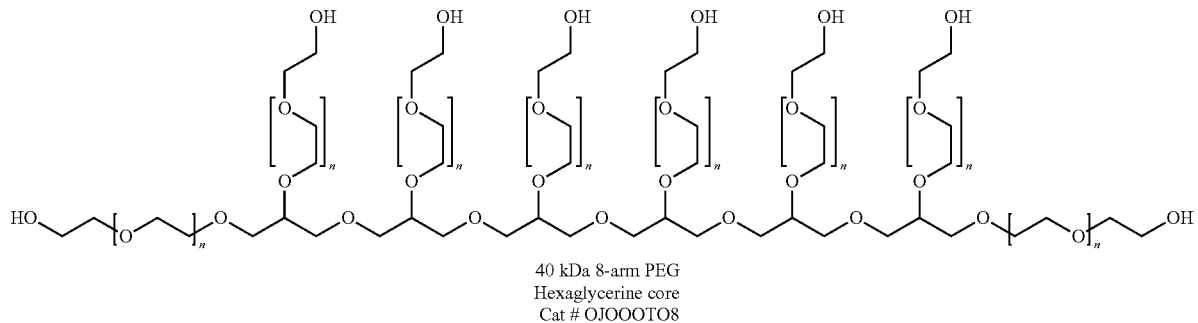

40 kDa 8-arm PEG
Hexaglycerine core
Cat # OJOOOTO8

Dendrimeric PEGs:

PEG Reagents available from NOF (40 kDa 4-arm)

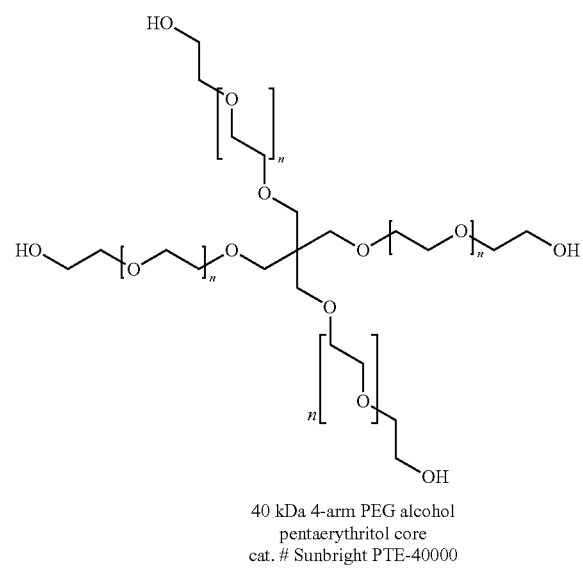

40 kDa 4-arm PEG alcohol
pentaerythritol core
cat. # Sunbright PTE-40000

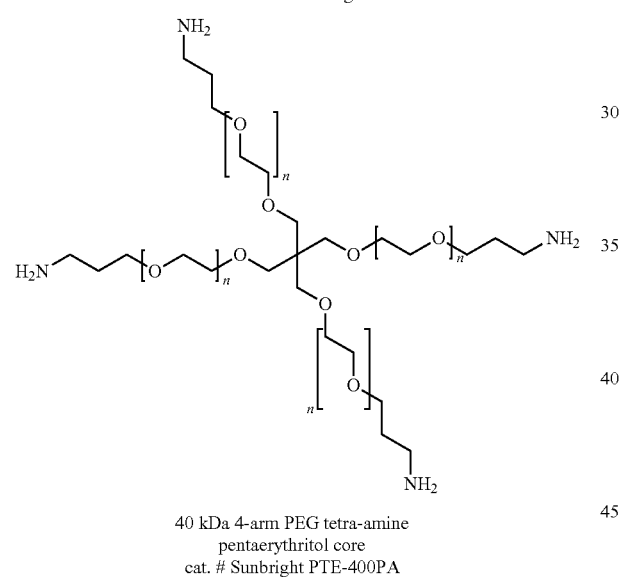

40 kDa 4-arm PEG tetra-amine
pentaerythritol core
cat. # Sunbright PTE-400PA

PEG Reagents available from NOF (40 kDa 3-arm)

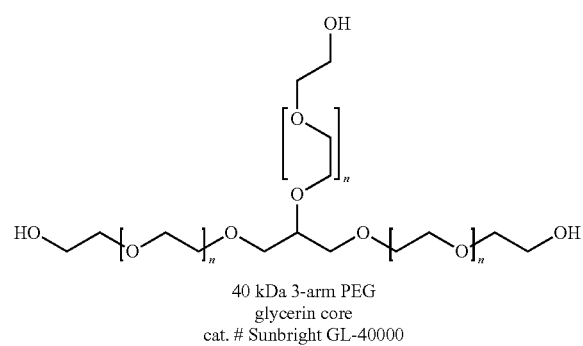

40 kDa 3-arm PEG
glycerin core
cat. # Sunbright GL-40000

40 kDa 3-arm PEG tri-amine
glycerin core
cat. # Sunbright GL-400PA

PEG Reagents available from SunBio (40 and 20 kDa)

Y-PEG Series (Aspartic acid core)

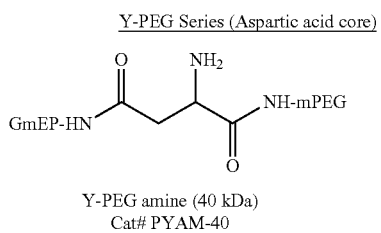

Y-PEG amine (40 kDa)
Cat# PYAM-40

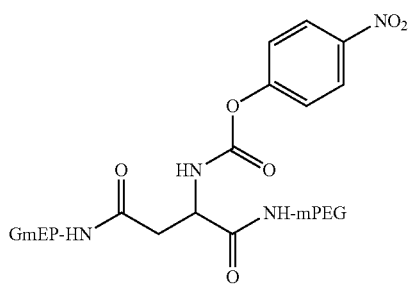

Y-PEG nitrophenyl carbamate (40 kDa)
Cat# PYNPC-40

6-Arm Series (Sorbitol Core)

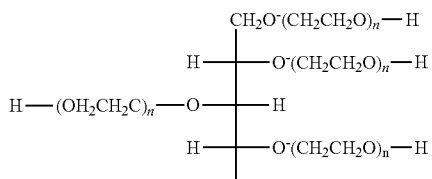

40 kDa 6-arm PEG
custom product

Lower molecular weights available in the sorbitol 6-arm series include 10, 15 and 20 kDa. Derivatives other than the alcohol include the 6-arm amine.

For example, the 10 kDa 6-arm amine (cat #P6AM-10) could be converted to a 40 kDa 6-arm hexa-amine (with Nektars 5 kDa BocNH-PEG-NHS ester) and then conjugated to a small molecule.

These PEG polymers may be further modified by extending the chains with PEG diamines through an appropriate linker, for example a carbamate (urethane) or a urea.

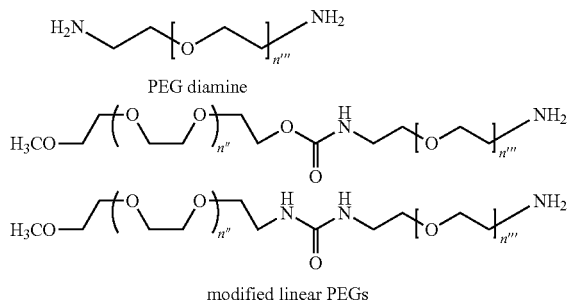

modified linear PEGs

"Pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

It is understood that in all substituted groups defined herein, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-(substituted aryl).

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Compound Preparation

The conjugates of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The conjugates of this invention preferably comprise a polymer moiety/optional branched-arm hub molecule containing 2 to about 20 substituents of Formula II:

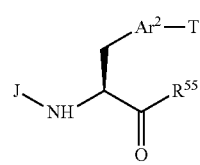

II

Specifically, the polymer moiety can be bound through a covalent bond to the $Ar^1$ substituent, the J substituent, the $Ar^2$ substituent and/or in the T substituent wherein the polymer moiety is either directly attached or is attached via a linker. In turn, the polymer moiety may optionally be bound to a branched-arm hub molecule.

In its simplest form, the compounds of this invention are divalent structures comprising a single polymer moiety having two substituents of formula II bound to both termini. In a representative case using a polymer moiety derived from PEG which is linked to a compound of formula II by a carbonyl linking group wherein the compound of formula II is represented by:

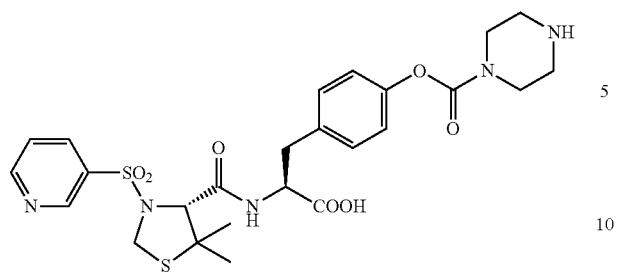

the resulting conjugate can be represented by the following formula:

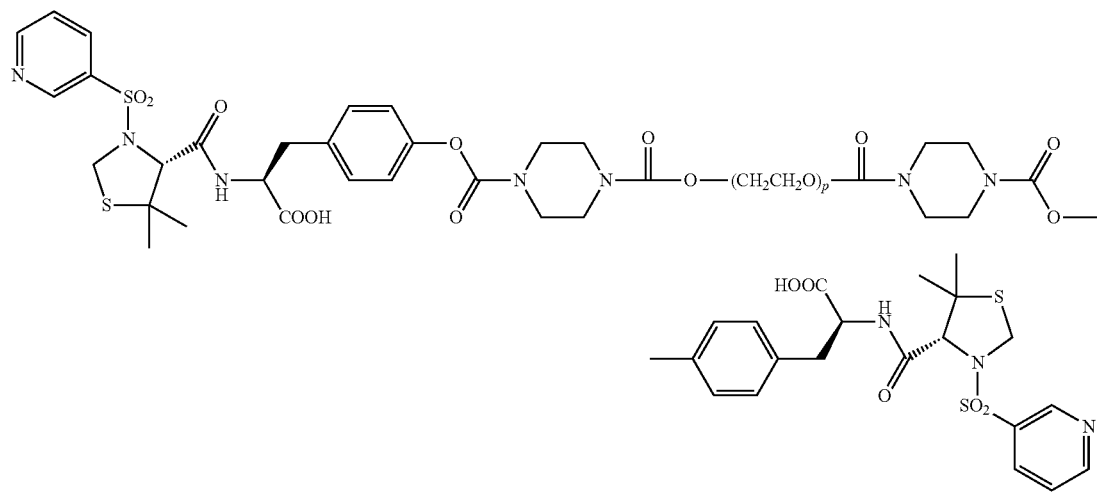

where p is preferably an integer of from about 100 to 1360.

In one example of a tetravalent form, the conjugate comprises four polymer moieties. In a representative case, one terminus of each polymer moiety is attached to a common a branched-arm hub molecule whereas the other terminus is attached to a compound of formula II optionally through a linker. Still further and again for illustrative purposes, each polymer moiety is derived from PEG and the common branched-arm hub molecule is pentaerythritol. In this exemplification, the other terminus of the PEG moiety is linked to a compound of formula II through a carbonyl linking group wherein the compound of formula II is represented by:

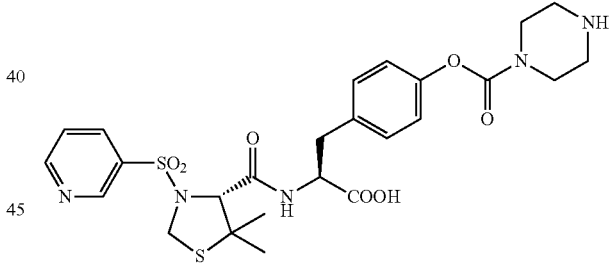

the resulting conjugate can be represented by the following formula:

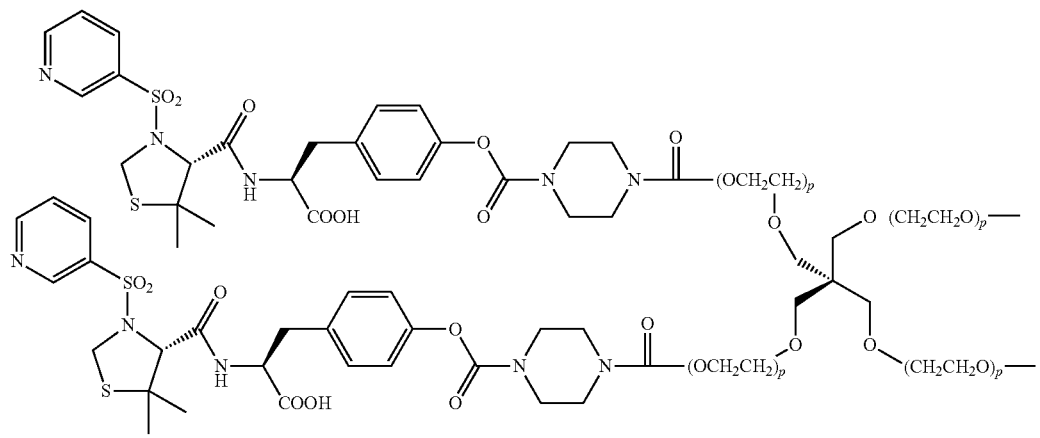

-continued

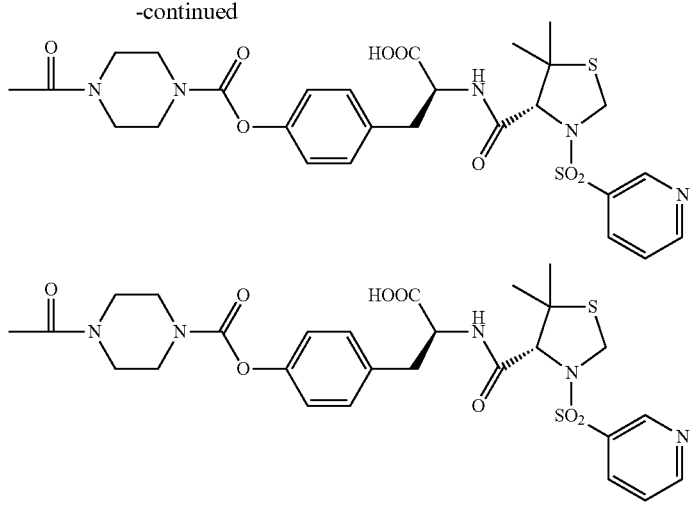

where the aggregate of the four p's is an integer preferably of from about 100 to 1360.

The synthetic protocol for forming the conjugates of formula I entails reaction of a functional group on the polymer moiety with either a linking group or directly with a compound of formula II thereby covalently binding the polymer moiety to the compound of formula II.

Initially, non-PEG substituted compounds of Formula IIb-IIh are well known in the art and are exemplified in a number of issued patents including, without limitation, U.S. Pat. Nos. 6,489,300 and 6,436,904 both of which are incorporated herein by reference in their entirety. Non-polymer variants of compounds of Formula II include those having complementary functional groups or groups derivatizable to complementary functional groups on one or more of the $Ar^1$, R, $Ar^2$ and T moieties. For illustrative purposes, compounds having a complementary functional group (—OH) on the $Ar^2$ moiety (e.g., tyrosine) are recited below as a suitable starting point for addition of a polymer moiety to the molecule either directly or through a linker.

Such compounds can be prepared by first coupling a heterocyclic amino acid, 1, with an appropriate aryl sulfonyl chloride as illustrated in Scheme 1 below:

Scheme 1

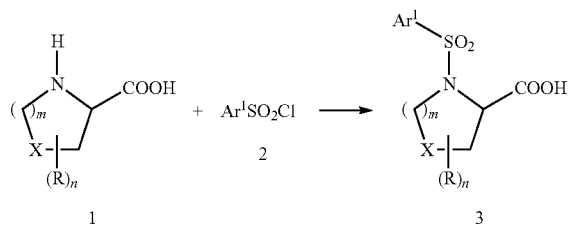

where R, $Ar^1$, X, m and n are as defined above.

Specifically, in Scheme 1 above, heterocyclic amino acid, 1, is combined with a stoichiometric equivalent or excess amount (preferably from about 1.1 to about 2 equivalents) of arylsulfonyl halide, 2, in a suitable inert diluent such as dichloromethane and the like. Generally, the reaction is conducted at a temperature ranging from about −70° C. to about 40° C. until the reaction is substantially complete, which typically occurs within 1 to 24 hours. Preferably, the reaction is conducted in the presence of a suitable base to scavenge the acid generated during the reaction. Suitable bases include, by way of example, tertiary amines, such as triethylamine, diisopropylethylamine, N-methyl-morpholine and the like. Alternatively, the reaction can be conducted under Schotten-Baumann-type conditions using an aqueous alkali solution such as an aqueous solution of sodium hydroxide, an aqueous phosphate solution buffered to pH 7.4, and the like. The resulting product, 3, can be recovered by conventional methods, such as chromatography, filtration, evaporation, crystallization, and the like or, alternatively, used in the next step without purification and/or isolation.

Heterocyclic amino acids, 1, employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-thiazolidine-4-carboxylic acid, L-(5,5-dimethyl)thiazolidine-4-carboxylic acid, L-thiamorpholine-3-carboxylic acid. If desired, the corresponding carboxylic acid esters of the amino acids, 1, such as the methyl esters, ethyl esters, t-butyl esters, and the like, can be employed in the above reaction with the arylsulfonyl chloride. Subsequent hydrolysis of the ester group to the carboxylic acid using conventional reagents and conditions, i.e., treatment with an alkali metal hydroxide in an inert diluent such as methanol/water, then provides the N-sulfonyl amino acid, 3.

Similarly, the arylsulfonyl chlorides, 2, employed in the above reaction are either known compounds or compounds that can be prepared from known compounds by conventional synthetic procedures. Such compounds are typically prepared from the corresponding sulfonic acid, i.e., from compounds of the formula $Ar^1SO_3H$ where $Ar^1$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the arylsulfonyl chlorides, 2, can be prepared from the corresponding thiol compound, i.e., from compounds of the $Ar^1$-SH where $Ar^1$ is as defined herein, by treating the thiol with chlorine ($Cl_2$) and water under conventional reaction conditions.

Alternatively, arylsulfonyl chlorides, 2, employed in the above reaction may be prepared by chlorosulfonylation of substituted benzene or heterocycloalkyl group using Cl—$SO_3$H.

Examples of arylsulfonyl chlorides suitable for use in this invention include, but are not limited to, benzenesulfonyl chloride, 1-naphthalenesulfonyl chloride, 2-naphthalenesulfonyl chloride, p-toluenesulfonyl chloride, o-toluenesulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamido-benzenesulfonyl chloride, 4-nitrobenzenesulfonyl chloride, 4-trifluoromethyl-benzenesulfonyl chloride, 4-trifluoromethoxybenzenesulfonyl chloride, 2,4,6-trimethylbenzenesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acid, 3.

The N-arylsulfonyl amino acid, 3, is then coupled to commercially available tyrosine esters as shown in Scheme 2 below:

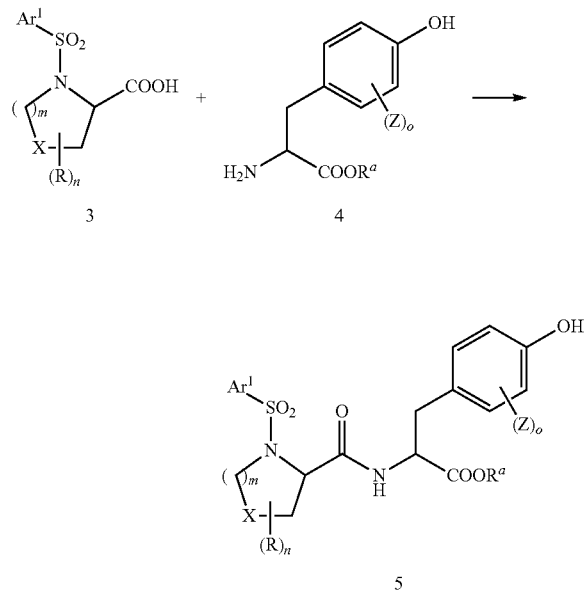

Scheme 2 where R, $Ar^1$, X, m and n are as defined above, $R^a$ is hydrogen or alkyl but preferably is an alkyl group such as t-butyl, Z represents optional substitution on the aryl ring and o is zero, one or two.

This coupling reaction is typically conducted using well-known coupling reagents such as carbodiimides, BOP reagent (benzotriazol-1-yloxy-tris(dimethylamino)-phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid, 3, with about 1 to about 2 equivalents of the coupling reagent and at least one equivalent, preferably about 1 to about 1.2 equivalents, of tyrosine derivative, 4, in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound 5 is recovered by conventional methods including neutralization, evaporation, extraction, precipitation, chromatography, filtration, and the like.

Alternatively, the N-sulfonyl amino acid, 3, can be converted into an acid halide which is then coupled with compound, 4, to provide compound 5. The acid halide can be prepared by contacting compound 3 with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide of N-sulfonyl amino acid, 3, is then contacted with at least one equivalent, preferably about 1.1 to about 1.5 equivalents, of the tyrosine derivative, 4, in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, compound 5 is recovered by conventional methods including neutralization, evaporation, extraction, precipitation, chromatography, filtration, and the like.

Alternatively, compound 5 can be prepared by first forming a diamino acid derivative and then coupling the diamino acid to the arylsulfonyl halide, 2, as shown in scheme 3 below:

Scheme 3

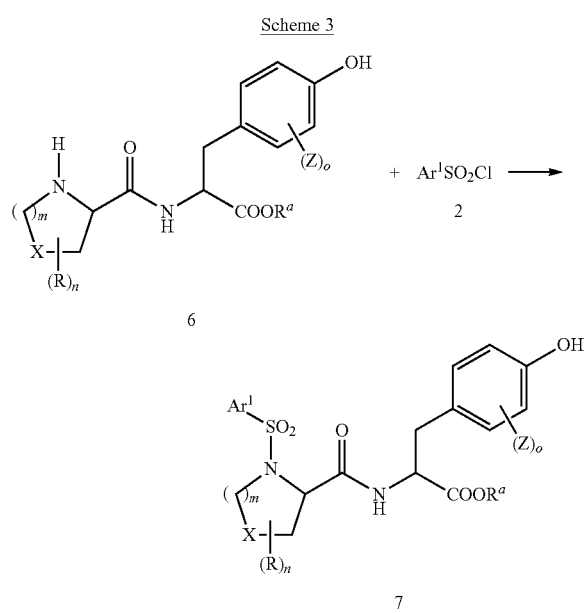

where R, $R^a$, $Ar^1$, X, Z, m, n and o are as defined above.

The diamino acid, 6, can be readily prepared by coupling amino acid, 1, with amino acid, 4, using conventional amino acid coupling techniques and reagents, such carbodiimides, BOP reagent and the like, as described above. Diamino acid, 6, can then be sulfonated using sulfonyl chloride, 2, and using the synthetic procedures described above to provide compound 7.

The tyrosine derivatives, 4, employed in the above reactions are either known compounds or compounds that can be prepared from known compounds by conventional synthetic procedures. For example, tyrosine derivatives, 4, suitable for use in the above reactions include, but are not limited to, L-tyrosine methyl ester, L-tyrosine t-butyl ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

The N-arylsulfonyl-heterocyclic amino acid-tyrosine derivative, 7, can be used as a starting point to attach a polymer moiety at the $Ar^2$ group by coupling reactions shown in Schemes 4-14 below which coupling reactions are illustrative only in demonstrating how polymer moieties can be introduced. In these Schemes, PEG is used as the polymer moiety for illustrative purposes only. It is understood that other suitable polymers could be used in place of PEG and that one of ordinary skill in the art would readily be able to modify the reaction schemes below to incorporate such other polymers. In some cases, the PEG moiety can be directly introduced onto the phenoxy group and, in other cases, the PEG moiety can be introduced by linkage through a linker moiety.

Specifically, Scheme 4 illustrates the following:

Scheme 4

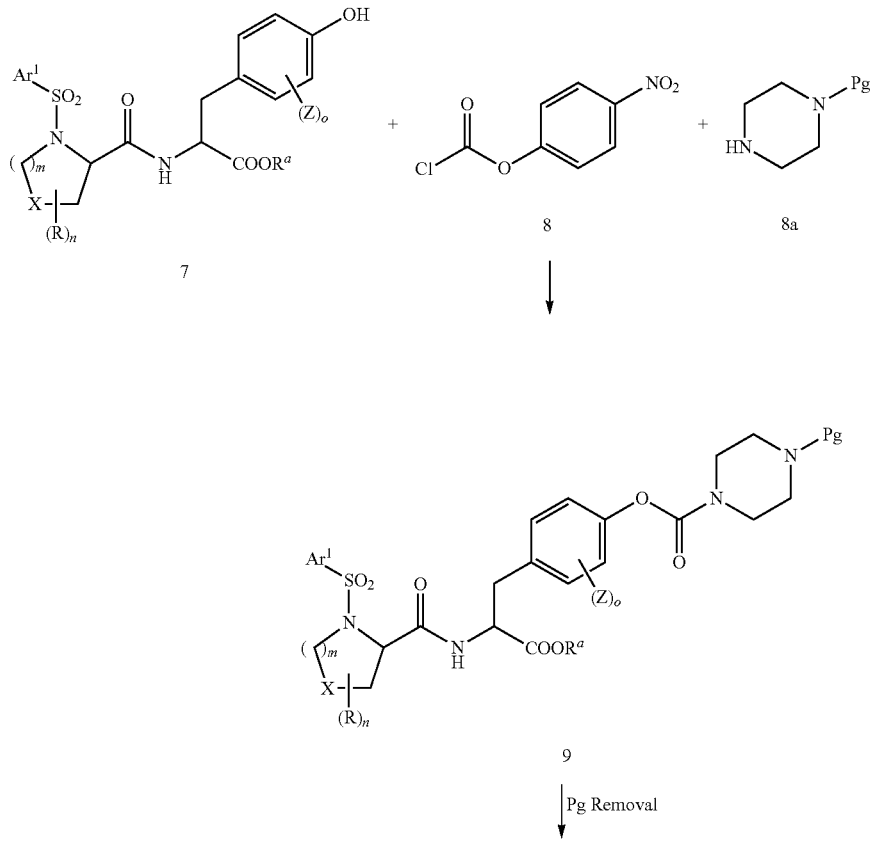

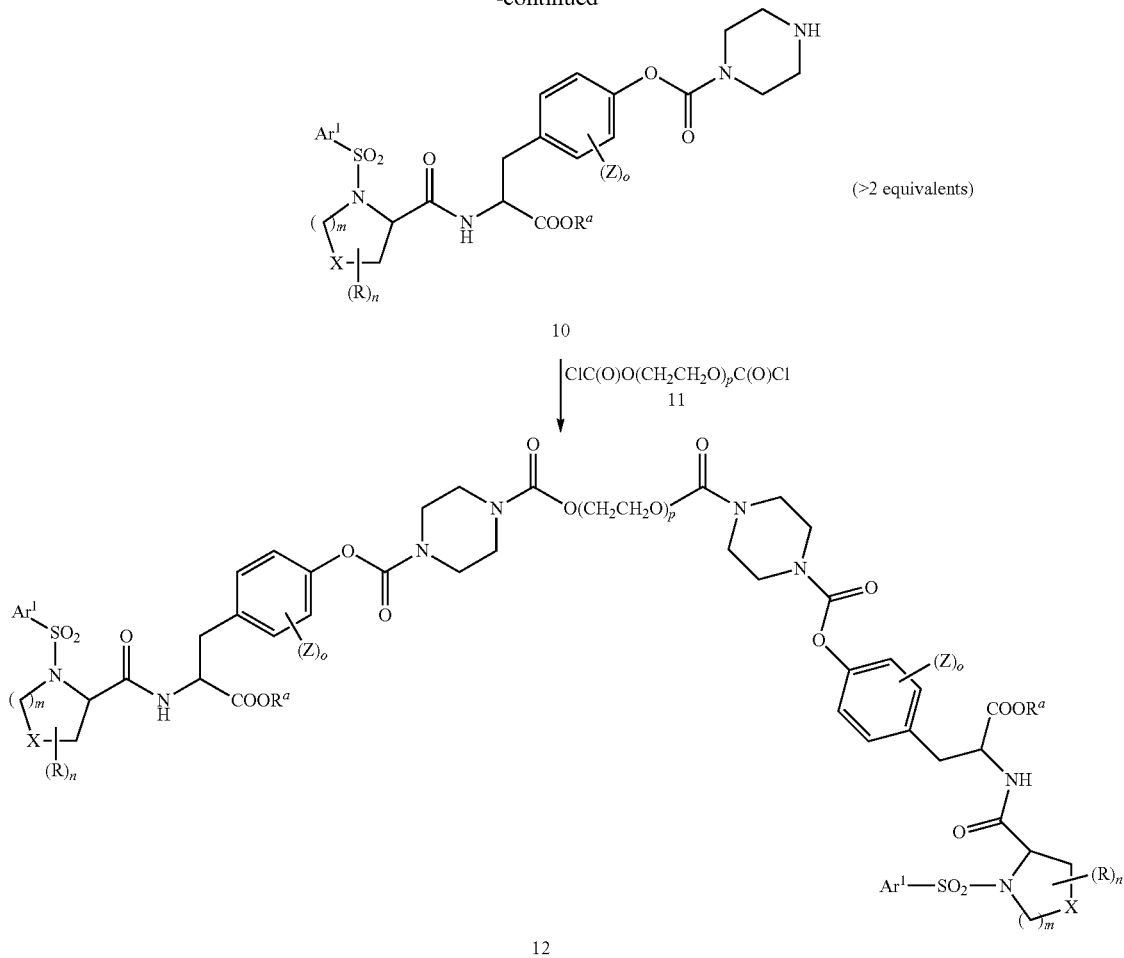

wherein $Ar^1$, R, $R^a$, m, n, o, X, and Z are as defined above, Pg is an amine protecting group such as CBZ, Boc, etc, which is preferably orthogonally removable as compared to the $R^a$ carboxyl protecting group and p is an integer preferably of from about 100 to 1360.

Specifically, in Scheme 4, compound 7, prepared as above, is combined with at least an equivalent and preferably an excess of 4-nitrophenyl chloroformate, 8, in a suitable solvent such as methylene chloride, chloroform and the like and preferably under an inert atmosphere. The reaction is preferably conducted at a temperature of from about −40° to about 0° C. in the presence of a suitable base to scavenge the acid generated. Suitable bases include, by way of example, triethylamine, diisopropylethylamine, and the like. After formation of the intermediate mixed carbonate (not shown), at least an approximately equimolar amount of N-Pg piperazine, 8a, is added to the reaction solution. This reaction is allowed to continue at room temperature for about 1 to 24 hours. Upon completion of the reaction, compound 9 is recovered by conventional methods including neutralization, evaporation, extraction, precipitation, chromatography, filtration, and the like, or, alternatively, is used in the next reaction without purification and/or isolation.

Conventional removal of the protecting group provides for the free piperazine derivative, 10. Removal is accomplished in accordance with the blocking group employed. For example, a trifluoromethylcarbonyl protecting group is readily removed via an aqueous solution of potassium carbonate. Further, suitable protecting groups for various functional groups as well as suitable conditions for protecting and deprotecting particular functional groups are well known in the art. See, for example, T. W. Greene and G. M. Wuts, *Protecting Groups in Organic Chemistry*, Second Edition, Wiley, New York, 1991, and references cited therein.

The free piperazine derivative, 10, is then combined with an α,ω-dichloroformate polyoxyethylene, compound 11, in a suitable inert diluent such as methylene chloride, chloroform, and the like and preferably under an inert atmosphere. Typically, at least 2 equivalents and preferably from about 2.5 to 10 equivalents of compound 10 per chloroformate entity are employed in combination with compound 11. The reaction is optionally conducted in the presence of a catalytic amount of DMAP and a base to scavenge the acid generated during reaction. The reaction is continued under ambient conditions until substantially complete which typically occurs within 4 to 24 hours. When $R^a$ is alkyl, subsequent hydrolysis of the ester derivative provides for the free carboxyl group or a salt thereof. The resulting dimer, 12, is recovered by conventional procedures such as neutralization, evaporation, extraction, precipitation, chromatography, filtration, and the like.

The α,ω-dichloroformate polyoxyethylene, compound 11, is readily prepared from commercially available polyoxyethylene by reaction with an excess of phosgene, typically from at least 2 to about 20 equivalents, in a suitable inert solvent such as methylene chloride, chloroform and the like. The reaction is preferably conducted under an inert atmosphere at ambient conditions until the reaction is substantially complete which typically occurs in from about 2 to 24 hours. Afterwards, the resulting α,ω-dichloroformate polyoxyethylene, compound 11, is recovered by convention procedures such as neutralization, evaporation, extraction, precipitation, chromatography, filtration, and the like.

A specific example of this reaction scheme up to formation of the piperazine derivative 28 is illustrated in Scheme 5 below:

Scheme 5

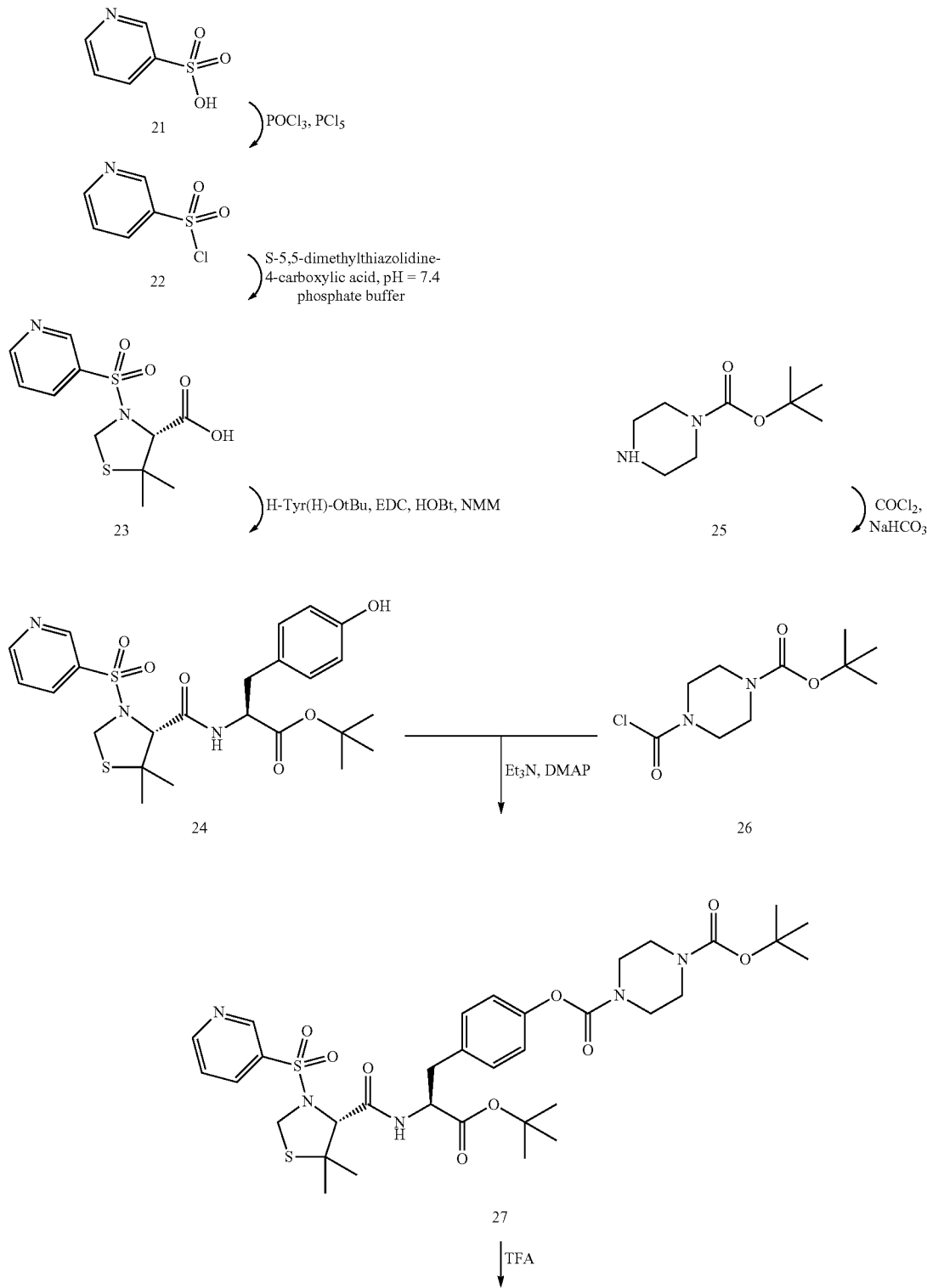

-continued

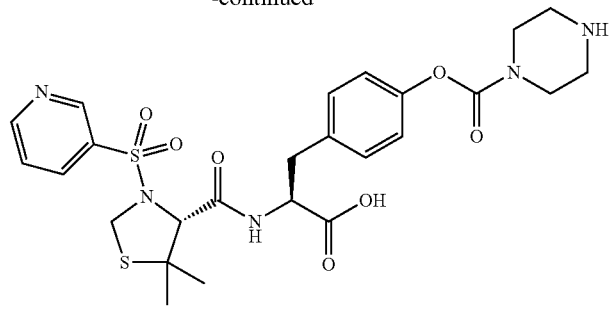

28

Specifically, commercially available 3-pyridinesulfonic acid, 21, is converted under conventional conditions to the corresponding sulfonyl chloride, 22, by contact with $POCl_3$/$PCl_5$ using conditions well known in the art. Coupling of sulfonyl chloride, 22, with commercially available S-5,5-dimethylthiazolidine-4-carboxylic acid, 23, is accomplished under conventional conditions preferably in the presence of a phosphate buffer (pH 7.4) using an excess of sulfonyl chloride. The reaction is preferably conducted at a temperature of from about −10 to 20° C. until the reaction is substantially complete, which typically occurs within 0.5 to 5 hours. The resulting product, 24, can be recovered by conventional methods, such as chromatography, filtration, evaporation, crystallization, and the like or, alternatively, used in the next step without purification and/or isolation.

The N-pyridinyl sulfonyl-5,5-dimethylthiazolidine-4-carboxylic acid compound, 23, is next coupled to t-butyl tyrosine using conventional amino acid coupling conditions. Specifically, this coupling reaction is conducted using well known coupling reagents such as 1-(3-dimethylaminopropyl)-3-ethylcarbodiimide (EDC), 1-hydroxy-benzotriazole (HOBt) and N-methylmorpholine to facilitate the coupling reaction.

This coupling reaction is typically conducted by contacting the N-sulfonylamino acid, 23, with about 1 to about 2 equivalents of the coupling reagent and at least one equivalent, preferably about 1 to about 1.2 equivalents, of tyrosine t-butyl ester in an inert diluent, such as dichloromethane, chloroform, acetonitrile, tetrahydrofuran, N,N-dimethylformamide and the like. Generally, this reaction is conducted at a temperature ranging from about 0° C. to about 22° C. for about 12 to about 24 hours. Upon completion of the reaction, the compound 24 is recovered by conventional methods including neutralization, evaporation, extraction, precipitation, chromatography, filtration, and the like or, alternatively, is employed in the next step without purification and/or isolation.

Separately, mono-N-Boc-piperazine, 25, is converted to the corresponding carbamyl chloride, 26, by reaction with phosgene in the manner described above. Upon completion of the reaction, the compound 26 is recovered by conventional methods including neutralization, evaporation, extraction, precipitation, chromatography, filtration, and the like or, alternatively, is employed in the next step without purification and/or isolation.

Coupling of compound 24 with compound 26 to provide for compound 27 proceeds under conventional conditions in an inert diluent such as dichloromethane, with a catalytic amount of DMAP and preferably in the presence of a base to scavenge the acid generate. The reaction is run at a temperature of about −20 to about 22° C. for about 2 to about 24 hours. Upon completion of the reaction, compound 27 is recovered by conventional methods including neutralization, evaporation, extraction, precipitation, chromatography, filtration, and the like or, alternatively, is employed in the next step without purification and/or isolation.

Removal of both the amino Boc protecting group and the t-butyl ester proceeds in the presence of trifluoroacetic acid to provide for compound 28 which can be recovered by conventional methods including neutralization, evaporation, extraction, precipitation, chromatography, filtration, and the like.

Scheme 6 below illustrates the preparation of a piperazine compound orthogonally protected on one of the amine groups relative to the carboxyl protecting group found on the phenylalanine compound such that after coupling, the piperazine protecting group can be removed differentially from that of the carboxyl protecting group. Such orthogonal protection is necessary if subsequent reactions on the resulting compound require a carboxyl protecting group to avoid undesired side reactions.

Scheme 6

-continued
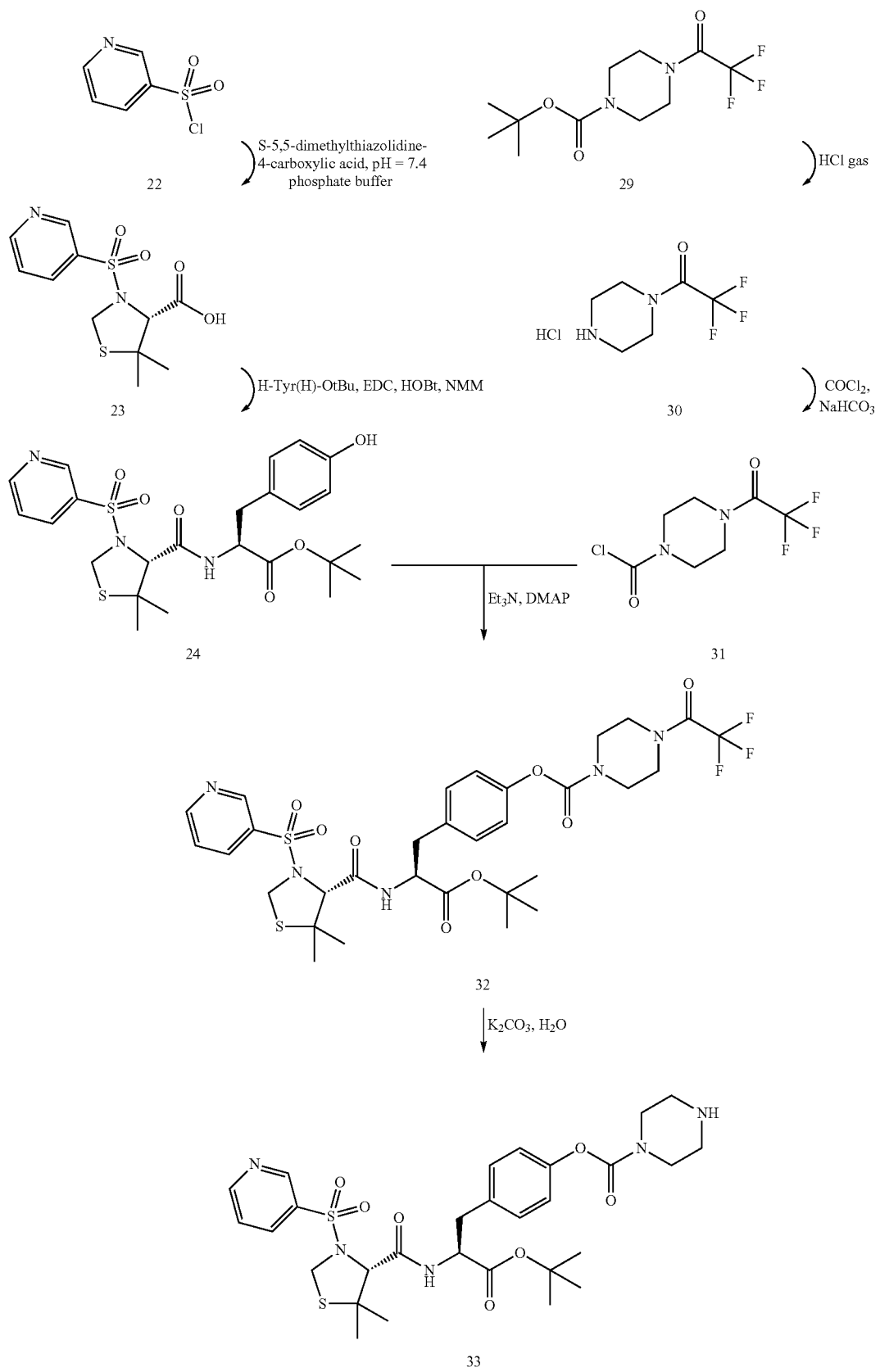

Specifically, in Scheme 6, compound 24 is prepared in the manner described above. N-t-Boc-piperazine, 25, is conventionally converted to N-t-Boc-N'-trifluoromethyl-carbonylpiperazine, 29, by contact with an excess of trifluoroacetic anhydride in the presence of a suitable amine such as triethylamine to scavenge the acid generated during reaction in a suitable solvent such as dichloromethane. Generally, this reaction is conducted at a temperature ranging from about −20° C. to about 22° C. for about 1 to about 24 hours. Upon completion of the reaction, compound 29 can be recovered by conventional methods including neutralization, evaporation, extraction, precipitation, chromatography, filtration, and the like or, alternatively and preferably, is employed in the next step without purification and/or isolation.

In turn, removal of the t-Boc protecting group on the N-t-Boc-N'-trifluoromethyl-carbonylpiperazine, 29, proceeds under conventional conditions using gaseous HCl bubbled through an inert solvent such as methylene chloride, EtOAc, EtO$_2$, and the like under ambient conditions to provide for the hydrochloride salt of N'-trifluoromethylcarbonylpiperazine, 30. Generally, this reaction is conducted at a temperature ranging from about −20° C. to about 22° C. for about 0.5 to about 4 hours. Upon completion of the reaction, compound 30 can be recovered by conventional methods including neutralization, evaporation, extraction, precipitation, chromatography, filtration, and the like or, alternatively and preferably, is employed in the next step without purification and/or isolation.

Conversion of N'-trifluoromethylcarbonylpiperazine, 30, to the N-carbamyl chloride derivative, 31, conventionally proceeds by contact with phosgene in the manner described above. Upon completion of the reaction, compound 31 can be recovered by conventional methods including neutralization, evaporation, extraction, precipitation, chromatography, filtration, and the like or, alternatively and preferably, is employed in the next step without purification and/or isolation.

Compounds 31 and 24 are coupled under conditions similar to those described above to provide for compound 32 which is orthogonally protected at the amino moiety of the piperazine group as well as the carboxyl moiety of the phenylalanine group. Selective removal of the trifluoromethylcarbonyl amino protecting group proceeds under conventional conditions using an aqueous solution of potassium carbonate to provide for compound 33.

Scheme 7 below illustrates modification of the polymer moiety prior to covalently binding the compound of formula II. For illustrative purposes only, the polymer moiety is a tetravalent PEG bound to a pentaerythritol. Scheme 7 illustrates that the length of the polymer moiety can be readily adjusted by conventional chemistry to provide for optimal lengths.

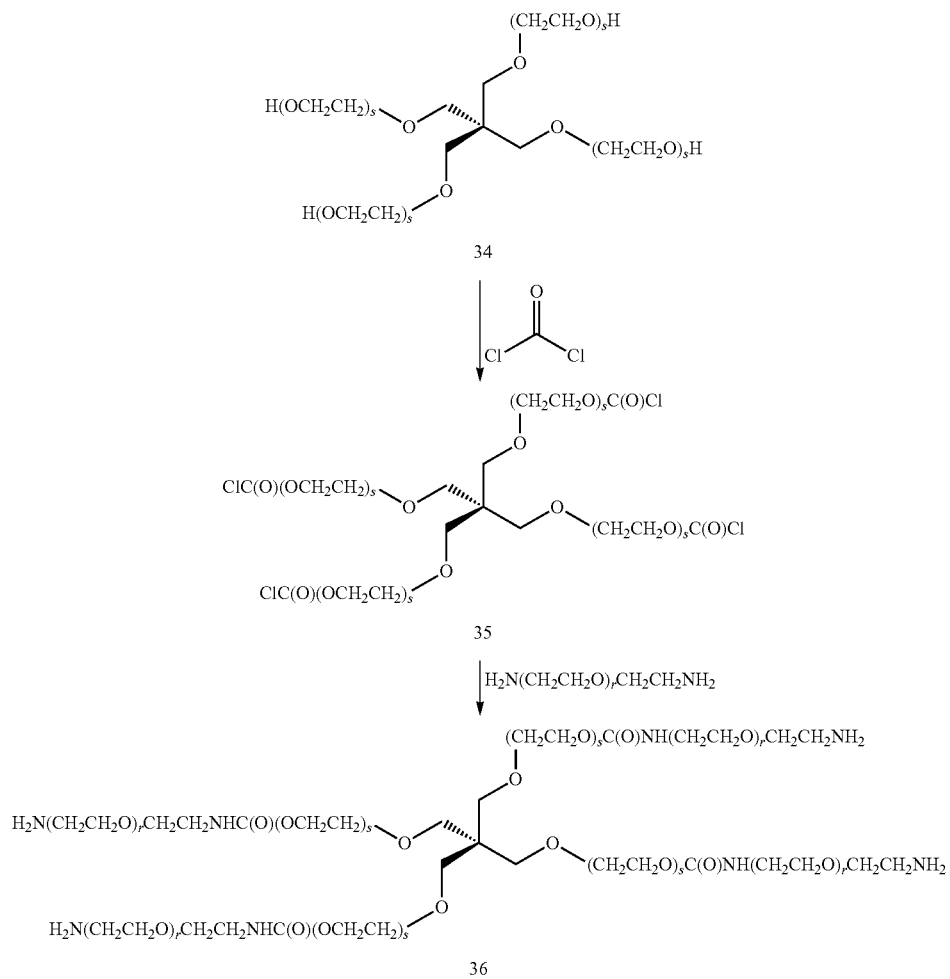

where the aggregate of the four r's and s's is an integer preferably from about 100 to 1360.

Specifically, commercially available tetra-pegylated pentaerythritol, compound 34, (e.g., a compound having a total molecular weight of approximately 20 kD and available from Sun Bio, Orinda, Calif., USA, as catalog no. P40H-20), is reacted with an excess of phosgene, typically from at least 4 to about 40 equivalents, in a suitable inert solvent such as methylene chloride, chloroform and the like. The reaction is preferably conducted under an inert atmosphere at ambient conditions until the reaction is substantially complete which typically occurs in from about 2 to 24 hours. Afterwards, the resulting tetrachloroformate polyoxyethylene, compound 35, is recovered by convention procedures such as neutralization, evaporation, extraction, precipitation, chromatography, filtration, and the like or is used in the next reaction step without purification and/or isolation.

Tetrachloroformate, compound 35, is then combined with an excess (typically 2.5 to 10 equivalents per chloroformate entity) of an α,ω-diaminopolyoxyethylene compound (e.g., a compound having a molecular weight of approximately 6 kD and available from Sun Bio, as catalog no. P2AM-6), under conventional conditions in an inert diluent such as dichloromethane, optionally in the presense of a catalytic amount of DMAP and a base to scavenge the acid generate. The reaction is typically conducted at a temperature of about −20 to about 22° C. for about 2 to about 24 hours or until substantial completion of the reaction. Upon completion, compound 36 is recovered by conventional methods including neutralization, evaporation, extraction, precipitation, chromatography, filtration, and the like or, alternatively, is employed in the next step without purification and/or isolation.

When the specific tetra-pegylated pentaerythritol from Sun Bio and the diamine from Sun Bio are employed, the resulting product, compound 36, has a molecular weight of approximately 45 kD. α,ω-Diaminopolyoxyethylenes are commercially available under the tradename Jeffamines® and typically have molecular weights of up to 10,000 or higher.

It is understood that a mono-amino protected α,ω-diaminopolyoxyethylene may be used in Scheme 7 in order to minimize cross-linking as well as cyclization. Upon reaction completion, the mono-amino protecting group is removed by conventional means well known in the art.

Scheme 8 illustrates a second route for derivatization to provide for polymer substitution. In this scheme, the amino moiety of the piperazine group is employed as a complementary functional group to an in situ formed activated carboxyl groups of an α,ω-dicarboxylic acid polymer. Again for the sake of illustration only, the α,ω-dicarboxylic acid polymer is an α,ω-dicarboxylic acid polyoxyethylene. In this embodiment, the dicarboxyl-PEG compound is represented by the formula HOOCCH$_2$(OCH$_2$CH$_2$)$_p$OCH$_2$COOH where p is as defined above and the resulting linker to the PEG group is represented by —C(O)CH$_2$—.

Scheme 8

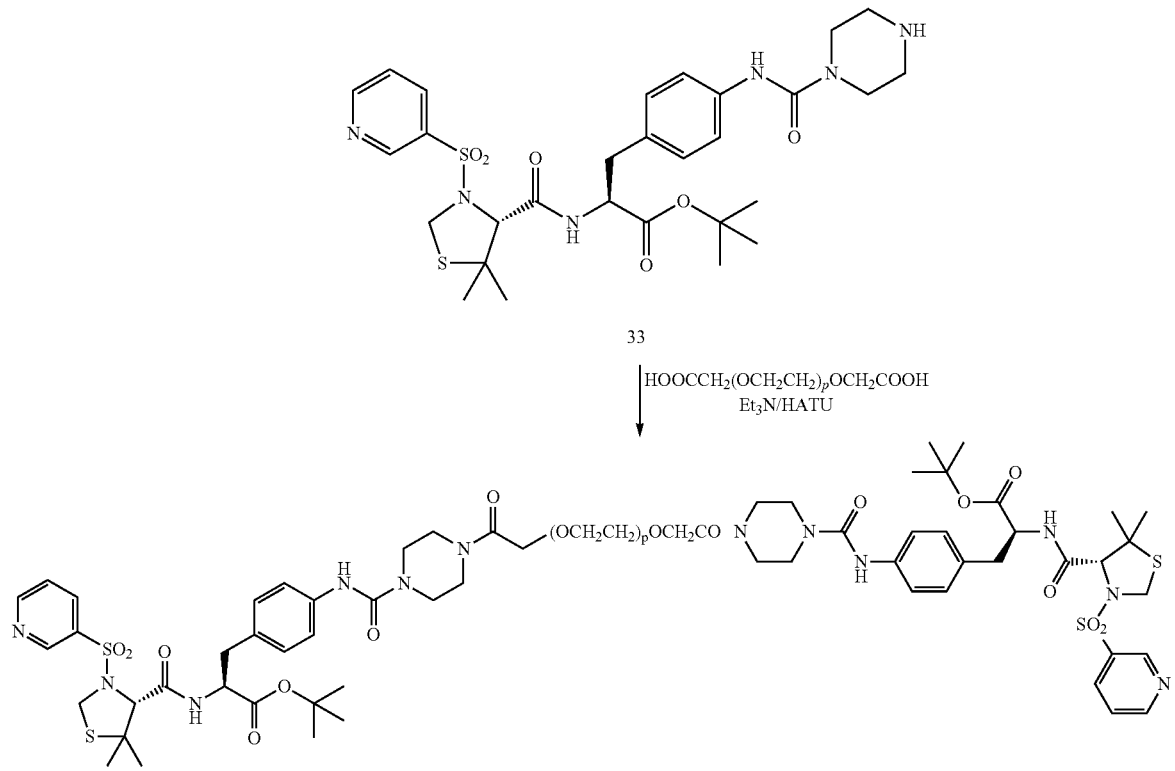

Specifically, in Scheme 8, an excess of compound 33 (e.g., 2.5 to 10 equivalents of compound 33 per carboxyl group), prepared as above, is added to the dicarboxyl-PEG compound which is converted in situ to an activated ester (not shown) by contact with at least two equivalents and preferably an excess of HATU [O-(7-azabenzotriazol-1-yl)-1,1,3,3,-tetramethyluronium hexafluorophosphate] in the presence of a suitable amine such as triethylamine. Coupling of the dicarboxyl-PEG compound to compound 33 preferably proceeds at a temperature of from about 0 to about 22° C. for about 2 to about 24 hours. Upon completion of the reaction, the compound 39 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides for a compound of Formula IA of this invention.

Scheme 9 illustrates still another route for derivatization to provide for polymer addition to compound A. In this scheme, the amino moiety of the piperazine group is employed as a complementary functional group to an in situ formed chloroformate of a polymer comprising an α,ω-diol. Again for illustrative purposes, the polymer comprising an α,ω-diol is PEG which is represented by the formula $HOCH_2CH_2(OCH_2CH_2)_pOH$ where p is as defined above and the resulting linker is represented by —C(O)—.

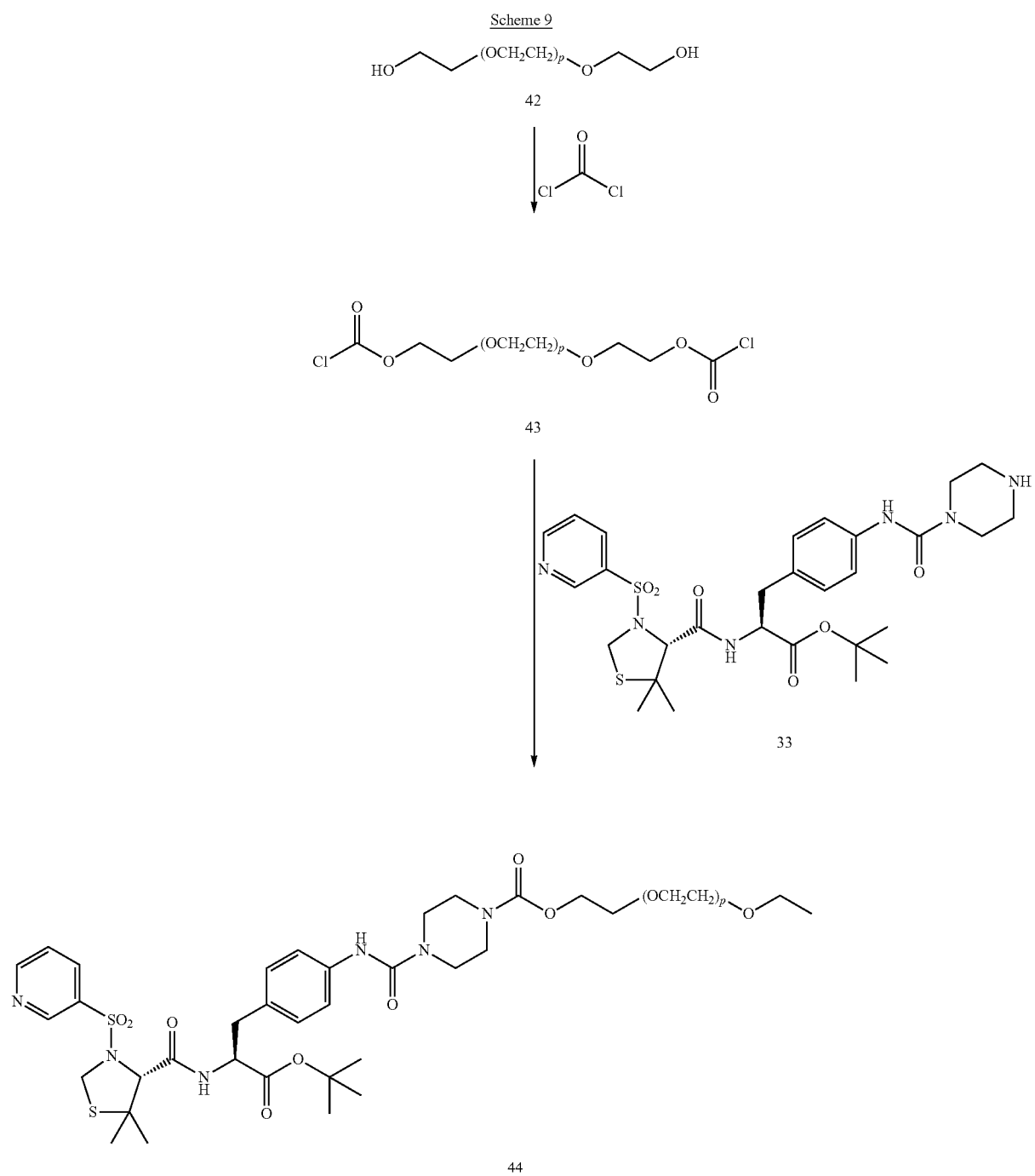

-continued

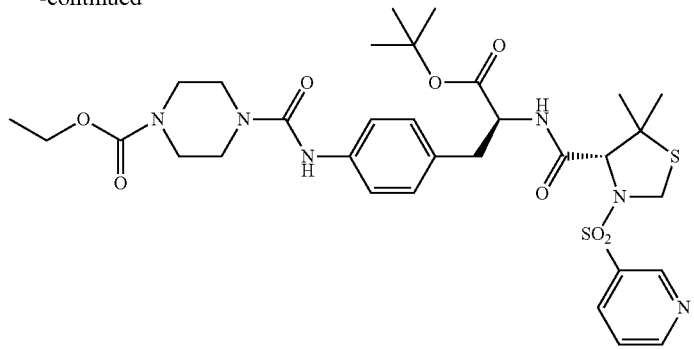

Specifically, in Scheme 9, the hydroxyl group of a commercially available dihydroxy PEG, 42, is converted to the corresponding chloroformate, 37 by reaction with phosgene in toluene (Fluka), in dichloromethane. The product is isolated by evaporation and is employed in the next step without further purification.

An excess of compound 33 (e.g., 2.5 to 10 equivalent of compound 33 per chloroformate entity) is contacted with dichloroformate, compound 43, prepared as above, in the presence of a suitable base such as triethylamine to scavenge the acid generated. Coupling of the dichloroformate-PEG compound to compound 33 preferably proceeds at a temperature of from about 0 to about 22° C. for about 2 to about 4 hours. Upon completion of the reaction, the compound 44 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides for a compound of Formula I of this invention.

The reactions depicted in Schemes 8 and 9 are simultaneously conducted at either end of the dicarboxylic acid (Scheme 8) or the dichloroformate (Scheme 9) thereby providing a one pot synthesis of a homomeric divalent or higher multivalent conjugate. It is understood, however, that these reactions can be conducted sequentially by use of protecting groups.

In the case of a dicarboxylic acid, one of the carboxyl groups can be protected while the other undergoes coupling to the amino group of the piperazine. Upon completion, the protecting group can be removed and then reacted with either the same or preferably a different compound A to provide for a heterodivalent structure. Still further, heterotrivalent, heterotetravalent and higher heteromultivalent structures can be prepared by use of orthogonal protecting groups on the carboxylic functionality. In the case of a diol (Scheme 9), one of the hdyroxyl groups can be protected while the other undergoes reaction with phosgene to form a chloroformate for subsequent addition to the amino group of the piperazine. Upon completion, the protecting group can be removed and then reacted with phosgene and subsequently with either the same or preferably a different compound A to provide for a heterodivalent structure. Still further, heterotrivalent, heterotetravalent and higher heteromultivalent structures can be prepared by use of orthogonal protecting groups on the alcohol functionality.

Scheme 10 illustrates the synthesis of N-carbamyl chloride and isocyanate intermediates useful for subsequent polymer addition. In this scheme, the amino moiety of the piperazine group is derivatized for subsequent polymer addition.

Scheme 10

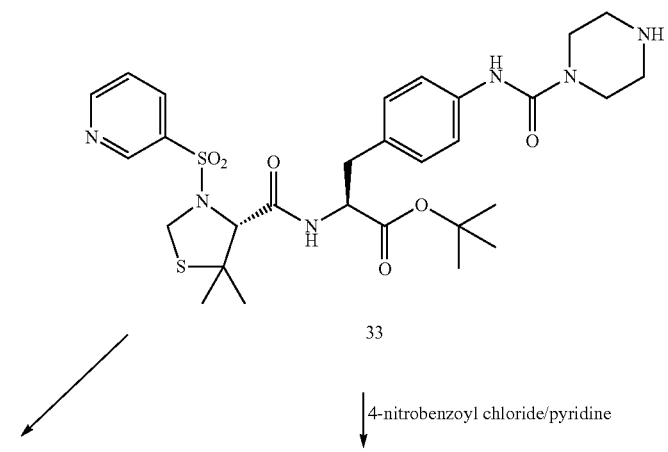

4-nitrobenzoyl chloride/pyridine

-continued

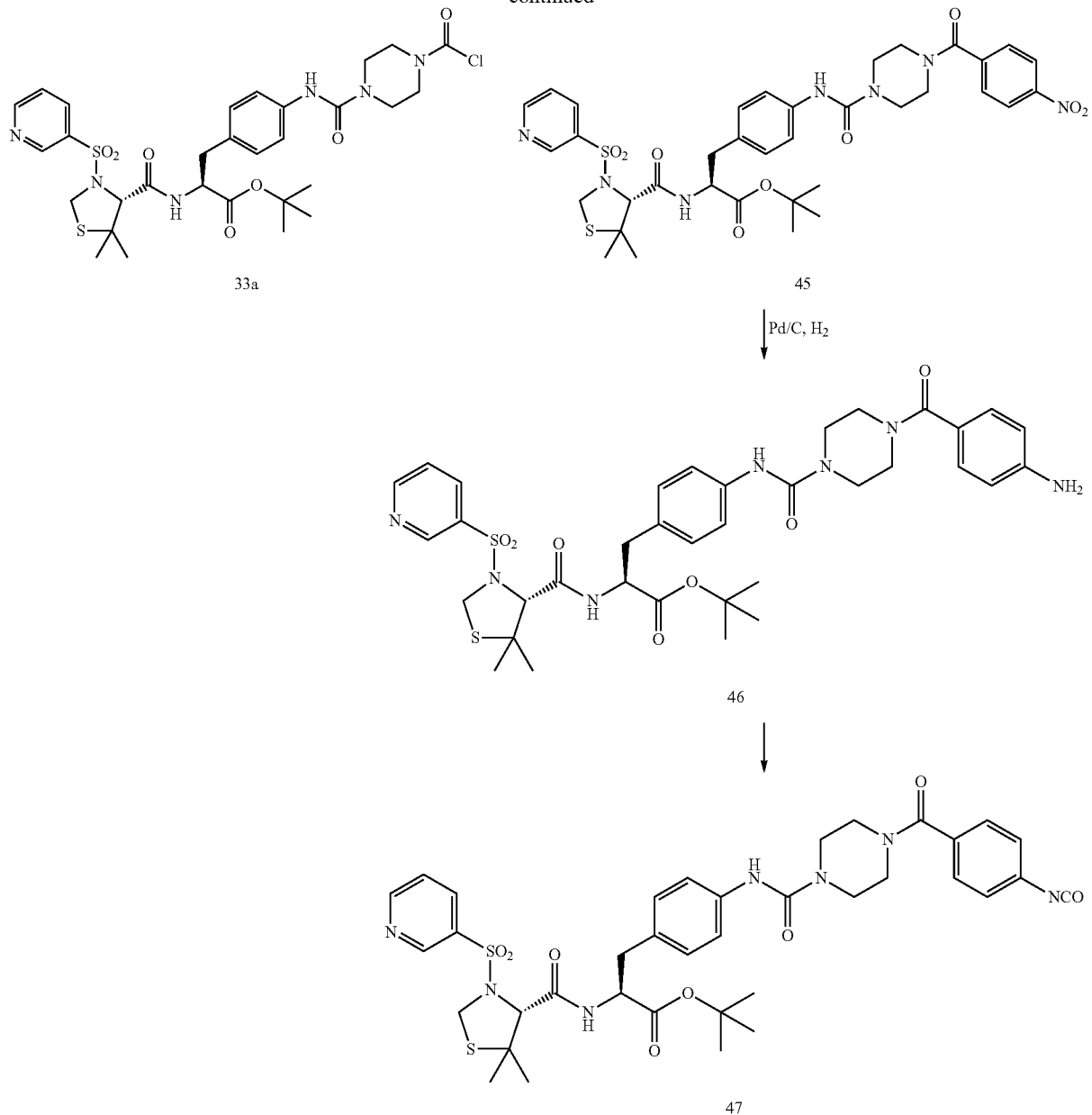

Specifically, in Scheme 10, conversion of the amino moiety of the piperazine group of compound 33, to the corresponding N-carbamyl chloride, compound 33a, proceeds by contact with an excess of phosgene in the presence of a suitable base such as sodium bicarbonate to scavenge the acid generated during reaction. Upon completion of the reaction, compound 33a can be recovered by conventional methods such as neutralization, evaporation, extraction, precipitation, chromatography, filtration, and the like or, alternatively and preferably is employed in the next (illustrated in Scheme 11) without purification and/or isolation.

Alternatively, the amino moiety of the piperazine group of compound 33 can be converted to the corresponding amide, compound 45, by reaction with at least an equivalent and preferably an excess of 4-nitrobenzoyl chloride in the presence of a base such as pyridine (which can also act as a solvent) to scavenge the acid generated during reaction. The reaction preferably proceeds at a temperature of from about 0 to about 22° C. for about 1 to about 24 hours. Upon completion of the reaction, compound 45 is recovered by conventional methods including neutralization, evaporation, extraction, precipitation, chromatography, filtration, and the like or, alternatively, is employed in the next step without purification and/or isolation.

Subsequent reduction of the para-nitro substituent of the phenyl group provides for the amine substituent in compound 46. Reduction is conventionally conducted using palladium/carbon under a hydrogen atmosphere typically at elevated pressures in a suitable diluent such as methanol. The reaction proceeds until substantial completion which typically occurs within about 24 to about 72 hours. During the reaction, additional catalyst is added as required to affect reaction completion. Upon completion of the reaction, the compound 46 is recovered by conventional methods including neutralization, evaporation, extraction, precipitation, chromatography, filtration, and the like or, alternatively, is employed in the next step without purification and/or isolation.

Conversion of the para-amino substituent of the phenyl group of compound 46 to the corresponding isocyanate, 47, occurs by reaction with an excess of phosgene in the presence of a suitable base such as sodium bicarbonate which scavenges the acid generated. The reaction proceeds until substantial completion which typically occurs within about 0.5 to about 5 hours at about 0° C. to about 22° C. Upon completion of the reaction, the compound 47 is recovered by conventional methods including neutralization, evaporation, extraction, precipitation, chromatography, filtration, and the like or, alternatively, is employed in the next step without purification and/or isolation.

Scheme 11 illustrates still a further route for derivatization to provide for polymer substitution. In this scheme, the carbamyl chloride moiety of the piperazine group of compound 33a is employed as a complementary functional group to form a carbamate or urea bond. For illustrative purposes only, the polymer employed is an α,ω-diol or diamine of a PEG and is represented by the formula $HQCH_2CH_2(OCH_2CH_2)_pQH$ where Q is NH or O.

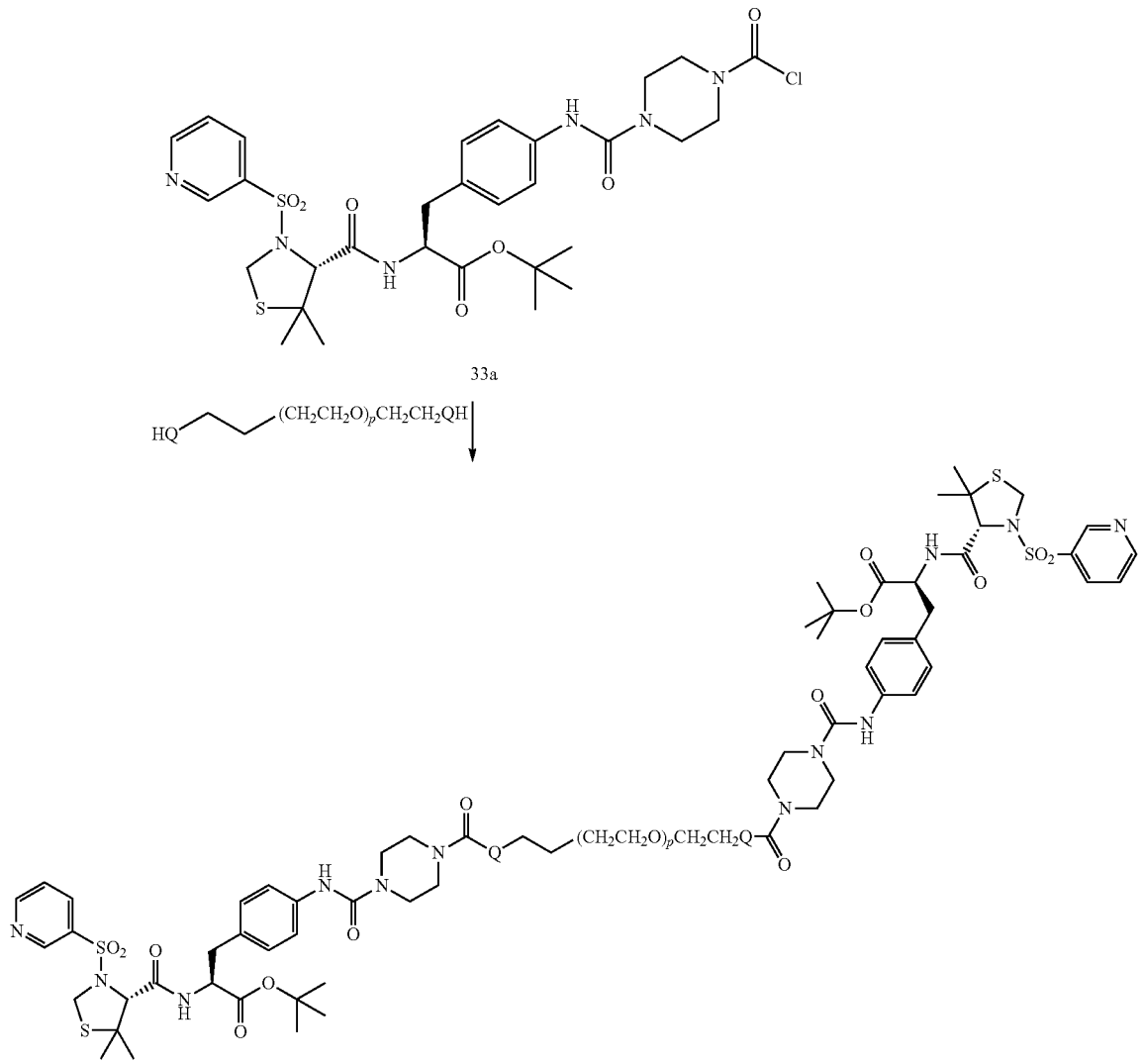

Scheme 11

48

Specifically, in Scheme 11, an excess (e.g., 2.5 to 10 equivalents of carbamyl chloride per each HQ moiety) of compound 33a, is contacted in an inert solvent such as dichloromethane with a suitable dihydroxy- or diamino-PEG compound preferably in the presence of a suitable base such as triethylamine and/or catalytic amounts of 4-N,N-dimethylaminopyridine (DMAP). The reaction proceeds until substantial completion which typically occurs within about 4 to about 48 hours. Upon completion of the reaction, the compound 48 is recovered by conventional methods including neutralization, evaporation, extraction, precipitation, chromatography, filtration, and the like or, alternatively, is employed in the next step without purification and/or isolation.

When Q is a hydroxyl group, the product contains a carbamate functionality covalently linking the PEG group to the VLA-4 antagonist through a linker represented by —C(O)—. When Q is an amino group, the product contains a urea functionality covalently linking the PEG group to the VLA-4 antagonist through a linker represented by —C(O)—Conventional removal of the t-butyl carboxyl protecting group with an excess of formic acid provides for a compound of this invention.

Scheme 12 illustrates yet another route for derivatization to provide for polymer substitution. In this scheme, the isocyanate of compound 47 is employed as a complementary functional group to form a carbamate or urea bond. For illustrative purposes only, the polymer employed is an α,ω-diol or diamine of a PEG and is represented by the formula $HQCH_2CH_2(OCH_2CH_2)_pQH$ where Q is NH or O.

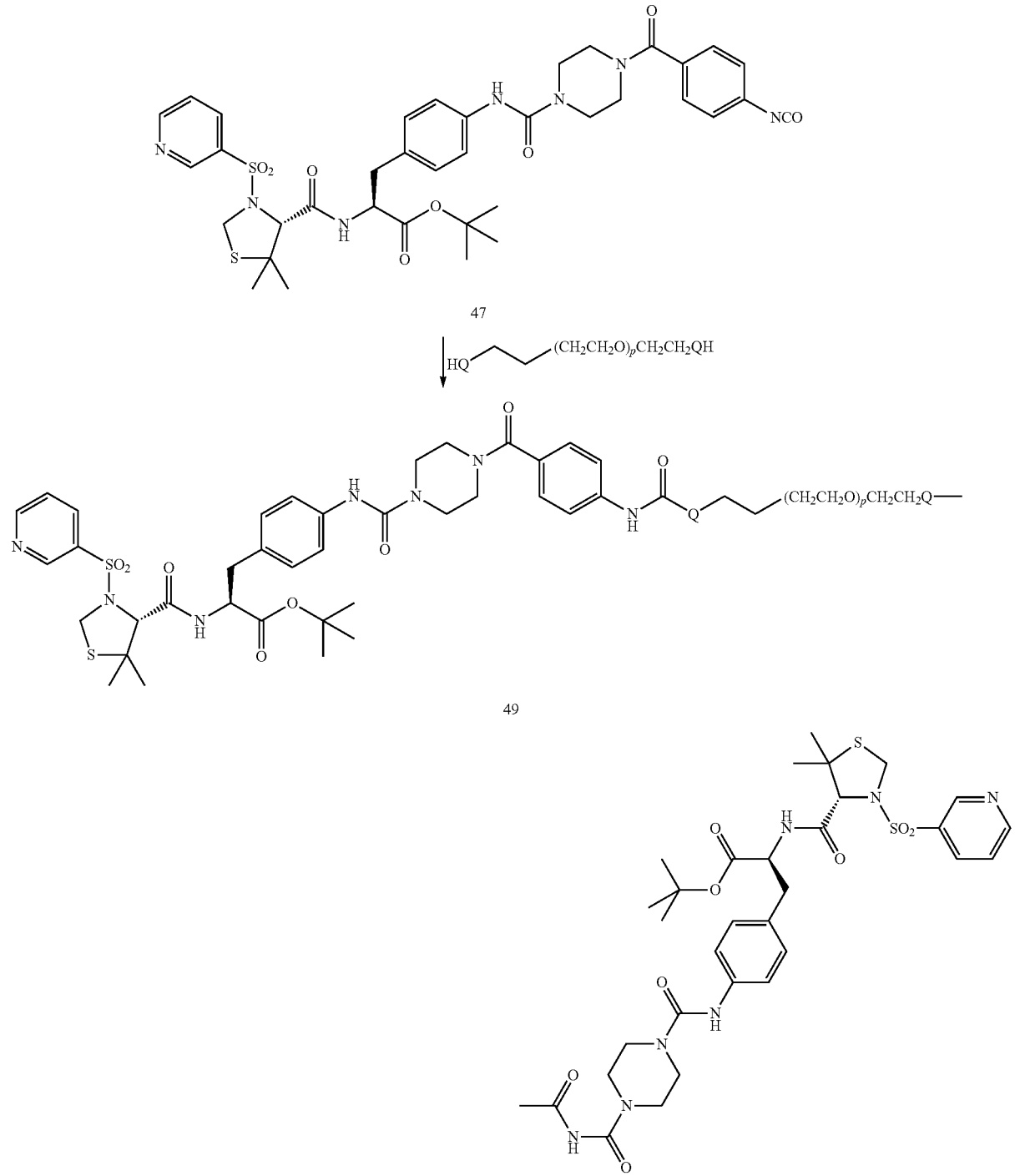

Specifically, in Scheme 12, an excess of isocyanate 47 (e.g., 2.5 to 10 equivalents of isocyanate 47 per each HQ moiety) is contacted with a suitable dihydroxy- or diamino-PEG compound in a suitable inert diluent such as dichloromethane or toluene. The reaction is preferably maintained at a temperature of from about 0° to about 105° C. until substantial completion which typically occurs within about 1 to about 24 hours. Upon completion of the reaction, compound 49 is recovered by conventional methods including neutralization, evaporation, extraction, precipitation, chromatography, filtration, and the like or, alternatively, is employed in the next step without purification and/or isolation.

When Q is a hydroxyl group, the resulting product contains a carbamate functionality covalently linking the PEG group to the VLA-4 antagonist through a —C(O)— linking group. When Q is an amino group, the resulting product contains a urea functionality covalently linking the PEG group to the VLA-4 antagonist through a —C(O)— linking group.

Conventional removal of the t-butyl carboxyl protecting group with an excess of formic acid provides for a mono-PEG compound, 47, of Formula I of this invention.

The reactions depicted in Schemes 11 and 12 are simultaneously conducted at both ends of the polymer (for dimer formation) thereby providing a one pot synthesis of a homomeric divalent or higher multivalent conjugate. It is understood, however, that these reactions can be conducted sequentially by use of protecting groups.

In the case of a diamine, one of the amine groups can be protected while the other undergoes coupling to either the carbamyl chloride of compound 33a or the isocyanate of compound 47. Upon completion, the protecting group can be removed and then reacted with either the same or preferably a different compound A to provide for a heterodivalent structure. Still further, heterotrivalent, heterotetravalent and higher heteromultivalent structures can be prepared by use of orthogonal protecting groups on one or more of the amine functionalities.

In the case of a diol, one of the hydroxyl groups can be protected while the other undergoes coupling to either the carbamyl chloride of compound 33a or the isocyanate of compound 47. Upon completion, the protecting group can be removed and then reacted with either the same or preferably a different compound A to provide for a heterodivalent structure. Still further, heterotrivalent, heterotetravalent and higher heteromultivalent structures can be prepared by use of orthogonal protecting groups on one or more of the hydroxyl functionalities.

In the Schemes above, amine moieties located on other portions of the molecule can be employed in the manner described above to covalently link a polymer group to the molecule. For example, amines located on $Ar^1$, on the heterocyclic amino acid or on $Ar^2$ can be similarly derivatized to provide for PEG substitution. The amine moieties can be included in these substituents during synthesis and appropriately protected as necessary. Alternatively, amine precursors can be employed. For example, as shown in Scheme 10, reduction of a nitro group provides for the corresponding amine. Similarly, reduction of a cyano group provides for a $H_2NCH_2$— group. Nitro and cyano substituted $Ar^1$ groups are provided in U.S. Pat. No. 6,489,300 as is an amino substituted $Ar^1$ group.

Further, the amino substitution can be incorporated into the heterocyclic amino acid functionality and then derivatized to include a polymer moiety. For example, the heterocyclic amino acid functionality can be 2-carboxylpiperazine depicted in U.S. Pat. No. 6,489,300. Alternatively, commercially available 3- or 4-hydroxyproline can be oxidized to the corresponding ketone and then reductively aminated with ammonia in the presence of sodium cyanoborohydride to form the corresponding amine moiety. Still further, 4-cyanoproline can be reduced to provide for a substituted alkyl group of the formula —$CH_2NH_2$ which can be derivatized through the amine.

Still further, the amine moiety can be incorporated into the $Ar^2$ functionality. Preferably, the amine moiety is present as an amine precursor such as a nitro or cyano group bound to $Ar^2$.

In the schemes above, the reactions of the amine with a complementary functional group can be reversed such that the carboxyl or hydroxyl group is on the VLA-4 antagonist of Formula II (without any polymer substituents) and the amine group could be part of the polymer moiety. In such cases, the amine group, preferably terminating the polymer moiety, can be converted to an isocyanate, using phosgene and $Et_3N$, and reacted with the hydroxyl group to form a carbamate as illustrated in Scheme 13 below:

Scheme 13

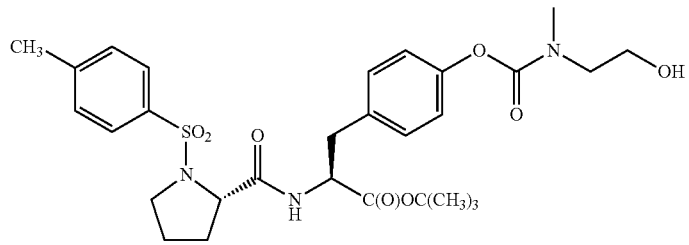

50

$$\downarrow OCN(CH_2CH_2O)_pCH_2CH_2NCO$$

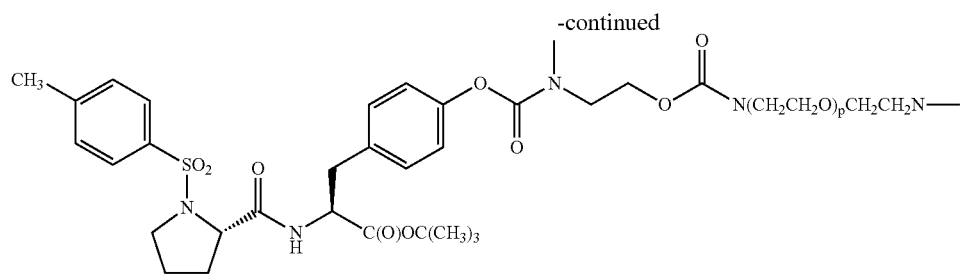

51

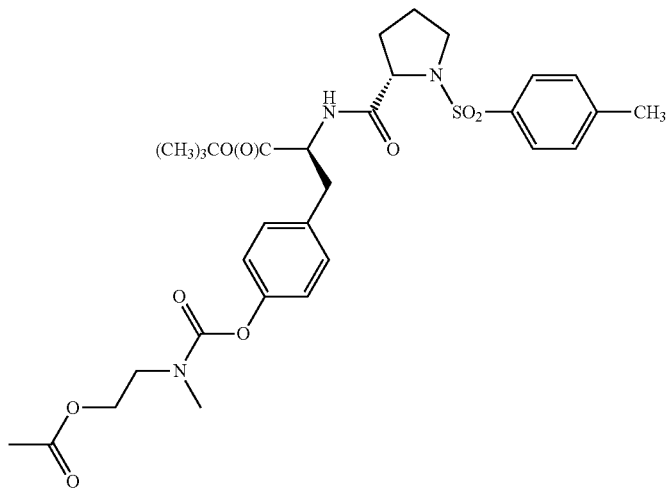

Specifically, an excess of compound 50 described in U.S. Pat. No. 6,489,300, is contacted with in the manner described above to provide for the corresponding carbamate, 51. Preferably, from about 2.5 to 10 equivalents of compound 50 per each isocyanate moiety is employed. Deprotection, as described above, then provides for the corresponding diacid (not shown).

Alternatively, in Scheme 13, the hydroxyl functionality can be reacted with phosgene to provide for the chlorocarbonyloxy derivative which reacts with an amine group of a diamine compound to provide for the carbamate.

Carboxyl functionality, for example on the $Ar^1$ moiety, can be converted to the corresponding amide by reaction with a di- or higher-aminopolymer in the manner described above in Scheme 8. Alternatively, Scheme 14 below illustrates one method for the generation of an amine functionality from the corresponding cyano group on the $Ar^1$ moiety.

Scheme 14

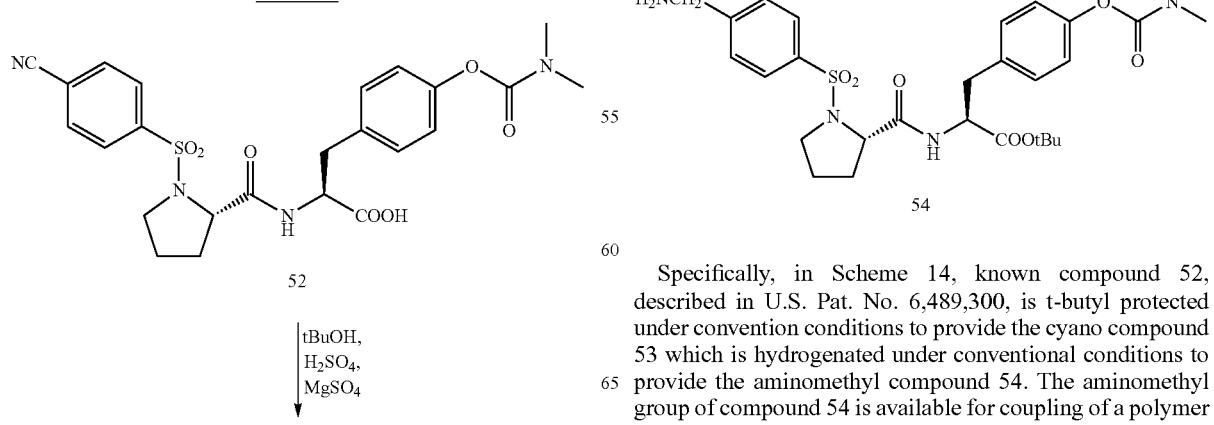

Specifically, in Scheme 14, known compound 52, described in U.S. Pat. No. 6,489,300, is t-butyl protected under convention conditions to provide the cyano compound 53 which is hydrogenated under conventional conditions to provide the aminomethyl compound 54. The aminomethyl group of compound 54 is available for coupling of a polymer moiety thereto in one on any of the schemes illustrated above.

Scheme 15 below illustrates an alternative synthesis of 3-aminopyrrolidinyl derivatives useful for coupling a polymer moiety thereto in any one of the schemes illustrated above.

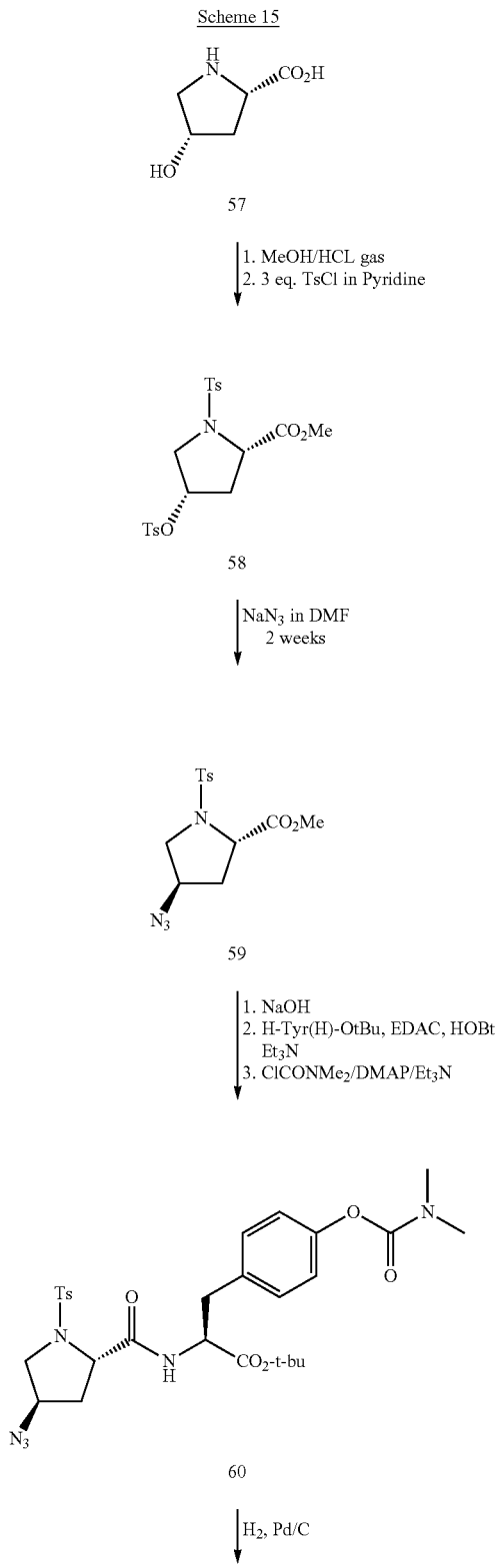

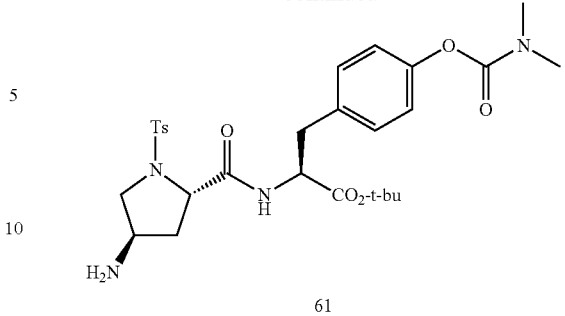

Using conventional methods, commercially available cis-4-hydroxy L-proline, 57, is treated with methanolic hydrogen chloride for several hours at reflux, followed by evaporation, and the so generated methyl ester hydrochloride is treated with excess tosyl chloride in pyridine for two days at room temperature, giving the product, 58. Compound 58 is isolated by neutralizing the pyridine using weak aqueous acid and extracting the product with an organic solvent such as EtOAc. The product 58 may be purified by crystallization, flash chromatography, or more preferably be used in subsequent steps without purification.

Reaction of 58 with a saturated solution of excess sodium azide in DMF at room temperature for 15 days affords compound 59. Compound 59 is isolated by dilution of the reaction mixture with water, followed by extraction with an organic solvent such as EtOAc. The product 59 may be purified by crystallization, flash chromatography, or more preferably be used in subsequent steps without purification.

Compound 59 is treated with sodium hydroxide, in a mixture of water and methanol, thus hydrolyzing the methyl ester and generating a carboxylic acid, which is isolated by acidification and extraction with an organic solvent such as EtOAc. The carboxylic acid is treated with L-tyrosine t-butyl ester [H-Tyr(H)-OtBu], EDAC, HOBt, and $Et_3N$ in DMF, generating a dipeptide, which is isolated by dilution with water and extraction with an organic solvent such as EtOAc. The dipeptide is treated with $ClCONMe_2$, $Et_3N$, and DMAP in DCM at reflux for 24 hours, generating the carbamate, 60, which is isolated by dilution with EtOAc, sequential washing with weak aqueous acid and base, and then evaporation. Compound 60 is rigorously purified by flash chromatography.

Finally, compound 61 is prepared by shaking of a solution of 60 in methanol, with a Pd/C catalyst under an atmosphere of hydrogen. The product, 61, is isolated by removal of the catalyst by filtration and evaporation.

Other methods for coupling of a compound of formula II with a polymer (optionally bound to a a branched-arm hub molecule) are well known in the art.

Other polymers suitable for conjugation to a compound of formula II include, without limitation, polyvinylpyrrolidone (PVP), polyacrylamide (PAAm), polydimethylacrylamide (PDAAm), polyvinyl alcohol (PVA), dextran, poly(L-glutamic acid) (PGA), styrene maleic anhydride (SMA), poly-N-(2-hydroxypropyl)methacrylamide (HPMA), poly-divinylether maleic anhydride (DIVEMA). By way of example, PVP, PAAm and PDAAm may be functionalized by introduction of co-monomers during radical polymerization. PVA and dextran each contain primary hydroxyl (OH) groups suitable for conjugation. Methods for synthesis of these biopolymers and for conjugating them to biological materials are well known in the art (see, for example, published U.S.

Patent Application 20040043030; U.S. Pat. No. 5,177,059; U.S. Pat. No. 6,716,821; U.S. Pat. No. 5,824,701; U.S. Pat. No. 6,664,331; U.S. Pat. No. 5,880,131; Kameda, Y. et al., Biomaterials 25: 3259-3266, 2004; Thanou, M. et al, Current Opinion in Investigational Drugs 4(6): 701-709, 2003; Veronese, F. M., et al., II Farmaco 54: 497-516, 1999, all of which are incorporated herein in their entireties).

Pharmaceutical Formulations

When employed as pharmaceuticals, the conjugates of this invention are usually administered in the form of pharmaceutical compositions. These conjugates can be administered by a variety of routes including oral, rectal, transdermal, subcutaneous, intravenous, intramuscular, sublingual, ophthalmic, or inhalation including administration by nasal or oral inhalation. Preferred administration routes include subcutaneous, intravenous, and inhalation. Such compositions are prepared in a manner well known in the pharmaceutical art and comprise at least one conjugate.

The invention also provides pharmaceutical compositions comprising a conjugate according to the invention, e.g., a conjugate of Formula I, in combination with a separate compound which is an $\alpha_4\beta_7$ inhibitor. Such compositions also comprise a pharmaceutically acceptable carrier or excipient and may be administered as discussed elsewhere herein.

This invention also includes pharmaceutical compositions which contain, as the active ingredient, one or more of the conjugate of formula I together with pharmaceutically acceptable carriers. In making the compositions of this invention, the active ingredient is usually mixed with an excipient, diluted by an excipient or enclosed within such a carrier which can be in, sterile injectable solutions, and sterile packaged powders. For subcutaneous administration, a simple carrier may comprise a sterile solution of water, Na2HPO4, NaH2PO4, and NaCl, in proportions that provide an isotonic and physiologically acceptable pH, known as PBS or phosphate-buffered saline. Another option is to administer the compounds in sterile isotonic saline adjusted to physiological pH if needed. Other options are known to those of skill in the art and include mixed solvent systems that can affect the rate of absorption and total exposure. These options include mixed solvent systems containing glycerin, Polyethylene glycol 400, and cottonseed oil. Also of potential use are ethanol, N,N'-dimethylacetamide, propylene glycol and benzyl alcohol all of which may be used to manipulate permeability enhancement and hypertonicity.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by subcutaneous or intravenous formulation is well known in the pharmaceutical industry. A subcutaneous or intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents:ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer: alendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer in the invention is sodium citrate/citric acid in the range of 5 to 50 mg per ml of sodium citrate to 1 to 15 mg per ml of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions may be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The conjugate is effective over a wide dosage range and is generally administered in a pharmaceutically effective amount. It, will be understood, however, that the amount of the conjugate actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner. For inhalation or insufflation administration, it is preferred that the total molecular weight of the conugate is between about 10,000 Daltons and 70,000 Daltons, more preferably between about 20,000 Daltons and 45,000 Daltons.

Polymer Conjugates

Compounds of this invention as formulated and administered are polymer conjugates. Polymer conjugates are anticipated to provide benefits over non-conjugated polymers, such as improved solubility and in vivo stability.

As such, single polymer molecule may be employed for conjugation with the compounds of the present invention, although it is also contemplated that more than one polymer molecule can be attached as well, typically through a carrier. The conjugated compounds of the present invention may find utility in both in vivo as well as non-in vivo applications. Additionally, it will be recognized that the conjugating polymer may utilize any other groups, moieties, or other conjugated species, as appropriate to the end use application. As an example, it may be advantageous in some applications to functionalize the polymer to render it reactive and enable it to conjugate to a compound of formula II and to enhance various properties or characteristics of the overall conjugated material. Accordingly, the polymer may contain any functionality, repeating groups, linkages, or other constituent structures which do not preclude the efficacy of the conjugated compounds of the present invention for its intended purpose.

Illustrative polymers that are usefully employed to achieve these desirable characteristics are described supra, as well as in PCT WO 01/54690 (to Zheng et al.,) incorporated by reference herein in its entirety. The polymer may be coupled to the compounds of the present invention (preferably via a linker moiety) to form stable bonds that are not significantly cleavable by human enzymes. Generally, for a bond to be not 'significantly' cleavable requires that no more than about 20% of the bonds connecting the polymer and the compounds of the present invention to which the polymer is linked, are cleaved within a 24 hour period, as measured by standard techniques in the art including, but not limited to, high pressure liquid chromatography (HPLC).

Generally, the compounds of this invention contain at least about 2 compounds of formula II bound to a polymer. The final amount is a balance between maximizing the extent of the reaction while minimizing non-specific modifications of the product and, at the same time, defining chemistries that will maintain optimum activity, while at the same time optimizing the half-life of the compounds of the present invention. Preferably, at least about 50% of the biological activity of the compounds of the present invention is retained, and most preferably 100% is retained.

As noted above in the preferred practice of the present invention, polyalkylene glycol residues of $C_2$-$C_4$ alkyl polyalkylene glycols, preferably polyethylene glycol (PEG), or poly(oxy)alkylene glycol residues of such glycols are advantageously incorporated in the polymer systems of interest. Thus, the polymer to which the compounds of the present invention are attached may be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained.

Examples of polyoxyethylated polyols include, but are not limited to, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

Those of ordinary skill in the art will recognize that the foregoing list is merely illustrative and that all polymer materials having the qualities described herein are contemplated. The polymer need not have any particular molecular weight, but it is preferred that the molecular weight be between about 100 and 100,000, preferably from about 10,000 to 80,000; more preferably from about 20,000 to about 70,000. In particular, sizes of 20,000 or more are most effective at preventing loss of the product due to filtration in the kidneys.

By PEG derivative is meant a polyethylene glycol polymer in which one or both of the terminal hydroxyl groups found in polyethylene glycol itself has been modified. Examples of suitable modifications include replacing one or both hydroxyl group(s) with alternative functional groups, which may be protected or unprotected, with low molecular weight ligands, or with another macromolecule or polymer. Modification of the terminal hydroxyl groups in the polyethylene glycol may be achieved by reacting the polyethylene glycol with compounds comprising complementary reactive functional groups, including functional groups which are able to undergo a reaction with the hydroxyl groups in polyethylene glycol. The PEG derivatives of the compounds of this invention may contain one or more polyethylene glycol (PEG) substituents covalently attached thereto by a linking group.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
|---|---|
| Active Ingredient | 50 mg · mL mg |
| Phosphate buffered saline | 1.0 ml |

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An intravenous formulation may be prepared as follows:

| Ingredient | Quantity |
|---|---|
| Active Ingredient | 250 mg |
| Isotonic saline | 100 ml |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Utility

The conjugates of this invention are alpha4 beta1(VLA-4) antagonists. Some also have at least a partial affinity for alpha4 beta7 integrins, making them mixed inhibitors of alpha4 integrin. The conjugates provide enhanced in vivo retention as compared to the non-conjugated compounds. The improved retention of the conjugate within the body results in lower required dosages of the drug, which in turn results in fewer side effects and reduced likelihood of toxicity. In addition, the drug formulation may be administered less frequently to the patient while achieving a similar or improved therapeutic effect.

The conjugates of this invention have improved inhibition, in vivo, of adhesion of leukocytes to endothelial cells mediated by inhibition of alpha4 beta1 or alpha4 beta7 binding to cellular receptors such as VCAM-1, fibronectin and MadCAM. Preferably, the conjugates of this invention can be used, e.g., by infusion, or by subcutaneous injection or oral administration, for the treatment of diseases mediated by alpha4 beta1 and/or alpha4 beta7 or, in general terms, leukocyte adhesion. The conjugates of the invention can be used to treat a variety of inflammatory brain disorders, especially central nervous system disorders in which the endothelium/leukocyte adhesion mechanism results in destruction to otherwise healthy brain tissue. Thus, the conjugates of the invention can be used for, e.g., the treatment of experimental autoimmune encephalomyelitis (EAE), multiple sclerosis (MS), meningitis, and encephalitis.

The conjugates of the invention can also be used to treat disorders and diseases due to tissue damage in other organ systems, i.e., where tissue damage also occurs via an adhesion mechanism resulting in migration or activation of leukocytes. Examples of such diseases in mammalian patients are inflammatory diseases such as asthma, Alzheimer's disease, atherosclerosis, AIDS dementia, diabetes (including acute juvenile onset diabetes), inflammatory bowel disease (including ulcerative colitis and Crohn's disease), rheumatoid arthritis, tissue transplantation rejection, tumor metastasis, stroke, and other cerebral traumas, nephritis, retinitis, atopic dermatitis, psoriasis, myocardial ischemia and acute leukocyte-mediated lung injury such as that which occurs in adult respiratory distress syndrome.

Still other disease conditions which may be treated using conjugates of the invention include erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

The invention also provides methods for treating a disease state caused or exacerbated at least in part by alpha 4 integrin-mediated lekocyte binding in a patient, which methods comprise co-administration of an effective amount of a conjugate of the invention, e.g., a conjugate of Formula I, and an effective amount of a separate compound which is an $\alpha_4\beta_7$ inhibitor. The co-administration can be carried out simultaneously or sequentially. For example, administration of the conjugate of the invention can precede administration of the $\alpha_4\beta_7$ inhibitor by minutes or hours. Alternatively, the $\alpha_4\beta_7$ inhibitor can be administered prior to the conjugate of the invention.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha 4$ integrins.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, Immunology (3d ed., Raven Press, 1993).

Another indication for the conjugates of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8+ cells, CD4 cells and monocytes are all involved in the rejection of transplant tissues. Conjugates of this invention which bind to alpha-4 integrin are useful, inter alia, to block alloantigen-induced immune responses in the donee thereby preventing such cells from participating in the destruction of the transplanted tissue or organ. See, e.g., Paul et al., Transplant International 9, 420-425 (1996); Georczynski et al., Immunology 87, 573-580 (1996); Georcyznski et al., Transplant. Immunol. 3, 55-61 (1995); Yang et al., Transplantation 60, 71-76 (1995); Anderson et al., APMIS 102, 23-27 (1994).

A related use for conjugates of this invention which bind to VLA-4 is in modulating the immune response involved in "graft versus host" disease (GVHD). See e.g., Schlegel et al., J. Immunol. 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

The formulations of the present invention are especially useful in the treatment of multiple sclerosis, rheumatoid arthritis and asthma.

A further use of the conjugates of this invention is inhibiting tumor metastasis. Several tumor cells have been reported to express VLA-4 and compounds which bind VLA-4 block adhesion of such cells to endothelial cells. Stein back et al., Urol. Res. 23, 175-83 (1995); Orosz et al., Int. J. Cancer 60, 867-71 (1995); Freedman et al., Leuk. Lymphoma 13, 47-52 (1994); Okahara et al., Cancer Res. 54, 3233-6 (1994).

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

A further use of the conjugates of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The therapeutic dosage of the conjugates of the present invention will vary according to, for example, the particular use for which the treatment is made, the manner of administration of the conjugate, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

Conjugates of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, conjugates of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187-2191. Compounds that bind $\alpha_e\beta_7$ integrin are also useful for the treatment of systemic lupus erythematosus (see, for example, M. Pang et al., *Arthritis Rheum.* 1998, 41(8), 1456-1463); Crohn's disease, ulcerative colitis and inflammatory bowel disease (IBD) (see, for example, D. Elewaut et al., *Scand J. Gastroenterol* 1998, 33(7) 743-748); Sjogren's syndrome (see, for example, U. Kroneld et al., *Scand J. Gastroenterol* 1998, 27(3), 215-218);

and rheumatoid arthritis (see, for example, *Scand J. Gastroenterol* 1996, 44(3), 293-298). And compounds that bind $\alpha_6\beta_1$ may be useful in preventing fertilization (see, for example, H. Chen et al., *Chem. Biol.* 1999, 6, 1-10).

In another aspect of the invention, the conjugates and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Inflammatory diseases that are included for treatment by the compositions, conjugates and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response. The conjugates, compositions and methods disclosed herein are not directed towards diseases and conditions wherein there is, for example, a genetic defect leading to improper myelin formation, e.g., dysmyelination.

The compositions, conjugates and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria, Tay-Sachs disease, Niemann-Pick disease, Gaucher's disease, Hurler's syndrome, Krabbe's disease and other leukodystrophies), neuropathies with abnormal myelination (e.g., Guillain Barré, chronic immune demyelinating polyneuropathy (CIDP), multifocal CIDP, anti-MAG syndrome, GALOP syndrome, anti-sulfatide antibody syndrome, anti-GM2 antibody syndrome, POEMS syndrome, perineuritis, IgM anti-GD1b antibody syndrome), drug related demyelination (e.g., caused by the administration of chloroquine, FK506, perhexyline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis or spinal cord injury) or diseases.

There are various disease models that can be used to study these diseases in vivo. For example, animal models include but are not limited to:

TABLE III

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

Multiple Sclerosis

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high—but not low—frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include: (1) treatment aimed at modification of the disease course, including treatment of acute exacerbation and directed to long-term suppression of the disease; (2) treatment of the symptoms of MS; (3) prevention and treatment of medical complications; and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Congenital Metabolic Disorders

Congenital metabolic disorders include phenylketonuria (PKU) and other aminoacidurias, Tay-Sachs disease, Niemann-Pick disease, Gaucher's disease, Hurler's syndrome, Krabbe's disease and other leukodystrophies that impact the developing sheath as described more fully below.

PKU is an inherited error of metabolism caused by a deficiency in the enzyme phenylalanine hydroxylase. Loss of this enzyme results in mental retardation, organ damage, unusual posture and can, in cases of maternal PKU, severely compromise pregnancy. A model for studying PKU has been discovered in mice. Preferably infants identified with PKU are sustained on a phenylalanine free or lowered diet. An aspect of the invention would be to combine such diets with the conjugates and compositions disclosed herein to prevent demyelination and remyelinate cells damaged due to PKU.

Classical Tay-Sachs disease appears in the subject at about age 6 months and will eventually result in the death of the subject by age 5 years. The disease is due to the lack of the enzyme, hexoaminidase A (hex A), which is necessary for degrading certain fatty substances in the brain and nerve cells. The substances in the absence of the enzyme accumulate and lead to the destruction of nerve cells. Another form of hex A enzyme deficiency occurs later in life and is referred to as juvenile, chronic and adult onset forms of hex A deficiency. Symptoms are similar to those that characterize classical Tay-Sachs disease. There is also an adult onset form of the enzyme deficiency. Currently there is no cure or treatment for the disease/deficiency, only the preventative measure of in utero testing of the fetus for the disease. Thus, the conjugates and compositions disclosed herein may be useful in ameliorating or preventing the destruction of nerve cells in such patients.

Niemann-Pick disease falls into three categories: the acute infantile form, Type B is a less common, chronic, non-neurological form, and Type C is a biochemically and genetically distinct form of the disease. In a normal individual, cellular cholesterol is imported into lysosomes for processing, after which it is released. Cells taken from subjects with Niemann-Pick have been shown to be defective in releasing cholesterol from lysosomes. This leads to an excessive build-up of cholesterol inside lysosomes, causing processing errors. NPC1 was found to have known sterol-sensing regions similar to those in other proteins, which suggests it plays a role in regulating cholesterol traffic. No successful therapies have been identified for Types A and C forms of Neumann-Pick. For Type C, patients are recommended to follow a low-cholesterol diet. Thus, the conjugates and compositions disclosed herein may be useful in ameliorating or preventing the destruction of the cells.

Gaucher's disease is an inherited illness caused by a gene mutation. Normally, this gene is responsible for an enzyme called glucocerebrosidase that the body needs to break down the fat, glucocerebroside. In patients with Gaucher's disease, the body is not able to properly produce this enzyme and the fat cannot be broken down. Like Tay-Sachs disease, Gaucher's disease is considerably more common in the descendants of Jewish people from Eastern Europe (Ashkenazi), although individuals from any ethnic group may be affected. Among the Ashkenazi Jewish population, Gaucher's disease is the most common genetic disorder, with an incidence of approximately 1 in 450 persons. In the general public, Gaucher's disease affects approximately 1 in 100,000 persons.

In 1991, enzyme replacement therapy became available as the first effective treatment for Gaucher's disease. The treatment consists of a modified form of the glucocerebrosidase enzyme given intravenously. It is contemplated that the compositions and conjugates disclosed herein can be used alone or more preferably in combination with glycocerebrosidase administration to treat the disease in an afflicted subject.

Hurler's syndrome, also known as mucopolysaccharidosis type I, is a class of overlapping diseases. These genetic diseases share in common the cellular accumulation of mucopolysaccharides in fibroblasts. The diseases are genetically distinguishable. Fibroblast and bone marrow transplantation does not seem to be helpful, thus conjugates and compositions useful in ameliorating disease severity and progression are needed. The conjugates and compositions disclosed herein may be administered to a subject to ameliorate disease progression and/or severity.

Krabbe's disease (also known as Globoid cell leukodystrophy) is an autosomal recessive condition resulting from galactosylceramidase (or galactocerebrosidase) deficiency, a lysosomal enzyme that catabolises a major lipid component of myelin. Incidence in France is an estimated 1:150,000 births. The disease leads to demyelination of the central and peripheral nervous system. Onset generally occurs during the first year of life and the condition is rapidly progressive, but juvenile, adolescent or adult onset forms have also been reported, with a more variable rate of progression. Diagnosis is established from enzyme assay (galactosylceramidase deficiency). There are several natural animal models (mouse, dog, monkey). Krabbe's disease, like all leukodystrophies, has no known cures or effective treatments. One embodiment of the instant invention is to use the compositions and conjugates disclosed herein to treat or ameliorate Krabbe's disease and other leukodystrophies:

Leukodystrophies are a group of genetically determined progressive disorders that affect the brain, spinal cord and peripheral nerves. They include adrenoleukodystrophy (ALD), adrenomyeloneuropathy (AMN), Aicardi-Goutiers syndrome, Alexander's disease, CACH (i.e., childhood ataxia with central nervous system hypomyelination or vanishing white matter disease), CADASIL (i.e., cerebral autosomal dominant arteriopathy with subcortical infarcts and leukoencephalopathy), Canavan disease (spongy degeneration), Cerebrotendinous Xanthomatosis (CTX), Krabbe's disease (discussed above), metachromatic leukodystrophy (MLD), neonatal adrenoleukodystrophy, ovarioleukodystrophy syndrome, Pelizaeus-Merzbacher disease (X-linked spastic paraplegia), Refsum disease, van der Knaap syndrome (vaculating leukodystrophy with subcortical cysts) and Zellweger syndrome. None of the diseases have effective treatments let alone cures. Consequently, means of treating or ameliorating the symptoms of the disease, such as by using the compositions and conjugates disclosed herein, is needed.

Neuropathies with Abnormal Myelination

A variety of chronic immune polyneuropathies exist which result in demyelination in the patient. The age of onset for the conditions varies by condition. Standard treatments for these diseases exist and could be combined with the compositions and conjugates disclosed herein. Alternatively, the compositions and conjugates disclosed can be used alone. Existing standard therapies include the following:

tain cancers. See for review Belka et al., 2001 *Br. J. Cancer* 85: 1233-9. However, radiation exposure may also be an issue for astronauts (Hopewell, 1994 *Adv. Space Res.* 14: 433-42) as well as in the event of exposure to radioactive substances.

Patients who have received drugs or been exposed accidentally or intentionally to radiation may experience a benefit by administered one of the conjugates or compositions disclosed herein to prevent demyelination or to promote remyelination.

Conditions Involving Demyelination

Additional inherited syndromes/diseases that result in demyelination include Cockayne's syndrome, congenital hypomyelinating, Farber's disease, metachromatic leukodystrophy, Peliszaeus-Merzbacher disease, Refsum, prion related conditions and Salla disease.

Cockayne's syndrome (CS) is a rare inherited disorder in which people are sensitive to sunlight, have short stature and have the appearance of premature aging. In the classical form of Cockayne's syndrome (Type I), the symptoms are progres-

TABLE IV

| Neuropathy | Clinical Features | Treatment |
| --- | --- | --- |
| Chronic Immune Demyelinating Polyneuropathy (CIDP) | Onset between 1-80 years. Characterized by weakness, sensory loss, and nerve hypertrophy. | T-cell immunosuppression with prednisone, cyclosporine A or methotrexate, HIG, plasma exchange |
| Multifocal CIDP | Onset between 28 to 58 years and characterized by asymmetric weakness, sensory loss with a course that is slowly progressive or relapsing-remitting. | T cell immunosuppression with prednisone Human immunoglobulin (HIG) |
| Multifocal Motor Neuropathy (MMN) | Onset ranges from 25 to 70 years, with twice as many men as women. Features include weakness, muscle atrophy, fasciculations, and cramps which are progressive over 1-30 years. | HIG B cell immunosuppression with plasma exchange cyclophosphamide, Rituxan |
| Neuropathy with IgM binding to Myelin- Associated Glycoprotein (MAG) | Onset is usually over age 50 and is characterized by sensory loss (100%), weakness, gain disorder, tremor which is all slowly progressive. | B-cell immunosuppression plasma exchange cyclophosphamide Rituxan α-interferon cladribine or fludarabine prednisone |
| GALOP Syndrome (Gait disorder, Autoantibody, Late-age, Onset, Polyneuropathy) | A gait disorder with polyneuropathy | HIG Plasma exchange cyclophosphamide |
| POEMS Syndrome (Polyneuropathy, Organomegaly, Endocrinopathy, M- Protein and Skin changes) also known as Crow-Fukase Syndrome and Takatsuki disease | Onset occurs between 27 and 80 years with weakness, sensory loss, reduced or absent tendon reflexes, skin disorders and other features. | Osteosclerotic lesions are treated with irradiation. Widespread lesions with chemotherapy (Melphalan and prednisone). |

Drug and Radiation Induced Demyelination

Certain drugs and radiation can induce demyelination in subjects. Drugs that are responsible for demyelination include but are not limited to chloroquine, FK506, perhexyline, procainamide, and zimeldine.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of cersive and typically become apparent after the age of one year. An early onset or congenital form of Cockayne's syndrome (Type II) is apparent at birth. Interestingly, unlike other DNA repair diseases, Cockayne's syndrome is not linked to cancer. CS is a multi-system disorder that causes both profound growth failure of the soma and brain and progressive cachexia, retinal, cochlear, and neurologic degeneration, with a leukodystrophy and demyelinating neuropathy without an increase in cancer. After exposure to UV (e.g., sunlight), subjects with Cockayne's syndrome can no longer perform transcription-coupled repair. Two genes defective in Cockayne's syndrome, CSA and CSB, have been identified so far. The CSA gene is found on chromosome 5. Both genes code for proteins that interacts with components of the transcriptional machinery and with DNA repair proteins.

To date, no cures or effective treatments for patients with this disease have been identified. Thus, one aspect of the invention is treatment of this disease with the conjugates and compositions disclosed herein.

Congenital hypomyelination has several names including congenital dysmyelinating neuropathy, congenital hypomyelinating polyneuropathy, congenital hypomyelination (Onion Bulb) polyneuropathy, congenital hypomyelination neuropathy, congenital neuropathy caused by hypomyelination, hypomyelination neuropathy and CHN. Hereditary peripheral neuropathies, among the most common genetic disorders in humans, are a complex, clinically and genetically heterogeneous group of disorders that produce progressive deterioration of the peripheral nerves. Congenital hypomyelination is one of a group of disorders. This group includes hereditary neuropathy with liability to pressure palsies, Charcot-Marie-Tooth disease, Dejerine-Sottas syndrome, and congenital hypomyelinating neuropathy. There are no known cures or effective treatments for any of these disorders.

Farber's disease has several names including: Farber lipogranulomatosis, ceremidase deficiency, acid ceramidase deficiency, AC deficiency, N-laurylsphingosine deacylase deficiency, and N-acylsphingosine amidohydrolase. As certain names reveal, the disease occurs due to a deficiency of acid ceramidase (also known as N-acylsphingosine amidohydrolase, ASAH). The lack of the enzyme results in an accumulation of non-sulfonated acid mucopolysaccharide in the neurons and glial cells. Patients with the disease usually die before the age of 2 years.

Metachromatic leukodystrophy (MLD) is a genetic disorder caused by a deficiency of the enzyme arylsulfatase A. It is one of a group of genetic disorders called the leukodystrophies that affect growth of the myelin sheath. There are three forms of MLD: late infantile, juvenile, and adult. In the late infantile form, which is the most common, onset of symptoms begins between ages 6 months and 2 years. The infant is usually normal at birth, but eventually loses previously gained abilities. Symptoms include hypotonia (low muscle tone), speech abnormalities, loss of mental abilities, blindness, rigidity (i.e., uncontrolled muscle tightness), convulsions, impaired swallowing, paralysis, and dementia. Symptoms of the juvenile form begin between ages 4 and 14, and include impaired school performance, mental deterioration, ataxia, seizures, and dementia. In the adult form, symptoms, which begin after age 16, may include impaired concentration, depression, psychiatric disturbances, ataxia, tremor, and dementia. Seizures may occur in the adult form, but are less common than in the other forms. In all three forms mental deterioration is usually the first sign.

Peliszaeus-Merzbacher disease (also known as perinatal sudanophilic leukodystrophy) is an X-linked genetic disorder that causes an abnormality of a proteolipid protein. The abnormality results in an infant's death typically before the age of one year. There are no known treatments or cures for the disease.

Refsum disease (also referred to as phytanic acid oxidase deficiency, heredopathia atactica polyneuritiformis or hereditary motor and sensory neuropathy IV, HMSN IV) is caused by mutations in the gene, which encodes phytanoyl-CoA hydroxylase (PAHX or PHYH). The major clinical features are retinitis pigmentosa, chronic polyneuropathy and cerebellar signs. Phytanic acid, an unusual branched chain fatty acid (3,7,11,15-tetramethyl-hexadecanoic acid) accumulates in the tissues and body fluids of patients with the disease and is unable to be metabolised due to the lack of PAHX. Plasmapheresis performed once or twice monthly effectively removes the acid from the body and permits liberalization of dietary restrictions limiting phytanic acid intake.

Prion related conditions include Gerstmann-Straussler disease (GSD), Creutzfeldt-Jakob disease (CJD), familial fatal insomnia and aberrant isoforms of the prion protein can act as infectious agents in these disorders as well as in kuru and scrapie (a disease found in sheep). The term prion derives from "protein infectious agent" (Prusiner, *Science* 216: 136-44, 1982). There is a proteolytic cleavage of the prion related protein (PRP) which results in an amyloidogenic peptide that polymerises into insoluble fibrils.

Salla disease and other types of sialurias are diseases involving problems with sialic acid storage. They are autosomal recessive neurodegenerative disorders that may present as a severe infantile form (i.e., ISSD) or as a slowly progressive adult form that is prevalent in Finland (i.e., Salla disease). The main symptoms are hypotonia, cerebellar ataxia and mental retardation. These conditions and diseases are also contemplated for palliative or ameliorating treatments.

Other conditions that result in demyelination include post-infectious encephalitis (also known as acute disseminated encephalomyelitis, ADEM), meningitis and injuries to the spinal cord. The compositions and conjugates disclosed herein are also contemplated for use in treating these other demyelinating conditions.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| ACN = | acetonitrile |
| bs = | broad singlet |
| d = | Doublet |
| dd = | doublet of doublets |
| $Et_3N$ = | triethylamine |
| g = | Grams |
| h and hr = | Hour |
| HPLC = | High performance (or pressure) liquid chromatography |
| kg = | kilogram |
| kDa = | kilodalton |
| L = | Liter |
| m = | multiplet |
| M = | Molar |
| mg = | milligram |
| min = | Minute |
| mL = | milliliter |
| mm = | millimeter |
| mM = | millimolar |
| mmol = | millimol |
| s = | Singlet |
| sat. = | saturated |
| t = | Triplet |
| TFA = | trifluoroacetic acid |
| TLC or tlc = | thin layer chromatography |
| Ts = | Tosyl |

| | |
|---|---|
| μL = | microliter |
| μg = | microgram |
| μm = | micron or micrometer |

ACN=acetonitrile
bs=broad singlet
d=Doublet
dd=doublet of doublets
Et₃N=triethylamine
g=Grams
h and hr=Hour
HPLC=High performance (or pressure) liquid chromatography
kg=kilogram
kDa=kilodalton
L=Liter
m=multiplet
M=Molar
mg=milligram
min=Minute
mL=milliliter
mm=millimeter
mM=millimolar
mmol=millimol
s=Singlet
sat.=saturated
t=Triplet
TFA=trifluoroacetic acid
TLC or tlc=thin layer chromatography
Ts=Tosyl
μL=microliter
μg=microgram
μm=micron or micrometer General Methods: Proton ($^1$H) and carbon ($^{13}$C) nuclear magnetic resonance spectra (NMR) were obtained using a Gemini 2000 or Bruker Avance 300 spectrometer. The presence of the polyethylene glycol (PEG) protons can be detected by a large, broad singlet at 3.6 ppm. The integration of this signal can vary depending on the size of the PEG moiety. Presence of the conjugated VLA-4 antagonist can also be detected in the $^1$H NMR spectra of conjugates. Thin layer chromatography was performed on pre-coated sheets of silica 60 F$_{254}$ (EMD 15341-1) or pre-coated MKC18F silica 60 Å (Whatman 4803-110). Mass spectrometry was performed on an Agilent mass spectrometer (LC/MSD VL) in positive ion single quad mode.

HPLC Methods for PEG Products and PEG Conjugates:
Preparative reverse phase HPLC was performed using a Varian Prep Star (Model SD-1) module with a Varian UV detector set at 210 nm. Method A: Samples of PEG products and PEG conjugates were purified using reverse phase HPLC on a Vydac C18, 300 Å pore size column (250 mm×21.2 mm), typically using a gradient of 35-50% ACN+0.1% TFA in 100 min at 20 mL/min. Method B: Samples of PEG products and conjugates were purified using reverse phase HPLC on a Vydac C18, 300 Å pore size column (250 mm×50 mm), typically using a gradient of 35-50% ACN+0.1% TFA in 100 min at 60 mL/min.

Method C: The purity of PEG products and conjugates was confirmed via reverse phase analytical HPLC using an Agilent Series 1100 Quaternary system equipped with a Waters Symmetry 300 Å pore size, 3.5μ C18 column (150 mm×4.6 mm), using a gradient of 40-50% ACN w/0.1% TFA at a flow rate of 1.5 mL/min. and coupled to an Agilent 1100 variable wavelength detector set at 210 nm and a Sedex 75 evaporative light scattering detector (40° C., gain=5)

PEG Reagents: PEG starting materials were acquired through NOF Corporation (Yebisu Garden Place Tower, 20-3 Ebisu 4-chome, Shibuya-ku, Tokyo 150-6019) or Nektar Therapeutics (150 Industrial Road, San Carlos, Calif. 94070) as follows: 30 kDa PEG diamine (NOF Cat. Sunbright DE-300PA); 5 kDa Boc-NH-PEG-NHS ester (Nektar Cat. 4M530H02); 20 kDa tetra-amine (NOF Cat. Sunbright PTE-200PA);

40 kDa 4-arm PEG alcohol (NOF Cat. Sunbright PTE-40000); 40 kDa 3-arm PEG alcohol (NOF Cat. Sunbright GL-400).

Example 1

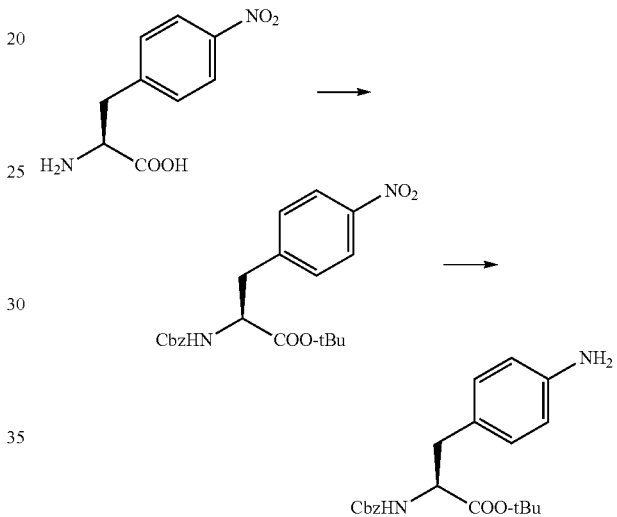

Sodium hydroxide (10 g, 0.25 m) is dissolved in water (300 ml). To this solution 4-nitrophenylalanine (50.3 g, 0.22 m) is added and stirred until complete dissolution. To the resulting solution the sodium carbonate (28.8 g, 0.26 m) is added and stirred suspension is cooled in an ice bath to +8° C. Benzyl chloroformate (44.7 g, 0.26 m) is added dropwise with vigorous stirring, maintaining internal temperature in +6° to +9° C. range. The mixture is stirred at +6° C. for additional 1 hr, transferred to the separatory funnel and washed with ether (2×150 ml). Aqueous phase is placed in a large Erlenmeyer flask (2 L) and is cautiously acidified with dil. aq. HCl to pH=2 and extracted with ethyl acetate (4×500 ml). The combined extracts are washed with water and dried with MgSO$_4$. The solution is filtered and filtrate evaporated, residue is dissolved in ethyl acetate (150 ml) and diluted with hexane (500 ml). Crystalline material is filtered off and rinsed with cold solvent, air dried to give Cbz-4-nitrophenylalanine, 75 g (99.5% yield). $^1$H-NMR, DMSO-d6, (δ): 12.85 (bs, 1H), 8.12 (d, 2H, J=9 Hz), 7.52 (d, 2H, J=9 Hz), 7.30 (m, 5H), 4.95 (s, 2H), 4.28 (m, 1H), 3.32 (bs, 1H), 3.10 (m, 2H). $^{13}$C-NMR (δ): 173.1, 156.3, 146.6, 137.3, 130.8, 128.5, 128.0, 127.8, 123.5, 65.6, 55.1, 36.6. MS (m/z): 367.1 [M+23].

The Cbz-4-nitrophenylalanine (75 g, 0.22 m) is dissolved in dioxane (300 ml). The resulted stirred solution is cooled in Dry Ice bath to −20° C. (internal). The liquefied isobutylene (approx. 290 ml) is added followed by conc. sulfuric acid (35 ml) added in three equal portions, 30 min apart. The addition of acid is a very exothermic process, accompanied by substantial degree of polymerization. Efficient mechanical stirring is essential at this stage. Resulted mixture is stirred for 20 hr, allowing to warm up to ambient temperature then is cautiously poured into sat. aq. sodium carbonate solution (2 L) and diluted with ethyl acetate (600 ml). Organic layer is separated and aqueous layer is extracted with ethyl acetate (2×200 ml). Combined extracts are washed with water and dried with sodium sulfate. The solution is filtered and evaporated to dryness. The residue is taken up in ethyl acetate/hexane mixture (500 ml; 1:1) and filtered through plug of silica gel (ca. 2×2 in). The silica is rinsed with an additional amount of the same solvent (2 L total) and the filtrates are evaporated to give fully protected 4-nitrophenylalanine as a viscous oil, 73 g (83% after two steps). $^1$H-NMR, CDCl$_3$, (δ): 8.12 (d, 2H, J=8.4 Hz), 7.36 (m, 7H), 5.35 (m, 1H), 5.10 (m, 2H), 4.57 (m, 1H), 3.31 (m, 2H), 1.43 (s, 9H). $^{13}$C-NMR, CDCl$_3$, (δ): 169.7, 155.3, 146.9, 143.9, 136.0, 130.2, 128.4, 128.2, 128.0, 123.3, 82.9, 66.9, 54.7, 38.2, 31.4, 27.8, 13.9. MS (m/z): 423.1 [M+23].

Protected 4-nitrophenylalanine (73 g, 0.18 m) is dissolved in ethanol (500 ml) and platinum oxide catalyst (1.5 g) is added. The resulting solution is vigorously stirred in hydrogen atmosphere (50-60 psi) at ambient temperature until further hydrogen adsorption ceased (3 hr). The catalyst is filtered off and the filtrate is evaporated to dryness, the residue is taken up in ethyl acetate (200 ml) and filtered through plug of silica gel (2×2 in) using ethyl acetate-hexane mixture (3:2, 2 L) to rinse silica. The filtrate is concentrated to approx. 200 ml and hexane (500 ml) is added. The crystalline product is filtered off, rinsed with cold solvent and air-dried. Yield—56 g, 84%. $^1$H-NMR, CDCl$_3$, (δ): 7.30 (bs, 5H), 6.92 (d, 2H, J=8.1 Hz), 6.58 (d, 2H, J=8.1 Hz), 5.21 (m, 1H), 5.10 (d, 2H, J=2.1 Hz), 4.46 (m, 1H), 3.59 (bs, 2H), 2.97 (s, 2H, J=5.4 Hz), 1.42 (s, 9H). $^{13}$C-NMR, CDCl$_3$, (δ): 170.6, 145.1, 136.3, 130.2, 128.3, 127.9, 125.6, 115.0, 81.9, 66.6, 55.2, 37.4, 27.8 MS (m/z): 393.1 [M+23].

Example 2

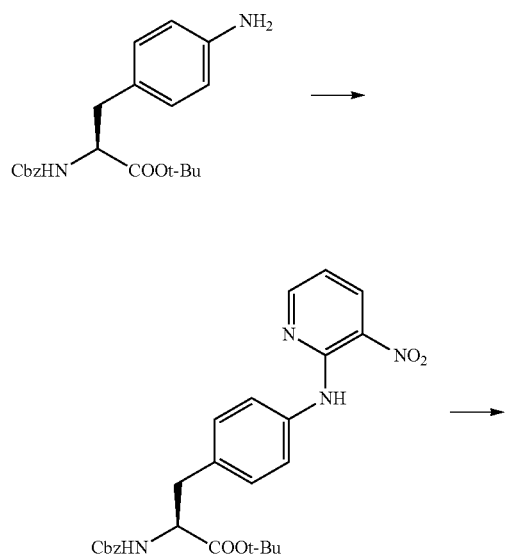

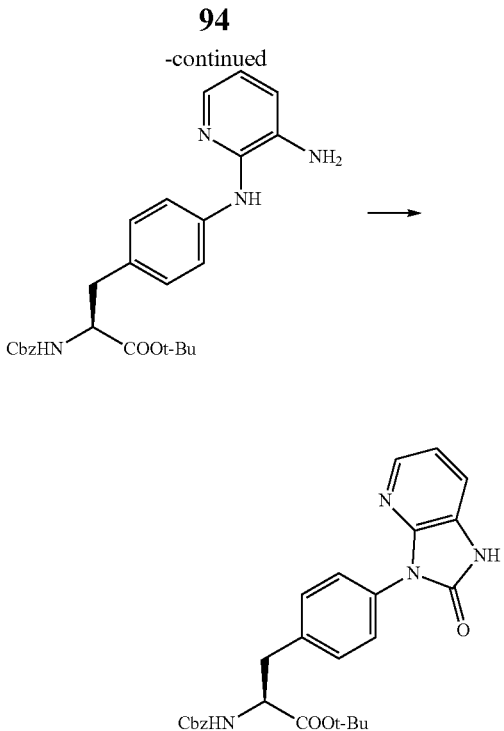

The product of Example 1, 4-aminophenylalanine, (20 g, 0.054 m) was dissolved in ethanol (200 ml) and treated with Hunig's base (21 g, 0.162 m, 3 eq) and 2-chloro-3-nitropyridine (10.3 g, 0.65 m, 1.2 eq). Resulted solution was stirred under nitrogen atmosphere and heated to reflux for 24 hr. LC analysis indicated presence of small amount of unreacted amine. The small additional amount of chloronitropyridine (1.1 g, 0.13 eq) was added and reflux continued for another 24 hr. Reaction mixture was cooled and evaporated to dryness. Residue was dissolved in ethyl acetate (600 ml) and obtained solution was washed with water (1×200 ml), dil. aq. citric acid (0.2 N, 2×200 ml), brine (1×200 ml) and dried with sodium sulfate. Solids were filtered off and filtrate evaporated to give 37 g of deep-red oil, containing expected product contaminated with excess of chloronitropyridine. Impure product was purified by flash chromatography (Biotage 75L system) eluting with ethyl acetate:hexane (3:17) mixture. Fractions containing pure product were combined and evaporated to give deep-red, viscous oil, 26 g (99%). $^1$H-NMR, CDCl$_3$, (δ): 10.10 (s, 1H), 8.49 (m, 2H), 7.57 (d, 2H, J=9 Hz), 7.35 (bs, 5H), 7.19 (d, 2H, J=9 Hz), 6.84 (m, 1H), 5.30 (m, 1H), 5.13 (d, 2H, J=3 Hz), 4.57 (m, 1H), 3.11 (m, 2H), 1.45 (s, 9H). $^{13}$C-NMR, CDCl$_3$, (δ): 170.4, 155.5, 155.1, 150.0, 136.7, 136.3, 135.4, 132.4, 129.9, 128.5, 128.3, 128.0, 127.9, 122.2, 113.7, 82.2, 66.7, 55.1, 37.7, 27.8, 20.9. MS (m/z): 493.1 [M+1], 515.1 [M+23].

The red nitro compound (26 g, 0.054 m) was dissolved in THF (350 ml) and platinum oxide catalyst (1.35 g) was added. Resulted mixture was vigorously stirred under hydrogen atmosphere (50-60 psi) until hydrogen adsorption ceased (2 hr). Catalyst was filtered off and filtrate evaporated to dryness. Residue was dissolved in ethyl acetate (100 ml) and diluted with hexane (50 ml) till beginning of crystallization. Mixture was further diluted with ethyl acetate/hexane (1:1) mixture (300 ml) and was left standing in refrigerator for 3 hr. Crystalline solids were filtered off, rinsed with cold solvent and air-dried to give product, 23 g, 94%. $^1$H-NMR, CDCl$_3$, (δ): 7.81 (dd, 1H, J1=1.5 Hz, J2=4.8 Hz), 7.33 (bs, 5H), 7.17 (d, 2H, J=8.4 Hz), 7.03 (d, 2H, J=8.4 Hz), 6.96 (dd, 1H, J1=1.5 Hz, J2=7.5 Hz), 6.75 (dd, 1H, J1=5.0 Hz, J2=7.7 Hz), 6.22 (s, 1H), 5.31 (m, 1H), 5.09 (bs, 2H), 4.50 (m, 1H), 3.41 (bs, 2H), 3.02 (m, 2H), 1.43 (s, 9H). $^{13}$C-NMR, CDCl$_3$, (δ): 170.6, 155.6, 145.5, 140.21, 138.8, 136.3, 130.8, 129.9, 128.5, 128.3, 127.9, 123.4, 118.2, 117.0, 82.0, 66.6, 55.2, 37.4, 27.9. MS (m/z): 407.1 [M−56], 463.1 [M+1], 485.1 [M+23].

The aminopyridine (19 g, 0.041 m) was suspended in dichloromethane (200 ml) and CDI (12 g, 0.074 m, 1.8 eq) was added. Resulted mixture was stirred at ambient temperature for 20 hr. Reaction mixture was washed with sat. aq. bicarbonate (2×100 ml), brine (1×100 ml) and dried with sodium sulfate. Solids were filtered off and filtrate evaporated to dryness. Residue was dissolved in ethyl acetate (hot, 300 ml) and set to crystallize. Crystalline product was filtered off, rinsed with cold ethyl acetate and air-dried to give 19.9 g, 81% of the imidazolone. $^1$H-NMR, CDCl$_3$, (δ): 10.63 (s, 1H), 8.06 (d, 1H, J=3 Hz), 7.66 (d, 2H, J=9 Hz), 7.32 (m, 8H), 7.05 (m, 1H), 5.36 (m, 1H), 5.13 (s, 2H), 4.59 (m, 1H), 3.17 (m, 2H), 1.45 (s, 9H). $^{13}$C-NMR, CDCl$_3$, (δ): 170.4, 155.6, 154.3, 143.8, 141.0, 136.2, 135.8, 131.8, 130.2, 128.3, 128.0, 125.9, 122.2, 118.3, 116.0, 82.4, 66.8, 55.0, 37.7, 27.8. MS (m/z): 433.1 [M−56], 489.2 [M+1], 511.2 [M+23].

Example 3

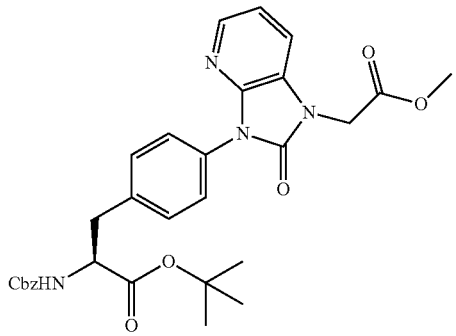

To a solution of the product of Example 2 (4.0 g, 8.19 mmol) in DMF (40 ml) crushed potassium carbonate (1.58 g, 11.47 mmol) was added followed by the addition of methyl bromoacetate (1.0 ml, 11.47 mmol). The reaction mixture was stirred under nitrogen at room temperature over night. The reaction mixture was concentrated in vacuo and the residue was taken up in ethyl acetate (100 ml). The organic phase was washed with H$_2$O, brine, dried over Na$_2$SO$_4$, filtered, and concentrated in vacuo. The crude material was purified by column chromatography (100% ethyl acetate) to yield 4.5 g (100%) of the title compound as a white foam. R$_f$=0.42 (5% MeOH/CH$_2$Cl$_2$). MS m/z=561, (M+H)$^+$. $^1$H NMR (CDCl$_3$) δ 8.10-8.08 (d, 1H), δ 7.67-7.65 (d, 2H), δ 7.37-7.30 (m, 7H), δ 7.20-7.17 (m, 1H), δ 7.10-7.05 (m, 1H), δ 5.30-5.27 (d, 1H), δ 5.11 (s, 2H), δ 4.58-4.55 (q, 1H), δ 3.81 (s, 3H), δ 3.16-3.14 (d, 2H), δ 1.42 (s, 9H).

Example 4

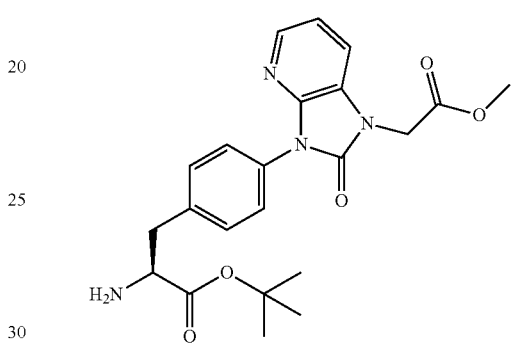

A solution of the product of Example 3 (2.25 g, 4.01 mmol) in MeOH (20 ml) with Degussa Pd/C catalyst (113 mgs) was placed under H$_2$ (55 psi) over night. The reaction mixture was filtered through Celite and concentrated in vacuo to yield 1.65 g (97%) of the title compound as a brown oil. R$_f$=0.32 (5% MeOH/CH$_2$Cl$_2$). MS m/z=449, (M+Na)$^+$. $^1$H NMR (CDCl$_3$) δ 8.11-8.09 (d, 1H), δ 7.68-7.65 (d, 2H), 67.41-7.38 (d, 2H), δ 7.20-7.17 (m, 1H), δ 7.10-7.06 (m, 1H), δ 4.73 (s, 2H), δ 3.81 (s, 3H), δ 3.67-3.62 (m, 1H), δ 3.16-3.09 (m, 1H), δ 2.91-2.84 (m, 1H), δ 1.46 (s, 9H).

Example 5

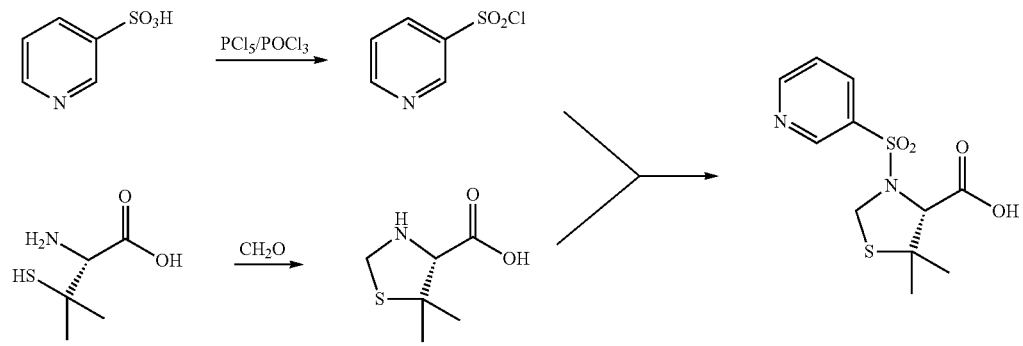

Pyridine-3-sulfonic acid (125 g, 0.78 m) was placed in a 1 L, 3-necked flask equipped with mechanical stirrer, reflux condenser, thermometer and nitrogen inlet. Next, the phosphorus pentachloride (250 g, 1.19 m, 1.5 eq) was added, followed immediately by the phosphorus oxychloride (330 ml, 3.8 m, 4.5 eq). The contents of flask were initially stirred at ambient temperature for 30 min, then brought slowly to gentle reflux (internal temp. approx. 110° C.) over the next hour, kept at this temperature for approx. 3.5 hr then allowed over the next 12 hr to cool back to ambient temperature. Gas evolution was observed during this time. The volatiles were stripped under reduced pressure (at 12 mmHg/40° C.) and yellow semi-solid residue was diluted with DCM (1 L). The slurry was poured slowly into the stirred, ice-cold sat. aq. bicarbonate, maintaining pH=7. Gas evolution was observed. The organic layer was separated and aqueous layer was back-extracted with DCM. The combined extracts were washed with cold sat. aq. bicarbonate, brine and dried with magnesium sulfate. The solids were filtered off and filtrate evaporated, leaving pyridine-3-sulfonyl chloride as a pale yellow, oily liquid, 123 g (93% pure; 88% theory). $^1$H-NMR, CDCl$_3$, (δ): 9.26 (d, 1H), 8.98 (dd, 1H), 8.34 (m, 1H), 7.62 (m, 1H). $^{13}$C-NMR, CDCl$_3$, (δ): 155.3, 147.4, 140.9, 134.6, 124.2. MS (m/z): 178.0 [M+1].

L-penicillamine (150 g, 1.0 m) was dissolved with stirring in DI water (1500 ml), cooled in ice-bath to +8° C. and treated with formalin (150 ml, 37% aq.). The reaction mixture was stirred at +8° C. for 2 hr, then cooling bath was removed and stirring continued for 12 hr. The clear solution was concentrated under reduced pressure (14 mmHg/50°) leaving white residue. The solids were re-suspended, then dissolved in hot MeOH (2500 ml) and left standing at ambient temperature for 12 hr. The white, fluffy precipitate was filtered off and rinsed with cold methanol. The filtrate was concentrated and set to crystallize again. The collected precipitate was combined with the first crop and dried in vacuum oven for 24 hr at 55° C. at 45 mmHg. The yield of (R)-5,5-dimethylthiazolidine-4-carboxylic acid was 138 g (>99% pure; 86% theory). $^1$H-NMR, DMSO-d6, (δ): 4.25 (d, 1H), 4.05 (d, 1H), 3.33 (s, 1H), 1.57 (s, 3H), 1.19 (s, 3H). $^{13}$C-NMR, DMSO-d6, (δ): 170.8, 74.4, 57.6, 51.8, 28.9, 27.9. MS (m/z): 162.3 [M+1].

In a 4 L reactor equipped with mechanical stirrer and thermometer, a buffer solution was prepared from potassium monobasic phosphate (43 g, 0.31 m) and potassium dibasic phosphate (188.7 g, 1.08 m) in DI water (2 L). The (R)-5,5-dimethylthiazolidine-4-carboxylic acid (107 g, 0.675 m) was added and stirred until complete dissolution. The solution was cooled in an ice-bath to +8° C. A separately prepared solution of pyridine-3-sulfonyl chloride (124 g, 0.695 m) in DCM (125 ml) was added dropwise to the reactor with vigorous stirring over the 1 hr. The pH of reaction mixture was monitored and after 4 hr, found to be pH=5 and adjusted to pH=6 by addition of solid bicarbonate. The mixture was allowed to warm up to ambient temperature over 18 hr. The pH was adjusted to 2 with dil. aq. sulfuric acid, stirred for 1 hr and precipitated yellow solids were filtered off, rinsed with water to neutral. The solid cake was transferred into 2 L Erlenmayer flask, suspended in DCM (500 ml) with occasional swirling for 5 min and filtered off again. The filter cake was washed with DCM and air-dried. The yield of the title compound, (R)-5,5-dimethyl-3-(pyridin-3-ylsulfonyl)thiazolidine-4-carboxylic acid was 148.9 g (98% pure; 73% theory). $^1$H-NMR, DMSO-d6, (δ): 9.05 (d, 1H), 8.89 (m, 1H), 8.32 (m, 1H), 7.69 (m, 1H), 4.68 (q, 2H), 4.14 (s, 1H), 1.35 (s, 3H), 1.29 (s, 3H). $^{13}$C-NMR, DMSO-d6, (δ): 170.0, 154.3, 147.9, 135.8, 134.1, 124.8, 72.6, 54.3, 50.2, 29.4, 25.0. MS (m/z): 303.2 [M+1].

Example 6

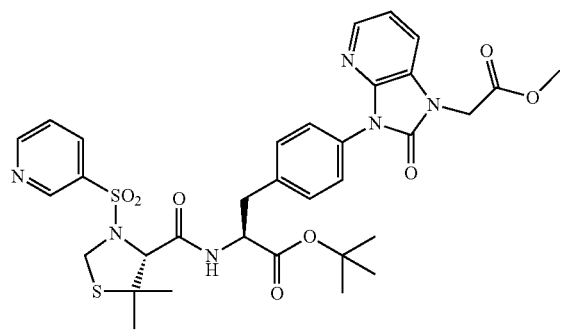

To a solution of the product of Example 4 (1.65 g, 3.88 mmol) in acetonitrile (35 ml) was added the product of Example 5 (1.06 g, 3.53 mmol), HATU (1.75 g, 3.88 mmol), and triethylamine (5.3 ml). The homogeneous brown solution was stirred under nitrogen for 72 hours. The organic reaction mixture was concentrated in vacuo, taken up in ethyl acetate (40 ml), washed with 1N HCl, sat. NaHCO$_3$, and brine. The organic layer was dried over Na$_2$SO$_4$, filtered, and concentrated in vacuo to yield 2.67 g (97%) 3 as an orange foam. R$_f$=0.36 (5% MeOH/CH$_2$Cl$_2$). MS m/z=711, (M+H)$^+$. $^1$H NMR (CDCl$_3$) δ 9.09-9.08 (d, 1H), δ 8.86-8.84 (m, 1H), δ 8.18-8.15 (m, 1H), δ 8.07-8.05 (m, 1H), δ 7.66-7.63 (d, 2H), δ 7.52-7.48 (m, 1H), δ 7.41-7.38 (d, 2H), δ 7.19-7.16 (m, 1H), δ 7.08-7.04 (m, 1H), δ 6.93-6.90 (d, 1H), δ 4.83-4.76 (q, 1H), δ 4.71 (s, 2H), δ 4.62-4.59 (d, 1H), δ 4.49-4.46 (d, 1H), δ 3.91 (s, 1H), δ 3.80 (s, 3H), δ 3.22-3.08 (m, 2H), δ 1.46 (s, 9H), δ 1.20-1.17 (d, 6H).

Example 7

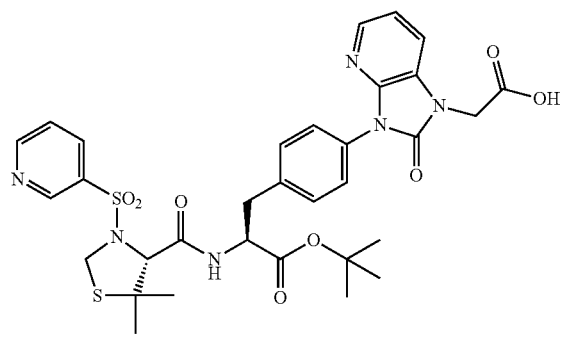

To a solution of the product of Example 6 (2.67 g, 3.75 mmol) in THF (12 ml) was added a solution of LiOH.H$_2$O (245 mgs, 5.97 mmol) in H$_2$O (3 ml). The reaction mixture was stirred at room temperature over night under nitrogen. Upon completion the reaction mixture was concentrated in vacuo, dissolved in H$_2$O (100 ml), and acidified to pH 4 with a 1M HCl solution. The desired product precipitated out as a white solid and was filtered and rinsed with H$_2$O to yield 1.87 g (72%) of the title compound. MS m/z=697, (M+H)$^+$. $^1$H NMR (CD$_3$OD) δ 9.02 (s, 1H), δ 9.80 (s, 1H), δ 8.47-8.44 (d, 1H), δ 8.21-8.19 (d, 1H), δ 7.98-7.96 (d, 1H), δ 7.63-7.59 (m, 3H), δ 7.52-7.48 (m, 3H), δ 7.17-7.13 (m, 1H), δ 4.75 (s, 2H), δ 4.72-4.61 (m, 3H), δ 4.14 (s, 1H), δ 3.22-3.16 (m, 2H), δ 1.45 (s, 9H), δ 1.25-1.19 (d, 6H). $^{13}$C NMR (CD$_3$OD) δ 169.9, 169.5, 168.9, 153.1, 152.8, 147.5, 142.8, 140.2, 136.6, 135.8, 134.0, 131.7, 129.9, 126.0, 124.2, 123.9, 117.8, 114.9, 81.8, 72.6, 54.1, 49.9, 41.3, 36.4, 28.5, 26.6, 23.4.

Example 8

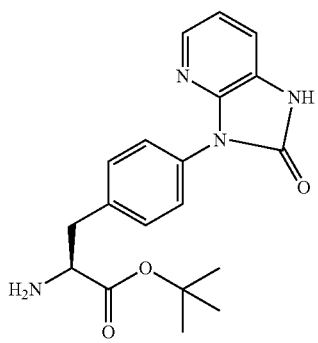

The product of Example 2 (52 g, 0.106 m) was slurried in MeOH (450 ml), hydrogenation catalyst (8.7 g, 5% Pd/C, Degussa) was added and the mixture was stirred under the hydrogen atmosphere (60 psi) until further absorption ceased (ca. 2 hrs). THF (150 ml) was added to dissolve precipitated solids and the solution was filtered through plug of Celite, using DCM to rinse the filter. The filtrate was evaporated to dryness, re-dissolved in DCM (300 ml) and stripped again. This operation was repeated twice. The foamy solids were kept under high vacuum for 3 hrs. The yield of title compound was 38.3 g (101% of theory). $^1$H-NMR, CDCl$_3$, (δ): 8.08 (m, 1H), 7.56 (AB q, 4H), 7.37 (m, 1H), 7.06 (m, 1H), 3.68 (m, 1H), 2.03 (m, 2H), 1.49 (s, 9H). $^{13}$C-NMR, CDCl$_3$, (δ): 173.8, 154.6, 143.9, 141.0, 137.4, 131.5, 130.2, 126.1, 122.3, 118.0, 116.1, 81.4, 56.0, 40.6, 27.9. MS (m/z): 299.3 [M−56], 355.4 [M+1], 377.4 [M+23].

Example 9

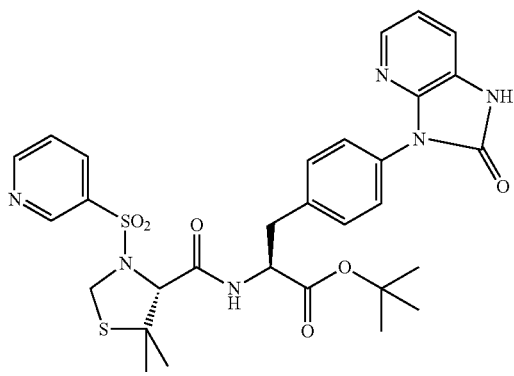

The product of Example 8 (38.3 g, assume 0.106 m) was dissolved in DCM (500 ml) and treated successively with: N-methylmorpholine (27 g, 30 ml, 0.266 m; 2.5 eq), HOBt (17.3 g, 0.128 m, 1.2 eq), and the product of Example 5 (33.8 g, 0.112 m; 1.06 eq). The resulting non-homogenous solution was cooled in an ice-bath to +4° C. and treated with EDC (22.5 g, 0.117 m; 1.1 eq) in one portion. The reaction mixture was stirred, allowing it to warm up to ambient temperature over the next 4 hr and then for 18 hr more. The solvent was stripped and residue dissolved in ethyl acetate (1.2 L), washed with sat. aq. bicarbonate (2×250 ml), water (250 ml), brine (300 ml) and dried with magnesium sulfate. The solution was filtered and evaporated to dryness, leaving a light orange, viscous oil, 76 g (>>100%). The crude product was purified by flash chromatography on silica gel (Biotage 75L, in ethyl-acetate/methanol (3%) mixture. Fractions, containing pure product, were combined and evaporated to give 54 g of the title compound (yield 83%). $^1$H-NMR, CDCl$_3$, (δ): 10.37 (s, 1H), 9.11 (s, 1H), 8.87 (m, 1H), 8.19 (m, 1H), 8.05 (m, 1H), 7.56 (AB q, 4H), 7.52 (m, 1H), 7.36 (m, 1H), 7.06 (m, 2H), 4.83 (m, 1H), 4.58 (AB a, 2H), 3.96 (s, 1H), 3.19 (m, 2H), 1.49 (s, 9H), 1.22 (s, 3H), 1.18 (s, 3H). $^{13}$C-NMR, CDCl$_3$, (δ): 169.7, 167.6, 153.9, 148.4, 143.8, 140.9, 135.8, 135.6, 132.9, 131.9, 130.2, 125.9, 123.8, 122.1, 118.0, 115.9, 82.8, 73.6, 60.3, 54.8, 53.7, 50.6, 37.8, 29.1, 27.8, 23.9, 14.1. MS (m/z): 583.3[M−56], 639.4 [M+1], 661.3 [M+23].

Example 10

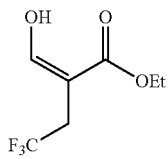

To an ice chilled solution of ethyl trifluorobutyrate (15 g, 89 mmol) and ethyl formate (36 mL, 444 mmol) in THF (200 mL) under N$_2$ was added a solution of 1 M KOtBu in THF (107 mmol, 107 mL) over a 25-minute period. After 15 minutes the ice bath was removed and the reaction mixture was stirred one hour at room temperature. Additional ethyl formate (18 mL, 222 mmol) was then added and the reaction mixture was stirred overnight. The reaction mixture was concentrated and the residue partitioned between cold ether (100 mL) and cold water (300 mL). The pH of the aqueous phase was adjusted to 2 with concentrated HCl. The product was extracted with dichloromethane (1×100 mL, 45×75 mL) and the combined organic extracts were washed with brine (1×100 mL), dried (MgSO$_4$), filtered, and concentrated to yield the title compound as thick oil which solidified upon standing, 10.2 g (58.5%). MS (m/z)=198 (M+H)$^+$.

Example 11

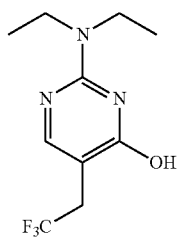

To a solution of the product of Example 10 (10 g, 51 mmol) and diethylguanidine sulfate (8.3 g, 25.2 mmol) in EtOH (60 mL) under N$_2$, was added NaOEt, 21% solution in EtOH (20.7 mL, 55.5 mmol) over a 10-minute period. The reaction mixture was then heated at reflux for 5 hours. The heterogeneous solution was cooled and poured into cold water (100 mL) to give a homogenous solution. The pH of the solution was adjusted to approximately 3.5 with conc. HCl and 1 N HCl. A solid precipitated from solution, which was collected by filtration. The light tan solid was washed with water and air-dried, yielding 2.9 g, (23%) of the title compound. MS (m/z)=250 (M+H)$^+$. $^1$H NMR (300 MHz, CD$_3$OD) δ 7.65 (br s, 1H), 3.55 (q, 4H), 3.30 (q, 2H), 1.25 (t, 6H).

Example 12

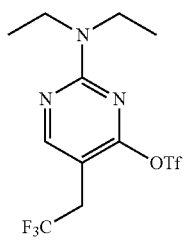

A flask was charged with the product of Example 11 (2.0 g, 8.02 mmol), DIEA (1.5 mL, 8.83 mmol), DMAP (0.98 g, 0.8 mmol), and dichloromethane (30 mL). The mixture was cooled to 0° C. and trifluoroacetic anhydride (1.5 mL, 8.83 mmol) was added. The reaction became homogeneous and was stirred at 0° C. for 3 hours. The mixture was quenched with sat. NaHCO$_3$ and extracted with dichlorormethane. The organic phase was washed with 0.2 N citric acid, dried over Na$_2$SO$_4$, filtered, and concentrated in vacuo to yield 2.87 g (94%) of the title compound as a brown solid. $^1$H NMR (300 MHz, CDCl$_3$) δ 8.28 (s, 1H), 3.65-3.52 (m, 4H), 3.29-3.19 (q, 2H), 1.22-1.17 (t, 6H).

Example 13

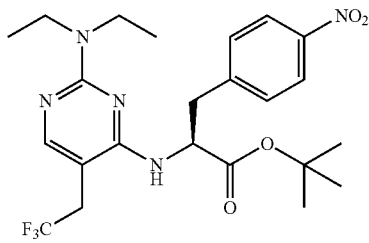

A solution of the product of Example 12 (1.3 g, 3.5 mmol), H-Phe(p-NO$_2$)OtBu (1.1 g, 4.2 mmol), and DIEA (0.9 mL, 5.3 mmol) in CH$_3$CN (14 mL) under N$_2$ was heated to reflux overnight. The next day additional H-Phe(p-NO$_2$)OtBu (0.8 g, 3 mmol) was added and reflux was continued for 3 days. The reaction mixture was then cooled and concentrated The residue taken-up in EtOAc (50 mL) and the organic portion washed with 0.5 N KHSO$_4$ (3×50 mL), water (1×50 mL), brine (1×10 mL), dried (MgSO$_4$), filtered and concentrated to a brownish gum. The crude material was purified by flash chromatography (5:1 hexanes/EtOAc) to yield 640 mg (38%) of the title compound as a golden gum. TLC: 3:1 hexanes/EtOAc, R$_f$=0.30, MS (m/z)=498 (M+H)$^+$, $^1$H NMR, (300 MHz, CDCl$_3$) δ 8.19 (d, 2H), 7.80 (s, 1H), 7.25 (d, 2H), 5.19 (br d, 1H), 4.95 (q, 1H), 3.70-3.50 (m, 4H), 3.45-3.25 (m, 2H), 3.10 (q, 2H), 1.40 (s, 9H), 1.05 (t, 6H).

Example 14

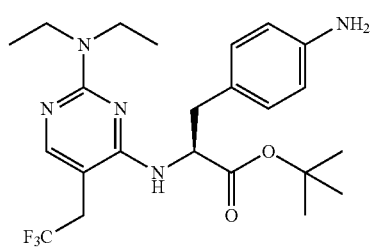

The product of Example 13 (635 mg, 1.27 mmol) was dissolved in absolute EtOH (5 mL) to which was added 35 mg of Pd/C, 10 wt %. The reaction was subjected to hydrogenation (45 psi H$_2$) for 2.5 hours at which time 50 mgs of Pd/C, 10 wt % was added and the reaction mixture again subjected to hydrogenation (45 psi H$_2$) overnight. The reaction mixture was filtered through a pad of Celite and the filtrate was concentrated to give 452 mg (76%) of the title compound. MS (m/z)=468 (M+H)$^+$, $^1$H NMR (300 MHz, CDCl$_3$) δ 7.75 (s, 1H), 6.90 (d, 2H), 6.60 (d, 2H), 5.05 (br d, 1H), 4.80 (q, 1H), 3.70-3.45 (m, 6H), 3.10-2.90 (m, 4H), 1.40 (s, 9H), 1.15 (t, 6H).

Example 15

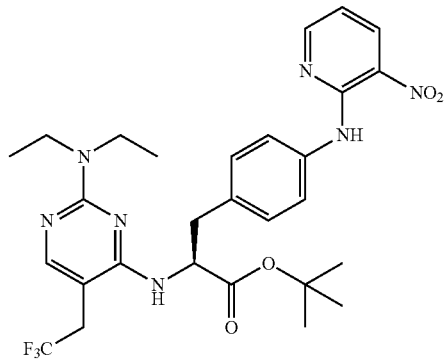

A solution of the product of Example 14 (598 mg, 1.28 mmol), 2-chloro-3-nitropyridine (243 mg, 1.53 mmol), and DIEA (0.67 mL, 3.83 mmol) in EtOH (5 mL) under N$_2$ was heated at reflux. The next day the reaction was cooled and additional 2-chloro-3-nitropyridine (40 mg, 0.25 mmol) and DIEA (0.11 mL, 0.60 mmol) was added and the reaction was heated at reflux for one day. The reaction mixture was then concentrated and the residue taken-up in EtOAc (20 mL). The organic phase was washed with water (2×20 mL). The combined aqueous washes was back extracted with EtOAc (2×10 mL). The combined organic extracts were washed with 0.2 N citric acid (3×20 mL), water (1×10 mL), sat. NaHCO$_3$ (3×20 mL), brine (1×10 mL), dried (MgSO$_4$), filtered and stripped to an orange gum. The crude product was purified by flash chromatography eluting with 4:1 hexanes/EtOAc (R$_f$=0.14) to yield 610 mg (81%) of the title compound as a red oil. MS (m/z)=590 (M+H)+, 1H NMR (300 MHz, CDCl3) δ 10.10 (s, 1H), 8.55 (d, 1H), 8.50 (m, 1H), 7.79 (s, 1H), 7.75 (d, 2H), 7.15 (d, 2H), 6.80 (q; 1H), 5.10 (br d, 1H), 4.90 (m, 1H), 3.70-3.45 (m, 4H), 3.25 (m, 2H), 3.10 (q, 2H), 1.40 (s, 9H), 1.10 (t, 6H).

Example 16

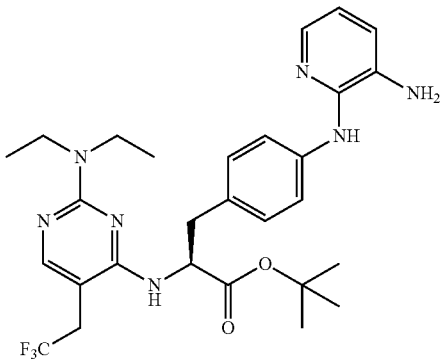

To a solution of the product of Example 15 (610 mg, 1.03 mmol) in absolute EtOH (5 mL) was added 60 mg of Pd/C, 10 wt %. The mixture was subjected to hydrogenation (45 psi H2) overnight. The next day the reaction mix was filtered through Celite and the filtrate concentrated to give 500 mg (87%) of the title compound. MS (m/z)=560 (M+H)+, 1H NMR (300 MHz, CDCl3) δ 7.85 (d, 2H), 7.80 (s, 1H), 7.20 (d, 2H), 7.05 (d, 2H), 7.00 (d, 1H), 7.75 (m, 1H), 6.20 (br s 1H), 5.15 (br s, 1H), 4.85 (m, 1H), 3.75-3.45 (m, 4H), 3.40 (br s, 2H), 3.15 (m, 2H), 3.05 (q, 2H), 1.40 (s, 9H), 1.15 (t, 6H).

Example 17

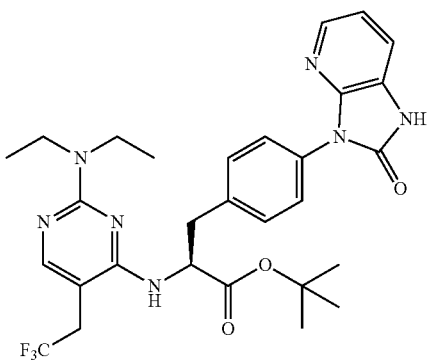

A solution of the product of Example 16 (141 mg, 0.250 mmol) and CDI (62 mg, 0.378 mmol) in CH2Cl2 (3 mL) was stirred overnight. The next day additional CDI (30 mg, 0.185 mmol) was added and the reaction was stirred another day. The reaction mixture was then concentrated and taken-up in EtOAc (10 mL) and the organic portion washed with 0.2 N citric acid (3×5 mL), water (1×5 mL), sat. NaHCO3 (3×5 mL), brine (1×5 mL), dried (MgSO4), filtered and concentrated to yield 69 mg (47%) the title compound as a foam which was used without further purification. MS (m/z)=586 (M+H)+, 1H NMR (300 MHz, CDCl3) δ 8.20 (br s, 1H), 8.05 (d, 1H), 7.80 (s, 1H), 7.65 (d, 2H), 7.90 (m, 3H), 7.05 (m, 1H), 5.15 (br d, 1H), 4.95 (m, 1H), 3.70-3.45 (m, 4H), 3.25 (app d, 2H), 3.10 (q, 2H), 1.40 (s, 9H), 1.15 (t, 6H).

Example 18

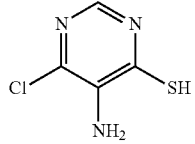

To a solution of 4,6-dichloro-5-aminopyrimidine (5.0 g, 30.7 mmol) in DMSO (30 mL) was added Na2S.9H2O (7.4 g, 30.8 mmol). The mixture was stirred at room temperature overnight. Water (40 mL) was then added to the mixture and the solution evaporated under reduced pressure to approximately 6 mL. To this solution was added conc. HCl (0.5 mL) and water to precipitate the product. The solution was filtered and the orange solid was washed with water and dried to afford 4.3 g (86%) of the title compound. 1H NMR (300 MHz, DMSO-d6) δ 5.84 (2H, s), 7.79 (1H, s), 14.37 (1H, br s); MS (m/z): MH+=162.

Example 19

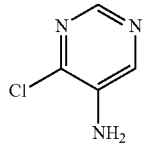

To the product of Example 18 (4.3 g, 26 mmol) dissolved in conc. NH4OH (4 mL) was added EtOH (40 mL). To this solution, Raney Nickel (excess) was added in portions. The reaction was stirred at room temperature overnight and then heated at 80° C. for 2 hrs. The mixture was filtered through Celite and the filtrate concentrated. The crude product was purified by flash chromatography on silica using EtOAc/hexanes to afford 1.6 g (47%) of the title compound as a yellow solid. 1H NMR (300 MHz, DMSO-d6) δ 5.90 (2H, s), 8.20 (2H, s); MS (m/z) MH+=130.

Example 20

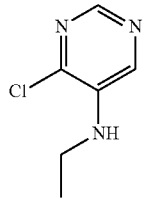

To the product of Example 19 (0.51 g, 3.9 mmol) in MeOH (20 mL) and HOAc (0.5 mL) was added CH3CHO (0.52 mL, 9.2 mmol). Then NaBH3CN (590 mg, 9.2 mmol) was added in one portion. The reaction was stirred at room temperature overnight and additional HOAc, CH3CHO, and NaBH3CN were added. The reaction was stirred overnight, concentrated, and the residue was taken up in EtOAc and sat. NaHCO$_3$. The separated aqueous layer was back extracted with EtOAc. The combined organic layer was dried and concentrated to a residue. The residue was dissolved in MeOH and treated with HOAc, CH$_3$CHO and NaBH$_3$CN as described above. Following the work up procedure described above the crude product was purified by flash chromatography on silica using EtOAc/hexanes, to afford 0.35 g (57%) of the title compound as a yellow oil. $^1$H NMR (300 MHz, CDCl$_3$) δ 1.35 (3H, q, J=12 Hz), 3.29 (2H, m), 4.21 (1H, bs), 8.04 (1H, s), 8.36 (1H, s); MS (m/z): MH$^+$=158.

Example 21

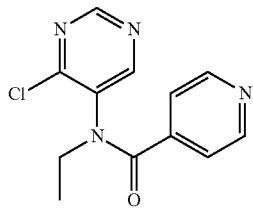

To the product of Example 20 (70 mg, 0.45 mmol) dissolved in DMF (1 mL) was added TEA (93 uL) and isonicotinoyl chloride (0.12 g, 0.67 mmol). The reaction mixture was stirred at room temperature for 2 days and then partitioned between EtOAc and sat. NaHCO$_3$. The separated aqueous layer was back extracted with EtOAc. The combined organic layer was dried and concentrated to give 67 mg (57%) of the title compound which was used without further purification. $^1$H NMR (300 MHz, CDCl$_3$) δ 1.26 (3H), 3.65-3.69 (1H), 4.21 (1H), 7.17 (2H), 8.43 (1H), 8.54 (2H), 8.86 (1H) Note: $^1$H NMR shows evidence of rotamers as demonstrated of broadness of all peaks; MS (m/z): MH$^+$=263.

Example 22

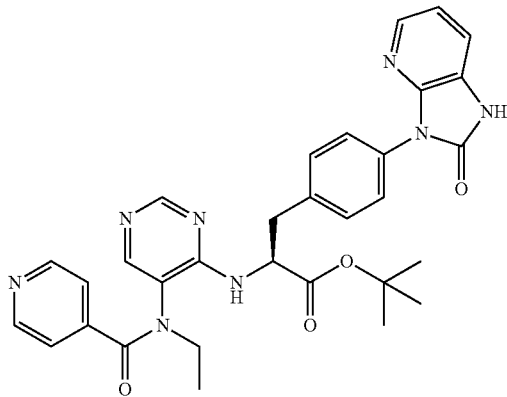

To a solution of the product of Example 21 (0.11 g, 0.42 mmol) and the product of Example 8 (0.135 g, 0.38 mmol) in IPA (2.5 ml) was added DIEA (0.35 ml, 1.9 mmol). The reaction mixture was stirred in a sealed tube at 130° C. for 2 days. The crude mixture was concentrated and the oil was purified by flash column chromatography with a solvent gradient of 0-10% MeOH in CH$_2$Cl$_2$ to yield the title compound as an oil. $^1$H NMR (300 MHz, CDCl$_3$) δ 1.16 (1.2H, m), 1.26-1.31 (1.8H, m), 1.50-1.53 (9H, d, J=9 Hz), 3.0 (1H, m), 3.2 (0.8H, m), 3.36 (1.2H, m), 4.12-4.18 (1.2H, m), 4.96-5.10 (0.8H, m), 5.80-5.95 (1H, m), 6.93-6.96 (1H, m), 7.07 (1H, m), 7.31-7.45 (5H, m), 7.66-7.75 (3H, m), 8.06 (1H, m), 8.44-8.51 (2H, m); HPLC/MS: single peak at 1.29 min, MH$^+$=581.

Example 23

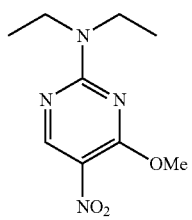

To 2,4-dichloro-5-nitropyrimidine (2.0 g, 10.3 mmol) in MeOH (7 mL) at 0° C. under N$_2$ was added NaOMe (0.5 M in MeOH, 25 mL) dropwise. After the addition was completed, the reaction mixture was stirred at 0 C for 15 min. Then diethylamine (5 mL) was added and the mixture was stirred at rt overnight. The reaction mixture was concentrated and the residue was partitioned between EtOAc and H$_2$O. The organic layer was dried and concentrated to a residue which was purified by flash chromatography on silica using EtOAc/Hexanes, to afford the title compouns as an off white solid (1.1 g, 4.9 mmol, 47% yield). $^1$H NMR (300 MHz, CDCl$_3$) δ 1.26 (6H, t, J=6.6 Hz), 3.70 (4H, m), 4.08 (3H, s), 9.01 (1H, s); HPLC/MS: MH$^+$=227.

Example 24

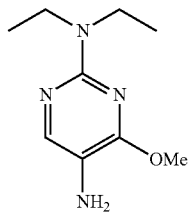

To the product of Example 23 (1.1 g, 4.9 mmol) in MeOH/EtOAc (1:1, 20 mL) was reduced with Pd/C (5% degussa, 0.5 g) and H$_2$ (50 psi) in a Parr shaker overnight. The reaction mixture was filtered and the filtrated was concentrated under reduced pressure to afford the title compound as a solid (0.85 g, 4.3 mmol, 88.5% yield). $^1$H NMR (300 MHz, CDCl$_3$) δ 1.18 (6H, t, J=6.9 Hz), 3.03 (2H, br), 3.57 (6H, t, J=6.9 Hz), 3.96 (3H, s), 7.71 (1H, s); HPLC/MS: MH$^+$=197.

Example 25

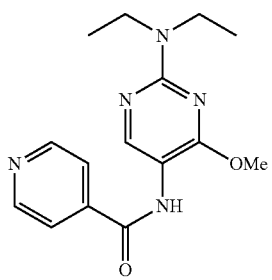

To the product of Example 24 (0.85 g, 4.3 mmol) in CH$_2$Cl$_2$ (15 mL) and TEA (1.4 mL, 10 mmol) was added isonicotinyl chloride HCl salt (1.13 g, 6.3 mmol). After 15 min, TLC showed no starting material. The mixture was extracted between EtOAc and sat. NaHCO$_3$. The aqueous layer was washed with EtOAc twice. The combined organic layers were washed with sat. NaHCO$_3$ and brine. It was dried over MgSO$_4$ and filtered. The filtrate was concentrated to give the title compound as a brown solid (1.3 g, 4.3 mmol, 100% yield). $^1$H NMR (300 MHz, CDCl$_3$) δ 1.20 (6H, t, J=6.9 Hz), 3.60 (4H, q, J=6.9 Hz), 3.96 (3H, s), 7.72 (2H, d, J=6.0 Hz), 7.75 (1H, bs), 8.80 (2H, d, J=6.0 Hz), 8.89 (1H, s); HPLC/MS: MH$^+$=302.

Example 26

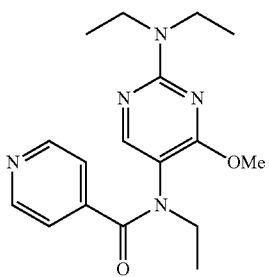

To the product of Example 25 (100 mg, 0.33 mmol) in THF (1 mL) was added KOtBu (1M in THF, 0.5 mL) slowly followed by EtI (40 μL, 0.5 mmol). The reaction mixture was stirred at rt overnight. TLC showed the disappearance of the starting material. The mixture was partitioned between EtOAc and H$_2$O. The aqueous layer was washed with EtOAc. The combined organic layers were washed with sat. NaHCO$_3$ and brine. It was dried and concentrated to give the title compound (90 mg, 0.27 mmol, 83%) that was used without further purification. $^1$H NMR (300 MHz, CDCl$_3$) δ 1.10 (9H, m), 3.47 (5H, m), 3.92 (1H, m), 7.14 (2H, d, J=6.0 Hz), 7.78 (1H, bs), 8.44 (2H, d, J=6.0 Hz); HPLC/MS: MH$^+$=330.

Example 27

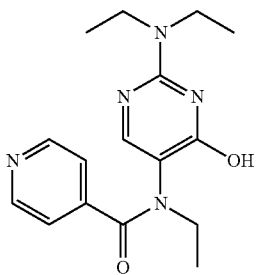

To the product of Example 26 (200 mg, 0.61 mmol) in DMF (4 mL) was added EtSNa (66 mg, 0.79 mmol) and the reaction mixture was heated at 100 C for 1 hr. LC/MS showed starting material still present. Another portion of NaSEt (66 mg, 0.79 mmol) was added and the reaction heated for another 2 hr. LC/MS showed product only. DMF was removed under reduced pressure and H$_2$O (10 mL) was added followed by conc. HCl (0.132 mL). Evaporating of the solvent left a residue. It was dissolved in EtOH and filtered. The filtrate was concentrated to yield the title compound (190 mg, 100%) that was used without further purification. $^1$H NMR (300 MHz, CD$_3$OD) δ 1.24 (9H, m), 3.60 (4H, m), 3.60-4.00 (2H, br), 8.12 (3H, d, J=5.7 Hz), 8.92 (2H, d, J=5.7 Hz); HPLC/MS: MH$^+$=316.

Example 28

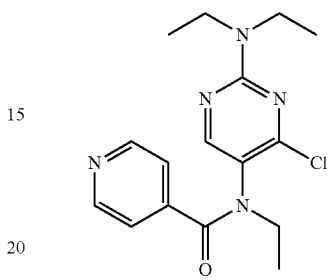

To the product of Example 27 (70 mg, 0.22 mmol) in POCl$_3$ (3 mL) at rt was added diethylaniline (30 μL). The reaction mixture was heated to 100 C for 30 min. Then it was concentrated. The residue was partitioned between EtOAc and H$_2$O. The organic layer was washed with H$_2$O twice. Then it was dried and concentrated to give the title compound (50 mg, 0.15 mmol, 68%) and used for the next reaction without further purification. HPLC/MS: MH$^+$=334

Example 29

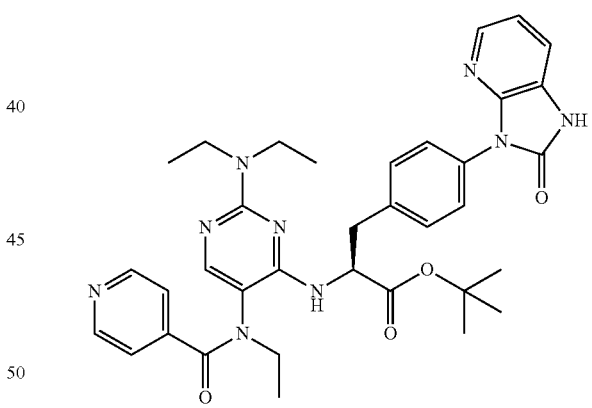

To a solution of the product of Example 28 (50 mg, 0.15 mmol) and the product of Example 8 (60 mg, 0.17 mmol) in IPA (0.75 mL) was added DIEA (0.15 mL, 0.8 mmol). The reaction mixture was stirred in a sealed tube at 130 degrees for 7 days. The crude mixture was concentrated and the residue was purified by preparative HPLC and silica gel flash chromatography to yield an off white solid (10 mg). $^1$H NMR (300 MHz, CDCl$_3$) δ 1.10-1.30 (9H, m), 1.48 (4.5H, s), 1.51 (4.5H, s), 2.80-3.38 (3H, m), 3.53 (4H, m), 4.05-4.30 (1H, m), 4.83 (0.5H, m), 4.96 (0.5H, m), 5.15-5.50 (1H, m), 6.95-7.10 (2H, m), 7.25-7.50 (5H, m), 7.69 (0.5H, d, J=8.4 Hz), 7.76 (0.5H, d, J=8.4 Hz), 8.08 (1H, d, J=5.1 Hz), 8.51 (2H, m), 8.83 (0.5H, br), 8.95 (0.5H, br);

HPLC/MS: MH+=652.

Example 30

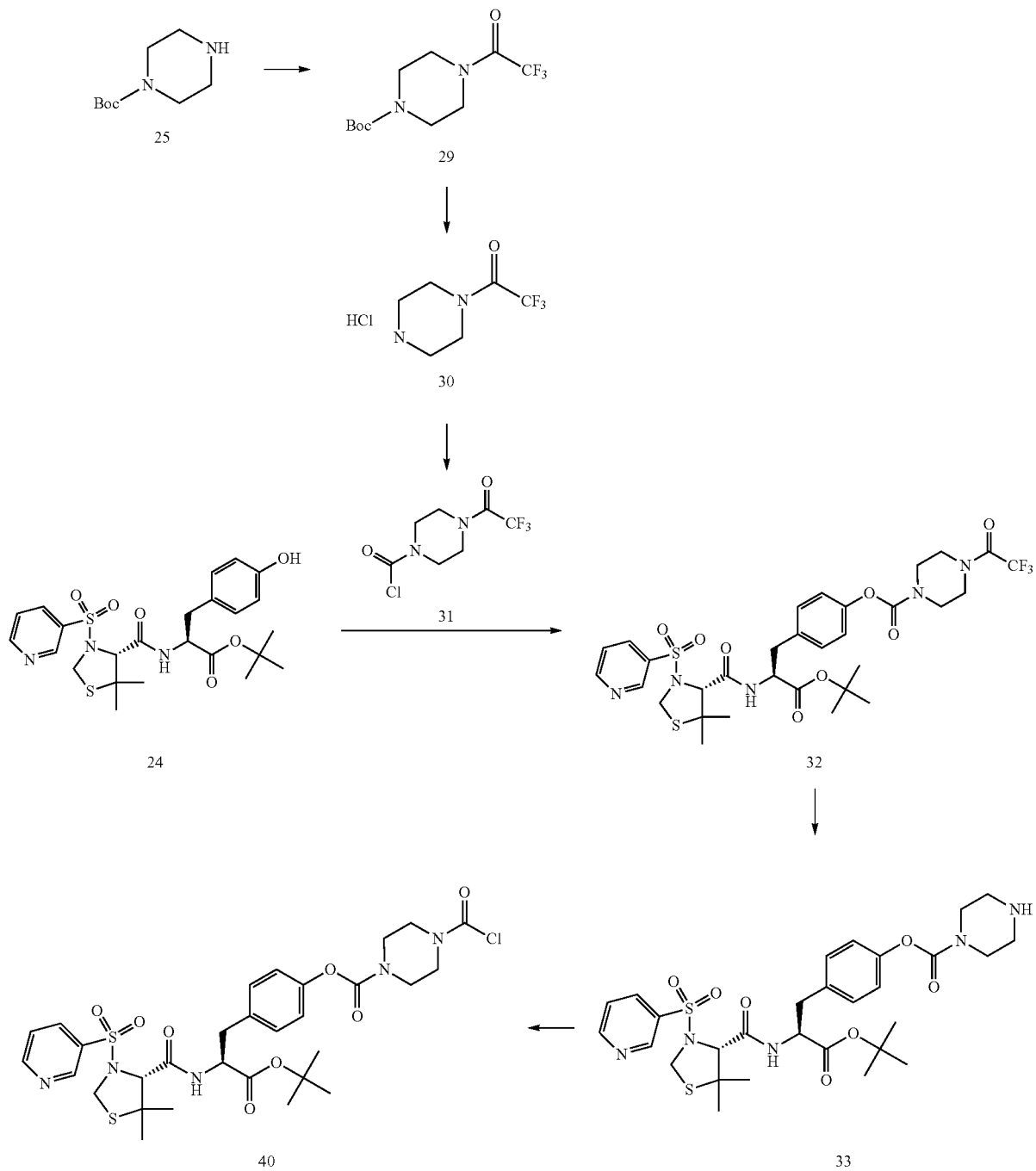

Compound 25 (20 g, 0.11 mol) was dissolved in CH$_2$Cl$_2$ (500 mL) under N$_2$. The reaction mixture was cooled to 0° C. Triethylamine (18.12 mL, 0.13 mol) was added, followed by trifluoroacetic anhydride (18.14 mL, 0.13 mol) in portions. The reaction was allowed to warm to room temperature overnight. The reaction mixture was concentrated in vacuo and the residue was taken up in ethyl acetate (200 mL). The organic phase was washed with H$_2$O, sat. NaHCO$_3$, brine, dried over Na$_2$SO$_4$, filtered, and concentrated in vacuo to yield 29.7 g (96%) 29 as a yellow solid. $^1$H NMR (CDCl$_3$) δ 3.64-3.60 (m, 2H), 3.55-3.53 (m, 2H), 3.49-3.45 (m, 4H), 1.44 (s, 9H). $^{13}$C NMR (CDCl$_3$) δ 155.7 (J$_{C-F}$=36 Hz), 154.3, 116.4 (J$_{C-F}$=288 Hz), 80.8, 45.7, 43.3, 28.3.

Compound 29 (29.26 g, 0.10 mol) was added in portions to a 500 mL flask containing a solution of 4N HCL in dioxane (200 mL) at 0° C. The reaction was stirred in ice bath for 4 hours when TLC (3:1 hexanes:ethyl acetate) showed 100% conversion to product. The reaction mixture was concentrated in vacuo and treated with ethyl ether (500 mL). The product was filtered and dried to yield 22.5 g (99%) 30 as a white mono-hydrochloride salt. $^1$H NMR (DMSO-d$_6$) δ 3.82-3.79

(m, 4H), 3.53 (s, 1H), 3.18-3.16 (m, 4H). $^{13}$C NMR (DMSO-d$_6$) δ 154.3 (J$_{C-F}$=35 Hz), 115.9 (J$_{C-F}$=289 Hz), 66.1, 42.0, 41.9, 41.5.

A 250 mL flask was charged with 30 (1.0 g, 4.6 mmol), CH$_2$Cl$_2$ (40 mL), and sat. NaHCO$_3$ (40 mL). The reaction mixture was stirred vigorously at 0° C. for 15 minutes. Stirring was ceased and the layers were allowed to separate. A 2.0 M solution of phosgene in toluene (9 mL, 18 mmol) was added to the reaction mixture which was stirred vigorously for 30 minutes, maintaining temperature at 0° C. The layers were separated and the aqueous phase was washed with CH$_2$Cl$_2$ (15 mL). The combined organic layers were washed with brine, dried over Na$_2$SO$_4$, filtered, and concentrated in vacuo. The residue was taken up in CH$_2$Cl$_2$ and concentrated in vacuo again to yield 1.0 g (92%) 31 as a white solid. MS (m/z) 245, (M+H)$^+$. $^1$H NMR (CDCl$_3$) δ 3.80-3.68 (m, 8H). $^{13}$C NMR (CDCl$_3$) δ 155.9 (J$_{C-F}$=37 Hz), 148.7 (J$_{C-F}$=12 Hz), 116.3 (J$_{C-F}$=289 Hz), 48.3, 47.8, 45.7, 45.3, 45.1, 42.9, 42.7.

A 25 mL flask was charged with 24 (5.97 g, 0.011 mol), DMAP (1.34 g, 0.011 mol), and CH$_2$Cl$_2$ (22 mL). Triethylamine (2.4 mL, 0.017 mol) was added followed by 31 (4.2 g, 0.017 mol). The reaction mixture was heated at reflux for 20 hours. The reaction mixture was concentrated in vacuo and the residue was taken up in ethyl acetate. The organic phase was washed with sat. NaHCO$_3$, H$_2$O, brine, dried over Na$_2$SO$_4$, filtered, and concentrated in vacuo to yield 9.3 g pink foam. The crude material was purified by flash chromatography (gradient of 50% ethyl acetate/hexanes to 75% ethyl acetate/hexanes) to yield 6.1 g (76%) 32 as a pale pink foam. R$_f$=0.14 (1:1 hexanes:ethyl acetate). MS (m/z) 730, (M+H)$^+$. $^1$H NMR (CDCl$_3$) δ 9.08-9.07 (m, 1H), 8.87-8.85 (m, 1H), 8.16-8.14 (m, 1H), 7.52-7.48 (m, 1H), 7.25-7.22 (d, 2H), 7.03-7.00 (d, 2H), 6.91-6.88 (d, 1H), 4.78-4.70 (q, 1H), 4.60-4.44 (dd, 2H), 3.88 (s, 1H), 3.75-3.60 (m, 8H), 3.09-3.06 (m, 2H), 1.42 (s, 9H), 1.18 (s, 3H), 1.16 (s, 3H).

To a solution of 32 (6.11 g, 8.4 mmol) dissolved in MeOH (90 mL) was added a solution of potassium carbonate (5.79 g, 42 mmol) in H$_2$O (10 mL). The reaction was stirred at room temperature for 15 minutes and then concentrated in vacuo. The residue was filtered and washed with copious amounts of H$_2$O to yield 4.65 g (88%) 33 as a white solid. R$_f$=0.08 (5% MeOH/CH$_2$Cl$_2$). MS (m/z) 634, (M+H)$^+$. $^1$H NMR (CDCl$_3$) δ 9.09-9.08 (m, 1H), 8.87-8.85 (m, 1H), 8.16-8.14 (m, 1H), 7.52-7.48 (m, 1H), 7.23-7.20 (d, 2H), 7.03-7.00 (d, 2H), 6.91-6.88 (d, 1H), 4.78-4.70 (q, 1H), 4.59-4.46 (dd, 2H), 3.89 (s, 1H), 3.65-3.50 (m, 4H), 3.09-3.06 (m, 2H), 2.92-2.88 (m, 4H), 1.43 (s, 9H), 1.19 (s, 3H), 1.17 (s, 3H). $^{13}$C NMR (CDCl$_3$) δ 170.1, 167.9, 154.5, 153.9, 150.7, 148.8, 136.0, 133.4, 133.2, 130.6, 124.1, 121.9, 83.0, 73.9, 55.0, 53.7, 50.7, 46.0, 45.7, 45.0, 37.9, 29.3, 28.0, 24.0.

A 250 mL flask was charged with 33 (2.5 g, 3.9 mmol), CH$_2$Cl$_2$ (40 mL), and sat. NaHCO$_3$ (40 mL). The reaction mixture was stirred vigorously at 0° C. for 15 minutes. Stirring was ceased and the layers were allowed to separate. A 2.0 M solution of phosgene in toluene (7.9 mL, 16 mmol) was quickly added to the reaction mixture, which was stirred vigorously for 60 minutes maintaining the temperature at 0° C. The layers were separated and the aqueous phase was washed with CH$_2$Cl$_2$ (30 mL). The combined organic layers were washed with 0.2 N citric acid, brine, dried over Na$_2$SO$_4$, filtered, and concentrated in vacuo to yield 2.8 g (100%) white foam. The crude material was purified through a silica plug, eluting with 100% ethyl acetate, to yield 2.2 g (78%) 40 as a white foam. R$_f$=0.43 (3:1 ethyl acetate:hexanes). $^1$H NMR (CDCl$_3$) δ 9.09-9.08 (m, 1H), 8.87-8.85 (m, 1H), 8.16-8.14 (d, 1H), 7.52-7.48 (m, 1H), 7.25-7.22 (d, 2H), 7.03-7.01 (d, 2H), 6.90-6.88 (d, 1H), 4.78-4.70 (q, 1H), 4.60-4.45 (dd, 2H), 3.88 (s, 1H), 3.79-3.65 (m, 8H), 3.10-3.07 (m, 2H), 1.43 (s, 9H), 1.18 (s, 3H), 1.17 (s, 3H). $^{13}$C NMR (CDCl$_3$) δ 169.9, 167.9, 154.1, 153.6, 150.2, 148.5, 136.1, 133.8, 130.6, 124.2, 121.7, 82.9, 73.7, 54.8, 53.8, 50.6, 48.3, 45.8, 37.7, 29.2, 27.9, 23.9.

Example 31

A. Synthesis of Carbamate-Linked Bis-PEG Conjugate t-Butyl Ester

Scheme 16

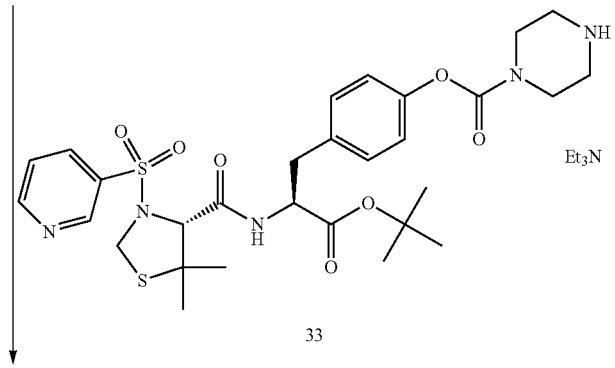

33

-continued

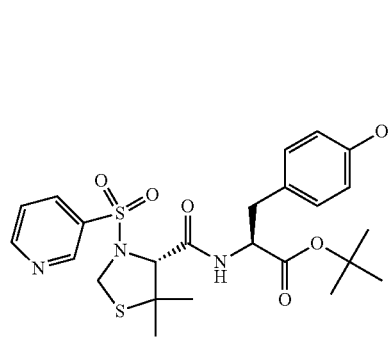
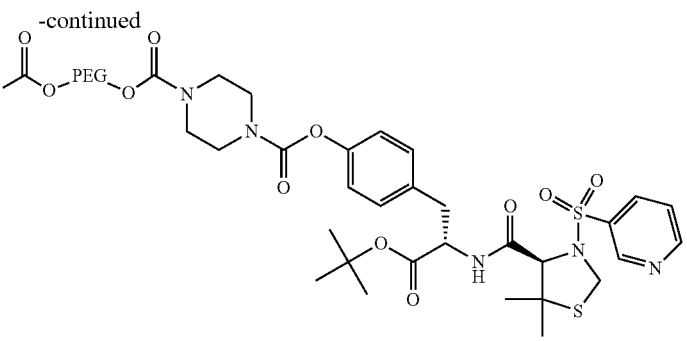

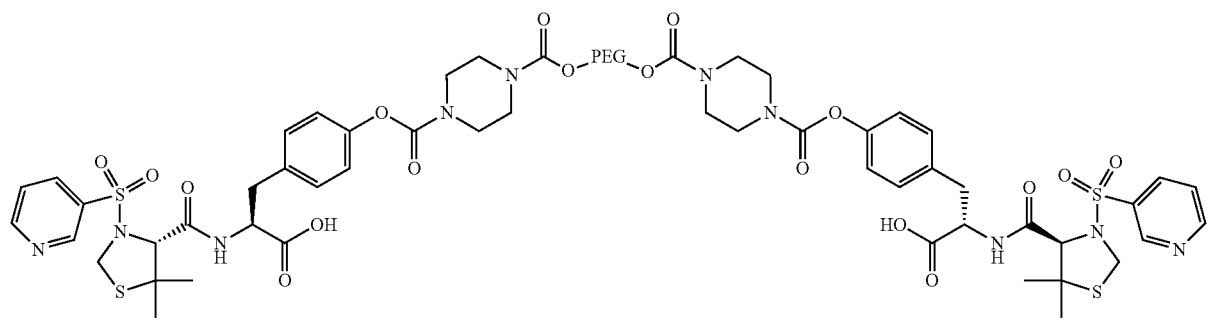

The carbamate linked conjugates were prepared based on a method modified from WO 92/16555, which is hereby incorporated by reference. Thus, the 6 kDa PEG-diol (500 mg, 0.083 mmol) was dissolved in a minimal amount of $CH_2Cl_2$ (0.1 mL). To this was added a 2.0 M solution of phosgene in toluene (0.6 mL, 1.2 mmol). The reaction mixture was stirred at room temperature for 18 hours and then concentrated in vacuo to yield 500 mg (100%) of the 6 kDa PEG bis-chloroformate as a white solid.

A solution of 33 (211 mg, 0.33 mmol) in $CH_2Cl_2$ (3 mL) (see example 30) was added to the 6 kDa PEG bis-chloroformate (500 mg, 0.08 mmol) dissolved in $CH_2Cl_2$ (2 mL). Triethylamine (11 µL, 0.08 mmol) was added, and the reaction mixture was stirred at room temperature for 18 hours. The reaction mixture was concentrated in vacuo, and the residue was dissolved in MeOH (10 mL). 2% cross-linked polystyrene sulfonic acid resin (410 mg) was added, and the reaction vessel was swirled for 2 hours. The mixture was filtered, and the filtrate was concentrated in vacuo to yield 500 mg (87%) of a white solid. A portion of the material (246 mg) was purified by HPLC, yielding 156 mg of the 6 kDa PEG bis-conjugate t-butyl ester as a white solid. HPLC determined the conjugate to be >99% pure (retention time 9.655 min).

$^1$H-NMR (CDCl$_3$) δ 9.07 (bs, 2H), 8.86-8.84 (m, 2H), 8.18-8.15 (d, 2H), 7.53-7.48 (m, 2H), 7.22-7.19 (d, 4H), 7.03-6.99 (d, 4H), 6.86-6.83 (d, 2H), 4.73-4.70 (m, 2H) 4.58-4.44 (dd, 4H), 4.27-4.24 (m, 4H), 3.62 (bs, 621H), 3.40-3.37 (m, 6H), 3.07-3.05 (m, 4H), 1.41 (s, 18H), 1.20-1.16 (d, 12H).

B. Synthesis of Carbamate-Linked Bis-PEG Conjugate

The purified 6 kDa carbamate-linked bis-PEG conjugate t-butyl ester (100 mg, 0.01 mmol) was dissolved in formic acid (5 mL) and heated at 40° C. for 24 hours. The reaction was concentrated in vacuo. The residue was dissolved in water, concentrated in vacuo, dissolved again in water, and lyophilized to yield 100 mg (100%) of the 6 kDa carbamate-linked bis-PEG conjugate carboxylic acid as a white powder. HPLC determined conjugate to be >99% pure (retention time 7.63 min).

$^1$H NMR (CDCl$_3$) δ 9.06 (bs, 2H), 8.84-8.83 (m, 2H), 8.17-8.14 (d, 2H), 7.53-7.49 (m, 2H), 7.24-7.21 (d, 4H), 7.02-6.99 (d, 4H), 6.94-6.92 (d, 2H), 4.81-4.79 (m, 2H), 4.57-4.48 (dd, 4H), 4.28-4.25 (m, 4H) 3.64 (bs, 621H), 3.41-3.38 (m, 6H), 3.23-3.08 (m, 4H), 1.23-1.18 (d, 12H).

US 8,263,063 B2
115
116
Example 32
A. Synthesis of Carbamate-Linked Octa-PEG Conjugate T-Butyl Ester
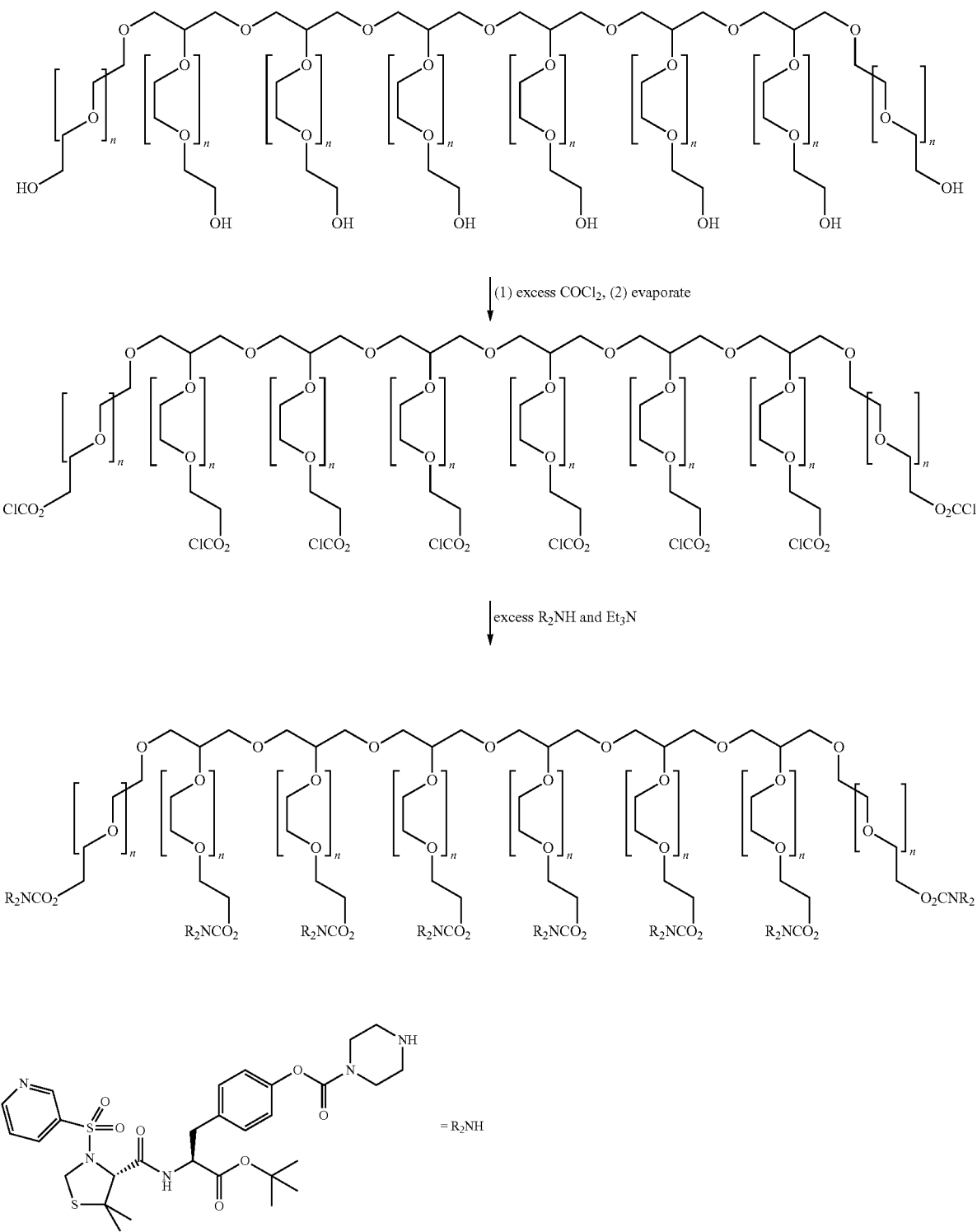

By following the procedures used in Example 31 above and employing an octa-pegylated hub molecule, the title compound was prepared.

Example 33

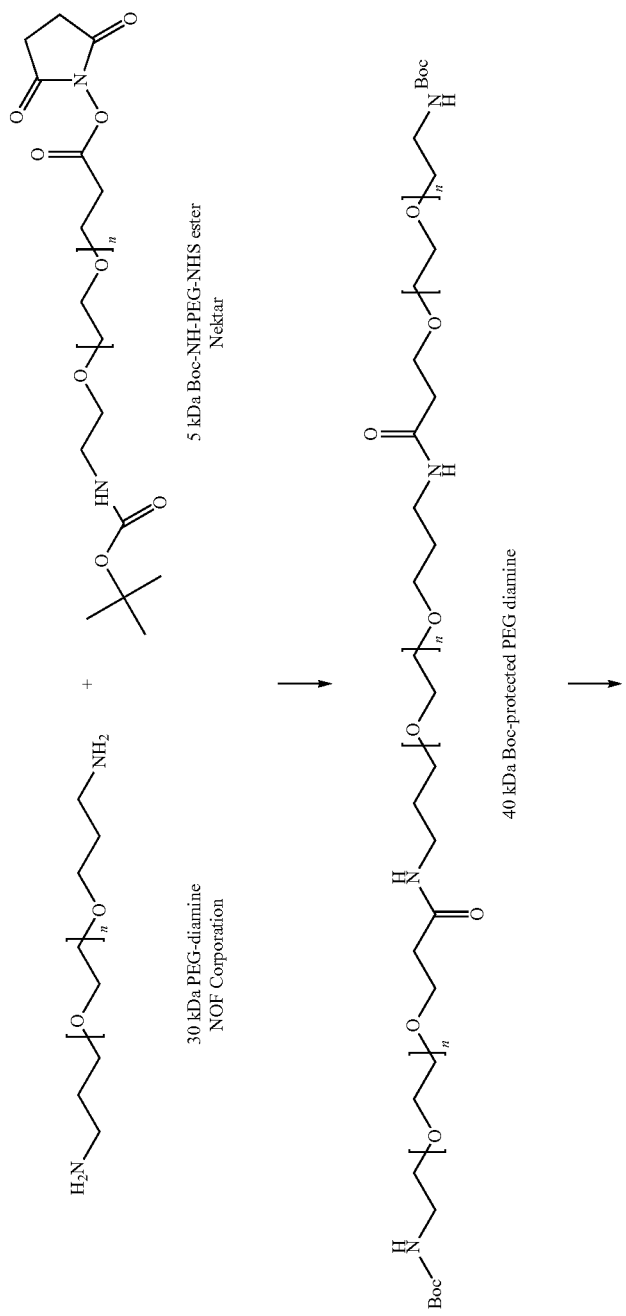

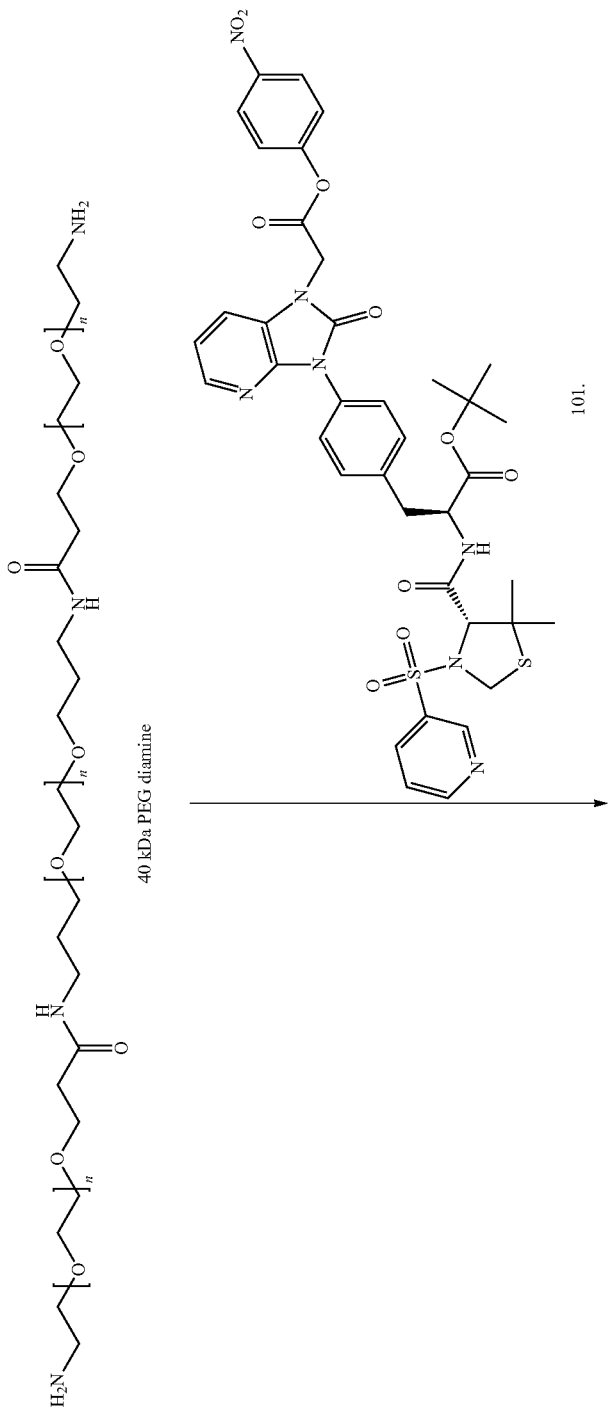

-continued
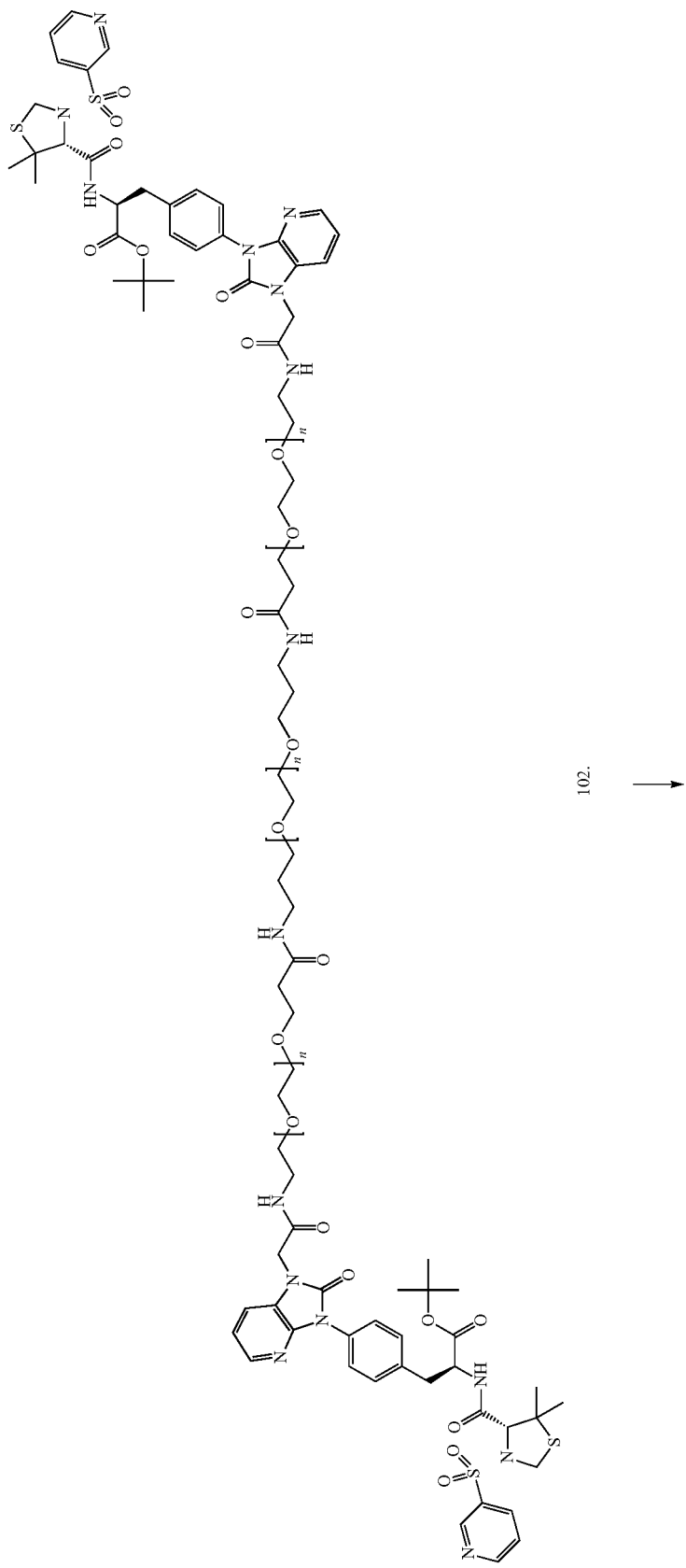
102.

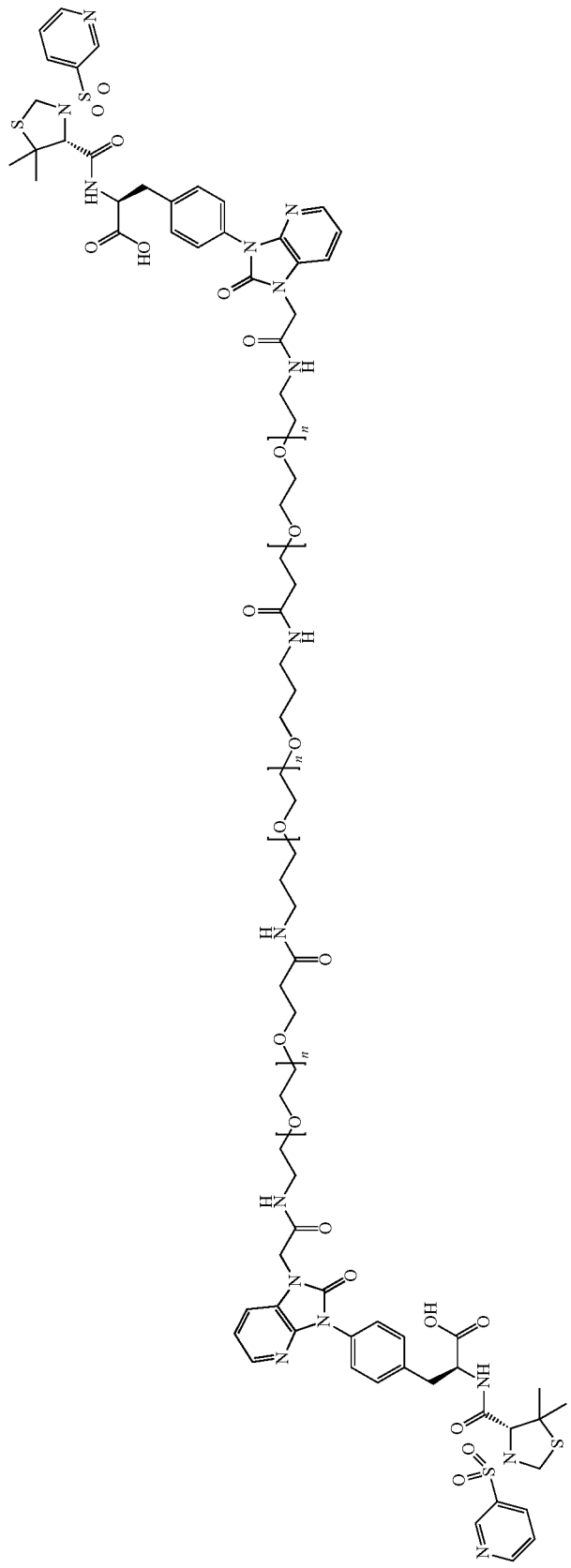

Nitro-Phenyl Ester (101)

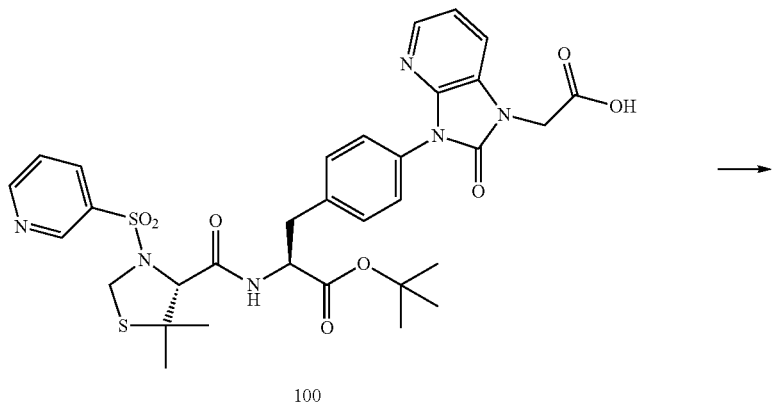

100

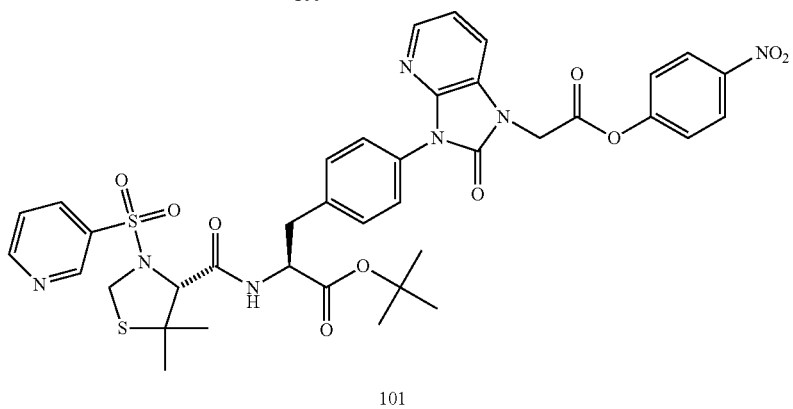

101

A solution of 100 (100 mg, 0.14 mmol) and 4-nitrophenol (24 mg, 0.17 mmol) in THF (0.7 mL) was cooled in an ice bath. A suspension of EDC (33 mg, 0.17 mmol) in CH$_2$Cl$_2$ (0.7 mL) was added and the reaction was stirred at 0° C. for 4 hours. The reaction was diluted with ethyl acetate (100 mL) and washed with 0.2 N citric acid. The organic layer was washed with 10% K$_2$CO$_3$, brine, dried over Na$_2$SO$_4$, filtered, and concentrated in vacuo to yield 90 mg (96%) of 101, which was used immediately. $^1$H NMR (CDCl$_3$) δ 9.07 (bs, 1H), 8.84-8.83 (d, 1H), 8.28-8.25 (d, 2H), 8.16-8.14 (d, 1H), 8.09-8.07 (d, 1H), 7.65-7.63 (d, 2H), 7.51-7.47 (dd, 1H), 7.41-7.39 (d, 2H), 7.36-7.35 (d, 2H), 7.12-7.07 (m, 1H), 6.95-6.92 (d, 1H), 5.00 (s, 2H), 4.82-4.76 (m, 1H), 4.62-4.45 (dd, 2H), 3.91 (s, 1H), 3.18-3.12 (m, 2H), 1.44 (s, 9H), 1.18-1.16 (d, 6H).

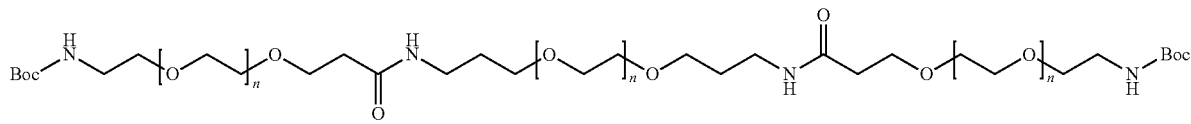

40 kDa Boc-Protected PEG Diamine

The 30 kDa PEG diamine (1 g, 0.033 mmol) and the 5 kDa Boc-NH-PEG-NHS ester (0.67 g, 0.13 mmol) were dissolved in CH$_2$Cl$_2$ (10 mL). Diisopropylethylamine (0.116 mL, 0.67 mmol) was added and the reaction stirred at room temperature for 18 hours. The reaction was concentrated in vacuo to yield crude product. The residue was purified according to HPLC Method B to yield 0.46 g of the 40 kDa Boc-protected PEG diamine as a white solid. HPLC Method C determined the product to be >96% pure (retention time=7.6 minutes). $^1$H NMR (CDCl$_3$) δ 6.75 (bs, 2H), 5.15 (bs, 2H) 3.64 (s, 2940H, PEG), 3.33-3.31 (m, 10H), 2.47-2.43 (m, 4H), 1.44 (s, 18H).

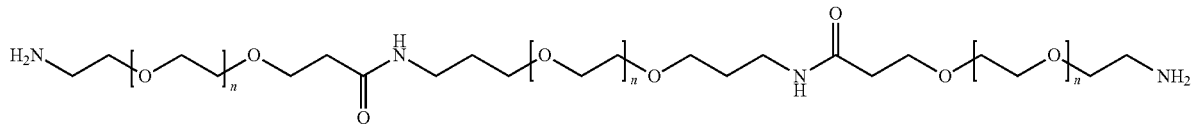

40 kDa PEG Diamine

The 40 kDa Boc-protected PEG diamine (0.2 g, 0.005 mmol) was dissolved in TFA (4 mL) and stirred at room temperature for 2 hours. The reaction was concentrated in vacuo to yield 200 mg (100%) crude 40 kDa PEG diamine as a beige residue. HPLC Method C determined the product to be >96% pure (retention time=6.5 minutes). $^1$H NMR (CDCl$_3$) δ 7.85 (bs, 1H), 6.75 (bs, 1H), 3.64 (s, 2432H, PEG), 3.34-3.32 (m, 10H), 2.47-2.45 (m, 4H).

T-Butyl Ester (102)

The 40 kDa PEG diamine (0.2 g, 0.005 mmol) was dissolved in CH$_2$Cl$_2$ (4 mL). Diisopropylethylamine (17 μL, 0.1 mmol) was added, followed by compound 101 (0.082 g, 0.1 mmol). Another portion of diisopropylethylamine (17 μL) was added and the reaction was stirred at room temperature for 18 hours. The reaction was concentrated in vacuo to yield 300 mg (150%) crude 102 as a white solid. HPLC Method C determined the product to be >70% pure (retention time 8.9 minutes). Crude product was used as is.

Conjugate 103

102 (0.3 g, 0.007 mmol) was dissolved in formic acid (5 mL) and heated at 40° C. for 24 hours. The reaction was concentrated in vacuo and purified according to HPLC Method A to yield 0.14 g (68%) of 103 as a white solid. HPLC Method C determined the conjugate to be >99% pure (retention time=7.3 minutes). $^1$H NMR (CDCl$_3$) δ 9.05 (bs, 2H), 8.82-8.81 (m, 2H), 8.17-8.14 (d, 2H), 8.05-8.04 (d, 2H), 7.65-7.58 (m, 4H), 7.54-7.48 (m, 2H), 7.41-7.34 (d, 4H), 7.10-7.05 (m, 2H) 6.95-6.93 (d, 2H), 4.90 (m, 2H), 4.63-4.49 (m, 6H), 3.64 (bs, 3042H, PEG), 3.35-3.29 (m, 6H), 3.22 (m, 5H), 2.45-2.41 (t, 4H), 1.79-1.74 (m, 4H), 1.29-1.27 (d, 12H).

Example 34

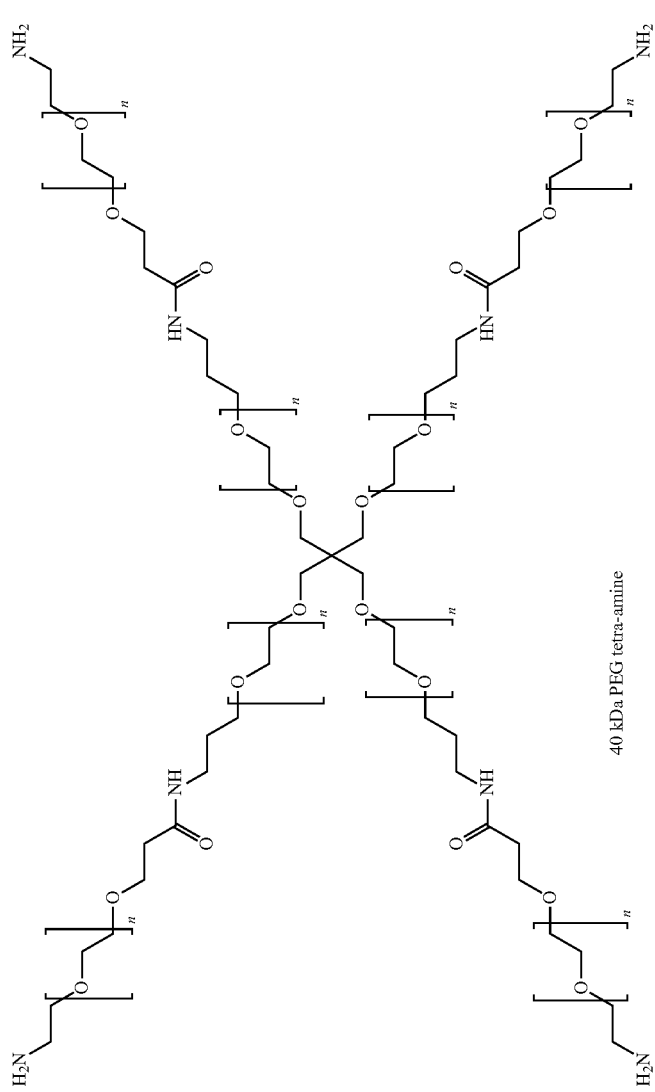
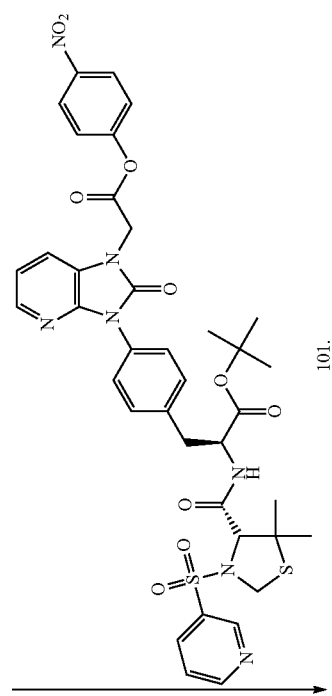
40 kDa PEG tetra-amine

-continued
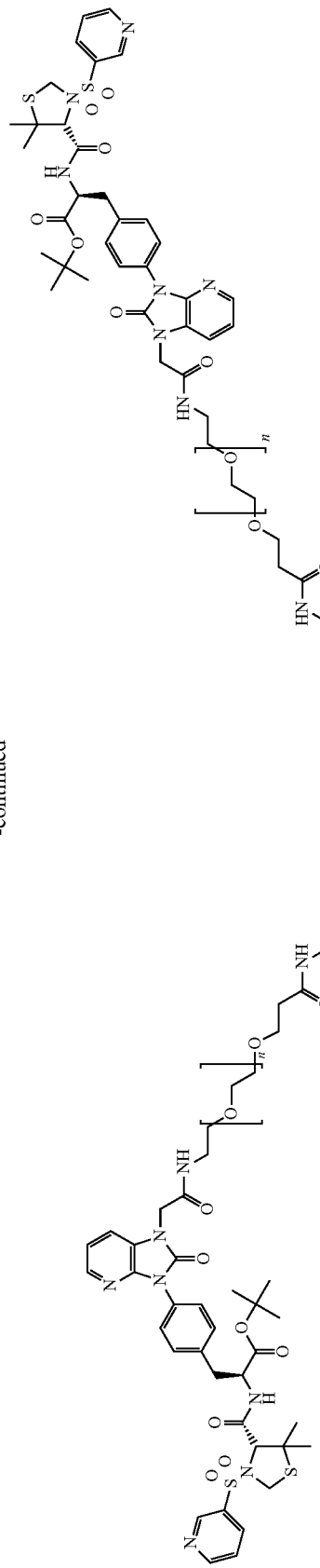
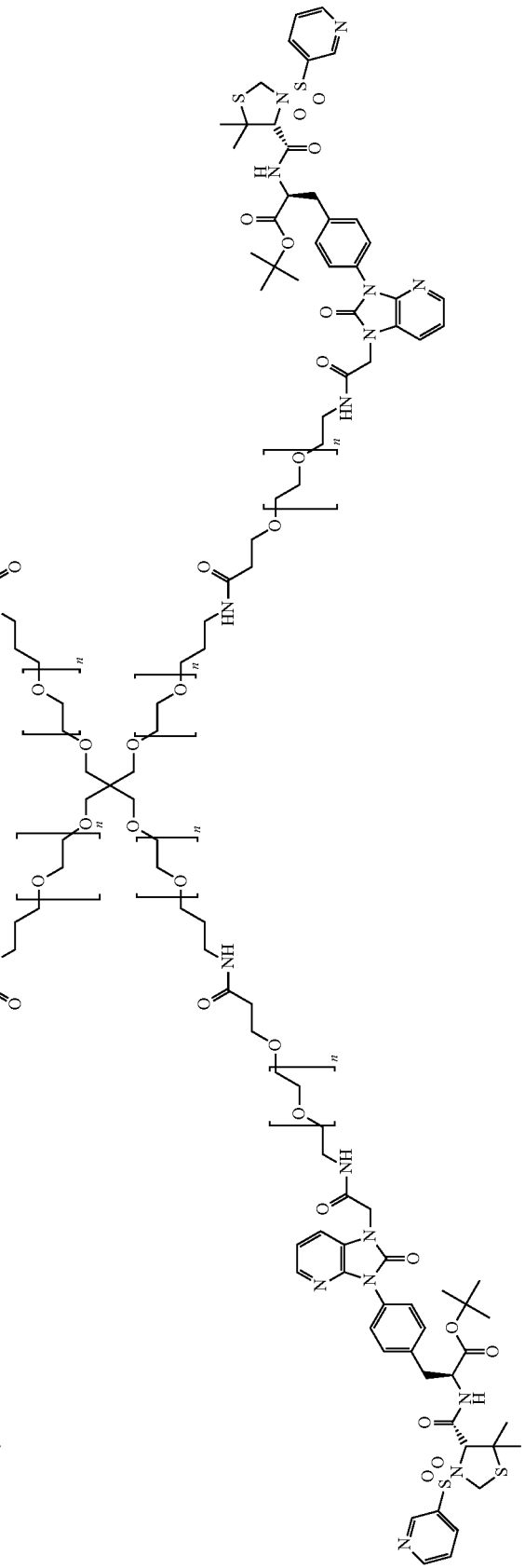
104.

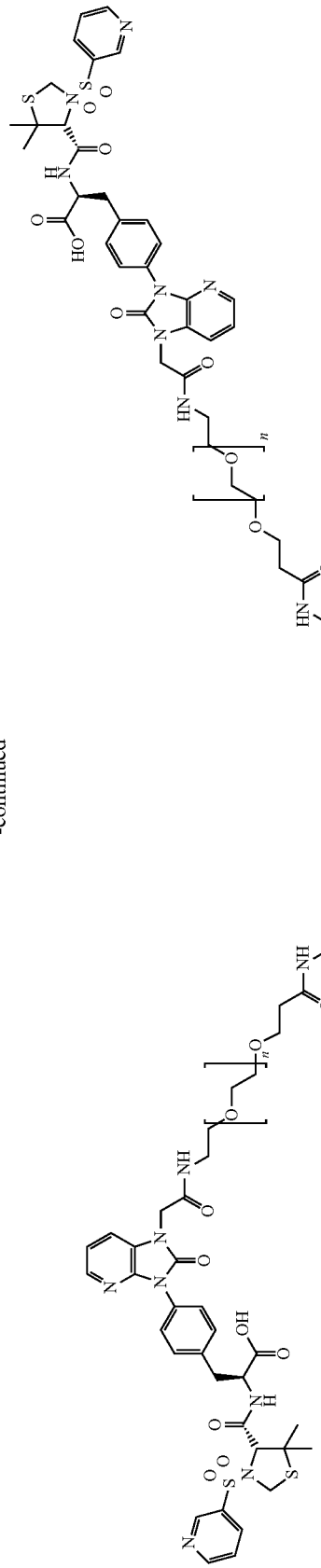
105.

Synthesis of Polymer:
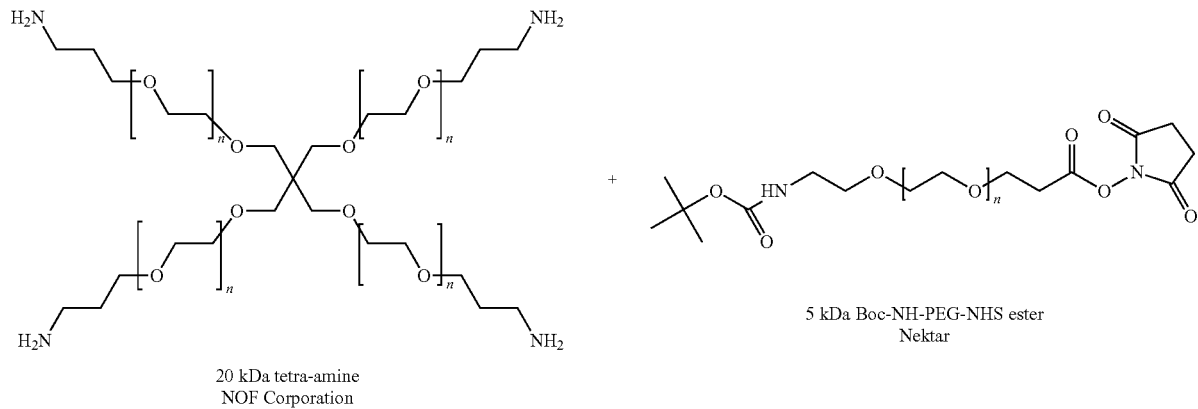
20 kDa tetra-amine
NOF Corporation
5 kDa Boc-NH-PEG-NHS ester
Nektar
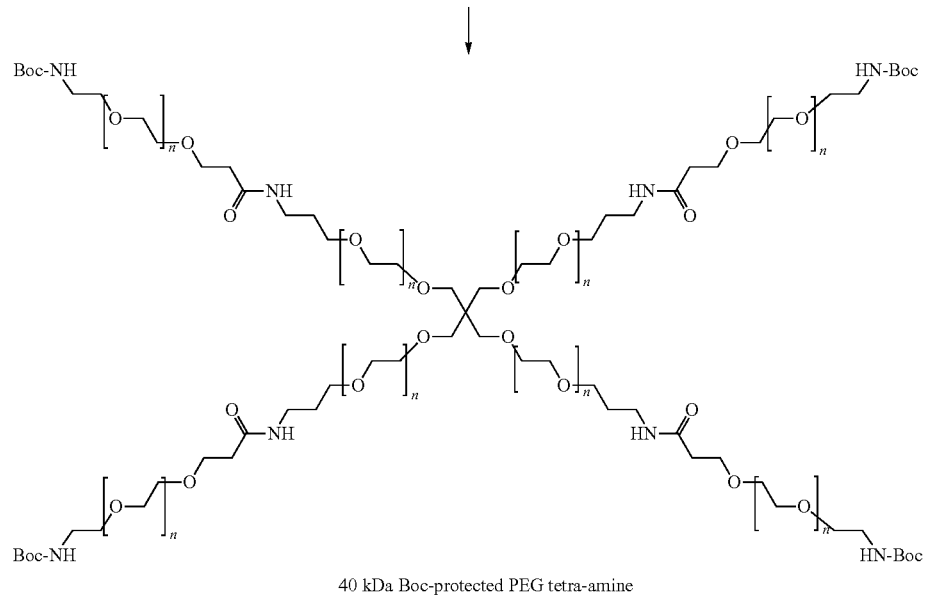
40 kDa Boc-protected PEG tetra-amine
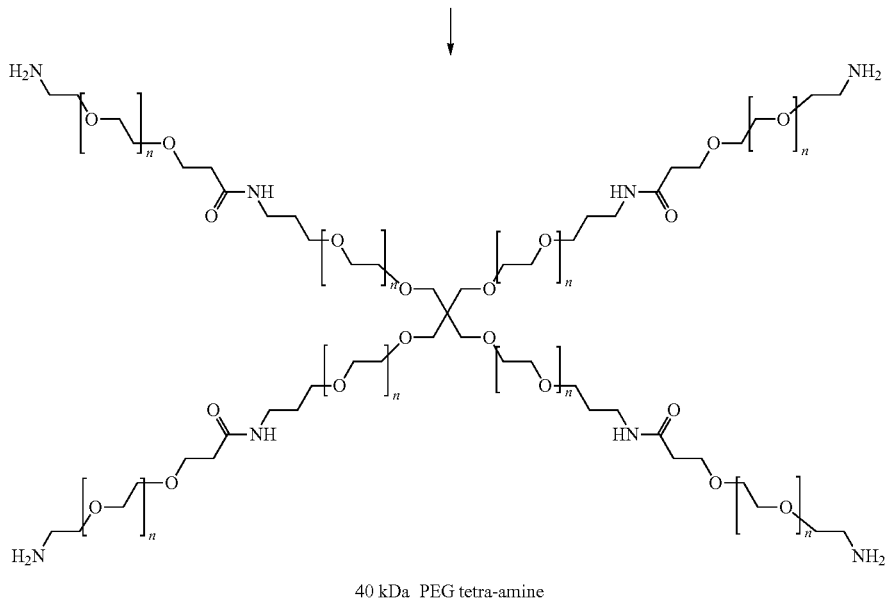
40 kDa PEG tetra-amine

40 kDa Boc-Protected PEG Tetra-Amine

The 20 kDa PEG tetra-amine (0.5 g, 0.025 mmol) and the 5 kDa Boc-NH-PEG-NHS ester (1 g, 0.2 mmol) were dissolved in $CH_2Cl_2$ (5 mL). Diisopropylethylamine (0.087 mL, 0.5 mmol) was added and the reaction stirred at room temperature for 18 hours. The reaction was concentrated in vacuo and taken up in MeOH (10 mL). 2% cross-linked polystyrene sulfonic acid resin (1.17 g) was added and the reaction vessel was swirled for 2 hours. The mixture was filtered and concentrated in vacuo to yield 1.4 g crude product as a beige solid. The residue was purified according to HPLC Method B to yield 0.44 g (44%) of the 40 kDa Boc-protected PEG tetra-amine as a white solid. HPLC Method C determined the product to be >96% pure (retention time=8.4 minutes). $^1$H NMR ($CDCl_3$) δ 6.75 (bs, 1H), 5.15 (bs, 1H), 3.64 (s, 2970H, PEG), 3.33-3.29 (m, 15H), 2.46-2.42 (t, 8H), 1.79-1.75 (m, 8H), 1.44 (s, 36H).

40 kDa PEG Tetra-Amine

The 40 kDa Boc-protected PEG tetra-amine (0.1 g, 0.0025 mmol) was dissolved in TFA (4 mL) and stirred at room temperature for 1.5 hours. The reaction was concentrated in vacuo to yield 120 mg 40 kDa PEG tetra-amine as a transparent residue. HPLC Method C determined the product to be >96% pure (retention time=6.2 minutes). $^1$H NMR ($CDCl_3$) δ 7.39 (bs, 1H), 6.75 (bs, 1H), 4.49-4.48 (m, 4H), 3.64 (s, 3253H, PEG), 3.35-3.33 (m, 15H), 2.49-2.46 (m, 8H), 1.80-1.75 (m, 8H).

T-Butyl Ester (104)

The 40 kDa PEG tetra-amine (0.1 g, 0.0025 mmol) was dissolved in $CH_2Cl_2$ (2 mL). Diisopropylethylamine (9 µL, 0.05 mmol) was added, followed by compound 101 (82 mg, 0.1 mmol). Another portion of diisopropylethylamine (9 µL) was added and the reaction was stirred at room temperature for 48 hours. The reaction was concentrated in vacuo to yield 110 mg crude 104 as a white solid. HPLC Method C determined the product to be >80% pure (retention time=10.9 minutes).

Conjugate 105

104 (0.1 g, 0.0024 mmol) was dissolved in formic acid (5 mL) and heated at 40° C. for 24 hours. The reaction was concentrated in vacuo and was purified according to HPLC Method A to yield 0.05 g (48%) of 105 as a white solid. HPLC Method C determined the conjugate to be >99% pure (retention time 7.6 minutes). $^1$H NMR ($CDCl_3$) δ 9.06 (bs, 4H), 8.83-8.82 (m, 4H), 8.20-8.17 (d, 4H), 8.05-8.03 (d, 4H), 7.63-7.61 (m, 8H), 7.53-7.49 (m, 4H), 7.42-7.33 (m, 8H), 7.09-7.05 (m, 4H) 6.70 (m, 4H), 4.84 (m, 4H), 4.62-4.50 (m, 12H), 3.64 (bs, 2357H, PEG), 3.36-3.29 (m, 12H), 2.46-2.42 (t, 8H), 1.79-1.74 (m, 8H), 1.30-1.25 (m, 24H).

Example 35

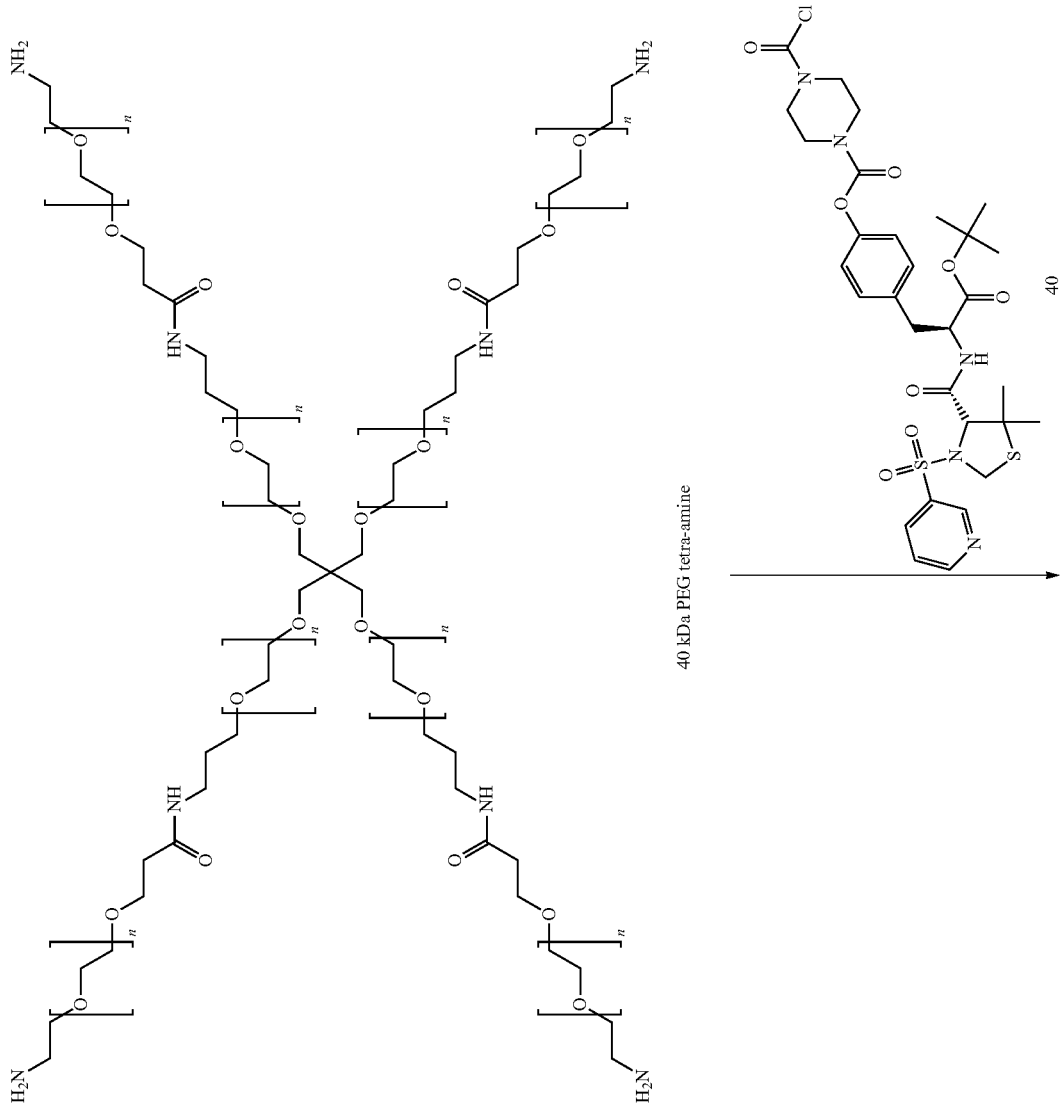

-continued
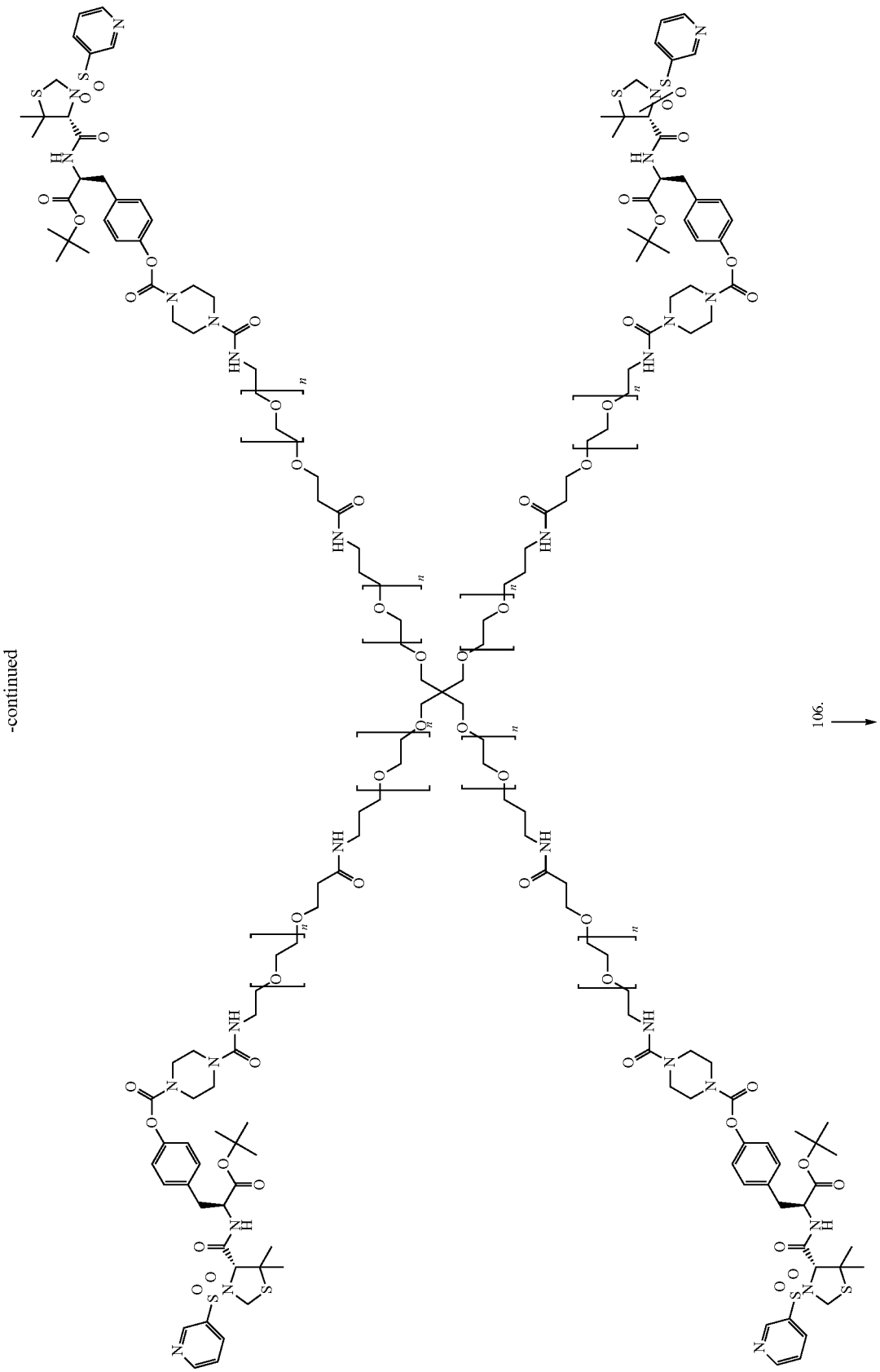
106.

-continued
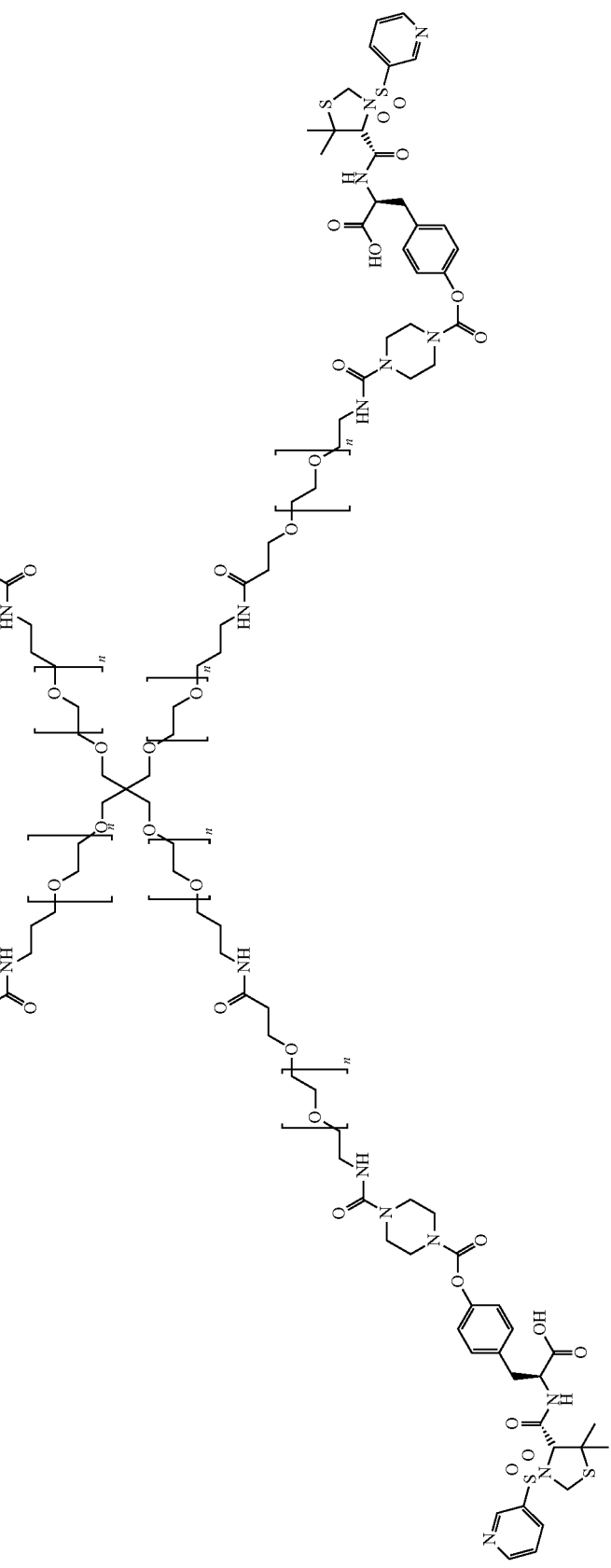
107.

T-Butyl Ester (106)

The 40 kDa PEG tetra-amine (37 mg, 0.000925 mmol) and DMAP (0.5 mg, 0.0037 mmol) were dissolved in $CH_2Cl_2$ (0.5 mL). Triethylamine (3 µL, 0.019 mmol) was added, followed by 40 (26 mg, 0.037 mmol). Another portion of triethylamine (3 µL) was added and the reaction was stirred at room temperature for 18 hours. The reaction was concentrated in vacuo to yield 34 mg crude 106 as a white solid. HPLC Method C determined the product to be >80% pure (retention time 10.9 minutes).

Conjugate 107

106 (34 mg, 0.0008 mmol) was dissolved in formic acid (4 mL) and heated at 40° C. for 24 hours. The reaction was concentrated in vacuo and purified according to HPLC Method A to yield 17 mg (50%) of 107 as a white solid. HPLC Method C determined the conjugate to be >99% pure (retention time=7.6 minutes). $^1$H NMR ($CDCl_3$) δ 9.06 (bs, 4H), 8.86 (bs, 4H), 8.17-8.15 (d, 4H), 7.52 (d, 4H), 7.26-7.23 (d, 8H), 7.02-6.99 (d, 8H), 6.72 (m, 4H), 5.69 (m, 4H), 4.80 (m, 4H), 4.60-4.47 (dd, 8H), 3.64 (bs, 1602H, PEG), 3.36-3.30 (dd, 8H), 3.16 (m, 8H), 2.46-2.42 (t, 8H), 1.24 (bs 24H).

Example 36

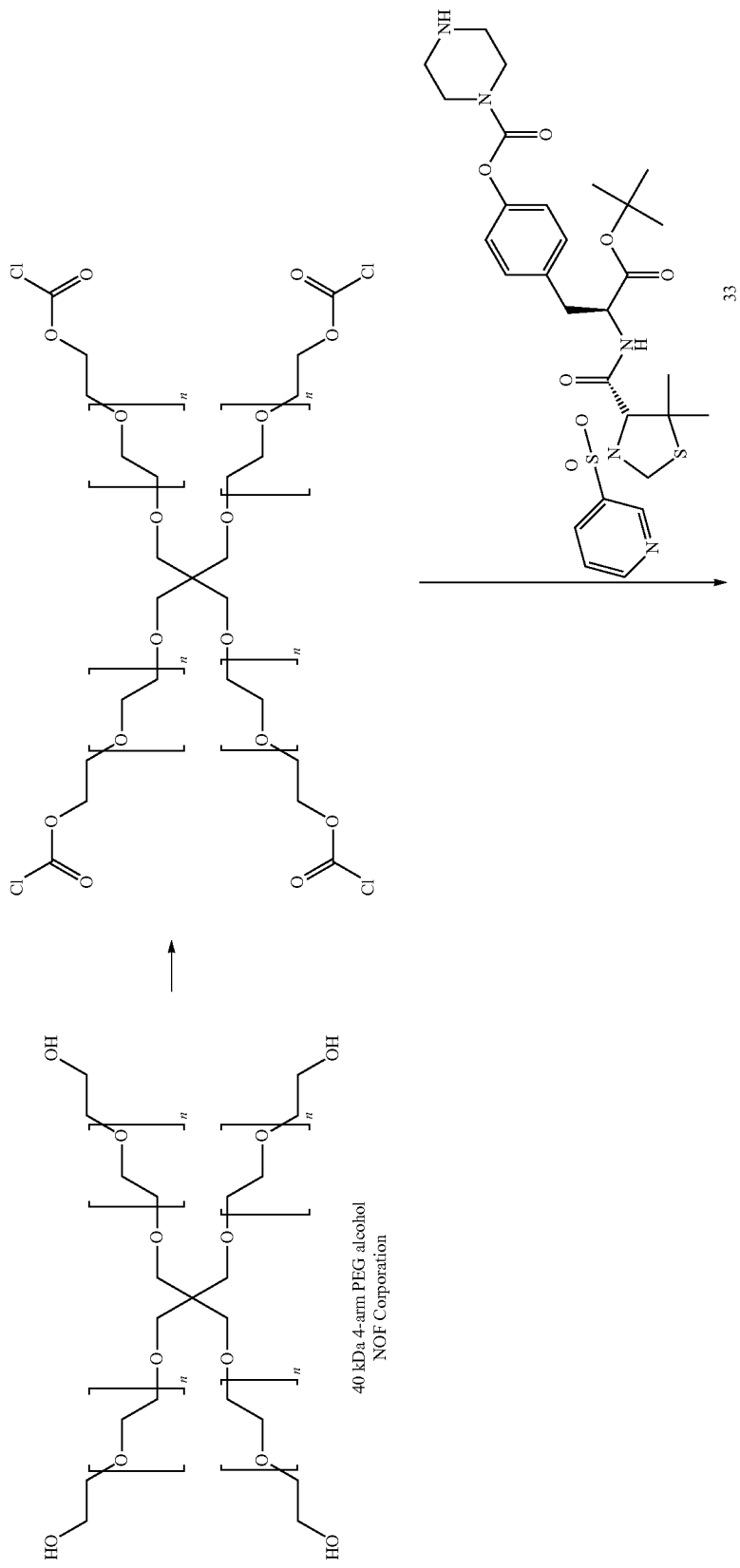

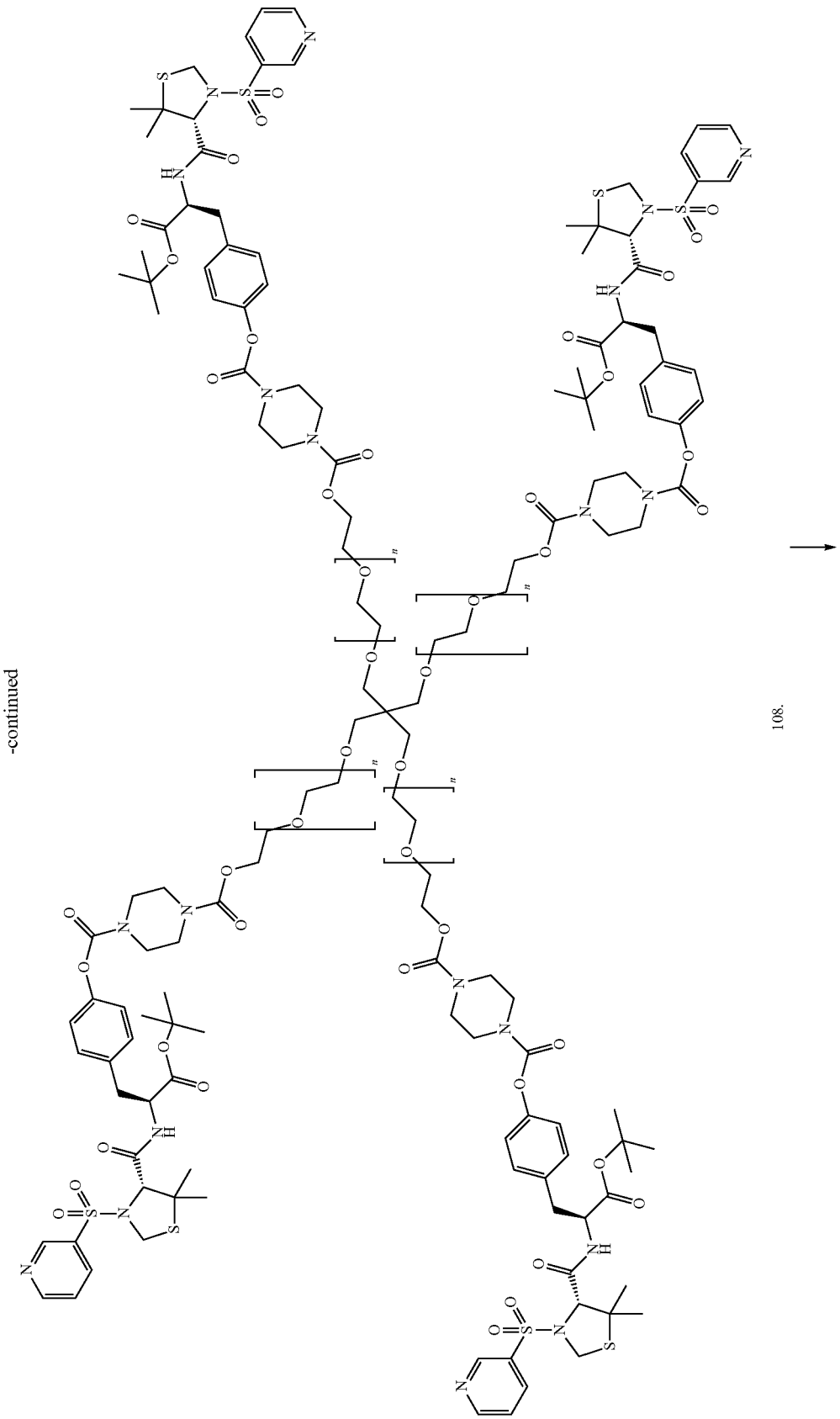

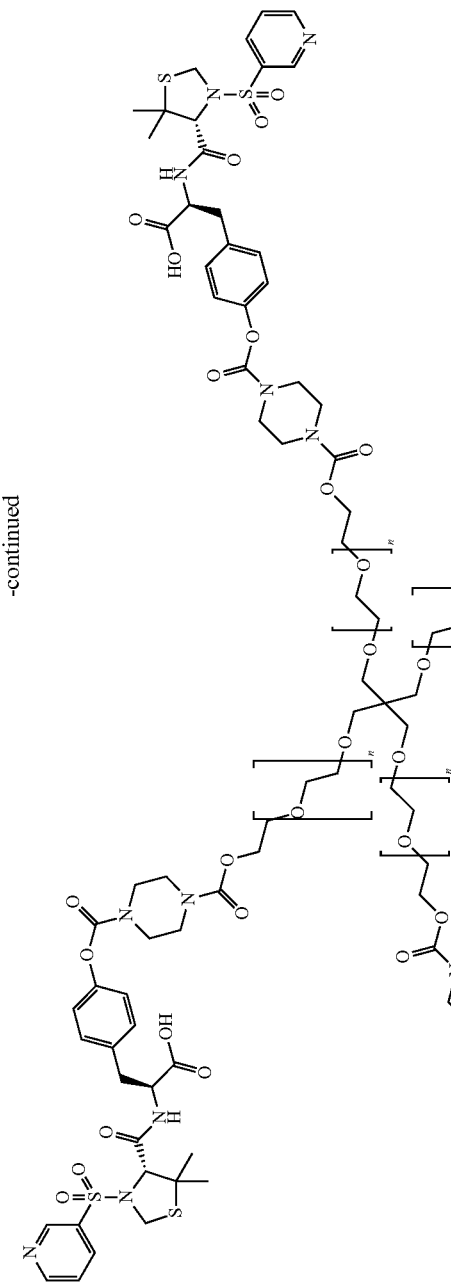
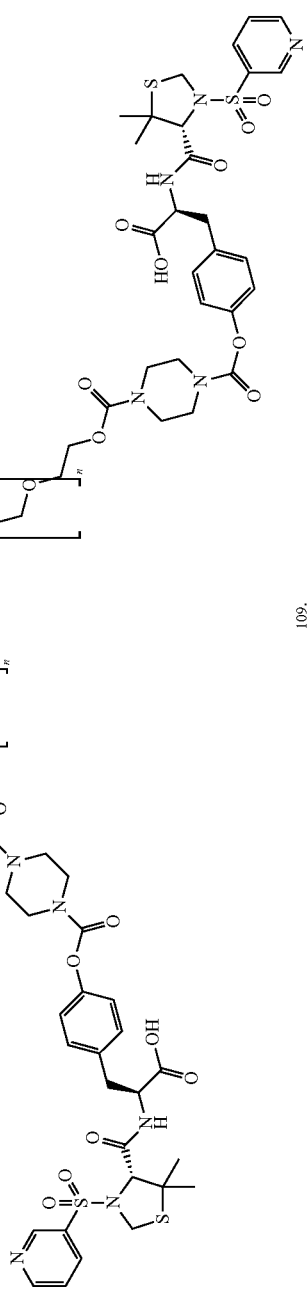
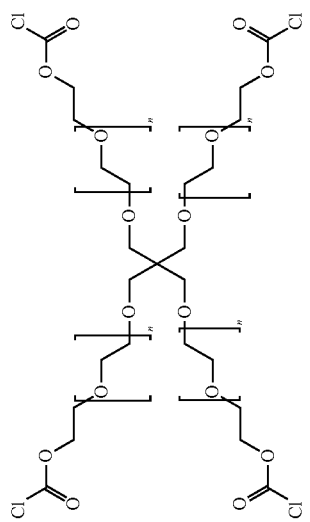

40 kDa PEG Tetra-Chloroformate

The 40 kDa 4-arm PEG alcohol (0.2 g, 0.005 mmol) was dissolved in CH$_2$Cl$_2$ (1 mL). To this was added a 2.0 M solution of phosgene in toluene (0.15 mL, 0.3 mmol). The reaction was stirred at room temperature for 18 hours. The reaction was concentrated in vacuo to yield 200 mg of the 40 kDa PEG tetra-chloroformate as a white solid.

T-Butyl Ester (108)

The 40 kDa PEG tetra-chloroformate (0.2 g, 0.005 mmol) was dissolved in CH$_2$Cl$_2$ (2 mL). To this was added 33 (63 mg, 0.1 mmol), followed by triethylamine (3.5 µL, 0.025 mmol). The reaction was stirred at room temperature for 72 hours. The reaction was concentrated in vacuo to yield 270 mg of 108 as a white solid.

Conjugate 109

108 (0.26 g, 0.006 mmol) was dissolved in formic acid (5 mL) and heated at 40° C. for 24 hours. The reaction was concentrated in vacuo and was purified according to HPLC Method A to yield 0.105 g (42%) of 109 as a white solid. HPLC Method C determined the conjugate to be >99% pure (retention time=8.3 minutes). $^1$H NMR (CDCl$_3$) δ 9.06 (bs, 4H), 8.85-8.84 (m, 4H), 8.17-8.14 (d, 4H), 7.53-7.49 (m, 4H), 7.26-7.22 (d, 8H), 7.01-6.98 (d, 8H), 4.81-4.78 (m, 4H), 4.59-4.46 (dd, 8H), 4.28-4.35 (m, 8H), 3.64 (bs, 3872H, PEG), 3.15-3.13 (m, 8H), 1.24-1.19 (m, 24H).

Example 37

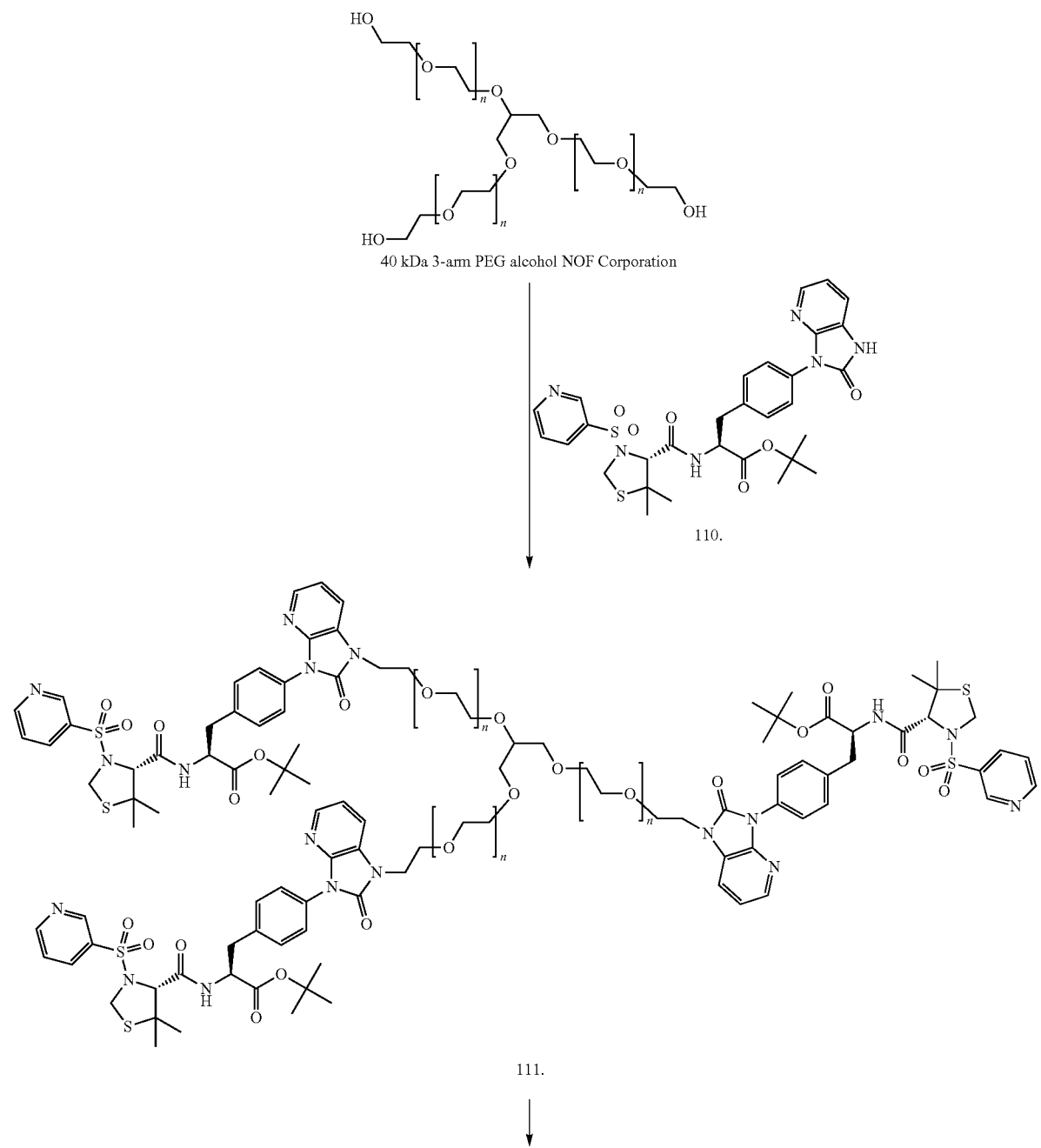

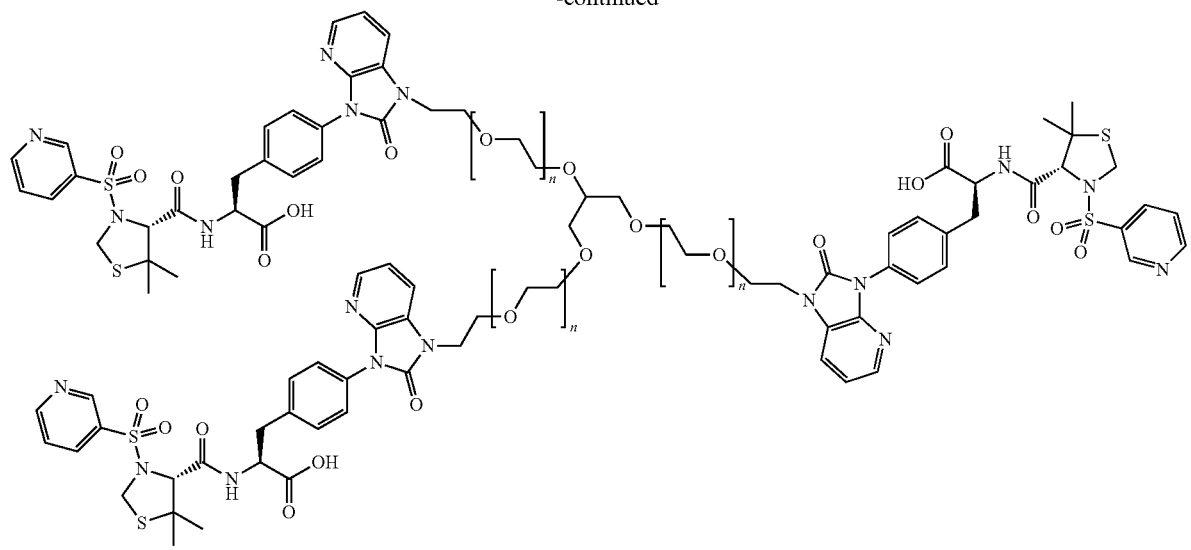

112.

T-Butyl Ester (111)

The 40 kDa 3-arm PEG alcohol (0.25 g, 0.00625 mmol), 110 (0.04 g, 0.056 mmol), and triphenylphosphine (0.025 g, 0.094 mmol) were dried by azeotropic distillation from toluene (5 mL). Half of the volume was distilled over (2.5 mL), and the mixture was cooled to room temperature. $CH_2Cl_2$ (0.5 mL) was added to make the reaction homogeneous. Diethylazodicarboxylate (0.015 mL, 0.094 mmol) was added dropwise and the reaction stirred for 48 hours. HPLC Method C showed the complete disappearance of the starting PEG alcohol. The reaction was concentrated in vacuo to yield the t-butyl ester 111 as a white solid.

Conjugate 112

111 (0.2 g, 0.005 mmol) was dissolved in formic acid (3 mL) and heated at 40° C. for 24 hours. The reaction was concentrated in vacuo and was purified according to HPLC Method A to yield 0.1 g (48%) of 112 as a white solid. HPLC Method C determined the conjugate to be >99% pure (retention time 8.1 minutes). $^1H$ NMR ($CDCl_3$) δ 9.08 (bs, 3H), 8.84 (bs, 3H), 8.18-8.16 (d, 3H), 8.02-8.00 (d, 3H), 7.67-7.61 (m, 6H), 7.47-7.38 (m, 9H), 7.08-7.04 (m, 3H), 6.91 (m, 3H), 4.88 (m, 3H), 4.62-4.49 (dd, 6H), 4.13 (m, 6H), 3.64 (bs, 5919H PEG), 3.23 (m, 6H), 1.25-1.24 (d, 18H).

Similar methods were used to synthesize the following conjugates:

Example 38

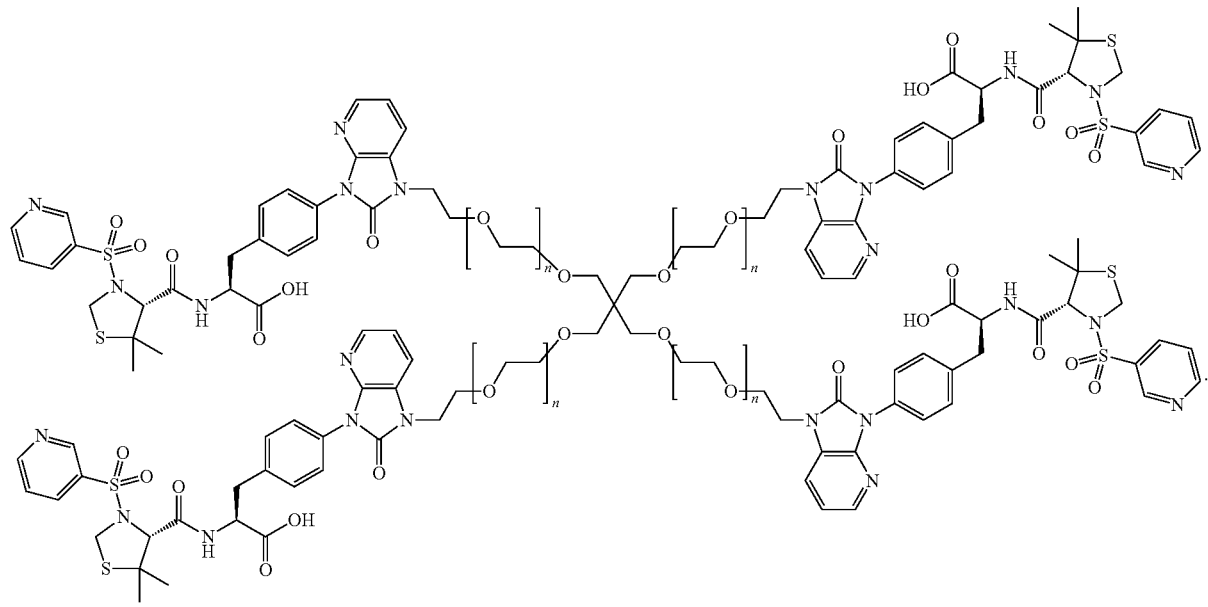

113

40 kDa 4-arm PEG alcohol was coupled to 110 and deprotected to final product using similar methods as with 112. The product was purified according to HPLC Method A. HPLC Method C determined the conjugate to be >95% pure (retention time 7.5-8.1 minutes). $^1$H NMR (CDCl$_3$) δ 9.08 (bs, 4H), 8.84 (bs, 4H), 8.18-8.16 (d, 4H), 8.02-8.00 (d, 4H), 7.67-7.61 (m, 8H), 7.47-7.38 (m, 12H), 7.08-7.04 (m, 4H), 6.91 (m, 4H), 4.88 (m, 4H), 4.62-4.49 (dd, 8H), 4.13 (m, 8H), 3.64 (bs, 10101H PEG), 3.23 (m, 8H), 1.25-1.24 (d, 24H).

Example 39

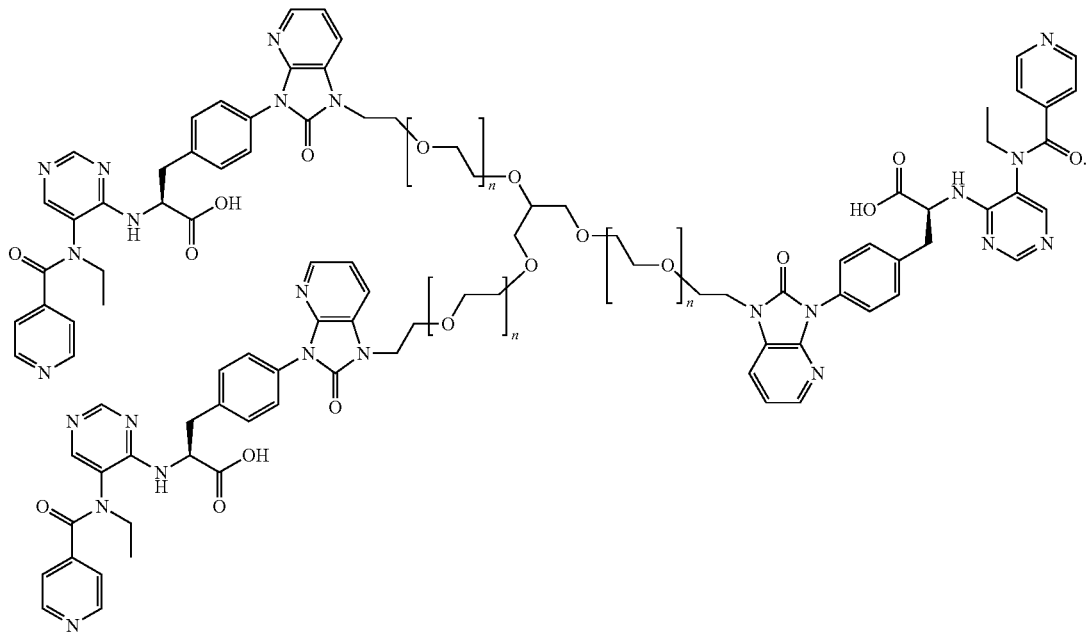

115

40 kDa 3-arm PEG alcohol was coupled to the t-butyl ester 114 (shown below) and deprotected to final product using similar methods as 112. The product was purified according to HPLC Method A. HPLC Method C determined the conjugate to be >95% pure (retention time 7.3 minutes). $^1$H NMR (CDCl$_3$) δ 8.66 (bs, 3H), 8.44 (bs, 3H), 8.04-8.02 (d, 3H), 7.75-7.30 (m, 24H), 7.10-7.06 (m, 3H), 6.93 (s, 3H), 5.60-5.50 (m, 3H), 4.15 (m, 6H), 3.66 (bs, 4270H PEG), 3.00 (m, 3H), 3.40-3.20 (m, 6H), 1.27 (d, 9H).

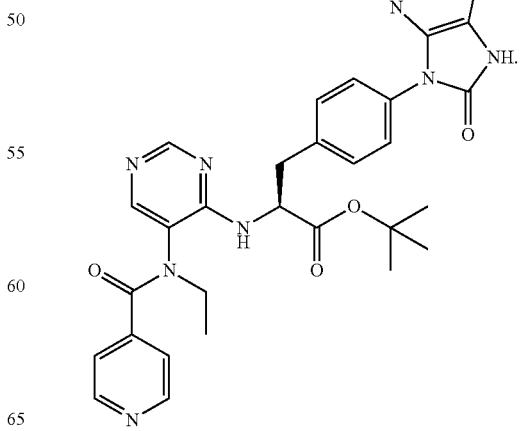

114

161
Example 40
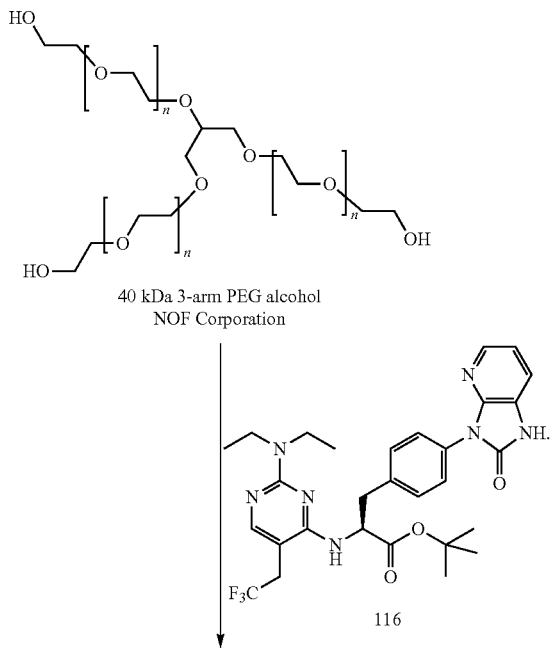
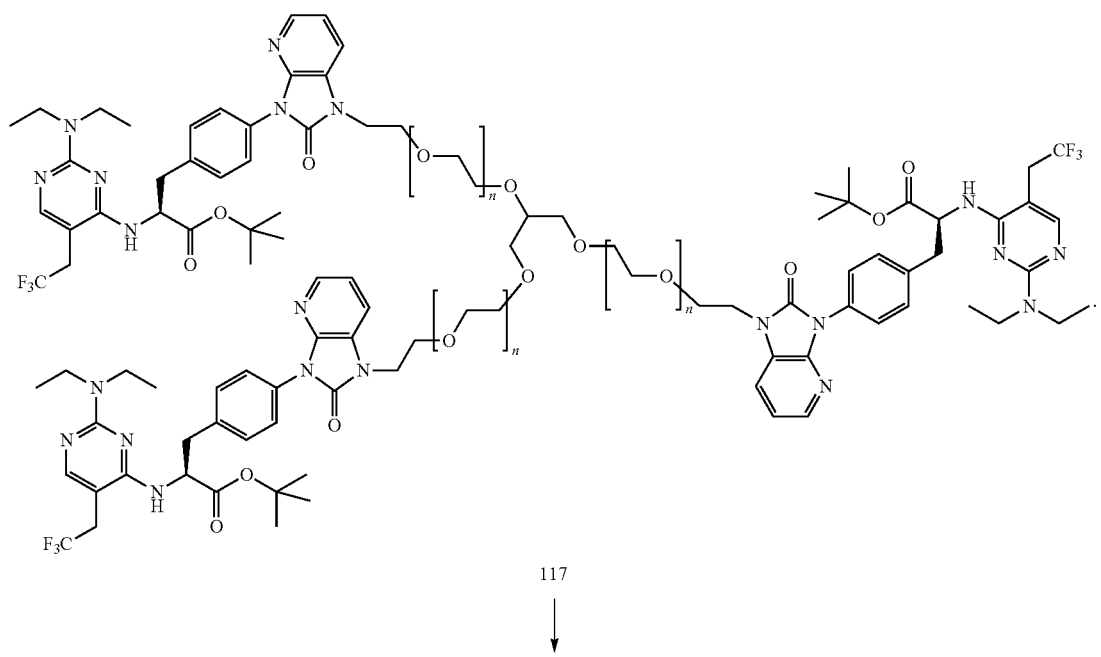

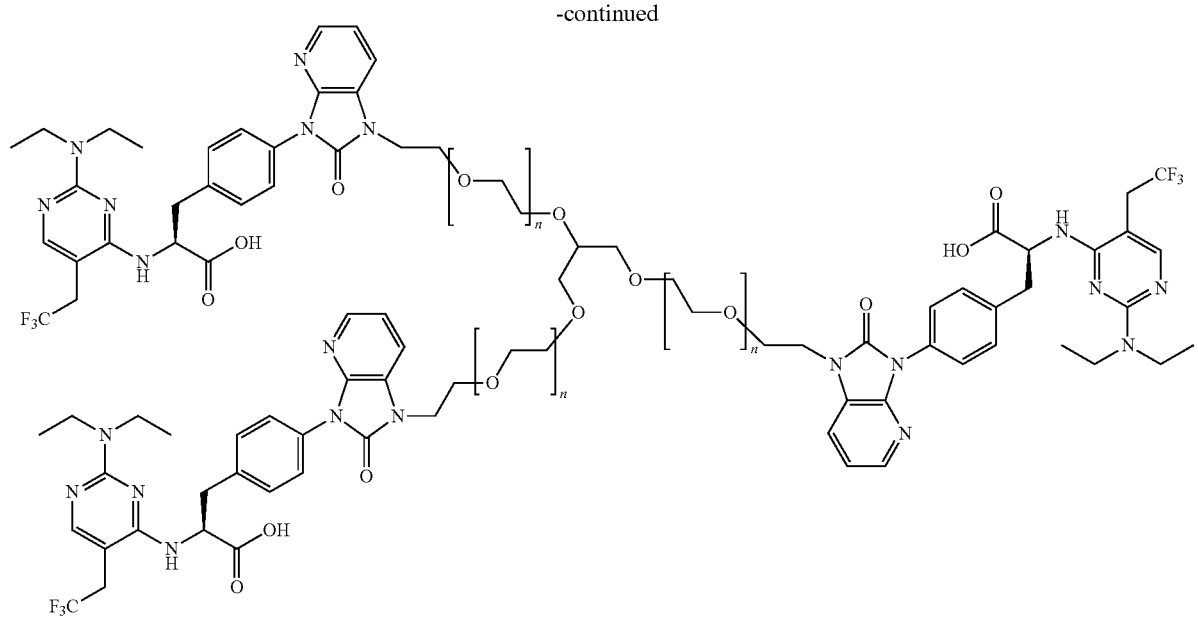

118.

T-Butyl Ester (117)

The 40 kDa 3-arm PEG alcohol (0.00625 mmol), 116 (0.056 mmol), and triphenylphosphine (0.094 mmol) are dried by azeotropic distillation from toluene (5 mL). Half of the volume is distilled over (2.5 mL), and the mixture is cooled to room temperature. $CH_2Cl_2$ (0.5 mL) is added to make the reaction homogeneous. Diethylazodicarboxylate (0.094 mmol) is added drop-wise and the reaction stirred for 48 hours. The reaction is concentrated in vacuo to yield the t-butyl ester 111.

Conjugate 118

118 (0.005 mmol) is dissolved in formic acid (3 mL) and heated at 40° C. for 24 hours. The reaction is concentrated in vacuo and is purified according to HPLC Method A to yield 112.

Example 41

Using the product of Example 29 and the PEG polymers used in Examples 38 and 39, the following conjugates are prepared:

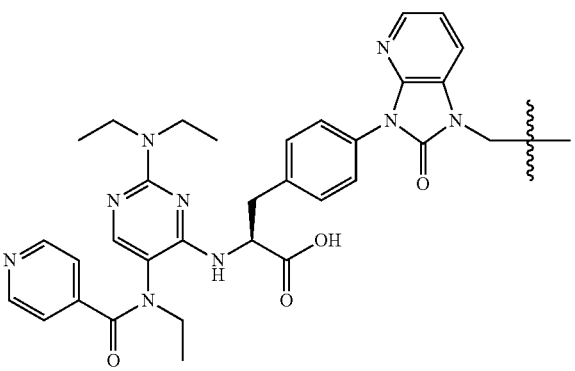

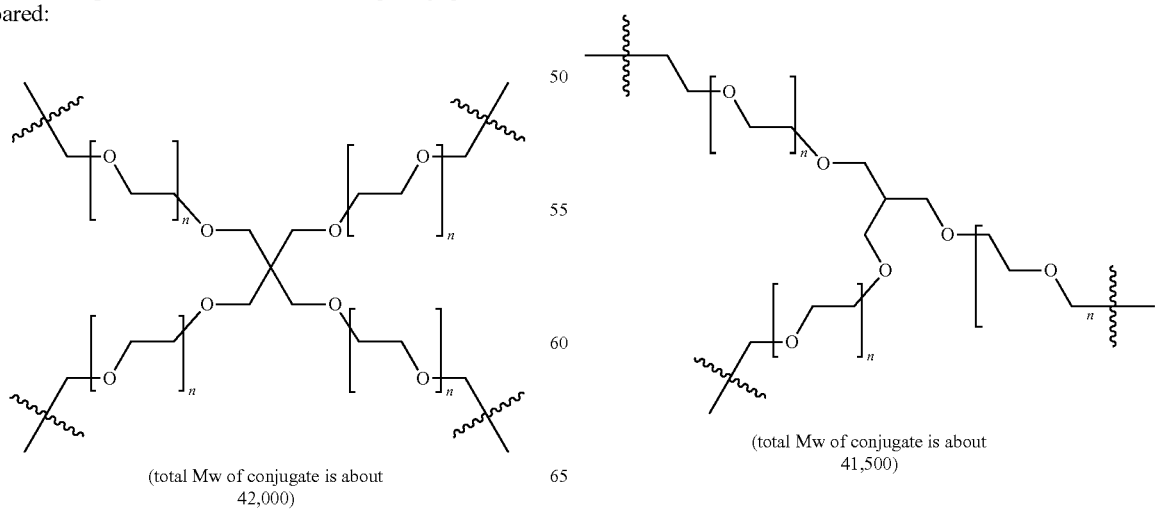

(total Mw of conjugate is about 42,000)

(total Mw of conjugate is about 41,500)

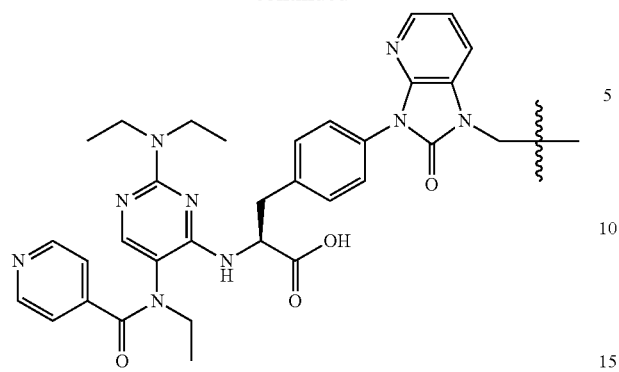
The following conjugates in Tables V and VI are prepared according to the examples and schemes described herein.

TABLE V

B—(A)$_t$

| Comp. No. | t | B Moieties | A Moieties |
|---|---|---|---|
| 1 | 2 homo-dimer | —C(O)(CH$_2$CH$_2$O)$_p$—C(O)— | (structure shown) |
| 2 | 3 homo-trimer | (branched structure with three —O—(CH$_2$CH$_2$O)$_p$C(O)— arms from a central carbon) | (structure shown) |

TABLE V-continued

| Comp. No. | t | B Moieties | A Moieties |
|---|---|---|---|
| 3 | 4 homo-tetramer | (pentaerythritol-based tetrameric PEG ester linker with —(OC(OCH₂CH₂)ₚ and —(CH₂CH₂O)ₚC(O)— arms) | (piperazine-N-carbonyloxy-phenyl)-CH₂-CH(COOH)-NH-C(O)-[5,5-dimethyl-3-(pyridin-3-ylsulfonyl)thiazolidin-4-yl] |
| 4 | 8 homo-octomer | Z | (piperazine-N-carbonyloxy-phenyl)-CH₂-CH(COOH)-NH-C(O)-[5,5-dimethyl-3-(pyridin-3-ylsulfonyl)thiazolidin-4-yl] |

TABLE V-continued

| Comp. No. | t | B Moieties | A Moieties |
|---|---|---|---|
| 5 | 2 homo-dimer | —C(O)O(CH₂CH₂O)ₚ—C(O)— | (structure) |
| 6 | homo-trimer | (branched tri-PEG ester structure) | (structure) |
| 7 | homo-tetramer | (pentaerythritol-based tetra-PEG ester structure) | (structure) |

TABLE V-continued

| Comp. No. | t | B Moieties | A Moieties |
|---|---|---|---|
| 8 | homo-octomer | Z | [structure: phenylsulfonyl-pyridyl-prolyl amide linked to tyrosine-COOH with O-C(O)-NH-CH₂CH₂-NH- terminus] |
| 9 | homo-dimer | —C(O)O(CH₂CH₂O)ₚ—C(O)— | [structure: —(OCH₂CH₂)ₙ—O-C(O)-NH-CH₂-phenyl-SO₂-prolyl amide linked to tyrosine with O-C(O)-N(CH₃)₂ terminus] |

TABLE V-continued

| Comp. No. | t | B Moieties | A Moieties |
|---|---|---|---|
| 10 | hetero-dimer | —C(O)O(CH₂CH₂O)ₚ—C(O)— | First A Moiety / Second A Moiety (see structures) |

$$B\!-\!\!(A)_t$$

Z = (see structure)

where in each of the structures the sum of all p's is from 200 to 1360.
TABLE VI
| B Moieties | A Moieties |
|---|---|
| ZZ (total Mw of conjugate is about 42,000) | 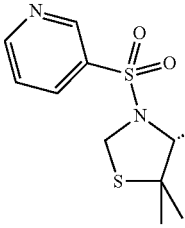 |
| ZZ (total Mw of conjugate is about 42,000) | 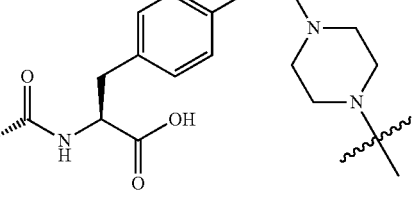 |
| ZZZ (total Mw of conjugate is about 41,000) | 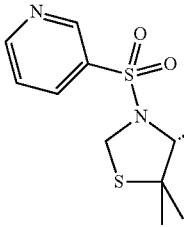 |
| 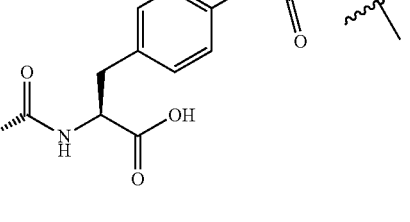 (total Mw of conjugate is about 42,000) | 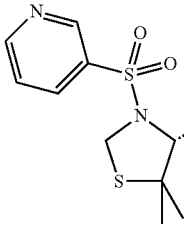 |

TABLE VI-continued
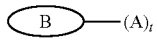
| B Moieties | A Moieties |
|---|---|
| 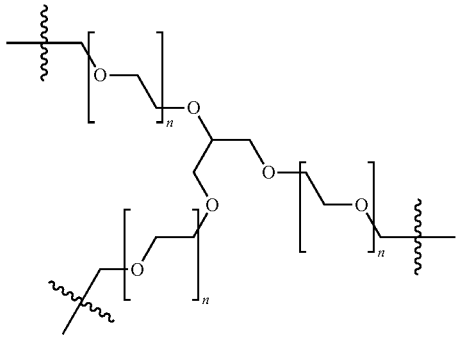<br>(total Mw of conjugate is about 41,500) | 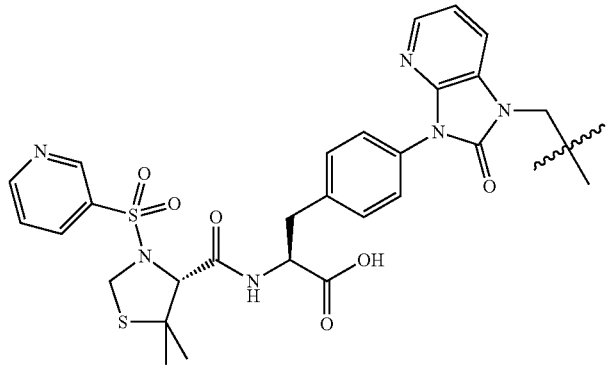 |
| 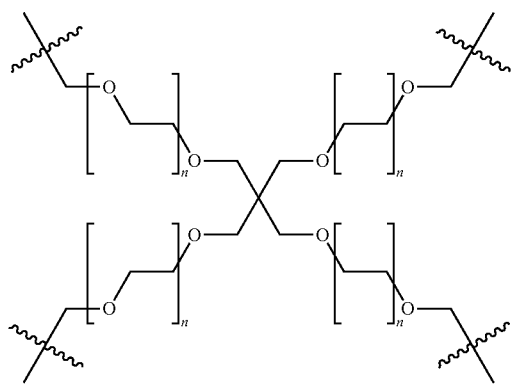<br>(total Mw of conjugate is about 42,000) | 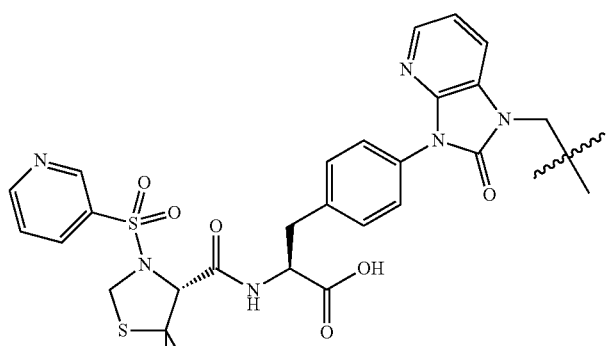 |
| 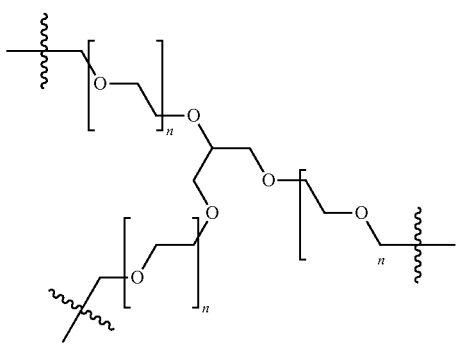<br>(total Mw of conjugate is about 41,500) | 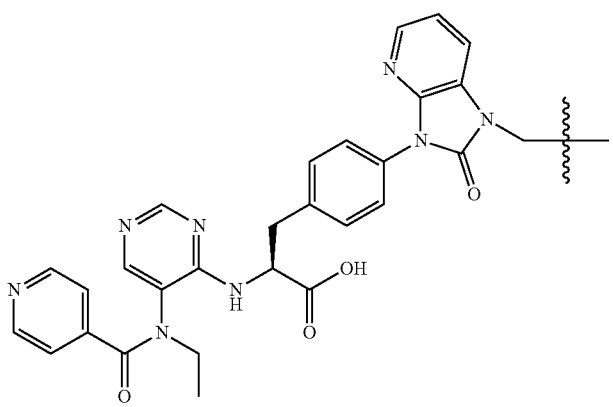 |

TABLE VI-continued

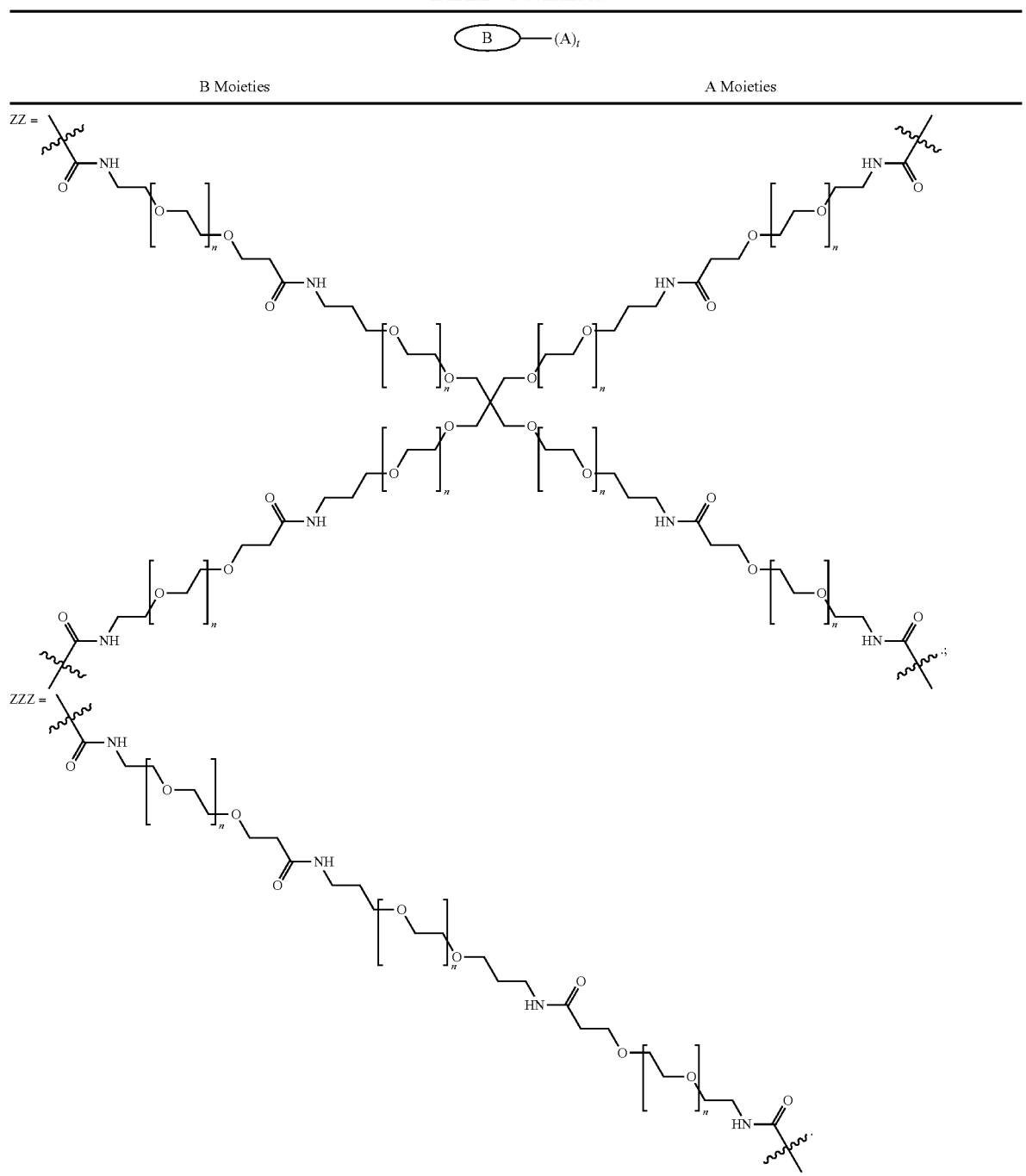

Biological Examples

Example A

In Vitro Assays for Determining Potency of Candidate Compounds

15/7 epitope induction on Jurkat TM (15/7 LIBS)

Log-phase Jurkat TM cells are incubated in a 96 wells Flexiplate under the following conditions: $10^5$ cells/100 μl/well in assay buffer (20 mM Hepes, 140 mM NaCl, 1 mM CaCl$_2$, 1 mM MgCl$_2$ and 0.3% BSA), 10 μg/ml 15/7 (Elan), and compound at a range of concentrations. The incubation is performed for 30 minutes at RT. Cells are then washed twice with assay buffer and incubated with Goat Fab'2 anti Ms IgG (Fc)-PE (Immunotech cat# PN IM0551) at 1:200 in assay buffer for 30 minutes on ice in the dark. Cells are then washed once and re-suspended in 300 μl cold assay buffer for FACS analysis (Becton-Dickinson).

Multivalent Ligand Competition Assay (MVCOMP)

Methods:

Integrin receptors mediate cell adhesion through a multivalent interaction with their specific ligands—multiple integrin receptors simultaneously engaging multiple ligand molecules within an adhesive substrate. To simulate this physiological interaction in a highly sensitive, quantitative assay, a multivalent ligand probe was developed that binds specifically to a4 integrin on the surface of lymphocytes. The probe consists of a small molecule ligand for a4 integrin, compound 200 (structure shown below), conjugated to a mouse IgG carrier molecule in a 6-10-fold molar excess (6-10 small molecule: 1 IgG). This binding is inhibited by 21/6, and antibody to α4. Once bound to the cell surface, the conjugate can be measured with a fluorescently-labeled secondary antibody against mouse IgG by FACS analysis. In this assay two different mouse monoclonal IgG carrier molecules have been used, TM2a and 27/1, neither of which bind to human lymphocytes unless conjugated with the a4 ligand.

200

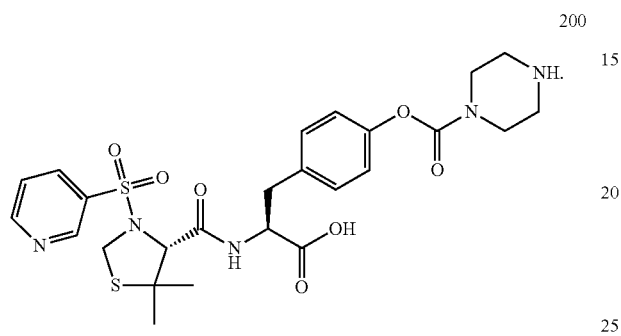

Small Molecule-Antibody Reagent Conjugation

Approximately 1 mg of TM2a or 27/1 (Elan) antibody was incubated with a 1:6 or 1:10 molar excess of compound 200 in the presence of [Bis(sulfosuccinimidyl)substrate] (Pierce) at 50-fold molar excess in a 1.0 ml total volume for 60 minutes at room temperature, with stirring. The reaction was then quenched with the amine-containing buffer TRIS-Cl at pH 7.5 for 20 minutes. The product was dialyzed twice for 24 hours against 4,000 volumes PBS at 4 degrees C. in 10 KD MW cutoff membrane cassettes to remove unbound small molecule and linking reagent.

Competitive Binding Assay

Jurkat cells (subline TM, subclone #15, Elan) were incubated with a titration of various test compounds in the presence of the TM2a or 27/1 conjugate diluted at 1:100 in assay buffer for 30 minutes at room temperature. Unbound reagent was then removed by several wash steps in which the cells were pelleted in a Beckman table top centrifuge at 300×g for 5 minutes, then resuspended in fresh buffer. Remaining bound antibody conjugate was detected by incubating the cells with Goat F(ab')$_2$ anti-mouse IgG (Fc)-Phycoerythrin (BeckmanCoulter) for 30-minutes at 4 degrees C., followed by washing and FACS analysis.

2G3 Epitope Induction on 8866 cells (2G3 Ligand Induced Binding Site)

Log-phase 8866 cells are incubated in a 96 wells Flexiplate under the following conditions: $10^5$ cells/100 Owen in assay buffer (PBS, 1 mM CaCl$_2$, 1 mM MgCl$_2$, 5% FBS), 10 μg/ml 2G3 (Elan), and compound at a range of concentrations. The incubation is performed for 30 minutes at RT. Cells are then washed twice with assay buffer and incubated with Goat Fab'2 anti Ms IgG (Fc)-PE (Immunotech cat# PN IM0551) at 1:200 in assay buffer for 30 minutes on ice in the dark. Cells are then washed once and re-suspended in 300 μl cold assay buffer for FACS analysis (Becton-Dickinson).

The invention claimed is:

1. A conjugate of the formula I:

I

B is a polyoxyalkylene polymer moiety comprising at least one polymeric unit, the polymer moiety having an average molecular weight of from about 20,000 to 60,000;

q is from about 2 to about 20;

A at each occurrence is independently a compound of formula II

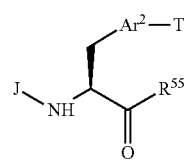

II or a pharmaceutically acceptable salt thereof, wherein each polymeric unit is derived only from alkylene oxide monomers selected from the group consisting of ethylene oxide, propylene oxide, isopropylene oxide, butylene oxide, and mixtures thereof, and the polymer moiety contains optional linker groups between polymeric units;

J is a group of formula (b):

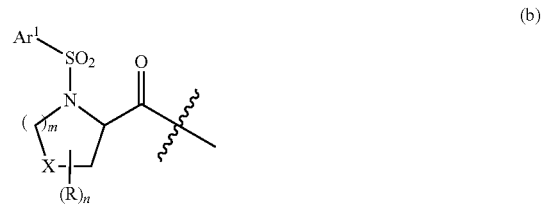

(b)

wherein m is 1;

n is an integer equal to 0, 1 or 2;

R is hydrogen, $R_{101}$, $R_{204}$, or $R_{205}$;

Ar$^1$ is selected from the group consisting of phenyl and heteroaryl wherein Ar$^1$ is optionally covalently bound to the polymer moiety wherein the polymer moiety optionally comprises a linker which covalently links the polymer moiety to Ar$^1$, and where Ar$^1$ is optionally substituted with from 1 to 3 groups that are independently $R_{201}$, $C_3$-$C_{10}$ cycloalkyl optionally substituted with $R_{201}$, heterocloalkyl optionally substituted with $R_{201}$, or $C_1$-$C_6$ alkyl optionally substituted with $R_{201}$;

Ar$^2$ is phenyl, wherein Ar$^2$ is optionally covalently bound to the polymer moiety and wherein the polymer moiety optionally comprises a linker which covalently links the polymer moiety to Ar$^2$, and where Ar$^2$ is optionally substituted with from 1 to 3 groups that are independentlu $R_{201}$, $C_3$-$C_{10}$ cycloalkyl optionally substituted with $R_{201}$ heterocloalkyl optionally substituted with $R_{201}$, or $C_1$-$C_6$ alkyl optionally substituted with $R_{201}$;

X is selected from the group consisting of —NR$^1$—, —O—, —S—, —SO—, —SO$_2$ and optionally substituted —CH$_2$— which is optionally covalently bound to the polymer moiety wherein, in each case, the polymer moiety optionally comprises a linker which covalently links the polymer moiety;

where $R^1$ is selected from the group consisting of hydrogen and alkyl;

T is a group of formula (d)

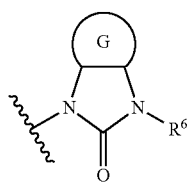

(d)

wherein G is optionally substituted pyrido group wherein said pyrido optionally further comprises a covalent bond to a polymer moiety which optionally comprises a linker;

$R^6$ is a covalent bond to a polymer moiety which optionally comprises a linker, or $R^6$ is —H, $R_{201}$ or —$CH_2C(O)R^{17}$, wherein $R^{17}$ is —OH, —$OR^{18}$, or —$NHR^{18}$, wherein $R^{18}$ is $R_{201}$, $R_{204}$, or $R_{205}$;

$R_{101}$ is alkyl optionally substituted with from 1 to 3 groups independently selected from $R_{201}$, $R_{202}$, $R_{203}$, $R_{204}$, and $R_{205}$, where $R_{201}$ is alkoxy, acyl, acylamino, acyloxy, amino, mono- or di($C_1$-$C_5$)alkyamino, aminoacyl, aryloxy, cyano, halogen, hydroxyl, nitro, carboxyl, —C(O)O—($C_1$-$C_6$)alkyl, or —C(O)O-aryl;

$R_{202}$ is $C_3$-$C_{10}$ cycloalkyl optionally substituted with from 1 to 5 groups which are independently oxo, thioxo, $R_{201}$ heterocycloalkyl optionally substituted with $R_{201}$, aryl optionally substituted with $R_{201}$, or heteroaryl optionally substituted with $R_{201}$;

$R_{203}$ is heterocycloalkyl optionally substituted with from 1 to groups which are independently oxo thioxo $R_{201}$, or $C_1$-$C_5$ alkyl optionally substituted with $R_{201}$;

$R_{204}$ is aryl optionally substituted with from 1 to 3 groups that are independently $R_{201}$, $C_3$-$C_{10}$ cycloalkyl optionally substituted with $R_{201}$, heterocycloalkyl optionally substituted with $R_{201}$, or $C_1$-$C_5$ alkyl optionally substituted with $R_{201}$;

$R_{205}$ is heteroaryl optionally substituted with from 1 to 3 groups that are independently $R_{201}$, $C_3$-$C_{10}$ cycloalkyl optionally substituted with $R_{201}$, heterocycloalkyl optionally substituted with $R_{201}$ or $C_1$-$C_5$ alkyl optionally substituted with $R_{201}$; and $R^{55}$ is —OH or a hydrolyzable ester, or $R^{55}$ forms a hydrolyzable polymer ester with the polymer moiety, optionally through a linker;

provided that:

A. at least one of J, $R^{55}$, and T contains a covalent bond to the polymer moiety; and B. the conjugate of formula I has a molecular weight of no more than about 80,000.

2. The conjugate according to claim 1, wherein only one of J, $R^{55}$ and T contains a covalent bond to a polymer moiety.

3. The conjugate according to claim 1, wherein n is 2, R at each occurrence is $C_1$-$C_3$ alkyl, and both R groups are on the same carbon.

4. The conjugate according to claim 1, wherein q is an integer of from 2 to about 8.

5. The conjugate according to claim 1, wherein A at each occurrence is independently a compound of formula IIi:

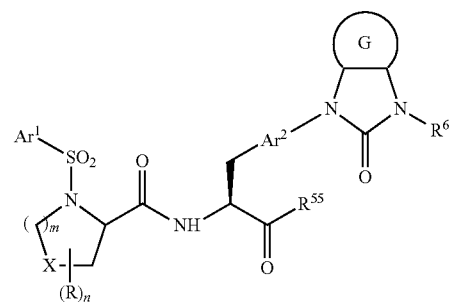

IIi or a pharmaceutically acceptable salt thereof.

6. The conjugate according to claim 5 wherein X is S, and R at each occurrence is independently selected from hydroxyl, alkyloxy, alkyl, or a covalent bond to the polymer moiety.

7. The conjugate according to claim 6 wherein n is 2, and R at both occurrences is methyl.

8. The conjugate according to claim 1, wherein A and B are as shown below:

| B Moieties | A Moieties |
|---|---|
| ZZ (total Mw of conjugate is about 42,000) | 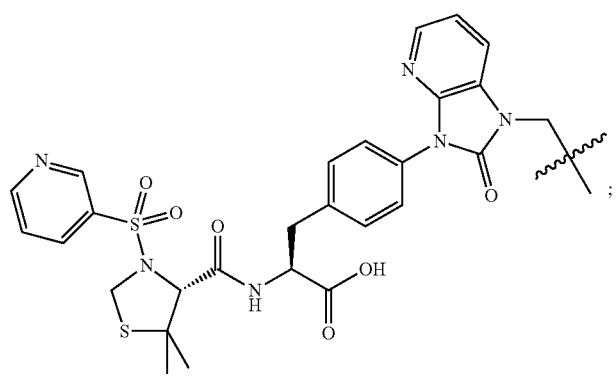 |

| B Moieties | A Moieties |
|---|---|
| ZZZ (total Mw of conjugate is about 41,000) | 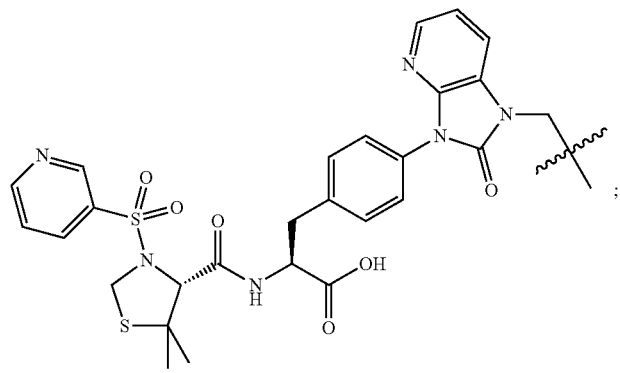 ; |
| 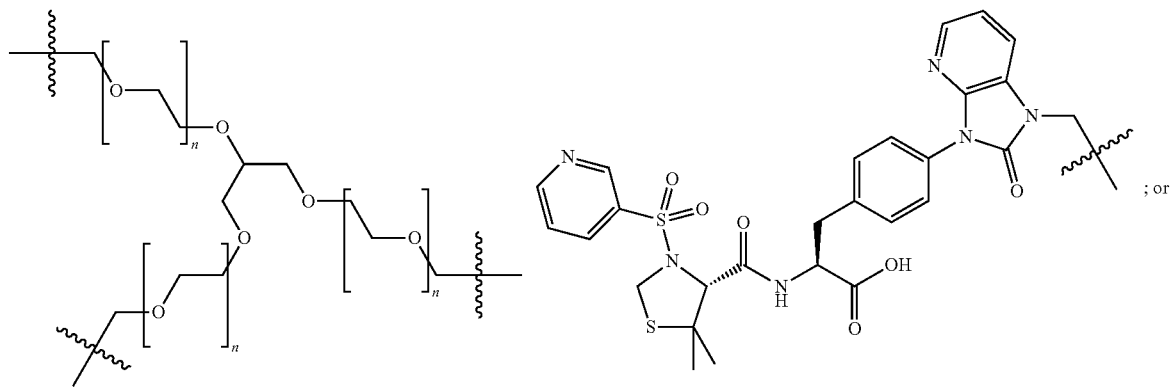 (total Mw of conjugate is about 41,500) | ; or |
| 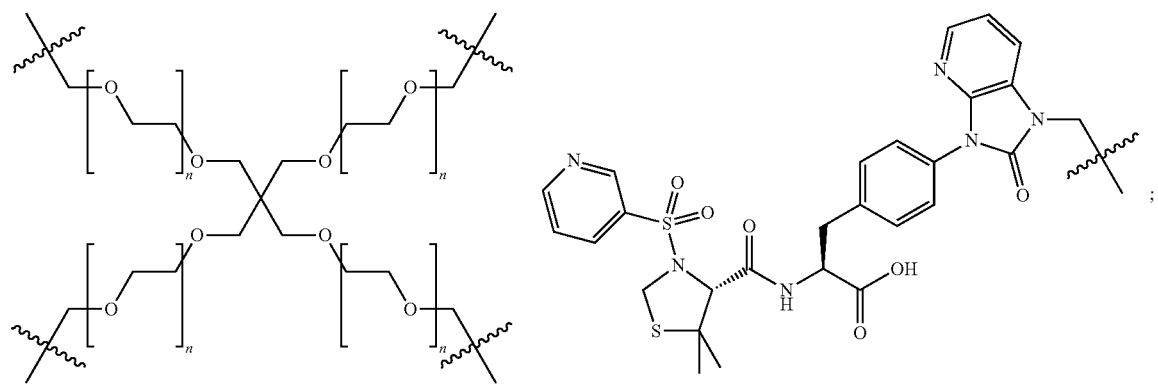 (total Mw of conjugate is about 42,000) | ; |

| B Moieties | A Moieties |
|---|---|
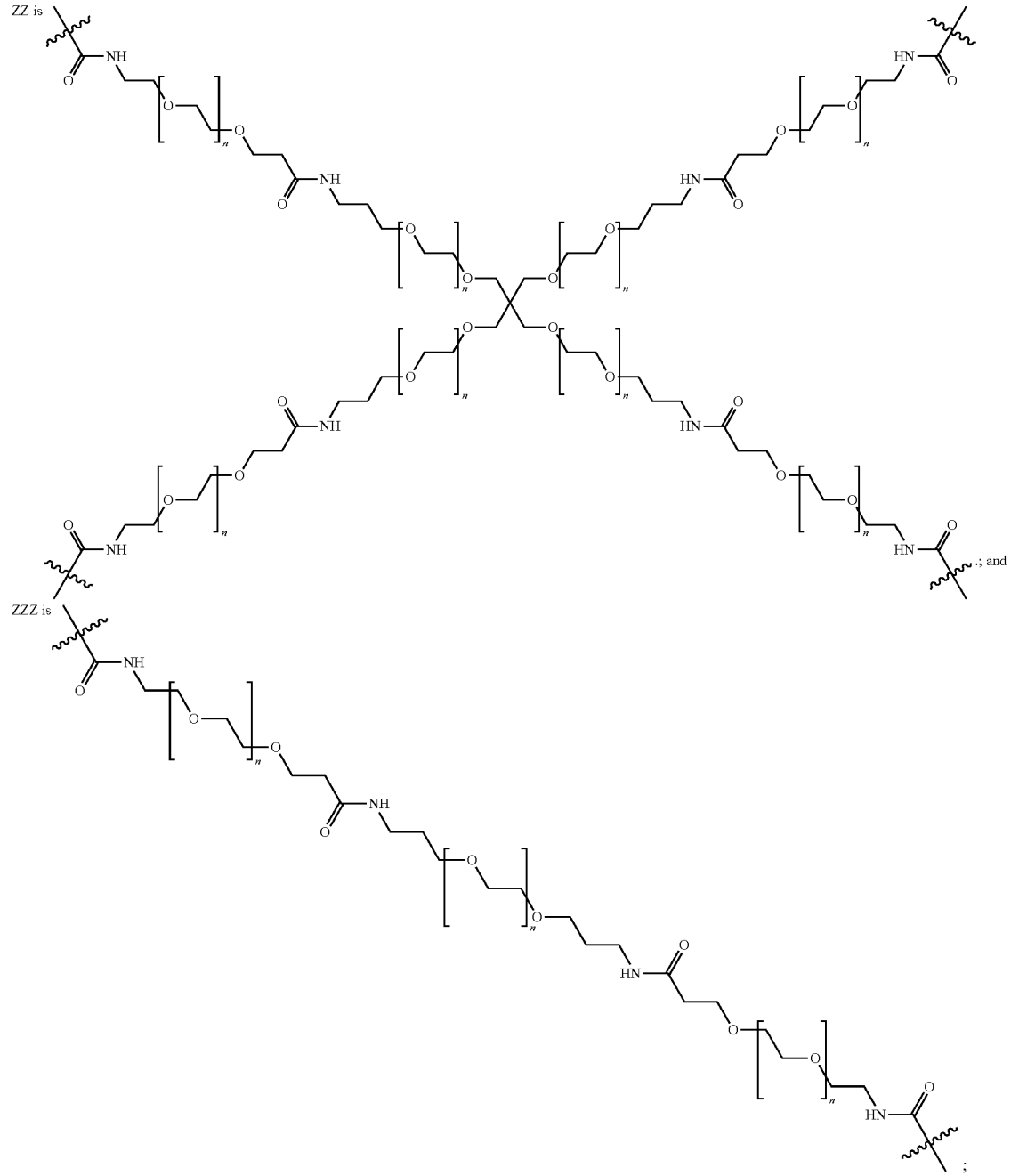
where the sum of all the n variables is from 100 to 1360.
9. A conjugate according to claim 1, selected from the group consisting of:

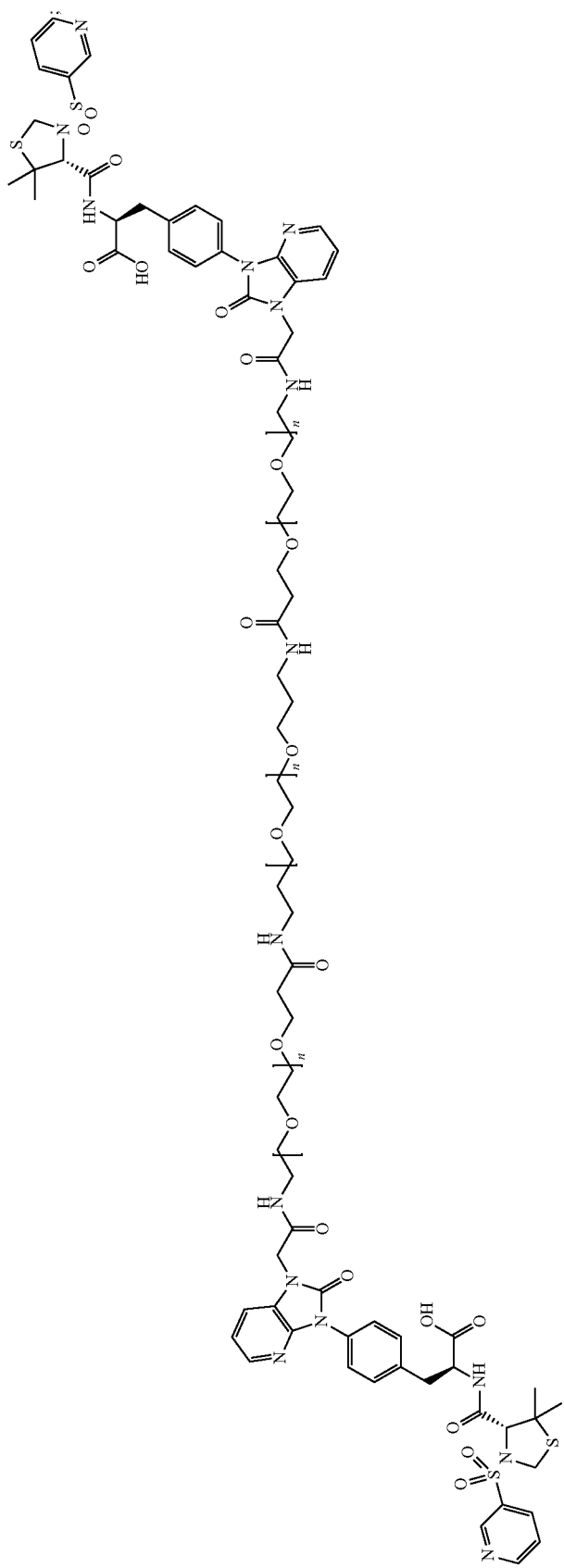

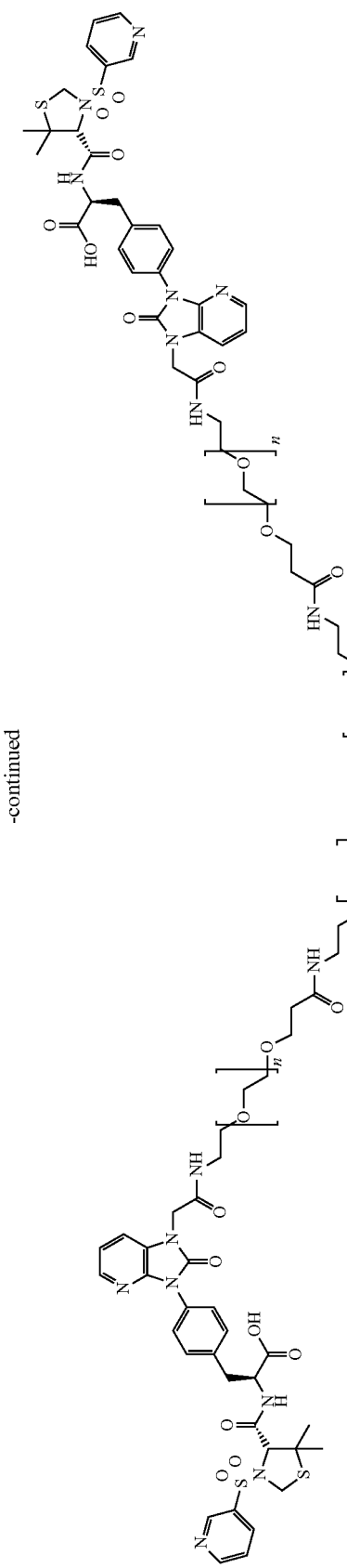

-continued
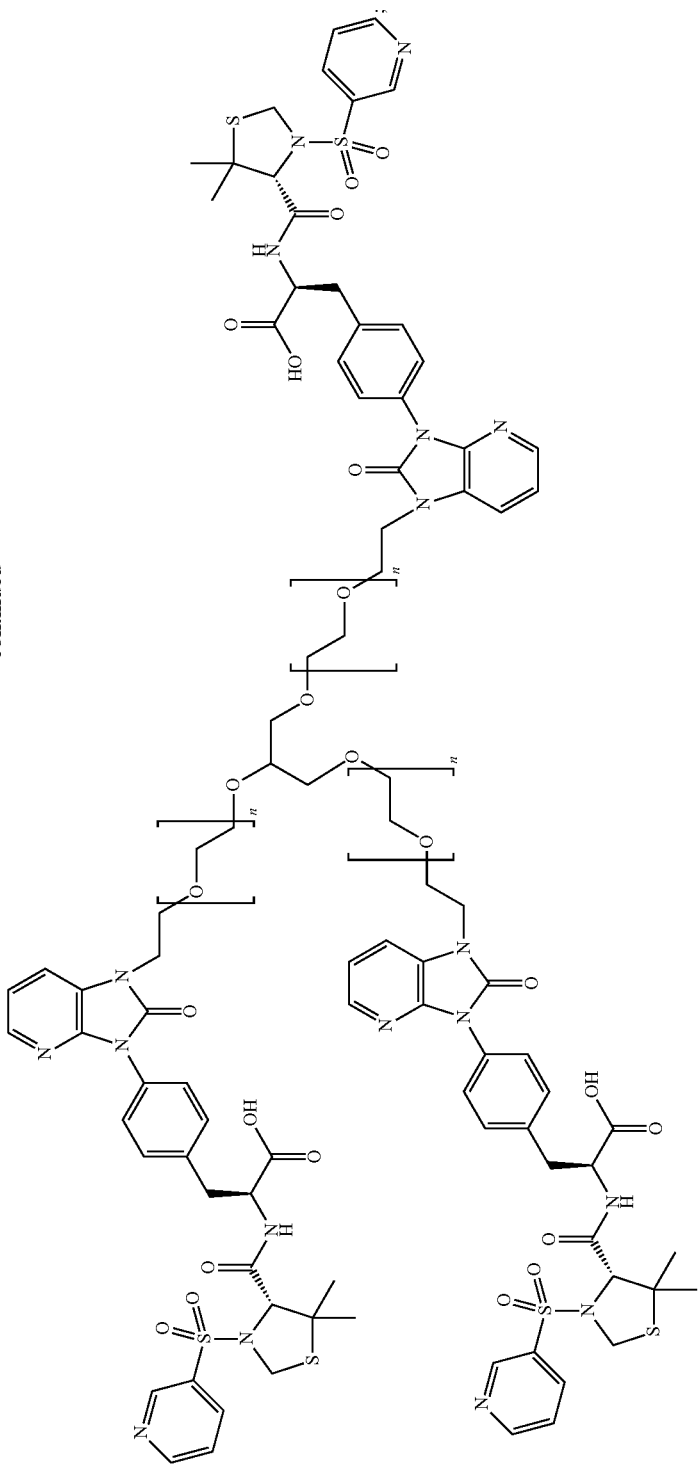

-continued
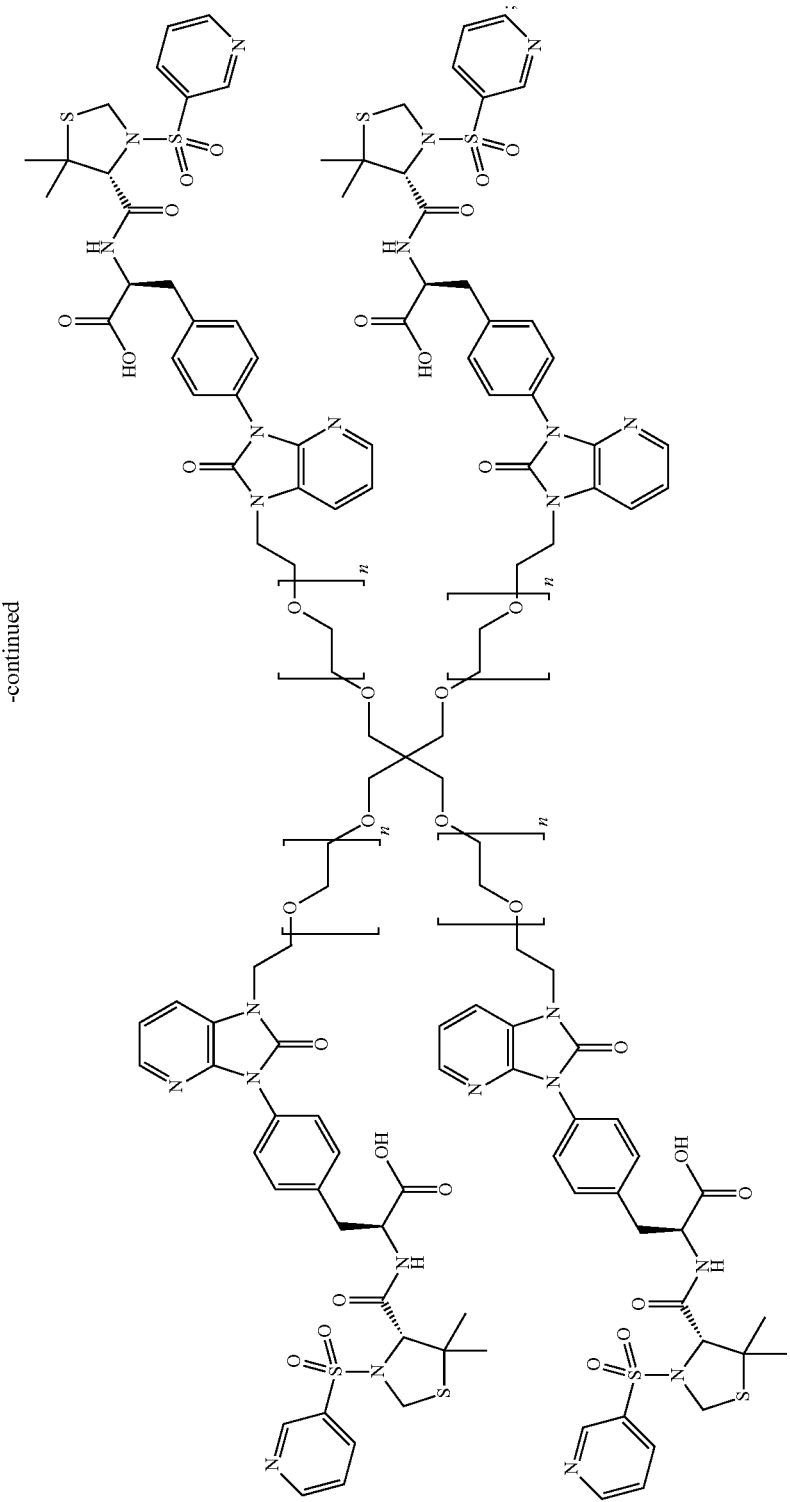

where the sum of all the n variables is from 100 to 1360 and a pharmaceutically acceptable salt thereof.

10. A pharmaceutical composition comprising a pharmaceutically acceptable carrier and a therapeutically effective amount of a conjugate according to claim 1 or mixtures thereof.

11. The conjugate according to claim 1, wherein the polyoxyalkylene polymer moiety is a homopolymer, copolymer, or block copolymer, and the polymer moiety contains optional linker groups between polymeric units.

12. The conjugate according to claim 1, wherein the linker groups between polymeric units are independently selected from branched arm hub molecules, —C(O)—, —O—, —$NR^3$—, —$NR^3$C(O)O—, —OC(O)$NR^3$—, —$NR^3$C(O)—, —C(O)$NR^3$—, —$NR^3$C(O)$NR^3$—, -alkylene-$NR^3$C(O)O-, -alkylene-$NR^3$C(O)$NR^3$—, -alkylene-OC(O)$NR^3$—, -alkylene-$NR^3$—, -alkylene-O—, -alkylene-$NR^3$C(O)—, -alkylene-C(O)$NR^3$—, —$NR^3$C(O)O-alkylene-, —$NR^3$C(O)$NR^3$-alkylene-, —OC(O)$NR^3$-alkylene, —$NR^3$-alkylene-, —O-alkylene-, —$NR^3$C(O)-alkylene-, —C(O)$NR^3$-alkylene-, -alkylene-$NR^3$C(O)O-alkylene-, -alkylene-$NR^3$C(O)$NR^3$-alkylene-, -alkylene-OC(O)$NR^3$-alkylene-, -alkylene-$NR^3$-alkylene-, alkylene-O-alkylene-, -alkylene-$NR^3$C(O)-alkylene-, —C(O)$NR^3$-alkylene-, —$NR^3$C(O)O-alkyleneoxy-, —$NR^3$C(O)$NR^3$-alkyleneoxy-, —OC(O)$NR^3$-alkyleneoxy, —$NR^3$-alkyleneoxy-, —O-alkyleneoxy-, —$NR^3$C(O)-alkyleneoxy-, —C(O)$NR^3$-alkyleneoxy-, and -alkyleneoxy-$NR^3$C(O)O-alkyleneoxy-, where each branched arm hub molecule is independently selected from the group consisting of glycerol, pentaerythitol, lysine, 1,2,4-benzenetriol, glucose, ethylenediamine tetraacetic acid, amino acids, 3- or 4-aminosalicylic acid, 1,3-diamino-2-hydroxypropane, glucosamine, and sialic acid, and where $R^3$ is independently selected from the group consisting of hydrogen, alkyl, and substituted alkyl.

13. The conjugate according to claim 1, wherein the polyoxyalkylene polymer moiety contains at least one branched arm hub molecule, where each branched arm hub molecule is independently selected from the group consisting of glycerol, pentaerythitol, lysine, 1,2,4-benzenetriol, glucose, ethylenediamine tetraacetic acid, amino acids, 3- or 4-aminosalicylic acid, 1,3-diamino-2-hydroxypropane, glucosamine, and sialic acid.

14. The conjugate according to claim 13, wherein the polyoxyalkylene polymer moiety contains one or more linker groups between polymeric units which are independently —C(O)—, —O—, —$NR^3$—, —$NR^3$C(O)O—, —OC(O)$NR^3$—, —$NR^3$C(O)—, —C(O)$NR^3$—, —$NR^3$C(O)$NR^3$—, -alkylene-$NR^3$C(O)O—, -alkylene-$NR^3$C(O)$NR^3$—, -alkylene-OC(O)$NR^3$—, -alkylene-$NR^3$—, -alkylene-O—, -alkylene-$NR^3$C(O)—, -alkylene-C(O)$NR^3$—, —$NR^3$C(O)O-alkylene-, —$NR^3$C(O)$NR^3$-alkylene-, —OC(O)$NR^3$-alkylene, —$NR^3$-alkylene-, —O-alkylene-, —$NR^3$C(O)-alkylene-, —C(O)$NR^3$-alkylene-, -alkylene-$NR^3$C(O)O-alkylene-, -alkylene-$NR^3$C(O)$NR^3$-alkylene-, -alkylene-OC(O)$NR^3$-alkylene-, -alkylene-$NR^3$-alkylene-, alkylene-O-alkylene-, -alkylene-$NR^3$C(O)-alkylene-, —C(O)$NR^3$-alkylene-, —$NR^3$C(O)O-alkyleneoxy-, —$NR^3$C(O)$NR^3$-alkyleneoxy-, —OC(O)$NR^3$-alkyleneoxy, —$NR^3$-alkyleneoxy-, —O-alkyleneoxy-, —$NR^3$C(O)-alkyleneoxy-, —C(O)$NR^3$-alkyleneoxy-, or -alkyleneoxy-$NR^3$C(O)O-alkyleneoxy-, where $R^3$ is independently selected from the group consisting of hydrogen, alkyl, and substituted alkyl.

15. The conjugate according to claim 14, wherein the polyoxyalkylene polymer moiety contains one or more linkers which are independently —C(O)—, —$NR^3$C(O)—, or —C(O)$NR^3$—.

16. The conjugate according to claim 14, wherein the polyoxyalkylene polymer moiety contains one or more linkers which are independently —$NR^3$C(O)— or —C(O)$NR^3$—.

17. The conjugate according to claim 13, wherein the polyoxyalkylene polymer moiety has a single branched arm hub molecule linker, and the branched arm hub molecule is glycerol.

18. The conjugate according to claim 1, wherein at least one polymeric unit is derived from ethylene oxide, propylene oxide, or mixtures thereof, and the polyoxyalkylene polymer moiety optionally contains one or more linker groups between polymeric units.

19. The conjugate according to claim 18, wherein at least one polymeric unit is derived from ethylene oxide, and the polyoxyalkylene polymer moiety optionally contains one or more linker groups between polymeric units.

20. A conjugate of the formula I:

B is a polymer moiety comprising at least one polymeric unit, the polymer moiety having an average molecular weight of from about 20,000 to 60,000;

q is from about 2 to about 20;

A at each occurrence is independently a compound of formula II

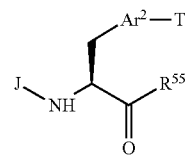

or a pharmaceutically acceptable salt thereof, wherein
each polymeric unit is derived only from alkylene oxide monomers selected from the group consisting of ethylene oxide, propylene oxide, isopropylene oxide, butylene oxide, and mixtures thereof, and the polymer moiety contains optional linker groups between polymeric units;

J is a group of formula (b):

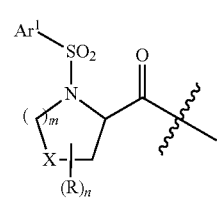

wherein
m is 1;
n is an integer equal to 0, 1 or 2; and
R is hydrogen, $R_{101}$, $R_{204}$, or $R_{205}$, Ar$^1$ is selected from the group consisting of phenyl and heteroaryl, wherein Ar$^1$ is optionally covalently bound to the polymer moiety wherein the polymer moiety optionally comprises a linker which covalently links the polymer moiety to Ar$^1$, and where Ar$^1$ is optionally substituted with from 1 to 3 groups that are independently R$_{201}$, C$_3$-C$_{10}$ cycloalkyl optionally substituted with R$_{201}$, heterocycloalkyl optionally substituted with R$_{201}$, or C$_1$-C$_6$ alkyl optionally substituted with R$_{201}$;

Ar$^2$ is phenyl, wherein Ar$^2$ is optionally covalently bound to the polymer moiety and wherein the polymer moiety optionally comprises a linker which covalently links the polymer moiety to Ar$^2$, and where Ar$^2$ is optionally substituted with from 1 to 3 groups that are independently R$_{201}$, C$_3$-C$_{10}$ cycloalkyl optionally substituted with R$_{201}$, heterocycloalkyl optionally substituted with R$_{201}$, or C$_1$-C$_6$ alkyl optionally substituted with R$_{201}$;

X is selected from the group consisting of —NR$^1$—, —O—, —S—, —SO—, —SO$_2$, and optionally substituted —CH$_2$— which is optionally covalently bound to the polymer moiety wherein, in each case, the polymer moiety optionally comprises a linker which covalently links the polymer moiety;

where R$^1$ is selected from the group consisting of hydrogen and alkyl;

T is a group of formula (d)

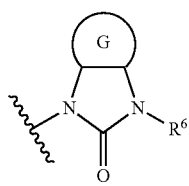

(d)

wherein G is optionally substituted pyrido, wherein said pyrido optionally further comprises a covalent bond to a polymer moiety which optionally comprises a linker;

R$^6$ is a covalent bond to a polymer moiety which optionally comprises a linker, or R$^6$ is —H, R$_{201}$, or —CH$_2$C(O)R$^{17}$, wherein R$^{17}$ is —OH, —OR$^{18}$, or —NHR$^{18}$, wherein R$^{18}$ is R$_{201}$, R$_{204}$, or R$_{205}$;

R$_{101}$ is alkyl optionally substituted with from 1 to 3 groups independently selected from R$_{201}$, R$_{202}$, R$_{203}$, R$_{204}$, and R$_{205}$, where R$_{201}$ is alkoxy, acyl, acylamino, acyloxy, amino, mono- or di(C$_1$-C$_5$)alkylamino, aminoacyl, aryloxy, cyano, halogen, hydroxyl, nitro, carboxyl, —C(O)O—(C$_1$-C$_6$)alkyl, or —C(O)O-aryl;

R$_{202}$ is C$_3$-C$_{10}$ cycloalkyl optionally substituted with from 1 to 5 groups which are independently oxo, thioxo, R$_{201}$, heterocycloalkyl optionally substituted with R$_{201}$, aryl optionally substituted with R$_{201}$, or heteroaryl optionally substituted with R$_{201}$;

R$_{203}$ is heterocycloalkyl optionally substituted with from 1 to 5 groups which are independently oxo, thioxo, R$_{201}$, or C$_1$-C$_5$ alkyl optionally substituted with R$_{201}$;

R$_{204}$ is aryl optionally substituted with from 1 to 3 groups that are independently R$_{201}$, C$_3$-C$_{10}$ cycloalkyl optionally substituted with R$_{201}$, heterocycloalkyl optionally substituted with R$_{201}$, or C$_1$-C$_5$ alkyl optionally substituted with R$_{201}$;

R$_{205}$ is heteroaryl optionally substituted with from 1 to 3 groups that are independently R$_{201}$, C$_3$-C$_{10}$ cycloalkyl optionally substituted with R$_{201}$, heterocycloalkyl optionally substituted with R$_{201}$, or C$_1$-C$_5$ alkyl optionally substituted with R$_{201}$; and R$^{55}$ is —OH or a hydrolyzable ester, or R$^{55}$ forms a hydrolyzable polymer ester with the polymer moiety, optionally through a linker;

wherein each heteroaryl contains up to 10 carbon atoms and 1 to 4 heteroatoms selected from the group consisting of oxygen, nitrogen and sulfur;

wherein each heterocycloalkyl independently contains up to 10 carbon atoms and from 1 to 4 hetero atoms selected from the group consisting of nitrogen, sulfur and oxygen;7 provided that:

A. at least one of J, R$^{55}$, and T contains a covalent bond to the polymer moiety; and B. the conjugate of formula I has a molecular weight of no more than about 80,000.

21. A conjugate according to claim 20 wherein

B is a polyoxyalkylene polymer moiety comprising at least one polymeric unit, the polymer moiety having an average molecular weight of from about 20,000 to 60,000;

Ar$^1$ is selected from the group consisting of phenyl, pyridinyl, indolizinyl, benzothienyl, pyrrolyl, indolyl, thiophenyl, furanyl, imidazolyl, pyrazolyl, pyrimidinyl, thienyl, quinolinyl, pyrazinyl, pyridazinyl, indolizinyl, isoindolyl, indolyl, indazolyl, purinyl, quinolizinyl, isoquinolinyl, phthalazinyl, quinoxalinyl, quinazolinyl, cinnolinyl, pteridinyl, isothiazolyl, isoxazolyl, thiazolyl, and benzo[b]thienyl, wherein Ar$^1$ is optionally covalently bound to the polymer moiety wherein the polymer moiety optionally comprises a linker which covalently links the polymer moiety to Ar$^1$, and where Ar$^1$ is optionally substituted with from 1 to 3 groups that are independently R$_{201}$, C$_3$-C$_{10}$ cycloalkyl optionally substituted with R$_{201}$, heterocycloalkyl optionally substituted with R$_{201}$, or C$_1$-C$_5$ alkyl optionally substituted with R$_{201}$;

and wherein each heterocycloalkyl is selected from the group consisting of piperidinyl, piperazinyl, morpholinyl, thiomorpholinyl, pyrrolidinyl, tetrahydrofuranyl, azetidinyl, dihydroindolyl, imidazolidinyl, imidazolinyl, indolinyl, 1,2,3,4-tetrahydro-isoquinolinyl, 1,4-dioxa-8-azaspiro[4.5]decanyl, 4,5,6,7-tetrahydrobenzo[b]thiophenyl, and thiazolidinyl.

22. The conjugate according to claim 21, wherein

Ar$^1$ is selected from the group consisting of phenyl, pyridinyl, indolizinyl, benzothienyl, pyrrolyl, indolyl, thiophenyl, furanyl, imidazolyl, pyrazolyl, pyrimidinyl, thienyl, and quinolinyl, wherein Ar$^1$ is optionally covalently bound to the polymer moiety and wherein the polymer moiety optionally comprises a linker which covalently links the polymer moiety to Ar$^1$, and where Ar$^1$ is optionally substituted with from 1 to 3 groups that are independently R$_{201}$, C$_3$-C$_{10}$ cycloalkyl optionally substituted with R$_{201}$, heterocycloalkyl optionally substituted with R$_{201}$, or C$_1$-C$_5$ alkyl optionally substituted with R$_{201}$.

23. The conjugate according to claim 21, wherein
W is selected from the group consisting of a covalent bond to a polymer moiety which optionally comprises a linker, and —NR²R³
wherein R² and R³ are independently selected from the group consisting of hydrogen and C₁-C₆ alkyl optionally substituted with R₂₀₁, or where R² and R³, together with the nitrogen atom bound thereto, form a piperidinyl, piperazinyl, morpholinyl, thiomorpholinyl, or pyrrolidinyl group, each of which is optionally substituted with C₁-C₆ alkyl or R₂₀₁, and
wherein each of the C₁-C₆ alkyl and the heterocycloalkyl within W is optionally covalently bound to a polymer moiety which further optionally comprises a linker.

24. The conjugate according to claim 1, wherein B is selected from the group selected from:

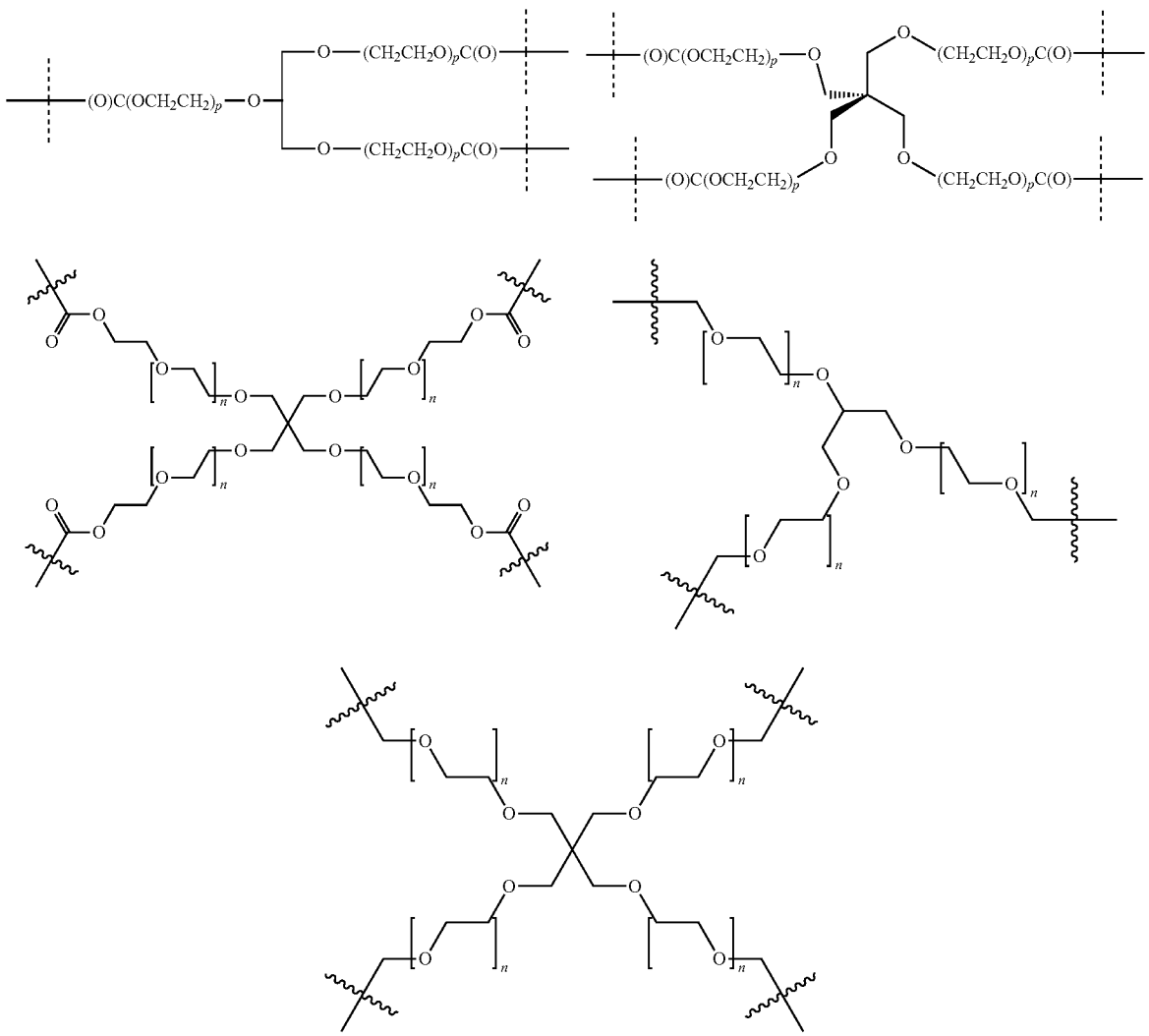

wherein
Z is

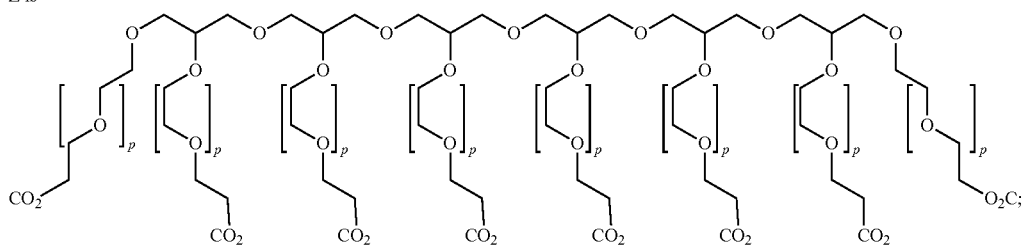

ZZ is
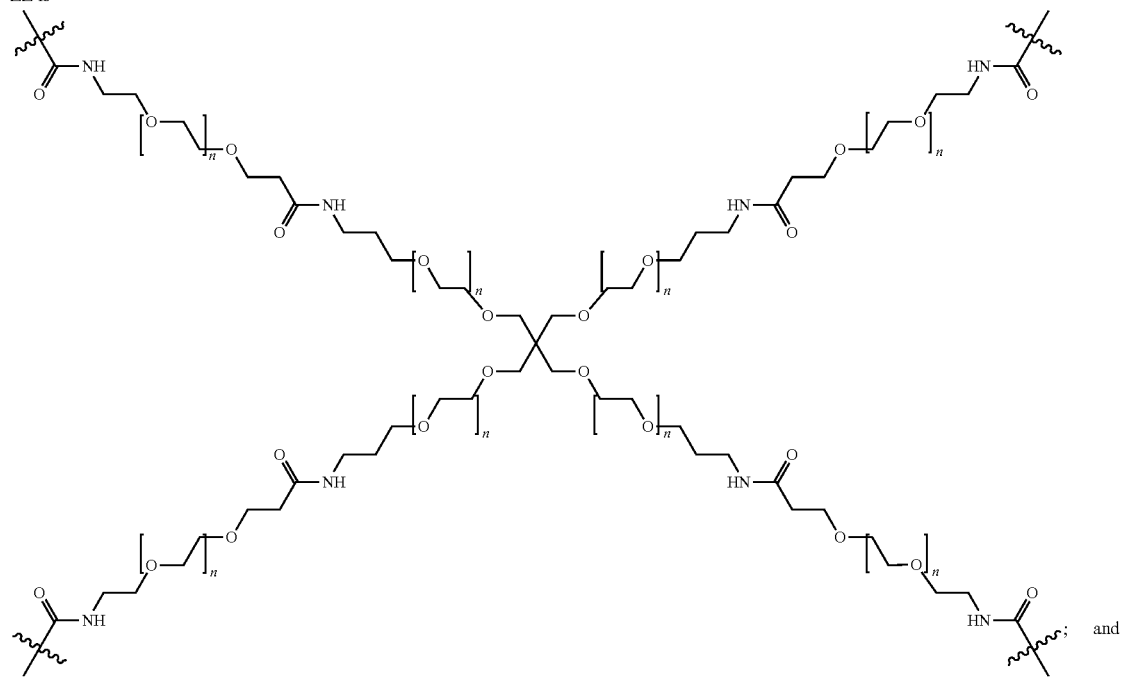
; and
ZZZ is
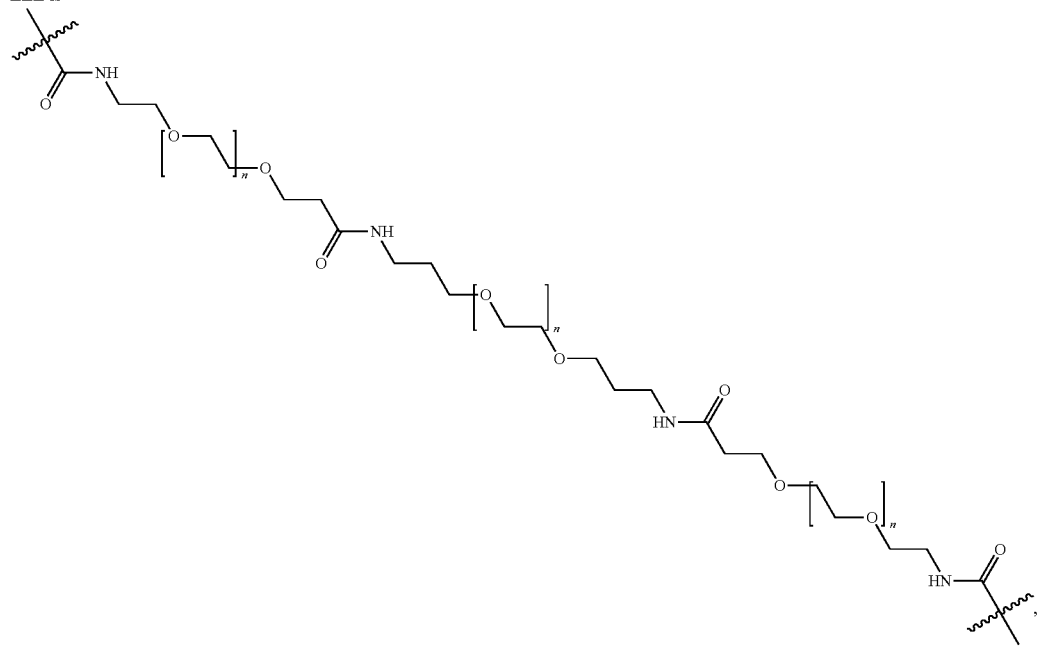
;
where the sum of all p variables or all n variables is from 100 to 1360.

25. The conjugate according to claim 20, wherein B is selected from the group selected from:
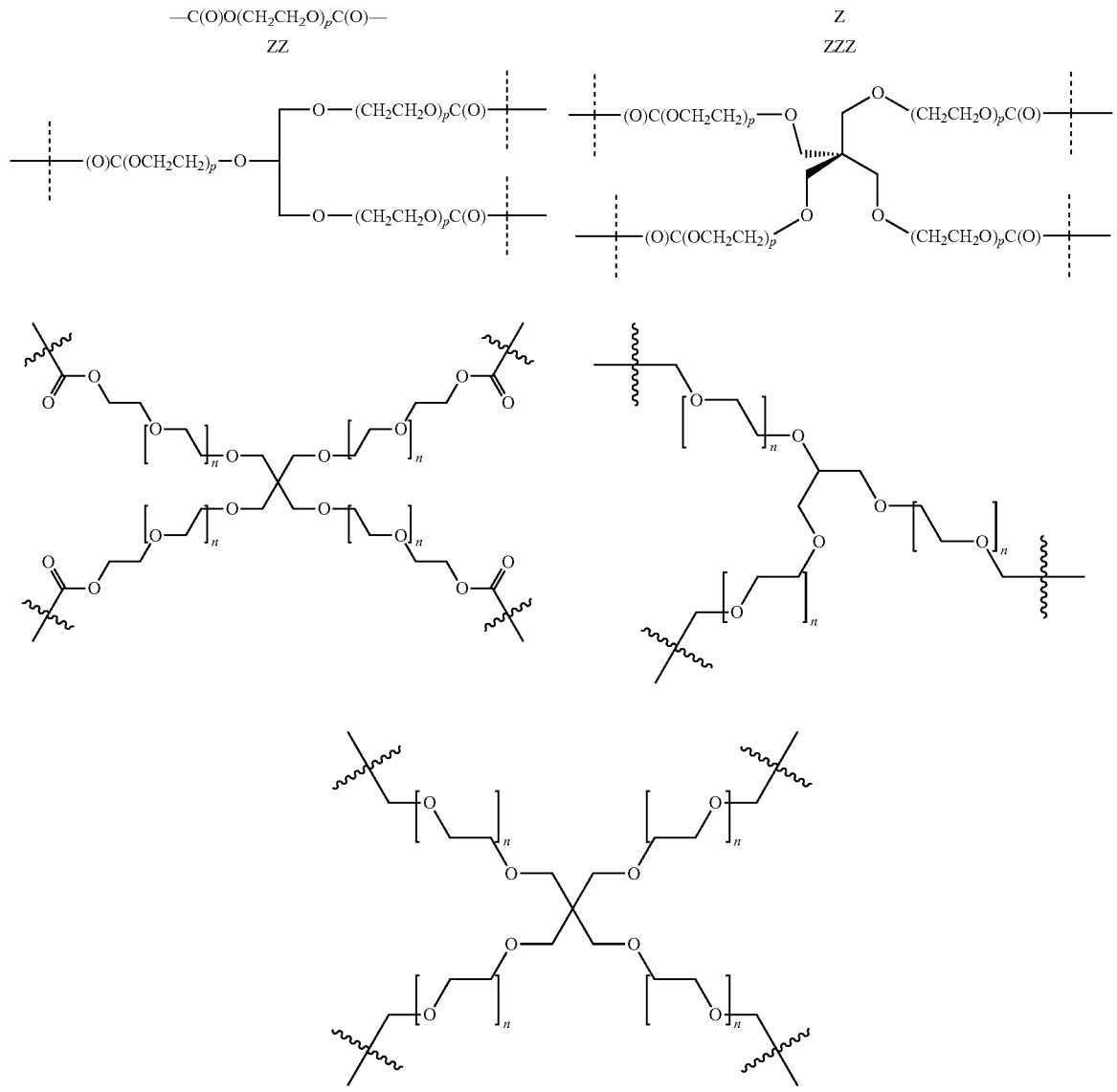
wherein
Z is
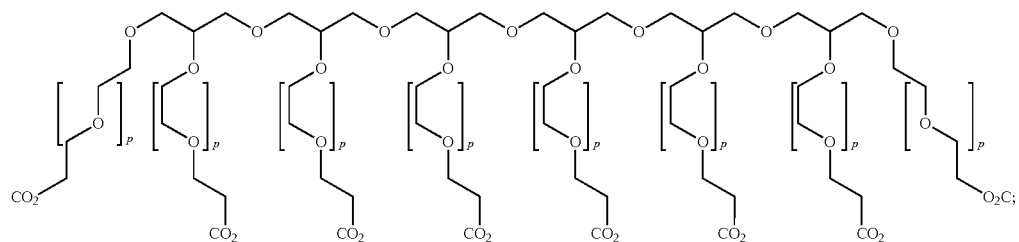

ZZ is
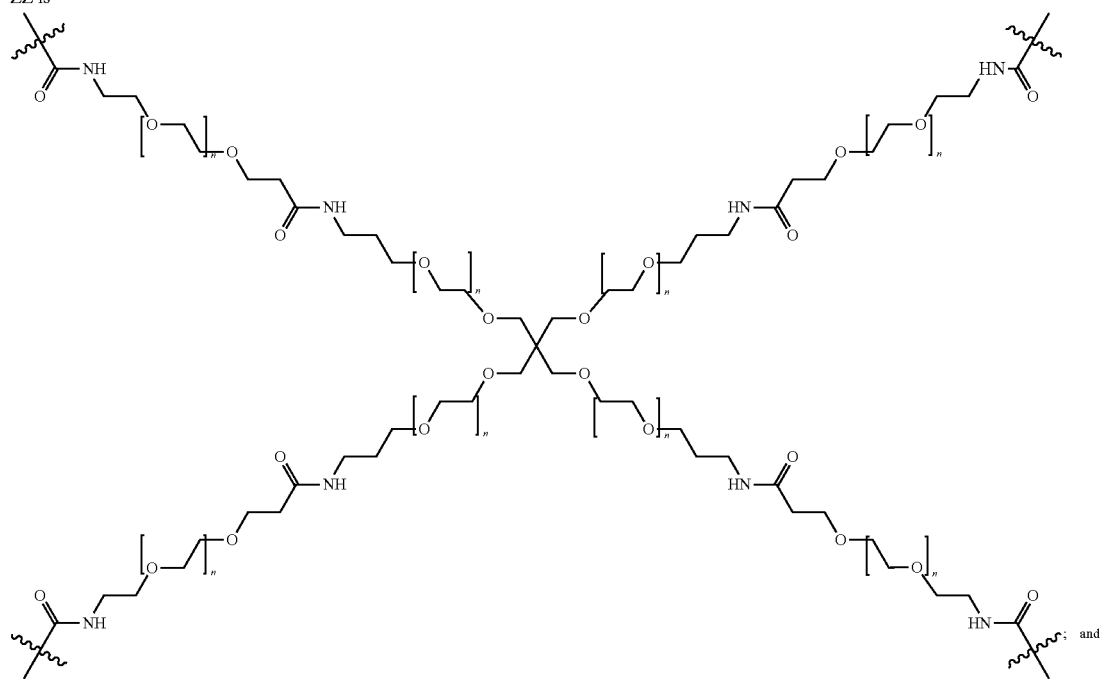
ZZZ is
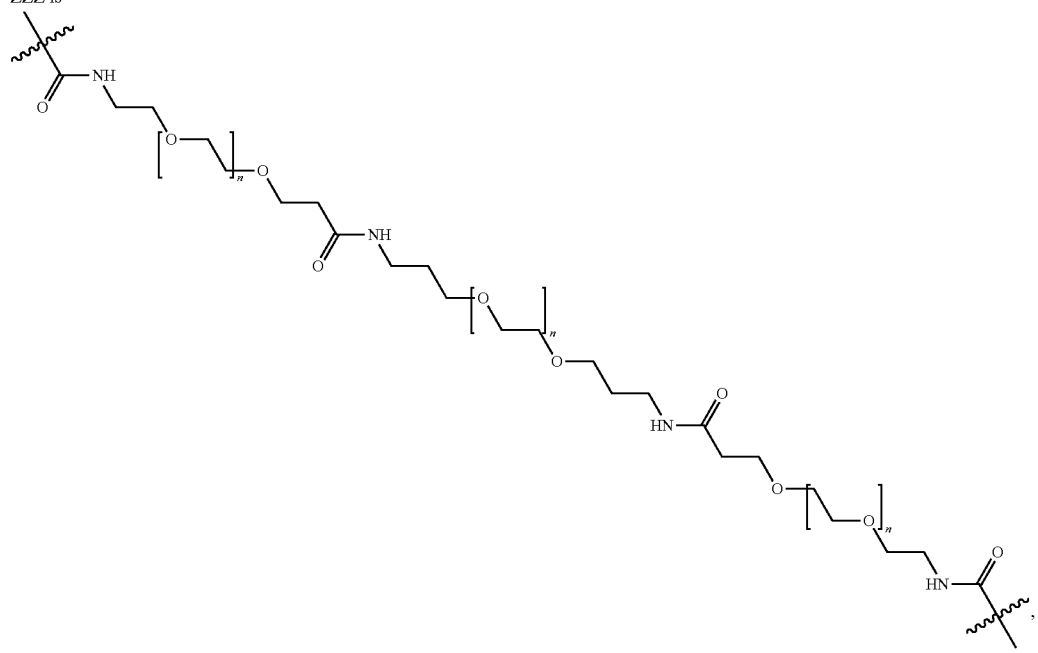
wherein
where the sum of all p variables or all n variables is from 100 to 1360,
or a pharmaceutically acceptable salt thereof.

26. A conjugate of the formula
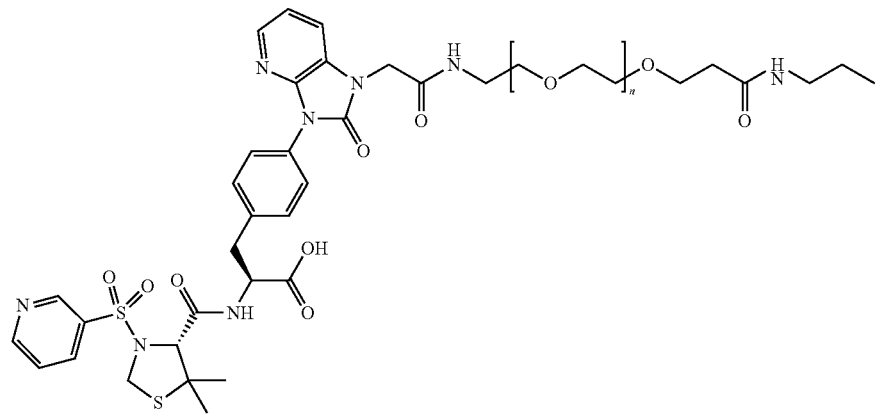
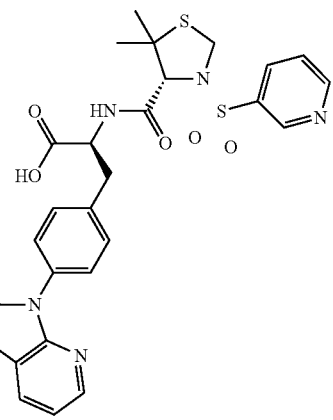
where the sum of all n variables is from 100 to 1360,
or a pharmaceutically acceptable salt thereof.
27. A conjugate of the formula 213 214
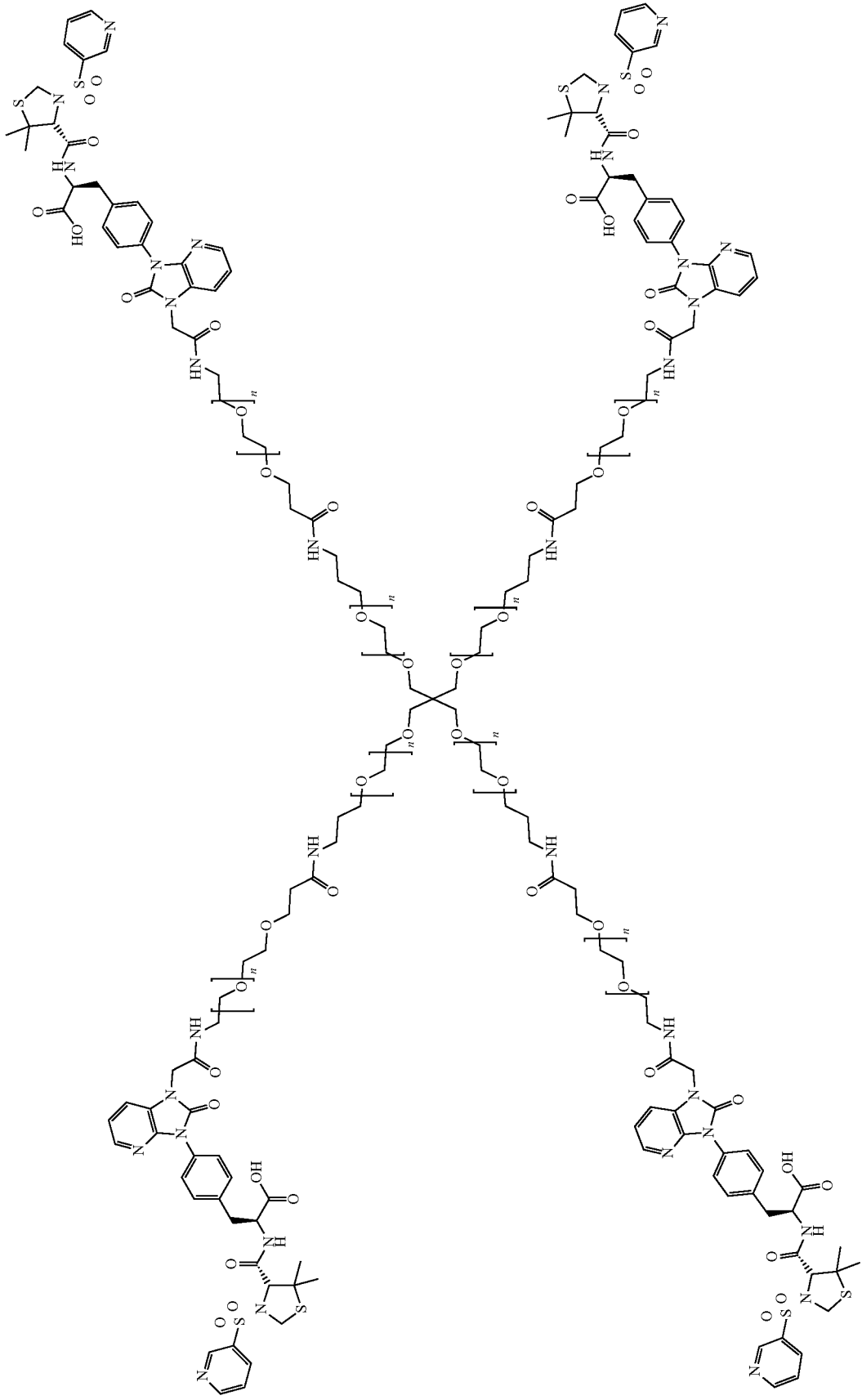

where the sum of all the n variables is from 100 to 1360, or a pharmaceutically acceptable salt thereof.

28. A conjugate of the formula

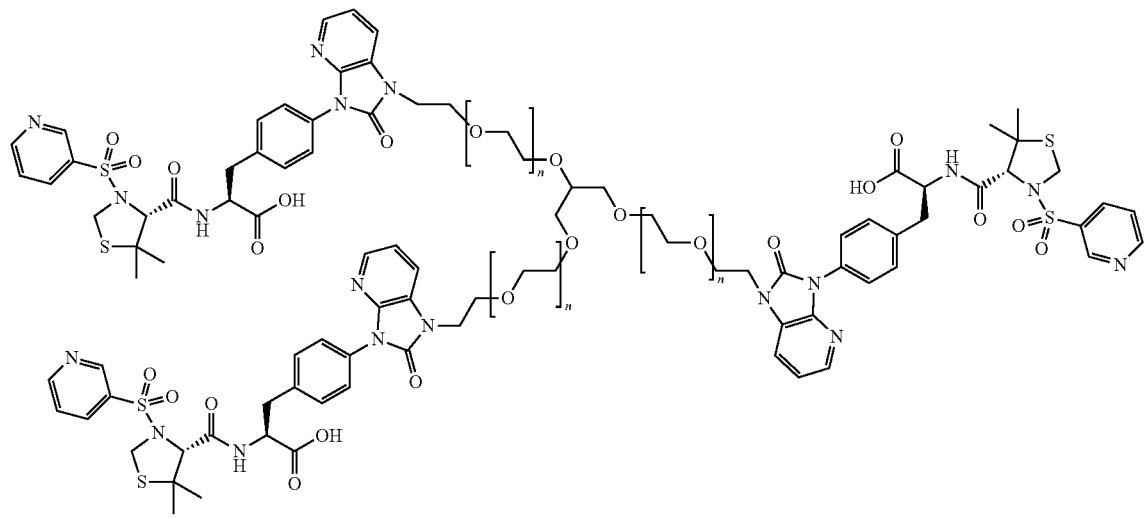

where the sum of all the n variables is from 100 to 1360, or a pharmaceutically acceptable salt thereof.

29. A conjugate of the formula

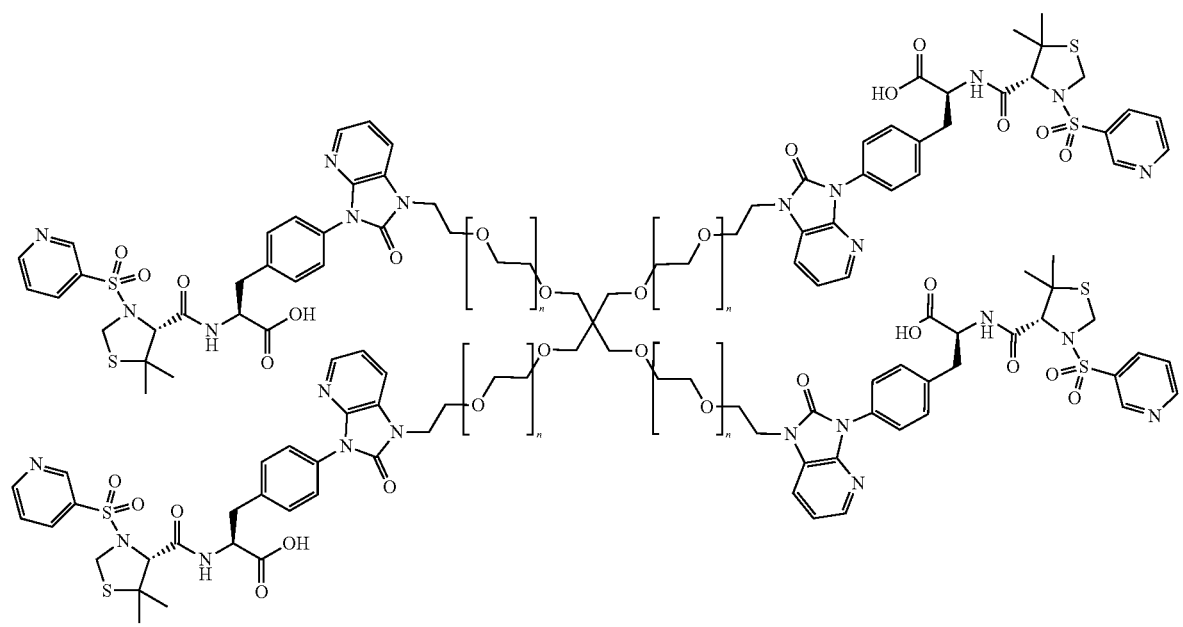

where the sum of all the n variables is from 100 to 1360.

30. A method for treating multiple sclerosis, which method comprises administering an effective amount of a conjugate according to claim 1 to a patient suffering from multiple sclerosis.

* * * * *